United States Patent [19]
Draetta et al.

[11] Patent Number: 5,981,699
[45] Date of Patent: Nov. 9, 1999

[54] HUMAN UBIQUITIN CONJUGATING ENZYME

[75] Inventors: Giulio Draetta, Winchester; Mark Rolfe, Newton Upper Falls; Jens W. Eckstein, Cambridge, all of Mass.

[73] Assignee: Mitotix, Inc., Cambridge, Mass.

[21] Appl. No.: 08/247,904

[22] Filed: May 23, 1994

Related U.S. Application Data

[63] Continuation-in-part of application No. 08/176,937, Jan. 4, 1994, abandoned.

[51] Int. Cl.$^6$ .......................... C07K 14/00; A61K 39/00
[52] U.S. Cl. ...................... 530/350; 530/324; 424/185.1; 424/192.1
[58] Field of Search .............................. 530/50, 324–330; 424/192.1, 185.1; 435/69.1–69.3, 69.7

[56] References Cited

FOREIGN PATENT DOCUMENTS

| | | |
|---|---|---|
| WO 89/09829 | 10/1989 | WIPO . |
| WO 89/12678 | 12/1989 | WIPO . |
| WO 91/17245 | 11/1991 | WIPO . |
| WO 92/20804 | 11/1992 | WIPO . |
| WO 93/09235 | 5/1993 | WIPO . |

OTHER PUBLICATIONS

Band et al., "Loss of p53 Protein in Human Papillomarvirus Type 16 E6–Immortalized Human Mammary Epithelial Cells" *Journal of Virology*, vol. 65, No. 12, pp. 6671–6676, Dec. 1991.
Berleth et al., "Inhibition of Ubiquitin–Protein Ligase (E3) by Mono–and Bifunctional Phenylarsenoxides" *The Journal of Biological Chemistry*, vol. 267, No. 23, pp. 16403–16411, Aug. 15, 1992.
Bissonnette et al., "Apoptotic cell death induced by c–myc is inhibited by bcl–2" *Nature*, vol. 359, pp. 552–556, Oct. 8, 1992.
Chen et al., "Multiple Ubiquitin–Conjugating Enzymes Participate in the In Vivo Degradation of the Yeast MATα2 Repressor" *Cell*, vol. 74, pp. 357–369, Jul. 30, 1993.
Crook et al., "Degradation of p53 Can Be Targeted by HPV E6 Sequences Distinct from Those Required for p53 Binding and Trans–Activation" *Cell*, vol. 67, pp. 547–556, Nov. 1, 1991.
Dohmen et al., "The N–end rule is mediated by the UBC2(RAD6) ubiquitin–conjugating enzyme" *Proceedings of the National Academy of Sciences*, vol. 88, pp. 7351–7355, Aug. 1991.
Ellison et al., "Epitope–tagged Ubiquitin" *The Journal of Biological Chemistry*, vol. 266, No. 31, pp. 21150–21157, Nov. 5, 1991.
Evan et al., "Induction of Apoptosis in Fibroblasts by c–myc Protein" *Cell*, vol. 69, pp. 119–128, Apr. 3, 1992.
Glotzer et al., "Cyclin is degraded by the ubiquitin pathway" *Nature*, vol. 349, pp. 132–138, Jan. 10, 1991.
Hartwell et al., "Defects in a Cell Cycle Checkpoint May Be Responsible for the Genomic Instability of Cancer Cells" *Cell*, vol. 71, pp. 543–546, Nov. 13, 1992.

Hershko et al., "Components of Ubiquitin–Protein Ligase System" *The Journal of Biological Chemistry*, vol. 258, No. 13, pp. 8206–8214, Jul. 10, 1983.
Hochstrasser et al., "In Vivo Degradation of a Transcriptional Regulator: The Yeast α2 Repressor" *Cell*, vol. 61, pp. 697–708, May 18, 1990.
Hoefer et al., "Purification and partial characterization of ubiquitin–activating enzyme from *Saccharomyces cerevisiae*" *FEBS Letters*, vol. 289, No. 1, pp. 54–58, Sep. 1991.
Holloway et al., "Anaphase Is Initiated by Proteolysis Rather Than by the Inactivation of Maturation–Promoting Factor" *Cell*, vol. 73, pp. 1393–1402, Jul. 2, 1993.
Huibregtse et al., "Localization of the E6–AP Regions That Direct Human Papillomavirus E6 Binding, Association with p53, and Ubiquitination of Associated Proteins" *Molecular and Cellular Biology*, vol. 13, No. 8, Aug. 1993.
Huibregtse et al., "Cloning and Expression of the cDNA for E6–AP, a Protein That Mediates the Interaction of the Human Papillomavirus E6 Oncoprotein with p53" *Molecular and Cellular Biology*, vol. 13, No. 2, pp. 775–784, Feb. 1993.
Hupp et al., "Regulation of the Specific DNA Binding Function of p53" *Cell*, vol. 71, pp. 875–886, Nov. 27, 1992.
Jacobs et al., "Rapid Assessment of Drug Susceptibilities of *Mycobacterium tuberculosis* by Means of Luciferase Reporter Phages" *Science*, vol. 260, pp. 819–822, May 7, 1993.
Jentsch et al., "The Ubiquitin–conjugation System" *Annu. Rev. Genet.*, vol. 26, pp. 179–207, 1992.
Jentsch et al., "Ubiquitin–dependent protein degradation: a cellular perspective" *Trends in Genetics*, vol. 2, pp. 98–103, Apr. 1992.
Klemperer et al., "A Novel, Arsenite–Sensitive E2 of the Ubiquitin Pathway: Purification and Properties" *Biochemistry*, vol. 28, pp. 6035–6041, 1989.
Koken et al., "Structural and Functional conservation of two human homologs of the yeast DNA repair gene RAD6" *Proceedings of the National Academy of Sciences*, vol. 88, pp. 8865–8869, Oct. 1991.
Milner et al., "p53 Is Associated with p34$^{cdc2}$ In Transformed Cells" *The EMBO Journal*, vol. 9, No. 9, pp. 2885–2889, 1990.

(List continued on next page.)

*Primary Examiner*—Ponnathapura Achutamurthy
*Attorney, Agent, or Firm*—Matthew P. Vincent; Beth E. Arnold; Foley, Hoag & Eliot LLP

[57] ABSTRACT

The present invention concerns a novel human ubiquitin-conjugating enzyme which is implicated in the ubiquitin-mediated inactivation of cell-cycle regulatory proteins, particularly p53. The present invention makes available diagnostic and therapeutic assays and reagents for detecting and treating transformed cells, such as may be useful in the detection of cancer. The present invention also provides reagents for altering the normal regulation cell proliferation in untransformed cells, such as by upregulating certain cell-cycle checkpoints, e.g. to protect normal cells against DNA damaging reagents.

26 Claims, 36 Drawing Sheets

OTHER PUBLICATIONS

Münger et al., "The E6 and E7 Genes of the Human Papillomavirus Type 16 Together Are Necessary and Sufficient for Transformation of Primary Human Keratinocytes" *Journal of Virology*, vol. 63, No. 10, pp. 4417–4421, Oct. 1989.

Nepveu et al., "Alternative modes of c–myc regulation in growth factor–stimulated and differentiating cells" *Oncogene*, vol. 1, pp. 243–250, 1987.

Rechsteiner et al., "Natural Substrates of the Ubiquitin Proteolytic Pathway" *Cell*, vol. 66, pp. 615–618, Aug. 23, 1991.

Schärer et al., "Mammalian p53 can function as a transcription factor in yeast" *Nucleic Acids Research*, vol. 20, No. 7, pp. 1539–1545, 1992.

Scheffner et al., "Interaction of the Human Papillomavirus Type 16 E6 Oncoprotein with Wild–Type and Mutant Human p53 Proteins" *Journal of Virology*, vol. 66, No. 8, pp. 5100–5105, Aug. 1992.

Schneffner et al., "The E6 Oncoprotein Encoded by Human Papi;;omavirus Types 16 and 18 Promotes the Degradation of p53" *Cell*, vol. 63, pp. 1129–1136, Dec. 21, 1990.

Scheffner et al., "Targeted degradation of the retinoblastoma protein by human papillomavirus E7–E6 fusion proteins" *The EMBO Journal*, vol. 11, No. 7, pp. 2425–2431, 1992.

Scheffner et al., "The HPV–16 E6 and E6–AP Complex Functions as a Ubiquitin–Protein Ligase in the Ubiquitination of p53" *Cell*, vol. 75, pp. 495–505, Nov. 5, 1993.

Treier et al., "Drosophila UbcD1 encodes a highly conserved ubiquitin–conjugating enzyme involved in selective protein degradation" *The EMBO Journal*, vol. 11, No. 1, pp. 367–372, 1992.

Tyers etal., "The Cin3–Cdc28 kinase complex of *S.cerevisiae* is regulated by proteolysis and phosphorylation" *The EMBO Journal*, vol. 11, No. 5, pp. 1773–1784, 1992.

Watanabe et al., "Human Papillomavirus Type 16 Transformation of Primary Human Embryonic Fibroblasts Requires Expression of Open Reading Frames E6 and E7" *Journal of Virplogy*, vol. 63, No. 2, pp. 965–969, Feb. 1989.

Zhen et al., "The ubc–2 Gene of *Caenorhabditis elegans* Encodes a Ubiquitin–Conjugating Enzyme Involved in Selective Protein Degradation" *Molecular and Cellular Biology*, vol. 13, No. 3, pp. 1371–1377, Mar. 1993.

Adams et al. (1993) "Rapid cDNA sequencing (expressed sequence tags) from a directionally cloned human infant brain cDNA library" *Nature Genetics* 4:373–380.

Cook et al. (1992) "Structure of a Diubiquitin Conjugate and a Model for Interaction with Ubiquitin Conjugating Enzyme (E2)" *The Journal of Biological Chemistry* 267(23):16467–16471.

Cook et al. (1993) "Tertiary Structures of Class I Ubiquitin–Conjugating Enzymes Are Highly Conserved: Crystal Structure of Yeast of Ubc4" *Biochemistry* 32(50):13809–13817.

Girod et al. (1993) "Homologs of the essential ubiquitin–conjugating enzymes UBC1, 4, and 5 in yeast are encoded by a multigene family in *Arabidopsis thaliana*" *The Plant Journal* 3(4):545–552.

Seufert and Jentsch (1990) "Ubiquitin–conjugating enzymes UBC4 and UBC5 mediate selective degradation of short–lived and abnormal proteins" *EMBO J* 9(2):543–550.

Sequence alignments to—Treier et al (1992) EMBO J. 11:367–372.

Sequence alignments to —Zhen et al (1993) Mol. Cell Biol 13:1371–1377.

| | | | | | | | | | |
|---|---|---|---|---|---|---|---|---|---|
| ATOM | 1 | N | ARG | 1 | 5 | 10.652 | 30.749 | 37.986 | 1.00 0.00 |
| ATOM | 2 | CA | ARG | 1 | 5 | 10.654 | 30.876 | 39.370 | 1.00 0.00 |
| ATOM | 3 | C | ARG | 1 | 5 | 9.386 | 31.560 | 39.753 | 1.00 0.00 |
| ATOM | 4 | O | ARG | 1 | 5 | 9.153 | 32.661 | 39.298 | 1.00 0.00 |
| ATOM | 5 | CB | ARG | 1 | 5 | 11.872 | 31.683 | 39.871 | 1.00 0.00 |
| ATOM | 6 | CG | ARG | 1 | 5 | 12.638 | 31.033 | 41.051 | 1.00 0.00 |
| ATOM | 7 | CD | ARG | 1 | 5 | 11.956 | 31.005 | 42.439 | 1.00 0.00 |
| ATOM | 8 | NE | ARG | 1 | 5 | 11.007 | 29.919 | 42.560 | 1.00 0.00 |
| ATOM | 9 | CZ | ARG | 1 | 5 | 10.281 | 29.677 | 43.686 | 1.00 0.00 |
| ATOM | 10 | NH1 | ARG | 1 | 5 | 10.417 | 30.413 | 44.773 | 1.00 0.00 |
| ATOM | 11 | NH2 | ARG | 1 | 5 | 9.411 | 28.694 | 43.623 | 1.00 0.00 |
| ATOM | 12 | 1H | ARG | 1 | 5 | 10.497 | 29.737 | 37.803 | 1.00 0.00 |
| ATOM | 13 | 2H | ARG | 1 | 5 | 9.927 | 31.348 | 37.541 | 1.00 0.00 |
| ATOM | 14 | 3H | ARG | 1 | T | 11.573 | 31.167 | 37.744 | 1.00 0.00 |
| ATOM | 15 | HE | ARG | 1 | 5 | 10.888 | 29.459 | 41.680 | 1.00 0.00 |
| ATOM | 16 | 1HH1 | ARG | 1 | 5 | 9.832 | 30.497 | 45.580 | 1.00 0.00 |
| ATOM | 17 | 2HH1 | ARG | 1 | 5 | 11.297 | 30.876 | 44.878 | 1.00 0.00 |
| ATOM | 18 | 1HH2 | ARG | 1 | 5 | 8.878 | 28.410 | 44.420 | 1.00 0.00 |
| ATOM | 19 | 2HH2 | ARG | 1 | 5 | 9.283 | 28.223 | 42.749 | 1.00 0.00 |
| ATOM | 20 | N | ILE | 1 | 6 | 8.510 | 30.841 | 40.468 | 1.00 0.00 |
| ATOM | 21 | CA | ILE | 1 | 6 | 7.082 | 31.170 | 40.678 | 1.00 0.00 |
| ATOM | 22 | C | ILE | 1 | 6 | 6.442 | 31.065 | 39.284 | 1.00 0.00 |
| ATOM | 23 | O | ILE | 1 | 6 | 5.956 | 29.988 | 38.915 | 1.00 0.00 |
| ATOM | 24 | CB | ILE | 1 | 6 | 6.853 | 32.470 | 41.413 | 1.00 0.00 |
| ATOM | 25 | CG1 | ILE | 1 | 6 | 7.651 | 32.561 | 42.727 | 1.00 0.00 |
| ATOM | 26 | CG2 | ILE | 1 | 6 | 5.366 | 32.803 | 41.630 | 1.00 0.00 |
| ATOM | 27 | CD1 | ILE | 1 | 6 | 6.834 | 32.009 | 43.915 | 1.00 0.00 |
| ATOM | 28 | H | ILE | 1 | 6 | 8.808 | 29.963 | 40.841 | 1.00 0.00 |
| ATOM | 29 | N | HIS | 1 | 7 | 6.540 | 32.257 | 38.639 | 1.00 0.00 |
| ATOM | 30 | CA | HIS | 1 | 7 | 6.197 | 32.320 | 37.173 | 1.00 0.00 |
| ATOM | 31 | C | HIS | 1 | 7 | 7.002 | 31.274 | 36.346 | 1.00 0.00 |
| ATOM | 32 | O | HIS | 1 | 7 | 8.174 | 30.919 | 36.611 | 1.00 0.00 |
| ATOM | 33 | CB | HIS | 1 | 7 | 6.233 | 33.740 | 36.613 | 1.00 0.00 |
| ATOM | 34 | CG | HIS | 1 | 7 | 7.507 | 34.441 | 37.147 | 1.00 0.00 |
| ATOM | 35 | ND1 | HIS | 1 | 7 | 8.661 | 34.555 | 36.453 | 1.00 0.00 |
| ATOM | 36 | CD2 | HIS | 1 | 7 | 7.660 | 35.160 | 38.373 | 1.00 0.00 |
| ATOM | 37 | CE1 | HIS | 1 | 7 | 9.552 | 35.219 | 37.259 | 1.00 0.00 |
| ATOM | 38 | NE2 | HIS | 1 | 7 | 8.924 | 35.642 | 38.428 | 1.00 0.00 |
| ATOM | 39 | H | HIS | 1 | 7 | 7.119 | 32.928 | 39.101 | 1.00 0.00 |
| ATOM | 40 | 1HD | HIS | 1 | 7 | 8.806 | 34.258 | 35.530 | 1.00 0.00 |
| ATOM | 41 | N | LYS | 1 | 8 | 6.366 | 30.860 | 35.208 | 1.00 0.00 |
| ATOM | 42 | CA | LYS | 1 | 8 | 6.776 | 29.679 | 34.371 | 1.00 0.00 |
| ATOM | 43 | C | LYS | 1 | 8 | 6.529 | 28.399 | 35.097 | 1.00 0.00 |
| ATOM | 44 | O | LYS | 1 | 8 | 5.719 | 27.551 | 34.809 | 1.00 0.00 |
| ATOM | 45 | CB | LYS | 1 | 8 | 8.237 | 29.782 | 33.828 | 1.00 0.00 |

FIG. 1A

| ATOM | 46 | CG | LYS | 1 | 8 | 8.500 | 29.320 | 32.392 | 1.00 | 0.00 |
| ATOM | 47 | CD | LYS | 1 | 8 | 9.916 | 29.656 | 31.893 | 1.00 | 0.00 |
| ATOM | 48 | CE | LYS | 1 | 8 | 9.996 | 29.567 | 30.420 | 1.00 | 0.00 |
| ATOM | 49 | NZ | LYS | 1 | 8 | 11.060 | 30.278 | 29.662 | 1.00 | 0.00 |
| ATOM | 50 | H | LYS | 1 | 8 | 5.445 | 31.225 | 35.069 | 1.00 | 0.00 |
| ATOM | 51 | 1HZ | LYS | 1 | 8 | 10.982 | 31.309 | 29.543 | 1.00 | 0.00 |
| ATOM | 52 | 1HZ | LYS | 1 | 8 | 12.021 | 29.906 | 29.803 | 1.00 | 0.00 |
| ATOM | 53 | 3HZ | LYS | 1 | 8 | 11.084 | 30.047 | 28.648 | 1.00 | 0.00 |
| ATOM | 54 | N | GLU | 1 | 9 | 7.274 | 28.215 | 36.215 | 1.00 | 0.00 |
| ATOM | 55 | CA | GLU | 1 | 9 | 6.995 | 27.070 | 37.159 | 1.00 | 0.00 |
| ATOM | 56 | C | GLU | 1 | 9 | 5.445 | 26.859 | 37.570 | 1.00 | 0.00 |
| ATOM | 57 | O | GLU | 1 | 9 | 4.977 | 25.769 | 37.789 | 1.00 | 0.00 |
| ATOM | 58 | CB | GLU | 1 | 9 | 7.951 | 27.203 | 38.425 | 1.00 | 0.00 |
| ATOM | 59 | CG | GLU | 1 | 9 | 9.433 | 26.780 | 38.356 | 1.00 | 0.00 |
| ATOM | 60 | CD | GLU | 1 | 9 | 10.169 | 27.525 | 39.767 | 1.00 | 0.00 |
| ATOM | 61 | OE1 | GLU | 1 | 9 | 9.570 | 27.669 | 40.887 | 1.00 | 0.00 |
| ATOM | 62 | OE2 | GLU | 1 | 9 | 11.354 | 27.904 | 39.613 | 1.00 | 0.00 |
| ATOM | 63 | H | GLU | 1 | 9 | 7.918 | 28.973 | 36.320 | 1.00 | 0.00 |
| ATOM | 64 | N | LEU | 1 | 10 | 4.816 | 27.970 | 37.728 | 1.00 | 0.00 |
| ATOM | 65 | CA | LEU | 1 | 10 | 3.434 | 28.097 | 38.068 | 1.00 | 0.00 |
| ATOM | 66 | C | LEU | 1 | 10 | 3.047 | 29.230 | 37.145 | 1.00 | 0.00 |
| ATOM | 67 | O | LEU | 1 | 10 | 3.769 | 30.204 | 37.045 | 1.00 | 0.00 |
| ATOM | 68 | CB | LEU | 1 | 10 | 3.176 | 28.409 | 39.531 | 1.00 | 0.00 |
| ATOM | 69 | CG | LEU | 1 | 10 | 2.041 | 27.485 | 40.074 | 1.00 | 0.00 |
| ATOM | 70 | CD1 | LEU | 1 | 10 | 0.728 | 27.903 | 39.503 | 1.00 | 0.00 |
| ATOM | 71 | CD2 | LEU | 1 | 10 | 2.366 | 26.000 | 39.832 | 1.00 | 0.00 |
| ATOM | 72 | H | LEU | 1 | 10 | 5.291 | 28.782 | 37.389 | 1.00 | 0.00 |
| ATOM | 73 | N | LEU | 1 | 11 | 1.850 | 29.001 | 36.566 | 1.00 | 0.00 |
| ATOM | 74 | CA | ASN | 1 | 11 | 1.355 | 29.849 | 35.463 | 1.00 | 0.00 |
| ATOM | 75 | C | ASN | 1 | 11 | -0.107 | 30.195 | 35.375 | 1.00 | 0.00 |
| ATOM | 76 | O | ASN | 1 | 11 | -0.745 | 29.756 | 34.411 | 1.00 | 0.00 |
| ATOM | 77 | CB | ASN | 1 | 11 | 2.047 | 29.486 | 34.124 | 1.00 | 0.00 |
| ATOM | 78 | CG | ASN | 1 | 11 | 1.754 | 30.546 | 33.096 | 1.00 | 0.00 |
| ATOM | 79 | OD1 | ASN | 1 | 11 | 1.217 | 31.610 | 33.377 | 1.00 | 0.00 |
| ATOM | 80 | ND2 | ASN | 1 | 11 | 1.971 | 30.162 | 31.811 | 1.00 | 0.00 |
| ATOM | 81 | H | ASN | 1 | 11 | 1.420 | 28.167 | 36.911 | 1.00 | 0.00 |
| ATOM | 82 | 1HD2 | ASN | 1 | 11 | 2.285 | 29.261 | 31.512 | 1.00 | 0.00 |
| ATOM | 83 | 2HD2 | ASN | 1 | 11 | 1.643 | 30.782 | 31.098 | 1.00 | 0.00 |
| ATOM | 84 | N | ASP | 1 | 12 | -0.619 | 30.939 | 36.323 | 1.00 | 0.00 |
| ATOM | 85 | CA | ASP | 1 | 12 | -2.064 | 31.262 | 36.250 | 1.00 | 0.00 |
| ATOM | 86 | C | ASP | 1 | 12 | -2.668 | 31.635 | 34.910 | 1.00 | 0.00 |
| ATOM | 87 | O | ASP | 1 | 12 | -3.709 | 31.008 | 34.539 | 1.00 | 0.00 |
| ATOM | 88 | CB | ASP | 1 | 12 | -2.517 | 32.237 | 37.409 | 1.00 | 0.00 |
| ATOM | 89 | CG | ASP | 1 | 12 | -1.293 | 32.675 | 38.157 | 1.00 | 0.00 |
| ATOM | 90 | OD1 | ASP | 1 | 12 | -0.497 | 33.446 | 37.645 | 1.00 | 0.00 |

FIG. 1B

| ATOM | 91 | OD2 | ASP | 1 | 12 | -1.057 | 32.123 | 39.266 | 1.00 | 0.00 |
| ATOM | 92 | H | ASP | 1 | 12 | -0.119 | 31.179 | 37.155 | 1.00 | 0.00 |
| ATOM | 93 | N | LEU | 1 | 13 | -2.099 | 32.601 | 34.132 | 1.00 | 0.00 |
| ATOM | 94 | CA | LEU | 1 | 13 | -2.827 | 33.180 | 32.995 | 1.00 | 0.00 |
| ATOM | 95 | C | LEU | 1 | 13 | -2.951 | 32.329 | 31.780 | 1.00 | 0.00 |
| ATOM | 96 | O | LEU | 1 | 13 | -3.808 | 32.567 | 30.921 | 1.00 | 0.00 |
| ATOM | 97 | CB | LEU | 1 | 13 | -2.337 | 34.600 | 32.584 | 1.00 | 0.00 |
| ATOM | 98 | CG | LEU | 1 | 13 | -3.491 | 35.515 | 32.232 | 1.00 | 0.00 |
| ATOM | 99 | CD1 | LEU | 1 | 13 | -4.133 | 36.006 | 33.554 | 1.00 | 0.00 |
| ATOM | 100 | CD2 | LEU | 1 | 13 | -2.935 | 36.524 | 31.217 | 1.00 | 0.00 |
| ATOM | 101 | H | LEU | 1 | 13 | -1.276 | 33.096 | 34.308 | 1.00 | 0.00 |
| ATOM | 102 | N | ALA | 1 | 14 | -2.089 | 31.252 | 31.763 | 1.00 | 0.00 |
| ATOM | 103 | CA | ALA | 1 | 14 | -2.227 | 30.131 | 30.792 | 1.00 | 0.00 |
| ATOM | 104 | C | ALA | 1 | 14 | -3.449 | 29.293 | 31.048 | 1.00 | 0.00 |
| ATOM | 105 | O | ALA | 1 | 14 | -3.724 | 28.399 | 30.301 | 1.00 | 0.00 |
| ATOM | 106 | CB | ALA | 1 | 14 | -1.062 | 29.249 | 30.600 | 1.00 | 0.00 |
| ATOM | 107 | H | ALA | 1 | 14 | -1.479 | 31.103 | 32.541 | 1.00 | 0.00 |
| ATOM | 108 | N | ARG | 1 | 15 | -4.037 | 29.445 | 32.285 | 1.00 | 0.00 |
| ATOM | 109 | CA | ARG | 1 | 15 | -5.241 | 28,633 | 32.573 | 1.00 | 0.00 |
| ATOM | 110 | C | ARG | 1 | 15 | -6.478 | 29.572 | 32.619 | 1.00 | 0.00 |
| ATOM | 111 | O | ARG | 1 | 15 | -7.563 | 29.184 | 32.147 | 1.00 | 0.00 |
| ATOM | 112 | CB | ARG | 1 | 15 | -5.074 | 27.850 | 33.877 | 1.00 | 0.00 |
| ATOM | 113 | CG | ARG | 1 | 15 | -5.256 | 26.348 | 33.808 | 1.00 | 0.00 |
| ATOM | 114 | CD | ARG | 1 | 15 | -6.599 | 25.816 | 34.374 | 1.00 | 0.00 |
| ATOM | 115 | NE | ARG | 1 | 15 | -7.738 | 26.515 | 33.767 | 1.00 | 0.00 |
| ATOM | 116 | CZ | ARG | 1 | 15 | -8.322 | 27.475 | 34.535 | 1.00 | 0.00 |
| ATOM | 117 | NH1 | ARG | 1 | 15 | -9.426 | 28.064 | 34.120 | 1.00 | 0.00 |
| ATOM | 118 | NH2 | ARG | 1 | 15 | -7.720 | 27.973 | 35.652 | 1.00 | 0.00 |
| ATOM | 119 | H | ARG | 1 | 15 | -3.720 | 30.097 | 32.975 | 1.00 | 0.00 |
| ATOM | 120 | HE | ARG | 1 | 15 | -8.062 | 26.201 | 32.875 | 1.00 | 0.00 |
| ATOM | 121 | 1HH1 | ARG | 1 | 15 | -9.878 | 28.795 | 34.631 | 1.00 | 0.00 |
| ATOM | 122 | 2HH1 | ARG | 1 | 15 | -9.779 | 27,853 | 33.209 | 1.00 | 0.00 |
| ATOM | 123 | 1HH2 | ARG | 1 | 15 | -8.137 | 28.803 | 36.022 | 1.00 | 0.00 |
| ATOM | 124 | 2HH2 | ARG | 1 | 15 | -6.866 | 27.700 | 36.093 | 1.00 | 0.00 |
| ATOM | 125 | N | ASP | 1 | 16 | -6.237 | 30.813 | 33.067 | 1.00 | 0.00 |
| ATOM | 126 | CA | ASP | 1 | 16 | -7.250 | 31.856 | 32.803 | 1.00 | 0.00 |
| ATOM | 127 | C | ASP | 1 | 16 | -6.824 | 33.136 | 32.067 | 1.00 | 0.00 |
| ATOM | 128 | O | ASP | 1 | 16 | -6.532 | 34.221 | 32.610 | 1.00 | 0.00 |
| ATOM | 129 | CB | ASP | 1 | 16 | -8.089 | 32.302 | 34.005 | 1.00 | 0.00 |
| ATOM | 130 | CG | ASP | 1 | 16 | -8.462 | 31.097 | 34.974 | 1.00 | 0.00 |
| ATOM | 131 | OD1 | ASP | 1 | 16 | -9.602 | 30.692 | 34.912 | 1.00 | 0.00 |
| ATOM | 132 | OD2 | ASP | 1 | 16 | -7.672 | 30.572 | 35.769 | 1.00 | 0.00 |
| ATOM | 133 | H | ASP | 1 | 16 | -5.451 | 31.212 | 33.539 | 1.00 | 0.00 |
| ATOM | 134 | N | PRO | 1 | 17 | -6.956 | 33.072 | 30.746 | 1.00 | 0.00 |
| ATOM | 135 | CA | PRO | 1 | 17 | -6.993 | 34.342 | 30.013 | 1.00 | 0.00 |

FIG. 1C

| ATOM | 136 | C | PRO | 1 | 17 | -8.205 | 35.156 | 30.521 | 1.00 | 0.00 |
| ATOM | 137 | O | PRO | 1 | 17 | -9.305 | 34.673 | 30.362 | 1.00 | 0.00 |
| ATOM | 138 | CB | PRO | 1 | 17 | -7.265 | 33.841 | 28.530 | 1.00 | 0.00 |
| ATOM | 139 | CG | PRO | 1 | 17 | -6.733 | 32.384 | 28.576 | 1.00 | 0.00 |
| ATOM | 140 | CD | PRO | 1 | 17 | -7.148 | 31.899 | 29.962 | 1.00 | 0.00 |
| ATOM | 141 | N | PRO | 1 | 18 | -7.965 | 36.355 | 31.086 | 1.00 | 0.00 |
| ATOM | 142 | CA | PRO | 1 | 18 | -9.083 | 37.138 | 31.627 | 1.00 | 0.00 |
| ATOM | 143 | C | PRO | 1 | 18 | -9.936 | 37.823 | 30.552 | 1.00 | 0.00 |
| ATOM | 144 | O | PRO | 1 | 18 | -10,510 | 37.184 | 29.678 | 1.00 | 0.00 |
| ATOM | 145 | CB | PRO | 1 | 18 | -8.415 | 37.993 | 32.696 | 1.00 | 0.00 |
| ATOM | 146 | CG | PRO | 1 | 18 | -6.972 | 38.217 | 32.269 | 1.00 | 0.00 |
| ATOM | 147 | CD | PRO | 1 | 18 | -6.703 | 36.974 | 31.360 | 1.00 | 0.00 |
| ATOM | 148 | N | ALA | 1 | 19 | -10.151 | 39.105 | 30.790 | 1.00 | 0.00 |
| ATOM | 149 | CA | ALA | 1 | 19 | -11.197 | 39.768 | 29.931 | 1.00 | 0.00 |
| ATOM | 150 | C | ALA | 1 | 19 | -10.607 | 40.086 | 28.534 | 1.00 | 0.00 |
| ATOM | 151 | O | ALA | 1 | 19 | -10.127 | 41.187 | 28.324 | 1.00 | 0.00 |
| ATOM | 152 | CB | ALA | 1 | 19 | -11.617 | 41.179 | 30.598 | 1.00 | 0.00 |
| ATOM | 153 | H | ALA | 1 | 19 | -9.561 | 39.653 | 31.383 | 1.00 | 0.00 |
| ATOM | 154 | N | GLN | 1 | 20 | -10.496 | 39.036 | 27.758 | 1.00 | 0.00 |
| ATOM | 155 | CA | GLN | 1 | 20 | -9.643 | 38.863 | 26.552 | 1.00 | 0.00 |
| ATOM | 156 | C | GLN | 1 | 20 | -8.342 | 39.556 | 26.683 | 1.00 | 0.00 |
| ATOM | 157 | O | GLN | 1 | 20 | -8.219 | 40.714 | 26.316 | 1.00 | 0.00 |
| ATOM | 158 | CB | GLN | 1 | 20 | -10.452 | 39.059 | 25.250 | 1.00 | 0.00 |
| ATOM | 159 | CG | GLN | 1 | 20 | -11.446 | 40.245 | 25.067 | 1.00 | 0.00 |
| ATOM | 160 | CD | GLN | 1 | 20 | -12.575 | 40.215 | 26.077 | 1.00 | 0.00 |
| ATOM | 161 | OE1 | GLN | 1 | 20 | -12.883 | 41.218 | 26.660 | 1.00 | 0.00 |
| ATOM | 162 | NE2 | GLN | 1 | 20 | -13.154 | 39.042 | 26.289 | 1.00 | 0.00 |
| ATOM | 163 | H | GLN | 1 | 20 | -11.149 | 38.324 | 28.017 | 1.00 | 0.00 |
| ATOM | 164 | 1HE2 | GLN | 1 | 20 | -12.901 | 38.240 | 25.748 | 1.00 | 0.00 |
| ATOM | 165 | 2HE2 | GLN | 1 | 20 | -13.792 | 38.993 | 27.058 | 1.00 | 0.00 |
| ATOM | 166 | N | CYS | 1 | 21 | -7.381 | 38.866 | 27.312 | 1.00 | 0.00 |
| ATOM | 167 | CA | CYS | 1 | 21 | -5.983 | 39.312 | 27.548 | 1.00 | 0.00 |
| ATOM | 168 | C | CYS | 1 | 21 | -5.049 | 38.159 | 27.644 | 1.00 | 0.00 |
| ATOM | 169 | O | CYS | 1 | 21 | -5.488 | 37.103 | 28.037 | 1.00 | 0.00 |
| ATOM | 170 | CB | CYS | 1 | 21 | -5.939 | 40.115 | 28.837 | 1.00 | 0.00 |
| ATOM | 171 | SG | CYS | 1 | 21 | -6.547 | 41.738 | 28.478 | 1.00 | 0.00 |
| ATOM | 172 | H | CYS | 1 | 21 | -7.581 | 37.909 | 27.521 | 1.00 | 0.00 |
| ATOM | 173 | N | SER | 1 | 22 | -3.768 | 38,479 | 27.242 | 1.00 | 0.00 |
| ATOM | 174 | CA | SER | 1 | 22 | -2.909 | 37.373 | 26.846 | 1.00 | 0.00 |
| ATOM | 175 | C | SER | 1 | 22 | -1.484 | 37.385 | 27.299 | 1.00 | 0.00 |
| ATOM | 176 | O | SER | 1 | 22 | -0.890 | 38.502 | 27.246 | 1.00 | 0.00 |
| ATOM | 177 | CB | SER | 1 | 22 | -3.010 | 37.109 | 25.307 | 1.00 | 0.00 |
| ATOM | 178 | OG | SER | 1 | 22 | -4.179 | 37.764 | 24.726 | 1.00 | 0.00 |
| ATOM | 179 | H | SER | 1 | 22 | -3.415 | 39.413 | 27.183 | 1.00 | 0.00 |
| ATOM | 180 | HG | SER | 1 | 22 | -3.987 | 37.872 | 23.804 | 1.00 | 0.00 |

FIG. 1D

| | | | | | | | | | |
|---|---|---|---|---|---|---|---|---|---|
| ATOM | 181 | N | ALA | 1 | 23 | -0.882 | 36.264 | 27.816 | 1.00 0.00 |
| ATOM | 182 | CA | ALA | 1 | 23 | 0.449 | 36.497 | 28.382 | 1.00 0.00 |
| ATOM | 183 | C | ALA | 1 | 23 | 1.533 | 35.875 | 27.516 | 1.00 0.00 |
| ATOM | 184 | O | ALA | 1 | 23 | 1.418 | 34.935 | 26.775 | 1.00 0.00 |
| ATOM | 185 | CB | ALA | 1 | 23 | 0.545 | 35.912 | 29.743 | 1.00 0.00 |
| ATOM | 186 | H | ALA | 1 | 23 | -1.458 | 35.449 | 27.752 | 1.00 0.00 |
| ATOM | 187 | N | GLY | 1 | 24 | 2.746 | 36.445 | 27.787 | 1.00 0.00 |
| ATOM | 188 | CA | GLY | 1 | 24 | 3.850 | 35.741 | 27.233 | 1.00 0.00 |
| ATOM | 189 | C | GLY | 1 | 24 | 5.127 | 36.253 | 27.699 | 1.00 0.00 |
| ATOM | 190 | O | GLY | 1 | 24 | 5.075 | 37.310 | 28.265 | 1.00 0.00 |
| ATOM | 191 | H | GLY | 1 | 24 | 3.000 | 37.253 | 28.319 | 1.00 0.00 |
| ATOM | 192 | N | PRO | 1 | 25 | 6.264 | 35.552 | 27.463 | 1.00 0.00 |
| ATOM | 193 | CA | PRO | 1 | 25 | 7.528 | 36.069 | 27.834 | 1.00 0.00 |
| ATOM | 194 | C | PRO | 1 | 25 | 7.954 | 37.302 | 27.064 | 1.00 0.00 |
| ATOM | 195 | O | PRO | 1 | 25 | 7.102 | 37.967 | 26.519 | 1.00 0.00 |
| ATOM | 196 | CB | PRO | 1 | 25 | 8.536 | 34.960 | 27.498 | 1.00 0.00 |
| ATOM | 197 | CG | PRO | 1 | 25 | 7.766 | 33.902 | 26.624 | 1.00 0.00 |
| ATOM | 198 | CD | PRO | 1 | 25 | 6.327 | 34.297 | 26.774 | 1.00 0.00 |
| ATOM | 199 | N | VAL | 1 | 26 | 9.251 | 37.652 | 27.070 | 1.00 0.00 |
| ATOM | 200 | CA | VAL | 1 | 26 | 9.831 | 38.466 | 25.975 | 1.00 0.00 |
| ATOM | 201 | C | VAL | 1 | 26 | 10.054 | 37.488 | 24.900 | 1.00 0.00 |
| ATOM | 202 | O | VAL | 1 | 26 | 9.071 | 36.906 | 24.424 | 1.00 0.00 |
| ATOM | 203 | CB | VAL | 1 | 26 | 11.032 | 39.240 | 26.509 | 1.00 0.00 |
| ATOM | 204 | CG1 | VAL | 1 | 26 | 10.726 | 40.772 | 26.799 | 1.00 0.00 |
| ATOM | 205 | CG2 | VAL | 1 | 26 | 11.723 | 38.692 | 27.823 | 1.00 0.00 |
| ATOM | 206 | H | VAL | 1 | 26 | 9.681 | 37.030 | 27.724 | 1.00 0.00 |
| ATOM | 207 | N | GLY | 1 | 27 | 11.292 | 37.168 | 24.590 | 1.00 0.00 |
| ATOM | 208 | CA | GLY | 1 | 27 | 11.482 | 35.738 | 24.271 | 1.00 0.00 |
| ATOM | 209 | C | GLY | 1 | 27 | 11.647 | 34.818 | 25.477 | 1.00 0.00 |
| ATOM | 210 | O | GLY | 1 | 27 | 11.513 | 35.432 | 26.503 | 1.00 0.00 |
| ATOM | 211 | H | GLY | 1 | 27 | 12.099 | 37.604 | 24.988 | 1.00 0.00 |
| ATOM | 212 | N | ASP | 1 | 28 | 12.041 | 33.489 | 25.391 | 1.00 0.00 |
| ATOM | 213 | CA | ASP | 1 | 28 | 12.052 | 32.693 | 26.625 | 1.00 0.00 |
| ATOM | 214 | C | ASP | 1 | 28 | 12.264 | 33.254 | 28.042 | 1.00 0.00 |
| ATOM | 215 | O | ASP | 1 | 28 | 11.812 | 32.613 | 29.013 | 1.00 0.00 |
| ATOM | 216 | CB | ASP | 1 | 28 | 12.848 | 31.459 | 26.313 | 1.00 0.00 |
| ATOM | 217 | CG | ASP | 1 | 28 | 12.220 | 30.275 | 26.971 | 1.00 0.00 |
| ATOM | 218 | OD1 | ASP | 1 | 28 | 11.048 | 29.929 | 26.718 | 1.00 0.00 |
| ATOM | 219 | OD2 | ASP | 1 | 28 | 12.910 | 29.622 | 27.780 | 1.00 0.00 |
| ATOM | 220 | H | ASP | 1 | 28 | 12.089 | 33.023 | 24.507 | 1.00 0.00 |
| ATOM | 221 | N | ASP | 1 | 29 | 13.052 | 34.361 | 28.176 | 1.00 0.00 |
| ATOM | 222 | CA | ASP | 1 | 29 | 13.109 | 34.931 | 29.560 | 1.00 0.00 |
| ATOM | 223 | C | ASP | 1 | 29 | 11.716 | 35.121 | 30.289 | 1.00 0.00 |
| ATOM | 224 | O | ASP | 1 | 29 | 10.664 | 35.488 | 29.732 | 1.00 0.00 |
| ATOM | 225 | CB | ASP | 1 | 29 | 14.006 | 36.222 | 29.650 | 1.00 0.00 |

FIG. 1E

| ATOM | 226 | CG  | ASP | 1 | 29 | 13.724 | 37.078 | 30.916 | 1.00 | 0.00 |
| ATOM | 227 | OD1 | ASP | 1 | 29 | 13.034 | 38.080 | 30.842 | 1.00 | 0.00 |
| ATOM | 228 | OD2 | ASP | 1 | 29 | 14.208 | 36.708 | 31.973 | 1.00 | 0.00 |
| ATOM | 229 | H   | ASP | 1 | 29 | 13.367 | 34.766 | 27.317 | 1.00 | 0.00 |
| ATOM | 230 | N   | MET | 1 | 30 | 11.742 | 34.874 | 31.593 | 1.00 | 0.00 |
| ATOM | 231 | CA  | MET | 1 | 30 | 10.513 | 34.871 | 32.347 | 1.00 | 0.00 |
| ATOM | 232 | C   | MET | 1 | 30 | 10.424 | 35.967 | 33.348 | 1.00 | 0.00 |
| ATOM | 233 | O   | MET | 1 | 30 | 9.395  | 36.073 | 34.009 | 1.00 | 0.00 |
| ATOM | 234 | CB  | MET | 1 | 30 | 10.024 | 33.562 | 32.904 | 1.00 | 0.00 |
| ATOM | 235 | CG  | MET | 1 | 30 | 8.608  | 33.344 | 32.660 | 1.00 | 0.00 |
| ATOM | 236 | SD  | MET | 1 | 30 | 8.121  | 33.393 | 30.892 | 1.00 | 0.00 |
| ATOM | 237 | CE  | MET | 1 | 30 | 6.473  | 32.740 | 31.116 | 1.00 | 0.00 |
| ATOM | 238 | H   | MET | 1 | 30 | 12.645 | 34.898 | 32.021 | 1.00 | 0.00 |
| ATOM | 239 | N   | PHE | 1 | 31 | 11.476 | 36.831 | 33.387 | 1.00 | 0.00 |
| ATOM | 240 | CA  | PHE | 1 | 31 | 11.426 | 37.966 | 34.248 | 1.00 | 0.00 |
| ATOM | 241 | C   | PHE | 1 | 31 | 10.748 | 39.124 | 33.639 | 1.00 | 0.00 |
| ATOM | 242 | O   | PHE | 1 | 31 | 10.171 | 39.983 | 34.265 | 1.00 | 0.00 |
| ATOM | 243 | CB  | PHE | 1 | 31 | 12.847 | 38.280 | 34.753 | 1.00 | 0.00 |
| ATOM | 244 | CG  | PHE | 1 | 31 | 13.502 | 36.936 | 35.115 | 1.00 | 0.00 |
| ATOM | 245 | CD1 | PHE | 1 | 31 | 14.835 | 36.780 | 34.734 | 1.00 | 0.00 |
| ATOM | 246 | CD2 | PHE | 1 | 31 | 12.856 | 35.900 | 35.819 | 1.00 | 0.00 |
| ATOM | 247 | CE1 | PHE | 1 | 31 | 15.477 | 35.585 | 34.972 | 1.00 | 0.00 |
| ATOM | 248 | CE2 | PHE | 1 | 31 | 13.540 | 34.632 | 36.102 | 1.00 | 0.00 |
| ATOM | 249 | CZ  | PHE | 1 | 31 | 14.843 | 34.454 | 35.587 | 1.00 | 0.00 |
| ATOM | 250 | H   | PHE | 1 | 31 | 12.277 | 36.803 | 32.788 | 1.00 | 0.00 |
| ATOM | 251 | N   | HIS | 1 | 32 | 10.865 | 39.200 | 32.331 | 1.00 | 0.00 |
| ATOM | 252 | CA  | HIS | 1 | 32 | 9.972  | 40.079 | 31.653 | 1.00 | 0.00 |
| ATOM | 253 | C   | HIS | 1 | 32 | 8.924  | 39.415 | 30.769 | 1.00 | 0.00 |
| ATOM | 254 | O   | HIS | 1 | 32 | 9.202  | 38.493 | 30.018 | 1.00 | 0.00 |
| ATOM | 255 | CB  | HIS | 1 | 32 | 10.760 | 41.083 | 30.810 | 1.00 | 0.00 |
| ATOM | 256 | CG  | HIS | 1 | 32 | 10.498 | 42.477 | 31.288 | 1.00 | 0.00 |
| ATOM | 257 | ND1 | HIS | 1 | 32 | 11.346 | 43.479 | 31.266 | 1.00 | 0.00 |
| ATOM | 258 | CD2 | HIS | 1 | 32 | 9.246  | 43.049 | 31.602 | 1.00 | 0.00 |
| ATOM | 259 | CE1 | HIS | 1 | 32 | 10.678 | 44.659 | 31.574 | 1.00 | 0.00 |
| ATOM | 260 | NE1 | HIS | 1 | 32 | 9.377  | 44.389 | 31.784 | 1.00 | 0.00 |
| ATOM | 261 | H   | HIS | 1 | 32 | 11.489 | 38.555 | 31.889 | 1.00 | 0.00 |
| ATOM | 262 | 1HD | HIS | 1 | 32 | 12.295 | 43.246 | 31.197 | 1.00 | 0.00 |
| ATOM | 263 | N   | TRP | 1 | 33 | 7.790  | 39.969 | 30.994 | 1.00 | 0.00 |
| ATOM | 264 | CA  | TRP | 1 | 33 | 6.604  | 39.493 | 30.279 | 1.00 | 0.00 |
| ATOM | 265 | C   | TRP | 1 | 33 | 6.205  | 40.551 | 29.240 | 1.00 | 0.00 |
| ATOM | 266 | O   | TRP | 1 | 33 | 6.438  | 41.689 | 29.500 | 1.00 | 0.00 |
| ATOM | 267 | CB  | TRP | 1 | 33 | 5.415  | 39.260 | 31.209 | 1.00 | 0.00 |
| ATOM | 268 | CG  | TRP | 1 | 33 | 5.641  | 38.164 | 32.176 | 1.00 | 0.00 |
| ATOM | 269 | CD1 | TRP | 1 | 33 | 6.812  | 37.983 | 32.936 | 1.00 | 0.00 |
| ATOM | 270 | CD2 | TRP | 1 | 33 | 4.801  | 37.018 | 32.425 | 1.00 | 0.00 |

FIG. 1F

| | | | | | | | | | |
|---|---|---|---|---|---|---|---|---|---|
| ATOM | 271 | NE1 | TRP | 1 | 33 | 6.752 | 36.776 | 33.576 | 1.00 0.00 |
| ATOM | 272 | CE2 | TRP | 1 | 33 | 5.536 | 36.139 | 33.304 | 1.00 0.00 |
| ATOM | 273 | CE3 | TRP | 1 | 33 | 3.526 | 36.671 | 31.930 | 1.00 0.00 |
| ATOM | 274 | CZ2 | TRP | 1 | 33 | 5.043 | 34.854 | 33.676 | 1.00 0.00 |
| ATOM | 275 | CZ3 | TRP | 1 | 33 | 3.036 | 35.429 | 32.346 | 1.00 0.00 |
| ATOM | 276 | CH2 | TRP | 1 | 33 | 3.758 | 34.524 | 33.185 | 1.00 0.00 |
| ATOM | 277 | H | TRP | 1 | 33 | 7.826 | 40.663 | 31.713 | 1.00 0.00 |
| ATOM | 278 | 1HE | TRP | 1 | 33 | 7.482 | 36.492 | 34.165 | 1.00 0.00 |
| ATOM | 279 | N | GLN | 1 | 34 | 5.696 | 40.048 | 28.134 | 1.00 0.00 |
| ATOM | 280 | CA | GLN | 1 | 34 | 4.869 | 40.836 | 27.220 | 1.00 0.00 |
| ATOM | 281 | C | GLN | 1 | 34 | 3.424 | 40.408 | 27.177 | 1.00 0.00 |
| ATOM | 282 | O | GLN | 1 | 34 | 3.094 | 39.240 | 27.133 | 1.00 0.00 |
| ATOM | 283 | CB | GLN | 1 | 34 | 5.470 | 40.924 | 25.800 | 1.00 0.00 |
| ATOM | 284 | CG | GLN | 1 | 34 | 6.917 | 41.448 | 25.783 | 1.00 0.00 |
| ATOM | 285 | CD | GLN | 1 | 34 | 7.429 | 41.452 | 24.291 | 1.00 0.00 |
| ATOM | 286 | OE1 | GLN | 1 | 34 | 7.612 | 42.380 | 23.559 | 1.00 0.00 |
| ATOM | 287 | NE1 | GLN | 1 | 34 | 7.489 | 40.260 | 23.927 | 1.00 0.00 |
| ATOM | 288 | H | GLN | 1 | 34 | 5.517 | 39.064 | 28.146 | 1.00 0.00 |
| ATOM | 289 | 1HE2 | GLN | 1 | 34 | 7.323 | 39.442 | 24.478 | 1.00 0.00 |
| ATOM | 290 | 2HE2 | GLN | 1 | 34 | 7.792 | 40.263 | 22.974 | 1.00 0.00 |
| ATOM | 291 | N | ALA | 1 | 35 | 2.538 | 41.366 | 27.220 | 1.00 0.00 |
| ATOM | 292 | CA | ALA | 1 | 35 | 1.184 | 40.851 | 27.117 | 1.00 0.00 |
| ATOM | 293 | C | ALA | 1 | 35 | 0.289 | 41.720 | 26.273 | 1.00 0.00 |
| ATOM | 294 | O | ALA | 1 | 35 | 0.110 | 42.908 | 26.564 | 1.00 0.00 |
| ATOM | 295 | CB | ALA | 1 | 35 | 0.621 | 40.755 | 28.550 | 1.00 0.00 |
| ATOM | 296 | H | ALA | 1 | 35 | 2.893 | 42.286 | 27.389 | 1.00 0.00 |
| ATOM | 297 | N | THR | 1 | 36 | -0.357 | 40.970 | 25.395 | 1.00 0.00 |
| ATOM | 298 | CA | THR | 1 | 36 | -1.550 | 41.487 | 24.753 | 1.00 0.00 |
| ATOM | 299 | C | THR | 1 | 36 | -2.696 | 41.829 | 25.712 | 1.00 0.00 |
| ATOM | 300 | O | THR | 1 | 36 | -3.280 | 41.022 | 26.401 | 1.00 0.00 |
| ATOM | 301 | CB | THR | 1 | 36 | -2.200 | 40.523 | 23.714 | 1.00 0.00 |
| ATOM | 302 | OG1 | THR | 1 | 36 | -1.176 | 39.765 | 22.985 | 1.00 0.00 |
| ATOM | 303 | CG2 | THR | 1 | 36 | -3.302 | 41.301 | 22.943 | 1.00 0.00 |
| ATOM | 304 | H | THR | 1 | 36 | 0.086 | 40.113 | 25.129 | 1.00 0.00 |
| ATOM | 305 | 1HG | THR | 1 | 36 | -1.335 | 40.089 | 22.109 | 1.00 0.00 |
| ATOM | 306 | N | ILE | 1 | 37 | -3.026 | 43.130 | 25.648 | 1.00 0.00 |
| ATOM | 307 | CA | ILE | 1 | 37 | -4.191 | 43.548 | 26.429 | 1.00 0.00 |
| ATOM | 308 | C | ILE | 1 | 37 | -5.298 | 44.216 | 25.630 | 1.00 0.00 |
| ATOM | 309 | O | ILE | 1 | 37 | -5.101 | 45.204 | 24.964 | 1.00 0.00 |
| ATOM | 310 | CB | ILE | 1 | 37 | -3.797 | 44.351 | 27.724 | 1.00 0.00 |
| ATOM | 311 | CG1 | ILE | 1 | 37 | -4.897 | 45.181 | 28.449 | 1.00 0.00 |
| ATOM | 312 | CG2 | ILE | 1 | 37 | -2.542 | 45.130 | 27.448 | 1.00 0.00 |
| ATOM | 313 | CD1 | ILE | 1 | 37 | -4.556 | 46.013 | 29.659 | 1.00 0.00 |
| ATOM | 314 | H | ILE | 1 | 37 | -2.472 | 43.740 | 25.081 | 1.00 0.00 |
| ATOM | 315 | N | ILE | 1 | 37 | -6.458 | 43.574 | 25.878 | 1.00 0.00 |

FIG. 1G

| ATOM | 316 | CA | MET | 1 | 38 | -7.586 | 44.220 | 25.347 | 1.00 | 0.00 |
| ATOM | 317 | C | MET | 1 | 38 | 8.605 | 44.872 | 26.322 | 1.00 | 0.00 |
| ATOM | 318 | O | MET | 1 | 38 | -8.349 | 45.935 | 26.893 | 1.00 | 0.00 |
| ATOM | 319 | CB | MET | 1 | 38 | -8.343 | 43.241 | 24.447 | 1.00 | 0.00 |
| ATOM | 320 | CG | MET | 1 | 38 | -7.470 | 42.311 | 23.603 | 1.00 | 0.00 |
| ATOM | 321 | SD | MET | 1 | 38 | -8.288 | 40.905 | 22.853 | 1.00 | 0.00 |
| ATOM | 322 | CE | MET | 1 | 38 | -9.622 | 41.838 | 22.065 | 1.00 | 0.00 |
| ATOM | 323 | H | MET | 1 | 38 | 6.505 | 42.757 | 26.452 | 1.00 | 0.00 |
| ATOM | 324 | N | GLY | 1 | 39 | -9.770 | 44.272 | 26.496 | 1.00 | 0.00 |
| ATOM | 325 | CA | GLY | 1 | 39 | -11.056 | 44.966 | 26.850 | 1.00 | 0.00 |
| ATOM | 326 | C | GLY | 1 | 39 | -12.298 | 44.411 | 26.038 | 1.00 | 0.00 |
| ATOM | 327 | O | GLY | 1 | 39 | -12.214 | 43.940 | 24.916 | 1.00 | 0.00 |
| ATOM | 328 | H | GLY | 1 | 39 | -9.966 | 43.294 | 26.425 | 1.00 | 0.00 |
| ATOM | 329 | N | PRO | 1 | 40 | -13.477 | 44.500 | 26.766 | 1.00 | 0.00 |
| ATOM | 330 | CA | PRO | 1 | 40 | -14.704 | 43.852 | 26.332 | 1.00 | 0.00 |
| ATOM | 331 | C | PRO | 1 | 40 | -15.431 | 44.406 | 25.096 | 1.00 | 0.00 |
| ATOM | 332 | O | PRO | 1 | 40 | -15.378 | 45.605 | 24.835 | 1.00 | 0.00 |
| ATOM | 333 | CG | PRO | 1 | 40 | -15.528 | 43.836 | 27.644 | 1.00 | 0.00 |
| ATOM | 334 | CG | PRO | 1 | 40 | -15.102 | 45.100 | 28.414 | 1.00 | 0.00 |
| ATOM | 335 | CD | PRO | 1 | 40 | -13.575 | 45.060 | 28.122 | 1.00 | 0.00 |
| ATOM | 336 | N | ASN | 1 | 41 | -16.104 | 43.478 | 24.432 | 1.00 | 0.00 |
| ATOM | 337 | CA | ASN | 1 | 41 | -16.866 | 43.806 | 23.227 | 1.00 | 0.00 |
| ATOM | 338 | C | ASN | 1 | 41 | -17.788 | 45.030 | 23.243 | 1.00 | 0.00 |
| ATOM | 339 | O | ASN | 1 | 41 | -18.334 | 45.404 | 24.266 | 1.00 | 0.00 |
| ATOM | 340 | CB | ASN | 1 | 41 | -17.505 | 42.566 | 22.629 | 1.00 | 0.00 |
| ATOM | 341 | CG | ASN | 1 | 41 | -17.457 | 42.783 | 21.100 | 1.00 | 0.00 |
| ATOM | 342 | OD1 | ASN | 1 | 41 | -16.424 | 42.515 | 20.518 | 1.00 | 0.00 |
| ATOM | 343 | ND2 | ASN | 1 | 41 | -18.580 | 43.205 | 20.495 | 1.00 | 0.00 |
| ATOM | 344 | H | ASN | 1 | 41 | -16.031 | 42.509 | 24.671 | 1.00 | 0.00 |
| ATOM | 345 | 1HD2 | ASN | 1 | 41 | -19.340 | 43.519 | 21.065 | 1.00 | 0.00 |
| ATOM | 346 | 2HD2 | ASN | 1 | 41 | -18.839 | 43.307 | 19.534 | 1.00 | 0.00 |
| ATOM | 347 | N | ASP | 1 | 42 | -17.706 | 45.666 | 22.075 | 1.00 | 0.00 |
| ATOM | 348 | CA | ASP | 1 | 42 | -18.549 | 46.827 | 21.646 | 1.00 | 0.00 |
| ATOM | 349 | C | ASP | 1 | 42 | -17.990 | 48.094 | 22.183 | 1.00 | 0.00 |
| ATOM | 350 | O | ASP | 1 | 42 | -17.904 | 49.099 | 21.503 | 1.00 | 0.00 |
| ATOM | 351 | CB | ASP | 1 | 42 | -20.049 | 46.643 | 22.001 | 1.00 | 0.00 |
| ATOM | 352 | CG | ASP | 1 | 42 | -20.617 | 45.386 | 21.248 | 1.00 | 0.00 |
| ATOM | 353 | OD1 | ASP | 1 | 42 | -21.189 | 44.546 | 22.019 | 1.00 | 0.00 |
| ATOM | 354 | OD2 | ASP | 1 | 42 | -20.505 | 45.329 | 19.972 | 1.00 | 0.00 |
| ATOM | 355 | H | ASP | 1 | 42 | -17.172 | 45.239 | 21.345 | 1.00 | 0.00 |
| ATOM | 356 | N | SER | 1 | 43 | -17.518 | 47.956 | 23.425 | 1.00 | 0.00 |
| ATOM | 357 | CA | SER | 1 | 43 | -16.981 | 49.076 | 24.283 | 1.00 | 0.00 |
| ATOM | 358 | C | SER | 1 | 43 | -15.645 | 49.654 | 23.703 | 1.00 | 0.00 |
| ATOM | 359 | O | SER | 1 | 43 | -14.885 | 49.017 | 22.898 | 1.00 | 0.00 |
| ATOM | 360 | CB | SER | 1 | 43 | -16.864 | 48.550 | 25.721 | 1.00 | 0.00 |

FIG. 1H

| | | | | | | | | | | |
|---|---|---|---|---|---|---|---|---|---|---|
| ATOM | 361 | OG | SER | 1 | 43 | -17.907 | 47.578 | 25.969 | 1.00 | 0.00 |
| ATOM | 362 | H | SER | 1 | 43 | -17.691 | 47.082 | 23.879 | 1.00 | 0.00 |
| ATOM | 363 | HG | SER | 1 | 43 | -17.668 | 46.770 | 25.535 | 1.00 | 0.00 |
| ATOM | 364 | N | PRO | 1 | 43 | -15.449 | 50.978 | 24.037 | 1.00 | 0.00 |
| ATOM | 365 | CA | PRO | 1 | 44 | -14.337 | 51.686 | 23.444 | 1.00 | 0.00 |
| ATOM | 366 | C | PRO | 1 | 44 | -12.965 | 51.042 | 23.266 | 1.00 | 0.00 |
| ATOM | 367 | O | PRO | 1 | 44 | -12.323 | 50.986 | 22.187 | 1.00 | 0.00 |
| ATOM | 368 | CB | PRO | 1 | 44 | -14.294 | 52.931 | 24.332 | 1.00 | 0.00 |
| ATOM | 369 | CG | PRO | 1 | 44 | -15.749 | 53.253 | 24.642 | 1.00 | 0.00 |
| ATOM | 370 | CD | PRO | 1 | 44 | -16.388 | 51.873 | 24.723 | 1.00 | 0.00 |
| ATOM | 371 | N | TYR | 1 | 45 | -12.499 | 50.612 | 24.469 | 1.00 | 0.00 |
| ATOM | 372 | CA | TYR | 1 | 45 | -11.173 | 49.936 | 24.432 | 1.00 | 0.00 |
| ATOM | 373 | C | TYR | 1 | 45 | -10.989 | 48.618 | 23.768 | 1.00 | 0.00 |
| ATOM | 374 | O | TYR | 1 | 45 | -9.874 | 48.082 | 23.625 | 1.00 | 0.00 |
| ATOM | 375 | CB | TYR | 1 | 45 | -10.642 | 49.821 | 25.898 | 1.00 | 0.00 |
| ATOM | 376 | CG | TYR | 1 | 45 | -10.263 | 51.093 | 26.551 | 1.00 | 0.00 |
| ATOM | 377 | CD1 | TYR | 1 | 45 | -11.055 | 51.437 | 27.637 | 1.00 | 0.00 |
| ATOM | 378 | CD2 | TYR | 1 | 45 | -9.186 | 51.866 | 26.062 | 1.00 | 0.00 |
| ATOM | 379 | CE1 | TYR | 1 | 45 | -10.678 | 52.632 | 28.338 | 1.00 | 0.00 |
| ATOM | 380 | CE2 | TYR | 1 | 45 | -8.954 | 53.120 | 26.707 | 1.00 | 0.00 |
| ATOM | 381 | CZ | TYR | 1 | 45 | -9.696 | 53.503 | 27.827 | 1.00 | 0.00 |
| ATOM | 382 | OH | TYR | 1 | 45 | -9.427 | 54.731 | 28.452 | 1.00 | 0.00 |
| ATOM | 383 | H | TYR | 1 | 45 | -12.786 | 50.950 | 25.365 | 1.00 | 0.00 |
| ATOM | 384 | HH | TYR | 1 | 45 | -9.015 | 55.269 | 27.788 | 1.00 | 0.00 |
| ATOM | 385 | N | GLN | 1 | 46 | -12.094 | 48.046 | 23.382 | 1.00 | 0.00 |
| ATOM | 386 | CA | GLN | 1 | 46 | -12.061 | 46.725 | 22.755 | 1.00 | 0.00 |
| ATOM | 387 | C | GLN | 1 | 46 | -11.454 | 46.729 | 21.459 | 1.00 | 0.00 |
| ATOM | 388 | O | GLN | 1 | 46 | -11.537 | 47.737 | 20.760 | 1.00 | 0.00 |
| ATOM | 389 | CB | GLN | 1 | 46 | -13.469 | 46.126 | 22.604 | 1.00 | 0.00 |
| ATOM | 390 | CG | GLN | 1 | 46 | -13.789 | 45.049 | 21.539 | 1.00 | 0.00 |
| ATOM | 391 | CD | GLN | 1 | 46 | -14.461 | 45.627 | 20.354 | 1.00 | 0.00 |
| ATOM | 392 | OE1 | GLN | 1 | 46 | -14.289 | 46.795 | 20.051 | 1.00 | 0.00 |
| ATOM | 393 | NE2 | GLN | 1 | 46 | -15.311 | 44.856 | 19.671 | 1.00 | 0.00 |
| ATOM | 394 | H | GLN | 1 | 46 | -12.898 | 48.611 | 23.201 | 1.00 | 0.00 |
| ATOM | 395 | 1HE2 | GLN | 1 | 46 | -15.436 | 43.884 | 19.867 | 1.00 | 0.00 |
| ATOM | 396 | 2HE2 | GLN | 1 | 46 | -15.796 | 45.251 | 18.890 | 1.00 | 0.00 |
| ATOM | 397 | N | GLY | 1 | 47 | -10.734 | 45.644 | 21.155 | 1.00 | 0.00 |
| ATOM | 398 | CA | GLY | 1 | 47 | -10.114 | 45.605 | 19.848 | 1.00 | 0.00 |
| ATOM | 399 | C | GLY | 1 | 47 | -8.629 | 45.843 | 19.905 | 1.00 | 0.00 |
| ATOM | 400 | O | GLY | 1 | 47 | -7.769 | 45.119 | 19.319 | 1.00 | 0.00 |
| ATOM | 401 | H | GLY | 1 | 47 | -10.775 | 44.822 | 21.723 | 1.00 | 0.00 |
| ATOM | 402 | N | GLY | 1 | 48 | -8.271 | 46.947 | 20.695 | 1.00 | 0.00 |
| ATOM | 403 | CA | GLY | 1 | 48 | -6.913 | 47.393 | 20.950 | 1.00 | 0.00 |
| ATOM | 404 | C | GLY | 1 | 48 | -6.009 | 46.228 | 21.154 | 1.00 | 0.00 |
| ATOM | 405 | O | GLY | 1 | 48 | -6.280 | 45.269 | 21.911 | 1.00 | 0.00 |

FIG. 1I

| ATOM | 406 | H   | GLY | 1 | 48 | -9.072 | 47.442 | 21.032 | 1.00 | 0.00 |
| ATOM | 407 | N   | VAL | 1 | 49 | -4.877 | 46.300 | 20.420 | 1.00 | 0.00 |
| ATOM | 408 | CA  | VAL | 1 | 49 | -3.846 | 45.346 | 20.774 | 1.00 | 0.00 |
| ATOM | 409 | C   | VAL | 1 | 49 | -2.700 | 46.129 | 21.429 | 1.00 | 0.00 |
| ATOM | 410 | O   | VAL | 1 | 49 | -1.856 | 46.847 | 20.841 | 1.00 | 0.00 |
| ATOM | 411 | CB  | VAL | 1 | 49 | -3.358 | 44.738 | 19.453 | 1.00 | 0.00 |
| ATOM | 412 | CG1 | VAL | 1 | 49 | -2.394 | 43.577 | 19.728 | 1.00 | 0.00 |
| ATOM | 413 | CG2 | VAL | 1 | 49 | -4.498 | 44.517 | 18.390 | 1.00 | 0.00 |
| ATOM | 414 | H   | VAL | 1 | 49 | -4.707 | 47.023 | 19.750 | 1.00 | 0.00 |
| ATOM | 415 | N   | PHE | 1 | 50 | -2.811 | 46.022 | 22.734 | 1.00 | 0.00 |
| ATOM | 416 | CA  | PHE | 1 | 50 | -1.793 | 46.690 | 23.383 | 1.00 | 0.00 |
| ATOM | 417 | C   | PHE | 1 | 50 | -0.835 | 45.766 | 23.937 | 1.00 | 0.00 |
| ATOM | 418 | O   | PHE | 1 | 50 | -1.082 | 44.564 | 24.001 | 1.00 | 0.00 |
| ATOM | 419 | CB  | PHE | 1 | 50 | -2.343 | 47.588 | 24.462 | 1.00 | 0.00 |
| ATOM | 420 | CG  | PHE | 1 | 50 | -3.767 | 48.162 | 24.266 | 1.00 | 0.00 |
| ATOM | 421 | CD1 | PHE | 1 | 50 | -4.158 | 48.819 | 23.058 | 1.00 | 0.00 |
| ATOM | 422 | CD2 | PHE | 1 | 50 | -4.648 | 48.064 | 25.365 | 1.00 | 0.00 |
| ATOM | 423 | CE1 | PHE | 1 | 50 | -5.442 | 49.326 | 22.959 | 1.00 | 0.00 |
| ATOM | 424 | CE2 | PHE | 1 | 50 | -5.989 | 48.477 | 25.179 | 1.00 | 0.00 |
| ATOM | 425 | CZ  | PHE | 1 | 50 | -6.378 | 49.138 | 23.978 | 1.00 | 0.00 |
| ATOM | 426 | H   | PHE | 1 | 50 | -3.535 | 45.534 | 23.221 | 1.00 | 0.00 |
| ATOM | 427 | N   | PHE | 1 | 51 |  0.269 | 46.369 | 24.384 | 1.00 | 0.00 |
| ATOM | 428 | CA  | PHE | 1 | 51 |  1.219 | 45.510 | 25.011 | 1.00 | 0.00 |
| ATOM | 429 | C   | PHE | 1 | 51 |  1.628 | 46.101 | 26.372 | 1.00 | 0.00 |
| ATOM | 430 | O   | PHE | 1 | 51 |  1.290 | 47.244 | 26.681 | 1.00 | 0.00 |
| ATOM | 431 | CB  | PHE | 1 | 51 |  2.558 | 45.235 | 24.183 | 1.00 | 0.00 |
| ATOM | 432 | CG  | PHE | 1 | 51 |  2.071 | 44.870 | 22.735 | 1.00 | 0.00 |
| ATOM | 433 | CD1 | PHE | 1 | 51 |  1.474 | 43.648 | 22.482 | 1.00 | 0.00 |
| ATOM | 434 | CD2 | PHE | 1 | 51 |  2.253 | 45.869 | 21.762 | 1.00 | 0.00 |
| ATOM | 435 | CE1 | PHE | 1 | 51 |  1.003 | 43.443 | 21.104 | 1.00 | 0.00 |
| ATOM | 436 | CE2 | PHE | 1 | 51 |  1.858 | 45.668 | 20.423 | 1.00 | 0.00 |
| ATOM | 437 | CZ  | PHE | 1 | 51 |  1.236 | 44.497 | 20.130 | 1.00 | 0.00 |
| ATOM | 438 | H   | PHE | 1 | 51 |  0.598 | 47.248 | 24.040 | 1.00 | 0.00 |
| ATOM | 439 | N   | LEU | 1 | 52 |  2.130 | 45.091 | 27.132 | 1.00 | 0.00 |
| ATOM | 440 | CA  | LEU | 1 | 52 |  2.325 | 45.227 | 28.576 | 1.00 | 0.00 |
| ATOM | 441 | C   | LEU | 1 | 52 |  3.524 | 44.445 | 29.054 | 1.00 | 0.00 |
| ATOM | 442 | O   | LEU | 1 | 52 |  3.530 | 43.203 | 29.019 | 1.00 | 0.00 |
| ATOM | 443 | CB  | LEU | 1 | 52 |  1.065 | 44.789 | 29.287 | 1.00 | 0.00 |
| ATOM | 444 | CG  | LEU | 1 | 52 |  0.938 | 45.233 | 30.789 | 1.00 | 0.00 |
| ATOM | 445 | CD1 | LEU | 1 | 52 | -0.220 | 46.185 | 30.933 | 1.00 | 0.00 |
| ATOM | 446 | CD2 | LEU | 1 | 52 |  0.653 | 44.204 | 31.814 | 1.00 | 0.00 |
| ATOM | 447 | H   | LEU | 1 | 52 |  2.068 | 44.177 | 26.732 | 1.00 | 0.00 |
| ATOM | 448 | N   | THR | 1 | 53 |  4.567 | 45.174 | 29.416 | 1.00 | 0.00 |
| ATOM | 449 | CA  | THR | 1 | 53 |  5.541 | 44.339 | 30.004 | 1.00 | 0.00 |
| ATOM | 450 | C   | THR | 1 | 53 |  5.394 | 44.249 | 31.552 | 1.00 | 0.00 |

FIG. 1J

| ATOM | 451 | O | THR | 1 | 53 | 5.698 | 45.208 | 32.281 | 1.00 | 0.00 |
| ATOM | 452 | CB | THR | 1 | 53 | 6.993 | 44.839 | 29.721 | 1.00 | 0.00 |
| ATOM | 453 | OG1 | THR | 1 | 53 | 7.141 | 46.178 | 30.117 | 1.00 | 0.00 |
| ATOM | 454 | OG2 | THR | 1 | 53 | 7.449 | 44.539 | 28.336 | 1.00 | 0.00 |
| ATOM | 455 | H | THR | 1 | 53 | 4.610 | 46.165 | 29.290 | 1.00 | 0.00 |
| ATOM | 456 | 1HG | THR | 1 | 53 | 6.693 | 46.593 | 29.392 | 1.00 | 0.00 |
| ATOM | 457 | N | ILE | 1 | 54 | 5.055 | 43.019 | 32.006 | 1.00 | 0.00 |
| ATOM | 458 | CA | ILE | 1 | 54 | 5.201 | 42.975 | 33.500 | 1.00 | 0.00 |
| ATOM | 459 | C | ILE | 1 | 54 | 6.483 | 42.187 | 33.824 | 1.00 | 0.00 |
| ATOM | 460 | O | ILE | 1 | 54 | 6.624 | 41.049 | 33.449 | 1.00 | 0.00 |
| ATOM | 461 | CB | ILE | 1 | 54 | 3.895 | 42.546 | 34.056 | 1.00 | 0.00 |
| ATOM | 462 | CG1 | ILE | 1 | 54 | 4.116 | 42.239 | 35.538 | 1.00 | 0.00 |
| ATOM | 463 | CG2 | ILE | 1 | 54 | 3.293 | 41.330 | 33.449 | 1.00 | 0.00 |
| ATOM | 464 | CD1 | ILE | 1 | 54 | 2.835 | 42.116 | 36.297 | 1.00 | 0.00 |
| ATOM | 465 | H | ILE | 1 | 54 | 4.883 | 42.200 | 31.459 | 1.00 | 0.00 |
| ATOM | 466 | N | HIS | 1 | 55 | 7.356 | 42.905 | 34.533 | 1.00 | 0.00 |
| ATOM | 467 | CA | HIS | 1 | 55 | 8.680 | 42.432 | 35.034 | 1.00 | 0.00 |
| ATOM | 468 | C | HIS | 1 | 55 | 8.488 | 41.851 | 36.430 | 1.00 | 0.00 |
| ATOM | 469 | O | HIS | 1 | 55 | 8.711 | 42.401 | 37.499 | 1.00 | 0.00 |
| ATOM | 470 | CB | HIS | 1 | 55 | 9.677 | 43.626 | 35.221 | 1.00 | 0.00 |
| ATOM | 471 | CG | HIS | 1 | 55 | 11.084 | 43.145 | 35.610 | 1.00 | 0.00 |
| ATOM | 472 | ND1 | HIS | 1 | 55 | 11.463 | 42.849 | 36.889 | 1.00 | 0.00 |
| ATOM | 473 | CD2 | HIS | 1 | 55 | 12.160 | 43.008 | 34.734 | 1.00 | 0.00 |
| ATOM | 474 | CE1 | HIS | 1 | 55 | 12.798 | 42.553 | 36.874 | 1.00 | 0.00 |
| ATOM | 475 | NE2 | HIS | 1 | 55 | 13.166 | 42.652 | 35.589 | 1.00 | 0.00 |
| ATOM | 476 | H | HIS | 1 | 55 | 6.985 | 43.825 | 34.656 | 1.00 | 0.00 |
| ATOM | 477 | 1HD | HIS | 1 | 55 | 10.779 | 42.792 | 37.588 | 1.00 | 0.00 |
| ATOM | 478 | N | PHE | 1 | 56 | 8.004 | 40.579 | 36.294 | 1.00 | 0.00 |
| ATOM | 479 | CA | PHE | 1 | 56 | 8.124 | 39.740 | 37.478 | 1.00 | 0.00 |
| ATOM | 480 | C | PHE | 1 | 56 | 9.564 | 39.404 | 37.759 | 1.00 | 0.00 |
| ATOM | 481 | O | PHE | 1 | 56 | 10.111 | 38.735 | 36.928 | 1.00 | 0.00 |
| ATOM | 482 | CB | PHE | 1 | 56 | 7.431 | 38.414 | 37.221 | 1.00 | 0.00 |
| ATOM | 483 | CG | PHE | 1 | 56 | 5.957 | 38.636 | 37.218 | 1.00 | 0.00 |
| ATOM | 484 | CD1 | PHE | 1 | 56 | 5.243 | 38.642 | 38.488 | 1.00 | 0.00 |
| ATOM | 485 | CD2 | PHE | 1 | 56 | 5.258 | 38.651 | 36.021 | 1.00 | 0.00 |
| ATOM | 486 | CE1 | PHE | 1 | 56 | 3.843 | 38.681 | 38.472 | 1.00 | 0.00 |
| ATOM | 487 | CE2 | PHE | 1 | 56 | 3.883 | 38.677 | 36.013 | 1.00 | 0.00 |
| ATOM | 488 | CZ | PHE | 1 | 56 | 3.180 | 38.671 | 37.227 | 1.00 | 0.00 |
| ATOM | 489 | H | PHE | 1 | 56 | 8.146 | 40.122 | 35.416 | 1.00 | 0.00 |
| ATOM | 490 | N | PRO | 1 | 57 | 10.161 | 40.000 | 38.828 | 1.00 | 0.00 |
| ATOM | 491 | CA | PRO | 1 | 57 | 11.669 | 39.843 | 38.911 | 1.00 | 0.00 |
| ATOM | 492 | C | PRO | 1 | 57 | 12.092 | 38.428 | 39.104 | 1.00 | 0.00 |
| ATOM | 493 | O | PRO | 1 | 57 | 11.362 | 37.470 | 39.343 | 1.00 | 0.00 |
| ATOM | 494 | CB | PRO | 1 | 57 | 12.003 | 40.789 | 40.050 | 1.00 | 0.00 |
| ATOM | 495 | CG | PRO | 1 | 57 | 10.739 | 40.883 | 40.945 | 1.00 | 0.00 |

FIG. 1K

| ATOM | 496 | CD  | PRO | 1 | 57 | 9.576  | 40.703 | 39.952 | 1.00 | 0.00 |
| ---- | --- | --- | --- | - | -- | ------ | ------ | ------ | ---- | ---- |
| ATOM | 497 | N   | THR | 1 | 58 | 13.424 | 38.247 | 38.912 | 1.00 | 0.00 |
| ATOM | 498 | CA  | THR | 1 | 58 | 14.071 | 37.056 | 39.470 | 1.00 | 0.00 |
| ATOM | 499 | C   | THR | 1 | 58 | 13.788 | 36.737 | 40.841 | 1.00 | 0.00 |
| ATOM | 500 | O   | THR | 1 | 58 | 13.926 | 35.629 | 41.294 | 1.00 | 0.00 |
| ATOM | 501 | CB  | THR | 1 | 58 | 15.541 | 37.145 | 39.032 | 1.00 | 0.00 |
| ATOM | 502 | OG1 | THR | 1 | 58 | 15.680 | 37.609 | 37.672 | 1.00 | 0.00 |
| ATOM | 503 | CG2 | THR | 1 | 58 | 16.131 | 35.762 | 39.182 | 1.00 | 0.00 |
| ATOM | 504 | H   | THR | 1 | 58 | 14.036 | 38.966 | 38.583 | 1.00 | 0.00 |
| ATOM | 505 | 1HG | THR | 1 | 58 | 16.524 | 37.297 | 37.373 | 1.00 | 0.00 |
| ATOM | 506 | N   | ASP | 1 | 59 | 13.457 | 37.777 | 41.583 | 1.00 | 0.00 |
| ATOM | 507 | CA  | ASP | 1 | 59 | 13.181 | 37.664 | 43.011 | 1.00 | 0.00 |
| ATOM | 508 | C   | ASP | 1 | 59 | 11.769 | 37.504 | 43.490 | 1.00 | 0.00 |
| ATOM | 509 | O   | ASP | 1 | 59 | 11.159 | 38.230 | 44.245 | 1.00 | 0.00 |
| ATOM | 510 | CB  | ASP | 1 | 59 | 13.889 | 38.750 | 43.734 | 1.00 | 0.00 |
| ATOM | 511 | CG  | ASP | 1 | 59 | 13.491 | 40.164 | 43.290 | 1.00 | 0.00 |
| ATOM | 512 | OD1 | ASP | 1 | 59 | 14.211 | 40.777 | 42.414 | 1.00 | 0.00 |
| ATOM | 513 | OD2 | ASP | 1 | 59 | 12.597 | 40.779 | 43.786 | 1.00 | 0.00 |
| ATOM | 514 | H   | ASP | 1 | 59 | 13.329 | 38.682 | 41.178 | 1.00 | 0.00 |
| ATOM | 515 | N   | TYR | 1 | 60 | 11.264 | 36.412 | 43.011 | 1.00 | 0.00 |
| ATOM | 516 | CA  | TYR | 1 | 60 | 9.821  | 36.218 | 43.226 | 1.00 | 0.00 |
| ATOM | 517 | C   | TYR | 1 | 60 | 9.406  | 35.407 | 44.477 | 1.00 | 0.00 |
| ATOM | 518 | O   | TYR | 1 | 60 | 10.033 | 34.441 | 44.781 | 1.00 | 0.00 |
| ATOM | 519 | CB  | TYR | 1 | 60 | 9.157  | 35.843 | 41.829 | 1.00 | 0.00 |
| ATOM | 520 | CG  | TYR | 1 | 60 | 7.838  | 36.612 | 41.789 | 1.00 | 0.00 |
| ATOM | 521 | CD1 | TYR | 1 | 60 | 8.034  | 37.990 | 41.682 | 1.00 | 0.00 |
| ATOM | 522 | CD2 | TYR | 1 | 60 | 6.546  | 36.030 | 41.874 | 1.00 | 0.00 |
| ATOM | 523 | CE1 | TYR | 1 | 60 | 6.972  | 38.870 | 41.721 | 1.00 | 0.00 |
| ATOM | 524 | CE2 | TYR | 1 | 60 | 5.438  | 36.950 | 41.740 | 1.00 | 0.00 |
| ATOM | 525 | CZ  | TYR | 1 | 60 | 5.729  | 38.357 | 41.751 | 1.00 | 0.00 |
| ATOM | 526 | OH  | TYR | 1 | 60 | 4.710  | 39.254 | 41.968 | 1.00 | 0.00 |
| ATOM | 527 | H   | TYR | 1 | 60 | 11.803 | 35.930 | 42.321 | 1.00 | 0.00 |
| ATOM | 528 | HH  | TYR | 1 | 60 | 4.929  | 39.846 | 42.676 | 1.00 | 0.00 |
| ATOM | 529 | N   | PRO | 1 | 61 | 8.341  | 35.745 | 45.277 | 1.00 | 0.00 |
| ATOM | 530 | CA  | PRO | 1 | 61 | 7.611  | 36.986 | 45.163 | 1.00 | 0.00 |
| ATOM | 531 | C   | PRO | 1 | 61 | 8.031  | 38.127 | 46.103 | 1.00 | 0.00 |
| ATOM | 532 | O   | PRO | 1 | 61 | 7.544  | 38.281 | 47.197 | 1.00 | 0.00 |
| ATOM | 533 | CB  | PRO | 1 | 61 | 6.241  | 36.440 | 45.549 | 1.00 | 0.00 |
| ATOM | 534 | CG  | PRO | 1 | 61 | 6.451  | 35.361 | 46.551 | 1.00 | 0.00 |
| ATOM | 535 | CD  | PRO | 1 | 61 | 7.874  | 34.846 | 46.340 | 1.00 | 0.00 |
| ATOM | 536 | N   | PHE | 1 | 62 | 8.921  | 39.015 | 45.665 | 1.00 | 0.00 |
| ATOM | 537 | CA  | PHE | 1 | 62 | 9.316  | 39.953 | 46.675 | 1.00 | 0.00 |
| ATOM | 538 | C   | PHE | 1 | 62 | 9.091  | 41.436 | 46.494 | 1.00 | 0.00 |
| ATOM | 539 | O   | PHE | 1 | 62 | 8.277  | 42.242 | 47.033 | 1.00 | 0.00 |
| ATOM | 540 | CB  | PHE | 1 | 62 | 10.835 | 39.726 | 47.093 | 1.00 | 0.00 |

FIG. 1L

| | | | | | | | | | |
|---|---|---|---|---|---|---|---|---|---|
| ATOM | 541 | CG | PHE | 1 | 62 | 11.170 | 38.343 | 47.627 | 1.00 | 0.00 |
| ATOM | 542 | CD1 | PHE | 1 | 62 | 10.256 | 37.516 | 48.364 | 1.00 | 0.00 |
| ATOM | 543 | CD2 | PHE | 1 | 62 | 12.483 | 37.929 | 47.366 | 1.00 | 0.00 |
| ATOM | 544 | CD1 | PHE | 1 | 62 | 10.701 | 36.264 | 48.835 | 1.00 | 0.00 |
| ATOM | 545 | CE2 | PHE | 1 | 62 | 12.959 | 36.670 | 47.863 | 1.00 | 0.00 |
| ATOM | 546 | CZ | PHE | 1 | 62 | 12.047 | 35.848 | 48.625 | 1.00 | 0.00 |
| ATOM | 547 | H | PHE | 1 | 62 | 9.595 | 38.814 | 44.954 | 1.00 | 0.00 |
| ATOM | 548 | N | LYS | 1 | 63 | 9.863 | 41.843 | 45.495 | 1.00 | 0.00 |
| ATOM | 549 | CA | LYS | 1 | 63 | 9.548 | 43.072 | 44.849 | 1.00 | 0.00 |
| ATOM | 550 | C | LYS | 1 | 63 | 8.397 | 43.143 | 43.796 | 1.00 | 0.00 |
| ATOM | 551 | O | LYS | 1 | 63 | 8.195 | 42.199 | 42.989 | 1.00 | 0.00 |
| ATOM | 552 | CB | LYS | 1 | 63 | 10.812 | 43.763 | 44.268 | 1.00 | 0.00 |
| ATOM | 553 | CG | LYS | 1 | 63 | 11.675 | 44.228 | 45.486 | 1.00 | 0.00 |
| ATOM | 554 | CD | LYS | 1 | 63 | 13.008 | 44.744 | 45.085 | 1.00 | 0.00 |
| ATOM | 555 | CE | LYS | 1 | 63 | 14.141 | 43.689 | 44.873 | 1.00 | 0.00 |
| ATOM | 556 | NZ | LYS | 1 | 63 | 13.885 | 43.084 | 43.628 | 1.00 | 0.00 |
| ATOM | 557 | H | LYS | 1 | 63 | 10.564 | 41.264 | 45.080 | 1.00 | 0.00 |
| ATOM | 558 | 1HZ | LYS | 1 | 63 | 13.607 | 43.721 | 42.854 | 1.00 | 0.00 |
| ATOM | 559 | 2HZ | LYS | 1 | 63 | 14.604 | 42.424 | 43.268 | 1.00 | 0.00 |
| ATOM | 560 | 3HZ | LYS | 1 | 63 | 13.094 | 42.434 | 43.815 | 1.00 | 0.00 |
| ATOM | 561 | N | PRO | 1 | 64 | 7.612 | 44.296 | 44.014 | 1.00 | 0.00 |
| ATOM | 562 | CA | PRO | 1 | 64 | 6.552 | 44.555 | 43.047 | 1.00 | 0.00 |
| ATOM | 563 | C | PRO | 1 | 64 | 7.019 | 44.767 | 41.595 | 1.00 | 0.00 |
| ATOM | 564 | O | PRO | 1 | 64 | 7.827 | 45.556 | 41.196 | 1.00 | 0.00 |
| ATOM | 565 | CB | PRO | 1 | 64 | 5.886 | 45.784 | 43.752 | 1.00 | 0.00 |
| ATOM | 566 | CG | PRO | 1 | 64 | 6.176 | 45.623 | 45.213 | 1.00 | 0.00 |
| ATOM | 567 | CD | PRO | 1 | 64 | 7.675 | 45.291 | 45.131 | 1.00 | 0.00 |
| ATOM | 568 | N | PRO | 1 | 65 | 6.468 | 43.847 | 40.815 | 1.00 | 0.00 |
| ATOM | 569 | CA | PRO | 1 | 65 | 6.866 | 43.890 | 39.421 | 1.00 | 0.00 |
| ATOM | 570 | C | PRO | 1 | 65 | 6.657 | 45.256 | 38.732 | 1.00 | 0.00 |
| ATOM | 571 | O | PRO | 1 | 65 | 5.727 | 46.018 | 38.928 | 1.00 | 0.00 |
| ATOM | 572 | CB | PRO | 1 | 65 | 6.066 | 42.674 | 38.836 | 1.00 | 0.00 |
| ATOM | 573 | CG | PRO | 1 | 65 | 5.450 | 41.854 | 39.988 | 1.00 | 0.00 |
| ATOM | 574 | CD | PRO | 1 | 65 | 5.640 | 42.744 | 41.175 | 1.00 | 0.00 |
| ATOM | 575 | N | LYS | 1 | 66 | 7.616 | 45.558 | 37.920 | 1.00 | 0.00 |
| ATOM | 576 | CA | LYS | 1 | 66 | 7.582 | 46.638 | 36.943 | 1.00 | 0.00 |
| ATOM | 577 | C | LYS | 1 | 66 | 6.677 | 46.420 | 35.758 | 1.00 | 0.00 |
| ATOM | 578 | O | LYS | 1 | 66 | 6.975 | 45.573 | 34.895 | 1.00 | 0.00 |
| ATOM | 579 | CB | LYS | 1 | 66 | 9.042 | 47.057 | 36.632 | 1.00 | 0.00 |
| ATOM | 580 | CG | LYS | 1 | 66 | 9.026 | 47.916 | 35.359 | 1.00 | 0.00 |
| ATOM | 581 | CD | LYS | 1 | 66 | 9.426 | 47.170 | 34.096 | 1.00 | 0.00 |
| ATOM | 582 | CE | LYS | 1 | 66 | 8.561 | 47.715 | 32.960 | 1.00 | 0.00 |
| ATOM | 583 | NZ | LYS | 1 | 66 | 7.593 | 46.650 | 32.604 | 1.00 | 0.00 |
| ATOM | 584 | H | LYS | 1 | 66 | 8.315 | 44.850 | 37.823 | 1.00 | 0.00 |
| ATOM | 585 | 1HZ | LYS | 1 | 66 | 7.202 | 46.096 | 33.393 | 1.00 | 0.00 |

FIG. 1M

| ATOM | 586 | 2HZ | LYS | 1 | 66 | 6.840 | 46.784 | 31.900 | 1.00 | 0.00 |
| ATOM | 587 | 3HZ | LYS | 1 | 66 | 8.051 | 45.940 | 31.997 | 1.00 | 0.00 |
| ATOM | 588 | N | VAL | 1 | 67 | 5.641 | 47.237 | 35.914 | 1.00 | 0.00 |
| ATOM | 589 | CA | VAL | 1 | 67 | 4.618 | 47.092 | 34.890 | 1.00 | 0.00 |
| ATOM | 590 | C | VAL | 1 | 67 | 4.669 | 48.202 | 33.838 | 1.00 | 0.00 |
| ATOM | 591 | O | VAL | 1 | 67 | 5.038 | 49.290 | 34.212 | 1.00 | 0.00 |
| ATOM | 592 | CB | VAL | 1 | 67 | 3.210 | 47.149 | 35.616 | 1.00 | 0.00 |
| ATOM | 593 | CG1 | VAL | 1 | 67 | 2.008 | 47.020 | 34.713 | 1.00 | 0.00 |
| ATOM | 594 | CG2 | VAL | 1 | 67 | 3.138 | 46.027 | 36.596 | 1.00 | 0.00 |
| ATOM | 595 | H | VAL | 1 | 67 | 5.652 | 47.816 | 36.730 | 1.00 | 0.00 |
| ATOM | 596 | N | ALA | 1 | 68 | 4.284 | 47.890 | 32.576 | 1.00 | 0.00 |
| ATOM | 597 | CA | ALA | 1 | 68 | 4.063 | 49.030 | 31.594 | 1.00 | 0.00 |
| ATOM | 598 | C | ALA | 1 | 68 | 3.210 | 48.782 | 30.295 | 1.00 | 0.00 |
| ATOM | 599 | O | ALA | 1 | 68 | 3.050 | 47.648 | 29.844 | 1.00 | 0.00 |
| ATOM | 600 | CB | ALA | 1 | 68 | 5.339 | 49.726 | 31.204 | 1.00 | 0.00 |
| ATOM | 601 | H | ALA | 1 | 68 | 3.936 | 46.964 | 32.435 | 1.00 | 0.00 |
| ATOM | 602 | N | PHE | 1 | 69 | 2.744 | 49.948 | 29.729 | 1.00 | 0.00 |
| ATOM | 603 | CA | PHE | 1 | 69 | 2.170 | 49.817 | 28.428 | 1.00 | 0.00 |
| ATOM | 604 | C | PHE | 1 | 69 | 3.003 | 49.993 | 27.243 | 1.00 | 0.00 |
| ATOM | 605 | O | PHE | 1 | 69 | 4.174 | 50.197 | 27.488 | 1.00 | 0.00 |
| ATOM | 606 | CB | PHE | 1 | 69 | 1.005 | 50.861 | 28.439 | 1.00 | 0.00 |
| ATOM | 607 | CG | PHE | 1 | 69 | -0.236 | 50.170 | 29.024 | 1.00 | 0.00 |
| ATOM | 608 | CD1 | PHE | 1 | 69 | -0.571 | 50.303 | 30.370 | 1.00 | 0.00 |
| ATOM | 609 | CD2 | PHE | 1 | 69 | -1.184 | 49.627 | 28.119 | 1.00 | 0.00 |
| ATOM | 610 | CE1 | PHE | 1 | 69 | -1.950 | 49.879 | 30.749 | 1.00 | 0.00 |
| ATOM | 611 | CE2 | PHE | 1 | 69 | -2.510 | 49.317 | 28.496 | 1.00 | 0.00 |
| ATOM | 612 | CZ | PHE | 1 | 69 | -2.919 | 49.553 | 29.836 | 1.00 | 0.00 |
| ATOM | 613 | H | PHE | 1 | 69 | 3.122 | 50.795 | 30.100 | 1.00 | 0.00 |
| ATOM | 614 | N | THR | 1 | 70 | 2.418 | 49.796 | 26.051 | 1.00 | 0.00 |
| ATOM | 615 | CA | THR | 1 | 70 | 3.174 | 50.059 | 24.865 | 1.00 | 0.00 |
| ATOM | 616 | C | THR | 1 | 70 | 2.540 | 50.869 | 23.691 | 1.00 | 0.00 |
| ATOM | 617 | O | THR | 1 | 70 | 3.101 | 51.454 | 22.774 | 1.00 | 0.00 |
| ATOM | 618 | CB | THR | 1 | 70 | 3.823 | 48.693 | 24.425 | 1.00 | 0.00 |
| ATOM | 619 | OG1 | THR | 1 | 70 | 4.392 | 47.934 | 25.445 | 1.00 | 0.00 |
| ATOM | 620 | OG2 | THR | 1 | 70 | 5.058 | 48.811 | 23.431 | 1.00 | 0.00 |
| ATOM | 621 | H | THR | 1 | 70 | 1.520 | 49.357 | 26.083 | 1.00 | 0.00 |
| ATOM | 622 | 1HG | THR | 1 | 70 | 4.658 | 48.583 | 26.082 | 1.00 | 0.00 |
| ATOM | 623 | N | THR | 1 | 71 | 1.197 | 50.942 | 23.754 | 1.00 | 0.00 |
| ATOM | 624 | CA | THR | 1 | 71 | 0.474 | 51.874 | 22.977 | 1.00 | 0.00 |
| ATOM | 625 | C | THR | 1 | 71 | 0.307 | 53.101 | 23.855 | 1.00 | 0.00 |
| ATOM | 626 | O | THR | 1 | 71 | 0.482 | 52.993 | 25.082 | 1.00 | 0.00 |
| ATOM | 627 | CB | THR | 1 | 71 | -0.890 | 51.230 | 22.586 | 1.00 | 0.00 |
| ATOM | 628 | OG1 | THR | 1 | 71 | -1.547 | 51.870 | 21.495 | 1.00 | 0.00 |
| ATOM | 629 | OG2 | THR | 1 | 71 | -1.785 | 51.219 | 23.771 | 1.00 | 0.00 |
| ATOM | 630 | H | THR | 1 | 71 | 0.626 | 50.488 | 24.439 | 1.00 | 0.00 |

FIG. 1N

| ATOM | 631 | 1HG | THR | 1 | 71 | -2.411 | 51.480 | 21.469 | 1.00 | 0.00 |
| ATOM | 632 | N | ARG | 1 | 72 | -0.235 | 54.173 | 23.226 | 1.00 | 0.00 |
| ATOM | 633 | CA | ARG | 1 | 72 | -0.698 | 55.208 | 24.180 | 1.00 | 0.00 |
| ATOM | 634 | C | ARG | 1 | 72 | -2.115 | 55.840 | 23.974 | 1.00 | 0.00 |
| ATOM | 635 | O | ARG | 1 | 72 | -2.217 | 57.065 | 23.776 | 1.00 | 0.00 |
| ATOM | 636 | CB | ARG | 1 | 72 | 0.288 | 56.308 | 24.307 | 1.00 | 0.00 |
| ATOM | 637 | CG | ARG | 1 | 72 | 0.826 | 56.516 | 25.720 | 1.00 | 0.00 |
| ATOM | 638 | CD | ARG | 1 | 72 | -0.223 | 57.282 | 26.573 | 1.00 | 0.00 |
| ATOM | 639 | NE | ARG | 1 | 72 | -0.810 | 58.398 | 25.780 | 1.00 | 0.00 |
| ATOM | 640 | CZ | ARG | 1 | 72 | -1.820 | 59.012 | 26.451 | 1.00 | 0.00 |
| ATOM | 641 | NH1 | ARG | 1 | 72 | -2.145 | 58.515 | 27.586 | 1.00 | 0.00 |
| ATOM | 642 | NH2 | ARG | 1 | 72 | -2.355 | 60.127 | 25.927 | 1.00 | 0.00 |
| ATOM | 643 | H | ARG | 1 | 72 | -0.234 | 54.315 | 22.236 | 1.00 | 0.00 |
| ATOM | 644 | HE | ARG | 1 | 72 | -0.329 | 58.774 | 24.988 | 1.00 | 0.00 |
| ATOM | 645 | 1HH1 | ARG | 1 | 72 | -2.785 | 59.051 | 28.137 | 1.00 | 0.00 |
| ATOM | 646 | 2HH1 | ARG | 1 | 72 | -1.825 | 57.675 | 28.024 | 1.00 | 0.00 |
| ATOM | 647 | 1HH2 | ARG | 1 | 72 | -3.097 | 60.500 | 26.484 | 1.00 | 0.00 |
| ATOM | 648 | 2HH2 | ARG | 1 | 72 | -2.152 | 60.596 | 25.068 | 1.00 | 0.00 |
| ATOM | 649 | N | ILE | 1 | 73 | -3.075 | 54.932 | 24.098 | 1.00 | 0.00 |
| ATOM | 650 | CA | ILE | 1 | 73 | -4.455 | 55.301 | 23.856 | 1.00 | 0.00 |
| ATOM | 651 | C | ILE | 1 | 73 | -5.133 | 55.989 | 25.011 | 1.00 | 0.00 |
| ATOM | 652 | O | ILE | 1 | 73 | -5.141 | 55.445 | 26.100 | 1.00 | 0.00 |
| ATOM | 653 | CB | ILE | 1 | 73 | -5.320 | 54.019 | 23.424 | 1.00 | 0.00 |
| ATOM | 654 | CG1 | ILE | 1 | 73 | -6.850 | 54.247 | 23.209 | 1.00 | 0.00 |
| ATOM | 655 | CG2 | ILE | 1 | 73 | -5.101 | 52.911 | 24.470 | 1.00 | 0.00 |
| ATOM | 656 | CD1 | ILE | 1 | 73 | -7.640 | 52.943 | 22.791 | 1.00 | 0.00 |
| ATOM | 657 | H | ILE | 1 | 73 | -2.810 | 53.985 | 24.276 | 1.00 | 0.00 |
| ATOM | 658 | N | TYR | 1 | 74 | -5.586 | 57.222 | 24.931 | 1.00 | 0.00 |
| ATOM | 659 | CA | TYR | 1 | 74 | -6.264 | 58.008 | 25.978 | 1.00 | 0.00 |
| ATOM | 660 | C | TYR | 1 | 74 | -6.963 | 57.448 | 27.192 | 1.00 | 0.00 |
| ATOM | 661 | O | TYR | 1 | 74 | -8.075 | 56.932 | 27.127 | 1.00 | 0.00 |
| ATOM | 662 | CB | TYR | 1 | 74 | -7.256 | 58.973 | 25.383 | 1.00 | 0.00 |
| ATOM | 663 | CG | TYR | 1 | 74 | -6.545 | 60.286 | 24.901 | 1.00 | 0.00 |
| ATOM | 664 | CD1 | TYR | 1 | 74 | -6.956 | 61.516 | 25.449 | 1.00 | 0.00 |
| ATOM | 665 | CD2 | TYR | 1 | 74 | -5.569 | 60.181 | 23.917 | 1.00 | 0.00 |
| ATOM | 666 | CE1 | TYR | 1 | 74 | -6.330 | 62.685 | 25.001 | 1.00 | 0.00 |
| ATOM | 667 | CE2 | TYR | 1 | 74 | -4.903 | 61.360 | 23.491 | 1.00 | 0.00 |
| ATOM | 668 | CZ | TYR | 1 | 74 | -5.267 | 62.542 | 24.077 | 1.00 | 0.00 |
| ATOM | 669 | OH | TYR | 1 | 74 | -4.459 | 63.643 | 23.767 | 1.00 | 0.00 |
| ATOM | 670 | H | TYR | 1 | 74 | -5.424 | 57.697 | 24.066 | 1.00 | 0.00 |
| ATOM | 671 | HH | TYR | 1 | 74 | -3.605 | 63.327 | 23.505 | 1.00 | 0.00 |
| ATOM | 672 | N | HIS | 1 | 75 | -6.244 | 57.542 | 28.315 | 1.00 | 0.00 |
| ATOM | 673 | CA | HIS | 1 | 75 | -6.712 | 57.415 | 29.691 | 1.00 | 0.00 |
| ATOM | 674 | C | HIS | 1 | 75 | -5.809 | 58.147 | 30.656 | 1.00 | 0.00 |
| ATOM | 675 | O | HIS | 1 | 75 | -4.618 | 58.037 | 30.567 | 1.00 | 0.00 |

FIG. 10

| ATOM | 676 | CB   | HIS | 1 | 75 | -6.903 | 55.932 | 30.164 | 1.00 | 0.00 |
| ATOM | 677 | CG   | HIS | 1 | 75 | -7.735 | 55.806 | 31.446 | 1.00 | 0.00 |
| ATOM | 678 | ND1  | HIS | 1 | 75 | -7.320 | 55.110 | 32.508 | 1.00 | 0.00 |
| ATOM | 679 | CD2  | HIS | 1 | 75 | -9.064 | 56.208 | 31.661 | 1.00 | 0.00 |
| ATOM | 680 | CE1  | HIS | 1 | 75 | -8.337 | 55.061 | 33.430 | 1.00 | 0.00 |
| ATOM | 681 | NE2  | HIS | 1 | 75 | -9.429 | 55.714 | 32.910 | 1.00 | 0.00 |
| ATOM | 682 | H    | HIS | 1 | 75 | -5.350 | 57.933 | 28.095 | 1.00 | 0.00 |
| ATOM | 683 | 1HD  | HIS | 1 | 75 | -6.505 | 54.575 | 32.609 | 1.00 | 0.00 |
| ATOM | 684 | N    | PRO | 1 | 76 | -6.406 | 58.853 | 31.622 | 1.00 | 0.00 |
| ATOM | 685 | CA   | PRO | 1 | 76 | -5.631 | 59.218 | 32.828 | 1.00 | 0.00 |
| ATOM | 686 | C    | PRO | 1 | 76 | -4.689 | 58.242 | 33.509 | 1.00 | 0.00 |
| ATOM | 687 | O    | PRO | 1 | 76 | -3.545 | 58.615 | 33.836 | 1.00 | 0.00 |
| ATOM | 688 | CB   | PRO | 1 | 76 | -6.733 | 59.744 | 33.703 | 1.00 | 0.00 |
| ATOM | 689 | CG   | PRO | 1 | 76 | -8.079 | 59.421 | 33.110 | 1.00 | 0.00 |
| ATOM | 690 | CD   | PRO | 1 | 76 | -7.793 | 59.273 | 31.629 | 1.00 | 0.00 |
| ATOM | 691 | N    | ASN | 1 | 77 | -5.120 | 56.969 | 33.592 | 1.00 | 0.00 |
| ATOM | 692 | CA   | ASN | 1 | 77 | -4.149 | 55.995 | 34.023 | 1.00 | 0.00 |
| ATOM | 693 | C    | ASN | 1 | 77 | -3.232 | 55.350 | 32.975 | 1.00 | 0.00 |
| ATOM | 694 | O    | ASN | 1 | 77 | -2.235 | 54.686 | 33.293 | 1.00 | 0.00 |
| ATOM | 695 | CB   | ASN | 1 | 77 | -4.544 | 55.069 | 35.221 | 1.00 | 0.00 |
| ATOM | 696 | CG   | ASN | 1 | 77 | -5.398 | 53.859 | 34.799 | 1.00 | 0.00 |
| ATOM | 697 | OD1  | ASN | 1 | 77 | -5.269 | 53.390 | 33.660 | 1.00 | 0.00 |
| ATOM | 698 | ND2  | ASN | 1 | 77 | -6.264 | 53.533 | 35.724 | 1.00 | 0.00 |
| ATOM | 699 | H    | ASN | 1 | 77 | -6.008 | 56.604 | 33.313 | 1.00 | 0.00 |
| ATOM | 700 | 1HD2 | ASN | 1 | 77 | -6.190 | 53.971 | 36.620 | 1.00 | 0.00 |
| ATOM | 701 | 2HD2 | ASN | 1 | 77 | -6.951 | 52.815 | 35.616 | 1.00 | 0.00 |
| ATOM | 702 | N    | ILE | 1 | 78 | -3.577 | 55.500 | 31.719 | 1.00 | 0.00 |
| ATOM | 703 | CA   | ILE | 1 | 78 | -2.428 | 55.111 | 30.819 | 1.00 | 0.00 |
| ATOM | 704 | C    | ILE | 1 | 78 | -1.366 | 56.277 | 30.720 | 1.00 | 0.00 |
| ATOM | 705 | O    | ILE | 1 | 78 | -1.137 | 56.911 | 29.708 | 1.00 | 0.00 |
| ATOM | 706 | CB   | ILE | 1 | 78 | -2.914 | 54.640 | 29.485 | 1.00 | 0.00 |
| ATOM | 707 | CG1  | ILE | 1 | 78 | -4.001 | 53.586 | 29.802 | 1.00 | 0.00 |
| ATOM | 708 | CG2  | ILE | 1 | 78 | -1.718 | 53.970 | 28.701 | 1.00 | 0.00 |
| ATOM | 709 | CD1  | ILE | 1 | 78 | -4.663 | 53.021 | 28.578 | 1.00 | 0.00 |
| ATOM | 710 | H    | ILE | 1 | 78 | -4.240 | 56.191 | 31.434 | 1.00 | 0.00 |
| ATOM | 711 | N    | ASN | 1 | 79 | -0.702 | 56.476 | 31.895 | 1.00 | 0.00 |
| ATOM | 712 | CA   | ASN | 1 | 79 |  0.362 | 57.504 | 31.918 | 1.00 | 0.00 |
| ATOM | 713 | C    | ASN | 1 | 79 |  1.462 | 57.177 | 30.980 | 1.00 | 0.00 |
| ATOM | 714 | O    | ASN | 1 | 79 |  1.783 | 56.010 | 30.852 | 1.00 | 0.00 |
| ATOM | 715 | CB   | ASN | 1 | 79 |  0.977 | 57.697 | 33.357 | 1.00 | 0.00 |
| ATOM | 716 | CG   | ASN | 1 | 79 |  1.977 | 58.941 | 33.383 | 1.00 | 0.00 |
| ATOM | 717 | OD1  | ASN | 1 | 79 |  3.102 | 58.857 | 32.913 | 1.00 | 0.00 |
| ATOM | 718 | ND2  | ASN | 1 | 79 |  1.421 | 59.936 | 34.047 | 1.00 | 0.00 |
| ATOM | 719 | H    | ASN | 1 | 79 | -0.879 | 55.970 | 32.740 | 1.00 | 0.00 |
| ATOM | 720 | 1HD2 | ASN | 1 | 79 |  0.480 | 59.871 | 34.380 | 1.00 | 0.00 |

FIG. 1P

| | | | | | | | | | |
|---|---|---|---|---|---|---|---|---|---|
| ATOM | 721 | 2HD2 | ASN | 1 | 79 | 1.919 | 60.793 | 34.181 | 1.00 | 0.00 |
| ATOM | 722 | N | SER | 1 | 80 | 2.012 | 58.274 | 30.296 | 1.00 | 0.00 |
| ATOM | 723 | CA | SER | 1 | 80 | 3.020 | 58.037 | 29.307 | 1.00 | 0.00 |
| ATOM | 724 | C | SER | 1 | 80 | 4.213 | 57.172 | 29.722 | 1.00 | 0.00 |
| ATOM | 725 | O | SER | 1 | 80 | 4.736 | 56.463 | 28.906 | 1.00 | 0.00 |
| ATOM | 726 | CB | SER | 1 | 80 | 3.540 | 59.374 | 28.740 | 1.00 | 0.00 |
| ATOM | 727 | OG | SER | 1 | 80 | 2.464 | 60.229 | 28.410 | 1.00 | 0.00 |
| ATOM | 728 | H | SER | 1 | 80 | 1.733 | 59.222 | 30.444 | 1.00 | 0.00 |
| ATOM | 729 | HG | SER | 1 | 80 | 2.142 | 59.977 | 27.555 | 1.00 | 0.00 |
| ATOM | 730 | N | ASN | 1 | 81 | 4.499 | 57.059 | 31.048 | 1.00 | 0.00 |
| ATOM | 731 | CA | ASN | 1 | 81 | 5.499 | 56.121 | 31.571 | 1.00 | 0.00 |
| ATOM | 732 | C | ASN | 1 | 81 | 5.049 | 54.722 | 31.893 | 1.00 | 0.00 |
| ATOM | 733 | O | ASN | 1 | 81 | 5.800 | 53.806 | 32.205 | 1.00 | 0.00 |
| ATOM | 734 | CB | ASN | 1 | 81 | 6.239 | 56.638 | 32.776 | 1.00 | 0.00 |
| ATOM | 735 | CG | ASN | 1 | 81 | 5.190 | 57.043 | 33.835 | 1.00 | 0.00 |
| ATOM | 736 | OD1 | ASN | 1 | 81 | 4.206 | 56.324 | 33.995 | 1.00 | 0.00 |
| ATOM | 737 | ND2 | ASN | 1 | 81 | 5.364 | 58.167 | 34.505 | 1.00 | 0.00 |
| ATOM | 738 | H | ASN | 1 | 81 | 4.021 | 57.645 | 31.702 | 1.00 | 0.00 |
| ATOM | 739 | 1HD2 | ASN | 1 | 81 | 6.256 | 58.616 | 34.550 | 1.00 | 0.00 |
| ATOM | 740 | 2HD2 | ASN | 1 | 81 | 4.596 | 58.637 | 34.941 | 1.00 | 0.00 |
| ATOM | 741 | N | GLY | 1 | 82 | 3.733 | 54.599 | 31.889 | 1.00 | 0.00 |
| ATOM | 742 | CA | GLY | 1 | 82 | 3.169 | 53.260 | 32.012 | 1.00 | 0.00 |
| ATOM | 743 | C | GLY | 1 | 82 | 2.883 | 52.770 | 33.467 | 1.00 | 0.00 |
| ATOM | 744 | O | GLY | 1 | 82 | 2.757 | 51.537 | 33.677 | 1.00 | 0.00 |
| ATOM | 745 | H | GLY | 1 | 82 | 3.081 | 55.355 | 31.943 | 1.00 | 0.00 |
| ATOM | 746 | N | SER | 1 | 83 | 2.699 | 53.686 | 34.408 | 1.00 | 0.00 |
| ATOM | 747 | CA | SER | 1 | 83 | 2.182 | 53.325 | 35.707 | 1.00 | 0.00 |
| ATOM | 748 | C | SER | 1 | 83 | 0.653 | 53.291 | 35.565 | 1.00 | 0.00 |
| ATOM | 749 | O | SER | 1 | 83 | 0.005 | 53.943 | 34.723 | 1.00 | 0.00 |
| ATOM | 750 | CB | SER | 1 | 83 | 2.747 | 54.306 | 36.709 | 1.00 | 0.00 |
| ATOM | 751 | OG | SER | 1 | 83 | 4.143 | 54.436 | 36.565 | 1.00 | 0.00 |
| ATOM | 752 | H | SER | 1 | 83 | 2.728 | 54.661 | 34.188 | 1.00 | 0.00 |
| ATOM | 753 | HG | SER | 1 | 83 | 4.292 | 55.334 | 36.830 | 1.00 | 0.00 |
| ATOM | 754 | N | ILE | 1 | 84 | 0.097 | 52.428 | 36.385 | 1.00 | 0.00 |
| ATOM | 755 | CA | ILE | 1 | 84 | -1.370 | 52.476 | 36.461 | 1.00 | 0.00 |
| ATOM | 756 | C | ILE | 1 | 84 | -1.850 | 52.509 | 37.900 | 1.00 | 0.00 |
| ATOM | 757 | O | ILE | 1 | 84 | -1.165 | 51.998 | 38.770 | 1.00 | 0.00 |
| ATOM | 758 | CB | ILE | 1 | 84 | -1.937 | 51.310 | 35.649 | 1.00 | 0.00 |
| ATOM | 759 | CG1 | ILE | 1 | 84 | -0.929 | 50.116 | 35.676 | 1.00 | 0.00 |
| ATOM | 760 | CG2 | ILE | 1 | 84 | -2.392 | 51.652 | 34.199 | 1.00 | 0.00 |
| ATOM | 761 | CD1 | ILE | 1 | 84 | -0.862 | 49.238 | 36.911 | 1.00 | 0.00 |
| ATOM | 762 | H | ILE | 1 | 84 | 0.585 | 51.890 | 37.073 | 1.00 | 0.00 |
| ATOM | 763 | N | CYS | 1 | 85 | -3.050 | 53.104 | 38.044 | 1.00 | 0.00 |
| ATOM | 764 | CA | CYS | 1 | 85 | -3.456 | 53.377 | 39.430 | 1.00 | 0.00 |
| ATOM | 765 | C | CYS | 1 | 85 | -3.946 | 52.219 | 40.300 | 1.00 | 0.00 |

FIG. 1Q

| ATOM | 766 | O   | CYS | 1 | 85 | -3.154 | 51.631 | 40.977 | 1.00 | 0.00 |
| ATOM | 767 | CB  | CYS | 1 | 85 | -4.494 | 54.530 | 39.493 | 1.00 | 0.00 |
| ATOM | 768 | SG  | CYS | 1 | 85 | -3.719 | 56.051 | 38.899 | 1.00 | 0.00 |
| ATOM | 769 | H   | CYS | 1 | 85 | -3.555 | 53.567 | 37.316 | 1.00 | 0.00 |
| ATOM | 770 | N   | LEU | 1 | 86 | -5.235 | 51.872 | 40.178 | 1.00 | 0.00 |
| ATOM | 771 | CA  | LEU | 1 | 86 | -5.836 | 50.570 | 40.669 | 1.00 | 0.00 |
| ATOM | 772 | C   | LEU | 1 | 86 | -5.198 | 49.716 | 41.738 | 1.00 | 0.00 |
| ATOM | 773 | O   | LEU | 1 | 86 | -4.347 | 48.854 | 41.497 | 1.00 | 0.00 |
| ATOM | 774 | CB  | LEU | 1 | 86 | -6.178 | 49.687 | 39.435 | 1.00 | 0.00 |
| ATOM | 775 | CG  | LEU | 1 | 86 | -5.062 | 49.502 | 38.390 | 1.00 | 0.00 |
| ATOM | 776 | CD1 | LEU | 1 | 86 | -4.529 | 48.072 | 38.326 | 1.00 | 0.00 |
| ATOM | 777 | CD2 | LEU | 1 | 86 | -5.429 | 49.889 | 36.984 | 1.00 | 0.00 |
| ATOM | 778 | H   | LEU | 1 | 86 | -5.624 | 52.275 | 39.349 | 1.00 | 0.00 |
| ATOM | 779 | N   | ASP | 1 | 87 | -5.646 | 49.975 | 42.971 | 1.00 | 0.00 |
| ATOM | 780 | CA  | ASP | 1 | 87 | -5.525 | 49.028 | 44.088 | 1.00 | 0.00 |
| ATOM | 781 | C   | ASP | 1 | 87 | -4.109 | 48.504 | 44.263 | 1.00 | 0.00 |
| ATOM | 782 | O   | ASP | 1 | 87 | -3.363 | 49.082 | 45.066 | 1.00 | 0.00 |
| ATOM | 783 | CB  | ASP | 1 | 87 | -6.527 | 47.893 | 43.964 | 1.00 | 0.00 |
| ATOM | 784 | CG  | ASP | 1 | 87 | -6.431 | 46.788 | 45.001 | 1.00 | 0.00 |
| ATOM | 785 | OD1 | ASP | 1 | 87 | -6.114 | 47.067 | 46.154 | 1.00 | 0.00 |
| ATOM | 786 | OD2 | ASP | 1 | 87 | -6.744 | 45.628 | 44.680 | 1.00 | 0.00 |
| ATOM | 787 | H   | ASP | 1 | 87 | -6.293 | 50.722 | 43.123 | 1.00 | 0.00 |
| ATOM | 788 | N   | ILE | 1 | 88 | -3.811 | 47.376 | 43.540 | 1.00 | 0.00 |
| ATOM | 789 | CA  | ILE | 1 | 88 | -2.601 | 46.573 | 43.737 | 1.00 | 0.00 |
| ATOM | 790 | C   | ILE | 1 | 88 | -1.296 | 47.330 | 43.558 | 1.00 | 0.00 |
| ATOM | 791 | O   | ILE | 1 | 88 | -0.504 | 47.300 | 44.477 | 1.00 | 0.00 |
| ATOM | 792 | CB  | ILE | 1 | 88 | -2.715 | 45.322 | 42.836 | 1.00 | 0.00 |
| ATOM | 793 | CG1 | ILE | 1 | 88 | -2.555 | 45.432 | 41.275 | 1.00 | 0.00 |
| ATOM | 794 | CG2 | ILE | 1 | 88 | -4.113 | 44.647 | 42.978 | 1.00 | 0.00 |
| ATOM | 795 | CD1 | ILE | 1 | 88 | -2.522 | 44.051 | 40.547 | 1.00 | 0.00 |
| ATOM | 796 | H   | ILE | 1 | 88 | -4.311 | 47.348 | 42.674 | 1.00 | 0.00 |
| ATOM | 797 | N   | LEU | 1 | 89 | -1.124 | 48.012 | 42.405 | 1.00 | 0.00 |
| ATOM | 798 | CA  | LEU | 1 | 89 | -0.037 | 48.937 | 42.290 | 1.00 | 0.00 |
| ATOM | 799 | C   | LEU | 1 | 89 | -0.284 | 50.287 | 42.862 | 1.00 | 0.00 |
| ATOM | 800 | O   | LEU | 1 | 89 | -0.472 | 51.269 | 42.113 | 1.00 | 0.00 |
| ATOM | 801 | CB  | LEU | 1 | 89 | -0.443 | 49.094 | 40.838 | 1.00 | 0.00 |
| ATOM | 802 | CG  | LEU | 1 | 89 | 1.420  | 48.043 | 40.288 | 1.00 | 0.00 |
| ATOM | 803 | CD1 | LEU | 1 | 89 | 2.636  | 47.915 | 41.237 | 1.00 | 0.00 |
| ATOM | 804 | CD2 | LEU | 1 | 89 | 0.675  | 46.722 | 39.962 | 1.00 | 0.00 |
| ATOM | 805 | H   | LEU | 1 | 89 | -1.933 | 48.260 | 41.873 | 1.00 | 0.00 |
| ATOM | 806 | N   | ARG | 1 | 90 | -0.418 | 50.340 | 44.189 | 1.00 | 0.00 |
| ATOM | 807 | CA  | ARG | 1 | 90 | -0.026 | 51.384 | 45.135 | 1.00 | 0.00 |
| ATOM | 808 | C   | ARG | 1 | 90 | -0.473 | 51.119 | 46.614 | 1.00 | 0.00 |
| ATOM | 809 | O   | ARG | 1 | 90 | 0.338  | 50.878 | 47.480 | 1.00 | 0.00 |
| ATOM | 810 | CB  | ARG | 1 | 90 | -0.202 | 52.892 | 44.694 | 1.00 | 0.00 |

FIG. 1R

| | | | | | | | | | |
|---|---|---|---|---|---|---|---|---|---|
| ATOM | 811 | CG | ARG | 1 | 90 | -1.614 | 53.327 | 44.386 | 1.00 0.00 |
| ATOM | 812 | CD | ARG | 1 | 90 | -1.771 | 54.741 | 43.914 | 1.00 0.00 |
| ATOM | 813 | NE | ARG | 1 | 90 | -3.140 | 55.176 | 43.940 | 1.00 0.00 |
| ATOM | 814 | CZ | ARG | 1 | 90 | -3.469 | 56.121 | 43.129 | 1.00 0.00 |
| ATOM | 815 | NH1 | ARG | 1 | 90 | -4.669 | 56.743 | 43.266 | 1.00 0.00 |
| ATOM | 816 | NH2 | ARG | 1 | 90 | -2.772 | 56.487 | 42.010 | 1.00 0.00 |
| ATOM | 817 | H | ARG | 1 | 90 | -0.600 | 49.477 | 44.659 | 1.00 0.00 |
| ATOM | 818 | HE | ARG | 1 | 90 | -3.649 | 54.776 | 44.702 | 1.00 0.00 |
| ATOM | 819 | 1HH1 | ARG | 1 | 90 | -4.832 | 57.565 | 42.721 | 1.00 0.00 |
| ATOM | 820 | 2HH1 | ARG | 1 | 90 | -5.240 | 56.526 | 44.058 | 1.00 0.00 |
| ATOM | 821 | 1HH2 | ARG | 1 | 90 | -3.123 | 57.247 | 41.464 | 1.00 0.00 |
| ATOM | 822 | 2HH2 | ARG | 1 | 90 | -1.861 | 56.172 | 41.743 | 1.00 0.00 |
| ATOM | 823 | N | SER | 1 | 91 | -1.779 | 51.132 | 46.880 | 1.00 0.00 |
| ATOM | 824 | CA | SER | 1 | 91 | -2.246 | 50.840 | 48.231 | 1.00 0.00 |
| ATOM | 825 | C | SER | 1 | 91 | -2.039 | 49.496 | 48.865 | 1.00 0.00 |
| ATOM | 826 | O | SER | 1 | 91 | -2.155 | 49.290 | 50.084 | 1.00 0.00 |
| ATOM | 827 | CB | SER | 1 | 91 | -3.706 | 51.221 | 48.212 | 1.00 0.00 |
| ATOM | 828 | OG | SER | 1 | 91 | -3.945 | 52.494 | 47.464 | 1.00 0.00 |
| ATOM | 829 | H | SER | 1 | 91 | -2.454 | 51.157 | 46.142 | 1.00 0.00 |
| ATOM | 830 | HG | SER | 1 | 91 | -4.217 | 53.128 | 48.114 | 1.00 0.00 |
| ATOM | 831 | N | GLN | 1 | 92 | -1.695 | 48.524 | 47.995 | 1.00 0.00 |
| ATOM | 832 | CA | GLN | 1 | 92 | -1.634 | 47.187 | 48.509 | 1.00 0.00 |
| ATOM | 833 | C | GLN | 1 | 92 | -0.236 | 46.696 | 48.873 | 1.00 0.00 |
| ATOM | 834 | O | GLN | 1 | 92 | 0.410 | 46.150 | 47.994 | 1.00 0.00 |
| ATOM | 835 | CB | GLN | 1 | 92 | -2.345 | 46.228 | 47.634 | 1.00 0.00 |
| ATOM | 836 | CG | GLN | 1 | 92 | -2.649 | 44.788 | 48.100 | 1.00 0.00 |
| ATOM | 837 | CD | GLN | 1 | 92 | -3.525 | 44.132 | 47.065 | 1.00 0.00 |
| ATOM | 838 | OE1 | GLN | 1 | 92 | -3.152 | 43.262 | 46.300 | 1.00 0.00 |
| ATOM | 839 | NE2 | GLN | 1 | 92 | -4.730 | 44.710 | 46.949 | 1.00 0.00 |
| ATOM | 840 | H | GLN | 1 | 92 | -1.391 | 48.636 | 47.050 | 1.00 0.00 |
| ATOM | 841 | 1HE2 | GLN | 1 | 92 | -5.066 | 45.404 | 47.585 | 1.00 0.00 |
| ATOM | 842 | 2HE2 | GLN | 1 | 92 | -5.388 | 44.626 | 46.200 | 1.00 0.00 |
| ATOM | 843 | N | TRP | 1 | 93 | 0.004 | 46.795 | 50.177 | 1.00 0.00 |
| ATOM | 844 | CA | TRP | 1 | 93 | 1.331 | 46.337 | 50.664 | 1.00 0.00 |
| ATOM | 845 | C | TRP | 1 | 93 | 1.379 | 44.847 | 50.786 | 1.00 0.00 |
| ATOM | 846 | O | TRP | 1 | 93 | 1.413 | 44.260 | 51.903 | 1.00 0.00 |
| ATOM | 847 | CB | TRP | 1 | 93 | 1.747 | 47.092 | 51.956 | 1.00 0.00 |
| ATOM | 848 | CG | TRP | 1 | 93 | 3.202 | 46.849 | 52.298 | 1.00 0.00 |
| ATOM | 849 | CD1 | TRP | 1 | 93 | 3.639 | 46.472 | 53.600 | 1.00 0.00 |
| ATOM | 850 | CD2 | TRP | 1 | 93 | 4.403 | 46.830 | 51.462 | 1.00 0.00 |
| ATOM | 851 | NE1 | TRP | 1 | 93 | 4.988 | 46.241 | 53.629 | 1.00 0.00 |
| ATOM | 852 | CE2 | TRP | 1 | 93 | 5.507 | 46.452 | 52349 | 1.00 0.00 |
| ATOM | 853 | CE3 | TRP | 1 | 93 | 4.729 | 47.037 | 50.081 | 1.00 0.00 |
| ATOM | 854 | CZ2 | TRP | 1 | 93 | 6.827 | 46.319 | 51.969 | 1.00 0.00 |
| ATOM | 855 | CZ3 | TRP | 1 | 93 | 6.089 | 46.803 | 49.652 | 1.00 0.00 |

FIG. 1S

| ATOM | 856 | CH2 | GLN | 1 | 93 | 7.087 | 46.544 | 50.614 | 1.00 | 0.00 |
| ATOM | 857 | H | TRP | 1 | 93 | -0.649 | 47.178 | 50.831 | 1.00 | 0.00 |
| ATOM | 858 | 1HE | TRP | 1 | 93 | 5.547 | 46.033 | 54.407 | 1.00 | 0.00 |
| ATOM | 859 | N | SER | 1 | 94 | 1.490 | 44.234 | 49.587 | 1.00 | 0.00 |
| ATOM | 860 | CA | SER | 1 | 94 | 1.669 | 42.774 | 49.495 | 1.00 | 0.00 |
| ATOM | 861 | C | SER | 1 | 94 | 2.312 | 42.502 | 48.181 | 1.00 | 0.00 |
| ATOM | 862 | O | SER | 1 | 94 | 1.754 | 42.899 | 47.152 | 1.00 | 0.00 |
| ATOM | 863 | CB | SER | 1 | 94 | 0.262 | 42.108 | 49.593 | 1.00 | 0.00 |
| ATOM | 864 | OG | SER | 1 | 94 | -0.412 | 42.387 | 48.358 | 1.00 | 0.00 |
| ATOM | 865 | H | SER | 1 | 94 | 1.514 | 44.787 | 48.753 | 1.00 | 0.00 |
| ATOM | 866 | HG | SER | 1 | 94 | -0.092 | 43.219 | 48.036 | 1.00 | 0.00 |
| ATOM | 867 | N | PRO | 1 | 95 | 3.435 | 41.722 | 48.161 | 1.00 | 0.00 |
| ATOM | 868 | CA | PRO | 1 | 95 | 3.724 | 41.167 | 46.814 | 1.00 | 0.00 |
| ATOM | 869 | C | PRO | 1 | 95 | 2.942 | 39.914 | 46.539 | 1.00 | 0.00 |
| ATOM | 870 | O | PRO | 1 | 95 | 3.473 | 38.913 | 46.075 | 1.00 | 0.00 |
| ATOM | 871 | CB | PRO | 1 | 95 | 5.243 | 40.974 | 46.986 | 1.00 | 0.00 |
| ATOM | 872 | CG | PRO | 1 | 95 | 5.541 | 40.527 | 48.437 | 1.00 | 0.00 |
| ATOM | 873 | CD | PRO | 1 | 95 | 4.449 | 41.477 | 49.162 | 1.00 | 0.00 |
| ATOM | 874 | N | ALA | 1 | 96 | 1.631 | 39.963 | 46.751 | 1.00 | 0.00 |
| ATOM | 875 | CA | ALA | 1 | 96 | 0.742 | 38.929 | 46.296 | 1.00 | 0.00 |
| ATOM | 876 | C | ALA | 1 | 96 | 0.008 | 39.214 | 45.017 | 1.00 | 0.00 |
| ATOM | 877 | O | ALA | 1 | 96 | -1.215 | 39.302 | 44.930 | 1.00 | 0.00 |
| ATOM | 878 | CB | ALA | 1 | 96 | -0.170 | 38.368 | 47.410 | 1.00 | 0.00 |
| ATOM | 879 | H | ALA | 1 | 96 | 1.330 | 40.893 | 46.964 | 1.00 | 0.00 |
| ATOM | 880 | N | LEU | 1 | 97 | 0.914 | 39.429 | 44.050 | 1.00 | 0.00 |
| ATOM | 881 | CA | LEU | 1 | 97 | -.494 | 39.917 | 42.699 | 1.00 | 0.00 |
| ATOM | 882 | C | LEU | 1 | 97 | 0.773 | 38.935 | 41.618 | 1.00 | 0.00 |
| ATOM | 883 | O | LEU | 1 | 97 | 1.827 | 38.934 | 40.926 | 1.00 | 0.00 |
| ATOM | 884 | CB | LEU | 1 | 97 | 1.151 | 41.281 | 42.350 | 1.00 | 0.00 |
| ATOM | 885 | CG | LEU | 1 | 97 | 1.297 | 42.490 | 43.278 | 1.00 | 0.00 |
| ATOM | 886 | CD1 | LEU | 1 | 97 | 1.815 | 43.697 | 42.585 | 1.00 | 0.00 |
| ATOM | 887 | CD2 | LEU | 1 | 97 | -0.071 | 42.794 | 44.045 | 1.00 | 0.00 |
| ATOM | 888 | H | LEU | 1 | 97 | 1.874 | 39.401 | 44.330 | 1.00 | 0.00 |
| ATOM | 889 | N | THR | 1 | 98 | -0.195 | 38.052 | 41.512 | 1.00 | 0.00 |
| ATOM | 890 | CA | THR | 1 | 98 | -0.030 | 37.084 | 40.473 | 1.00 | 0.00 |
| ATOM | 891 | C | THR | 1 | 98 | -0.990 | 37.340 | 39.335 | 1.00 | 0.00 |
| ATOM | 892 | O | THR | 1 | 98 | -2.041 | 37.953 | 39.480 | 1.00 | 0.00 |
| ATOM | 893 | CB | THR | 1 | 98 | -0.163 | 35.572 | 41.034 | 1.00 | 0.00 |
| ATOM | 894 | OG1 | THR | 1 | 98 | 0.762 | 34.750 | 40.274 | 1.00 | 0.00 |
| ATOM | 895 | CG2 | THR | 1 | 98 | -1.504 | 35.029 | 41.173 | 1.00 | 0.00 |
| ATOM | 896 | H | THR | 1 | 98 | -1.027 | 38.138 | 42.060 | 1.00 | 0.00 |
| ATOM | 897 | 1HG | THR | 1 | 98 | 0.266 | 34.090 | 39.808 | 1.00 | 0.00 |
| ATOM | 898 | N | ILE | 1 | 99 | -0.363 | 37.052 | 38.234 | 1.00 | 0.00 |
| ATOM | 899 | CA | ILE | 1 | 99 | -0.894 | 37.527 | 37.020 | 1.00 | 0.00 |
| ATOM | 900 | C | ILE | 1 | 99 | -2.380 | 37.698 | 36.697 | 1.00 | 0.00 |

FIG. 1T

| ATOM | 901 | O   | ILE | 1 | 99  | -2.724 | 38.764 | 36.246 | 1.00 | 0.00 |
|------|-----|-----|-----|---|-----|--------|--------|--------|------|------|
| ATOM | 902 | CB  | ILE | 1 | 99  | -0.082 | 37.024 | 35.825 | 1.00 | 0.00 |
| ATOM | 903 | CG1 | ILE | 1 | 99  | -0.308 | 37.613 | 34.450 | 1.00 | 0.00 |
| ATOM | 904 | CG2 | ILE | 1 | 99  | -0.305 | 35.483 | 35.600 | 1.00 | 0.00 |
| ATOM | 905 | CD1 | ILE | 1 | 99  | 0.494  | 38.884 | 34.205 | 1.00 | 0.00 |
| ATOM | 906 | H   | ILE | 1 | 99  | 0.345  | 36.354 | 38.343 | 1.00 | 0.00 |
| ATOM | 907 | N   | SER | 1 | 100 | -3.270 | 36.706 | 36.849 | 1.00 | 0.00 |
| ATOM | 908 | CA  | SER | 1 | 100 | -4.724 | 36.906 | 36.744 | 1.00 | 0.00 |
| ATOM | 909 | C   | SER | 1 | 100 | -5.204 | 38.211 | 37.355 | 1.00 | 0.00 |
| ATOM | 910 | O   | SER | 1 | 100 | -5.742 | 39.096 | 36.685 | 1.00 | 0.00 |
| ATOM | 911 | CB  | SER | 1 | 100 | -5.415 | 35.624 | 37.222 | 1.00 | 0.00 |
| ATOM | 912 | OG  | SER | 1 | 100 | -4.736 | 35.233 | 38.459 | 1.00 | 0.00 |
| ATOM | 913 | H   | SER | 1 | 100 | -2.868 | 35.938 | 37.348 | 1.00 | 0.00 |
| ATOM | 914 | HG  | SER | 1 | 100 | -5.204 | 34.561 | 38.936 | 1.00 | 0.00 |
| ATOM | 915 | N   | LYS | 1 | 101 | -4.768 | 38.359 | 38.639 | 1.00 | 0.00 |
| ATOM | 916 | CA  | LYS | 1 | 101 | -5.113 | 39.564 | 39.413 | 1.00 | 0.00 |
| ATOM | 917 | C   | LYS | 1 | 101 | -4.402 | 40.879 | 39.024 | 1.00 | 0.00 |
| ATOM | 918 | O   | LYS | 1 | 101 | -4.754 | 41.953 | 39.522 | 1.00 | 0.00 |
| ATOM | 919 | CB  | LYS | 1 | 101 | -4.912 | 39.238 | 40.866 | 1.00 | 0.00 |
| ATOM | 920 | CG  | LYS | 1 | 101 | -5.274 | 40.259 | 42.002 | 1.00 | 0.00 |
| ATOM | 921 | CD  | LYS | 1 | 101 | -3.984 | 40.688 | 42.680 | 1.00 | 0.00 |
| ATOM | 922 | CE  | LYS | 1 | 101 | -4.365 | 40.819 | 44.136 | 1.00 | 0.00 |
| ATOM | 923 | NZ  | LYS | 1 | 101 | -3.203 | 41.272 | 44.871 | 1.00 | 0.00 |
| ATOM | 924 | H   | LYS | 1 | 101 | -4.189 | 37.616 | 38.973 | 1.00 | 0.00 |
| ATOM | 925 | 1HZ | LYS | 1 | 101 | -2.880 | 42.183 | 44.487 | 1.00 | 0.00 |
| ATOM | 926 | 2HZ | LYS | 1 | 101 | -3.296 | 41.474 | 45.887 | 1.00 | 0.00 |
| ATOM | 927 | 3HZ | LYS | 1 | 101 | -2.424 | 40.594 | 44.747 | 1.00 | 0.00 |
| ATOM | 928 | N   | VAL | 1 | 102 | -3.475 | 40.750 | 38.077 | 1.00 | 0.00 |
| ATOM | 929 | CA  | VAL | 1 | 102 | -2.860 | 41.961 | 37.557 | 1.00 | 0.00 |
| ATOM | 930 | C   | VAL | 1 | 102 | -3.510 | 42.388 | 36.239 | 1.00 | 0.00 |
| ATOM | 931 | O   | VAL | 1 | 102 | -3.849 | 43.567 | 35.957 | 1.00 | 0.00 |
| ATOM | 932 | CB  | VAL | 1 | 102 | -1.348 | 41.798 | 37.381 | 1.00 | 0.00 |
| ATOM | 933 | CG1 | VAL | 1 | 102 | -0.665 | 43.196 | 37.067 | 1.00 | 0.00 |
| ATOM | 934 | CG2 | VAL | 1 | 102 | -0.609 | 41.199 | 38.633 | 1.00 | 0.00 |
| ATOM | 935 | H   | VAL | 1 | 102 | -3.259 | 39.834 | 37.736 | 1.00 | 0.00 |
| ATOM | 936 | N   | LEU | 1 | 103 | -3.744 | 41.406 | 35.354 | 1.00 | 0.00 |
| ATOM | 937 | CA  | LEU | 1 | 103 | -4.192 | 41.772 | 34.076 | 1.00 | 0.00 |
| ATOM | 938 | C   | LEU | 1 | 103 | -5.690 | 42.032 | 34.111 | 1.00 | 0.00 |
| ATOM | 939 | O   | LEU | 1 | 103 | -6.211 | 42.990 | 33.448 | 1.00 | 0.00 |
| ATOM | 940 | CB  | LEU | 1 | 103 | -3.726 | 40.740 | 32.995 | 1.00 | 0.00 |
| ATOM | 941 | CG  | LEU | 1 | 103 | -2.507 | 41.346 | 32.267 | 1.00 | 0.00 |
| ATOM | 942 | CD1 | LEU | 1 | 103 | -1.795 | 40.254 | 31.459 | 1.00 | 0.00 |
| ATOM | 943 | CD2 | LEU | 1 | 103 | -2.903 | 42.587 | 31.541 | 1.00 | 0.00 |
| ATOM | 944 | H   | LEU | 1 | 103 | -3.911 | 40.514 | 35.773 | 1.00 | 0.00 |
| ATOM | 945 | N   | LEU | 1 | 104 | -6.424 | 41.145 | 34.856 | 1.00 | 0.00 |

FIG. 1U

| ATOM | 946 | CA  | LEU | 1 | 104 | -7.810  | 41.575  | 35.127 | 1.00 | 0.00 |
| ATOM | 947 | C   | LEU | 1 | 104 | -7.855  | 42.961  | 35.724 | 1.00 | 0.00 |
| ATOM | 948 | O   | LEU | 1 | 104 | -8.500  | 43.819  | 35.130 | 1.00 | 0.00 |
| ATOM | 949 | CB  | LEU | 1 | 104 | -8.506  | 40.520  | 35.983 | 1.00 | 0.00 |
| ATOM | 950 | CG  | LEU | 1 | 104 | -9.953  | 40.895  | 36.094 | 1.00 | 0.00 |
| ATOM | 951 | CD1 | LEU | 1 | 104 | -10.722 | 40.812  | 34.846 | 1.00 | 0.00 |
| ATOM | 952 | CD2 | LEU | 1 | 104 | -10.702 | 40.028  | 37.125 | 1.00 | 0.00 |
| ATOM | 953 | H   | LEU | 1 | 104 | -6.131  | 40.287  | 35.278 | 1.00 | 0.00 |
| ATOM | 954 | N   | SER | 1 | 105 | -7.118  | 43.132  | 36.833 | 1.00 | 0.00 |
| ATOM | 955 | CA  | SER | 1 | 105 | -7.386  | 44.418  | 37.550 | 1.00 | 0.00 |
| ATOM | 956 | C   | SER | 1 | 105 | -6.973  | 45.720  | 36.778 | 1.00 | 0.00 |
| ATOM | 957 | O   | SER | 1 | 105 | -7.602  | 46.7373 | 36.986 | 1.00 | 0.00 |
| ATOM | 958 | CB  | SER | 1 | 105 | -6.761  | 44.419  | 38.909 | 1.00 | 0.00 |
| ATOM | 959 | OG  | SER | 1 | 105 | -7.437  | 43.369  | 39.676 | 1.00 | 0.00 |
| ATOM | 960 | H   | SER | 1 | 105 | -6.570  | 42.378  | 37.194 | 1.00 | 0.00 |
| ATOM | 961 | HG  | SER | 1 | 105 | -7.053  | 42.532  | 39.449 | 1.00 | 0.00 |
| ATOM | 962 | N   | ILE | 1 | 106 | -5.953  | 45.587  | 35.942 | 1.00 | 0.00 |
| ATOM | 963 | CA  | ILE | 1 | 106 | -5.565  | 46.649  | 34.950 | 1.00 | 0.00 |
| ATOM | 964 | C   | ILE | 1 | 106 | -6.694  | 46.937  | 33.906 | 1.00 | 0.00 |
| ATOM | 965 | O   | ILE | 1 | 106 | -7.039  | 48.044  | 33.459 | 1.00 | 0.00 |
| ATOM | 966 | CB  | ILE | 1 | 106 | -4.240  | 46.330  | 34.320 | 1.00 | 0.00 |
| ATOM | 967 | CG1 | ILE | 1 | 106 | -3.013  | 46.371  | 35.246 | 1.00 | 0.00 |
| ATOM | 968 | CG2 | ILE | 1 | 106 | -3.926  | 47.235  | 33.094 | 1.00 | 0.00 |
| ATOM | 969 | CD1 | ILE | 1 | 106 | -1.919  | 45.558  | 34.629 | 1.00 | 0.00 |
| ATOM | 970 | H   | ILE | 1 | 106 | -5.752  | 44.610  | 35.861 | 1.00 | 0.00 |
| ATOM | 971 | N   | CYS | 1 | 107 | -7.274  | 45.781  | 33.409 | 1.00 | 0.00 |
| ATOM | 972 | CA  | CYS | 1 | 107 | -8.520  | 45.970  | 32.586 | 1.00 | 0.00 |
| ATOM | 973 | C   | CYS | 1 | 107 | -9.757  | 46.433  | 33.338 | 1.00 | 0.00 |
| ATOM | 974 | O   | CYS | 1 | 107 | -10.600 | 47.145  | 32.731 | 1.00 | 0.00 |
| ATOM | 975 | CB  | CYS | 1 | 107 | -8.856  | 44.670  | 31.741 | 1.00 | 0.00 |
| ATOM | 976 | SG  | CYS | 1 | 107 | -7.429  | 44.342  | 30.720 | 1.00 | 0.00 |
| ATOM | 977 | H   | CYS | 1 | 107 | -7.117  | 44.941  | 33.928 | 1.00 | 0.00 |
| ATOM | 978 | N   | SER | 1 | 108 | -9.830  | 46.108  | 34.695 | 1.00 | 0.00 |
| ATOM | 979 | CA  | SER | 1 | 108 | -11.060 | 46.479  | 35.328 | 1.00 | 0.00 |
| ATOM | 980 | C   | SER | 1 | 108 | -11.219 | 47.952  | 35.369 | 1.00 | 0.00 |
| ATOM | 981 | O   | SER | 1 | 108 | -12.337 | 48.405  | 35.150 | 1.00 | 0.00 |
| ATOM | 982 | CB  | SER | 1 | 108 | -11.152 | 45.799  | 36.770 | 1.00 | 0.00 |
| ATOM | 983 | OG  | SER | 1 | 108 | -11.173 | 44.322  | 36.587 | 1.00 | 0.00 |
| ATOM | 984 | H   | SER | 1 | 108 | -9.241  | 45.357  | 34.991 | 1.00 | 0.00 |
| ATOM | 985 | HG  | SER | 1 | 108 | -11.732 | 44.168  | 35.837 | 1.00 | 0.00 |
| ATOM | 986 | N   | LEU | 1 | 109 | -10.155 | 48.631  | 35.780 | 1.00 | 0.00 |
| ATOM | 987 | CA  | LEU | 1 | 109 | -10.220 | 50.104  | 35.653 | 1.00 | 0.00 |
| ATOM | 988 | C   | LEU | 1 | 109 | -9.817  | 50.687  | 34.332 | 1.00 | 0.00 |
| ATOM | 989 | O   | LEU | 1 | 109 | -9.444  | 51.821  | 34.154 | 1.00 | 0.00 |
| ATOM | 990 | CB  | LEU | 1 | 109 | -9.558  | 50.849  | 36.830 | 1.00 | 0.00 |

FIG. 1V

| ATOM | 991 | CG | LEU | 1 | 109 | -10.330 | 50.611 | 38.192 | 1.00 | 0.00 |
| ATOM | 992 | CD1 | LEU | 1 | 109 | -9.530 | 51.170 | 39.297 | 1.00 | 0.00 |
| ATOM | 993 | CD2 | LEU | 1 | 109 | -11.727 | 51.119 | 38.162 | 1.00 | 0.00 |
| ATOM | 994 | H | LEU | 1 | 109 | -9.232 | 48.266 | 35.900 | 1.00 | 0.00 |
| ATOM | 995 | N | LEU | 1 | 110 | -9.934 | 49.766 | 33.374 | 1.00 | 0.00 |
| ATOM | 996 | CA | LEU | 1 | 110 | -10.049 | 50.216 | 32.023 | 1.00 | 0.00 |
| ATOM | 997 | C | LEU | 1 | 110 | -11.371 | 49.745 | 31.298 | 1.00 | 0.00 |
| ATOM | 998 | O | LEU | 1 | 110 | -11.455 | 49.615 | 30.102 | 1.00 | 0.00 |
| ATOM | 999 | CB | LEU | 1 | 110 | -8.751 | 49.816 | 31.312 | 1.00 | 0.00 |
| ATOM | 1000 | CG | LEU | 1 | 110 | -7.942 | 50.875 | 30.483 | 1.00 | 0.00 |
| ATOM | 1001 | CD1 | LEU | 1 | 110 | -7.368 | 51.879 | 31.470 | 1.00 | 0.00 |
| ATOM | 1002 | CD2 | LEU | 1 | 110 | -6.829 | 50.314 | 29.656 | 1.00 | 0.00 |
| ATOM | 1003 | H | LEU | 1 | 110 | -10.041 | 48.784 | 33.533 | 1.00 | 0.00 |
| ATOM | 1004 | N | CYS | 1 | 111 | -12.308 | 49.338 | 32.152 | 1.00 | 0.00 |
| ATOM | 1005 | CA | CYS | 1 | 111 | -13.548 | 48.999 | 31.551 | 1.00 | 0.00 |
| ATOM | 1006 | C | CYS | 1 | 111 | -14.398 | 50.255 | 31.331 | 1.00 | 0.00 |
| ATOM | 1007 | O | CYS | 1 | 111 | -14.130 | 50.937 | 30.370 | 1.00 | 0.00 |
| ATOM | 1008 | CB | CYS | 1 | 111 | -14.416 | 48.026 | 32.492 | 1.00 | 0.00 |
| ATOM | 1009 | SG | CYS | 1 | 111 | -14.116 | 46.278 | 32.379 | 1.00 | 0.00 |
| ATOM | 1010 | H | CYS | 1 | 111 | -12.026 | 49.328 | 33.112 | 1.00 | 0.00 |
| ATOM | 1011 | N | ASP | 1 | 112 | -15.364 | 50.587 | 32.178 | 1.00 | 0.00 |
| ATOM | 1012 | CA | ASP | 1 | 112 | -15.593 | 51.987 | 32.403 | 1.00 | 0.00 |
| ATOM | 1013 | C | ASP | 1 | 112 | -14.518 | 52.650 | 33.331 | 1.00 | 0.00 |
| ATOM | 1014 | O | ASP | 1 | 112 | -14.507 | 52.386 | 34.545 | 1.00 | 0.00 |
| ATOM | 1015 | CB | ASP | 1 | 112 | -17.121 | 52.182 | 32.807 | 1.00 | 0.00 |
| ATOM | 1016 | CG | ASP | 1 | 112 | -17.888 | 52.937 | 31.766 | 1.00 | 0.00 |
| ATOM | 1017 | OD1 | ASP | 1 | 112 | -19.113 | 52.989 | 31.785 | 1.00 | 0.00 |
| ATOM | 1018 | OD2 | ASP | 1 | 112 | -17.199 | 53.537 | 30.912 | 1.00 | 0.00 |
| ATOM | 1019 | H | ASP | 1 | 112 | -15.765 | 49.992 | 32.874 | 1.00 | 0.00 |
| ATOM | 1020 | N | PRO | 1 | 113 | -13.531 | 53.288 | 32.615 | 1.00 | 0.00 |
| ATOM | 1021 | CA | PRO | 1 | 113 | -12.199 | 53.281 | 33.187 | 1.00 | 0.00 |
| ATOM | 1022 | C | PRO | 1 | 113 | -12.012 | 54.384 | 34.243 | 1.00 | 0.00 |
| ATOM | 1023 | O | PRO | 1 | 113 | -12.637 | 55.445 | 34.025 | 1.00 | 0.00 |
| ATOM | 1024 | CB | PRO | 1 | 113 | -11.398 | 53.419 | 31.897 | 1.00 | 0.00 |
| ATOM | 1025 | CG | PRO | 1 | 113 | -12.171 | 54.275 | 30.881 | 1.00 | 0.00 |
| ATOM | 1026 | CD | PRO | 1 | 113 | -13.610 | 53.875 | 31.275 | 1.00 | 0.00 |
| ATOM | 1027 | N | ASN | 1 | 114 | -11.261 | 54.180 | 35.336 | 1.00 | 0.00 |
| ATOM | 1028 | CA | ASN | 1 | 114 | -11.182 | 55.245 | 36.355 | 1.00 | 0.00 |
| ATOM | 1029 | C | ASN1 | 1 | 114 | -10.597 | 56.637 | 35.865 | 1.00 | 0.00 |
| ATOM | 1030 | O | ASN | 1 | 114 | -9.378 | 56.803 | 35.714 | 1.00 | 0.00 |
| ATOM | 1031 | CB | ASN | 1 | 114 | -10.330 | 54.764 | 37.541 | 1.00 | 0.00 |
| ATOM | 1032 | CG | ASN | 1 | 114 | -10.137 | 55.772 | 38.647 | 1.00 | 0.00 |
| ATOM | 1033 | OD1 | ASN | 1 | 114 | -9.345 | 56.731 | 38.656 | 1.00 | 0.00 |
| ATOM | 1034 | ND2 | ASN | 1 | 114 | -10.980 | 55.677 | 39.678 | 1.00 | 0.00 |
| ATOM | 1035 | H | ASN | 1 | 114 | -10.615 | 53.417 | 35.332 | 1.00 | 0.00 |

FIG. 1W

| ATOM | 1036 | 1HD2 | ASN | 1 | 114 | -11.523 | 54.841 | 39.754 | 1.00 | 0.00 |
| ATOM | 1037 | 2HD2 | ASN | 1 | 114 | -11.318 | 56.332 | 40.354 | 1.00 | 0.00 |
| ATOM | 1038 | N | PRO | 1 | 115 | -11.568 | 57.547 | 35.930 | 1.00 | 0.00 |
| ATOM | 1039 | CA | PRO | 1 | 115 | -11.202 | 58.938 | 35.634 | 1.00 | 0.00 |
| ATOM | 1040 | C | PRO | 1 | 115 | -10.529 | 59.625 | 36.725 | 1.00 | 0.00 |
| ATOM | 1041 | O | PRO | 1 | 115 | -9.921 | 60.690 | 36.497 | 1.00 | 0.00 |
| ATOM | 1042 | CB | PRO | 1 | 115 | -12.673 | 59.470 | 35.330 | 1.00 | 0.00 |
| ATOM | 1043 | CG | PRO | 1 | 115 | -13.720 | 58.740 | 58.740 | 1.00 | 0.00 |
| ATOM | 1044 | CD | PRO | 1 | 115 | -12.975 | 57.417 | 36.159 | 1.00 | 0.00 |
| ATOM | 1045 | N | ASP | 1 | 116 | -10.763 | 59.056 | 37.948 | 1.00 | 0.00 |
| ATOM | 1046 | CA | ASP | 1 | 116 | -10.371 | .59.852 | 39.097 | 1.00 | 0.00 |
| ATOM | 1047 | C | ASP | 1 | 116 | -8.965 | 60.130 | 39.381 | 1.00 | 0.00 |
| ATOM | 1048 | O | ASP | 1 | 116 | -8.729 | 61.091 | 40.080 | 1.00 | 0.00 |
| ATOM | 1049 | CB | ASP | 1 | 116 | -11.112 | 59.169 | 40.210 | 1.00 | 0.00 |
| ATOM | 1050 | CG | ASP | 1 | 116 | -12.562 | 59.525 | 40.004 | 1.00 | 0.00 |
| ATOM | 1051 | OD1 | ASP | 1 | 116 | -12.897 | 60.693 | 40.229 | 1.00 | 0.00 |
| ATOM | 1052 | OD2 | ASP | 1 | 116 | -13.360 | 58.645 | 39.645 | 1.00 | 0.00 |
| ATOM | 1053 | H | ASP | 1 | 116 | -11.087 | 58.122 | 38.101 | 1.00 | 0.00 |
| ATOM | 1054 | N | ASP | 1 | 117 | -8.046 | 59.379 | 38.889 | 1.00 | 0.00 |
| ATOM | 1055 | CA | ASP | 1 | 117 | -6.667 | 59.696 | 39.115 | 1.00 | 0.00 |
| ATOM | 1056 | C | ASP | 1 | 117 | -6.000 | 60.362 | 37.956 | 1.00 | 0.00 |
| ATOM | 1057 | O | ASP | 1 | 117 | -5.912 | 59.906 | 36.817 | 1.00 | 0.00 |
| ATOM | 1058 | CB | ASP | 1 | 117 | -5.812 | 58.462 | 39.672 | 1.00 | 0.00 |
| ATOM | 1059 | CG | ASP | 1 | 117 | -5.071 | 58.862 | 40.969 | 1.00 | 0.00 |
| ATOM | 1060 | OD1 | ASP | 1 | 117 | -5.706 | 59.224 | 41.919 | 1.00 | 0.00 |
| ATOM | 1061 | OD2 | ASP | 1 | 117 | -3.839 | 58.861 | 40.982 | 1.00 | 0.00 |
| ATOM | 1062 | H | ASP | 1 | 117 | -8.297 | 58.676 | 38.225 | 1.00 | 0.00 |
| ATOM | 1063 | N | PRO | 1 | 118 | -5.510 | 61.616 | 38.265 | 1.00 | 0.00 |
| ATOM | 1064 | CA | PRO | 1 | 118 | -4.974 | 62.450 | 37.154 | 1.00 | 0.00 |
| ATOM | 1065 | C | PRO | 1 | 118 | -3.551 | 62.218 | 36.754 | 1.00 | 0.00 |
| ATOM | 1066 | O | PRO | 1 | 118 | -2.677 | 63.093 | 36.734 | 1.00 | 0.00 |
| ATOM | 1067 | CB | PRO | 1 | 118 | -5.149 | 63.800 | 37.805 | 1.00 | 0.00 |
| ATOM | 1068 | CG | PRO | 1 | 118 | -4.936 | 63.597 | 39.311 | 1.00 | 0.00 |
| ATOM | 1069 | CD | PRO | 1 | 118 | -5.578 | 62.267 | 39.561 | 1.00 | 0.00 |
| ATOM | 1070 | N | LEU | 1 | 119 | -3.257 | 60.906 | 36.463 | 1.00 | 0.00 |
| ATOM | 1071 | CA | LEU | 1 | 119 | -1.905 | 60.688 | 35.982 | 1.00 | 0.00 |
| ATOM | 1072 | C | LEU | 1 | 119 | -1.307 | 61.479 | 34.745 | 1.00 | 0.00 |
| ATOM | 1073 | O | LEU | 1 | 119 | -0.441 | 62.318 | 34.908 | 1.00 | 0.00 |
| ATOM | 1074 | CB | LEU | 1 | 119 | -1.456 | 59.254 | 35.930 | 1.00 | 0.00 |
| ATOM | 1075 | CG | LEU | 1 | 119 | -1.532 | 58.349 | 37.167 | 1.00 | 0.00 |
| ATOM | 1076 | CD1 | LEU | 1 | 119 | -0.912 | 56.912 | 36.972 | 1.00 | 0.00 |
| ATOM | 1077 | CD2 | LEU | 1 | 119 | -0.790 | 58.990 | 38.341 | 1.00 | 0.00 |
| ATOM | 1078 | H | LEU | 1 | 119 | -3.921 | 60.164 | 36.368 | 1.00 | 0.00 |
| ATOM | 1079 | N | VAL | 1 | 120 | -1.971 | 61.216 | 33.617 | 1.00 | 0.00 |
| ATOM | 1080 | CA | VAL | 1 | 120 | -1.959 | 62.209 | 32.538 | 1.00 | 0.00 |

FIG. 1X

| ATOM | 1081 | C | VAL | 1 | 120 | 3.329 | 62.894 | 32.518 | 1.00 | 0.00 |
|---|---|---|---|---|---|---|---|---|---|---|
| ATOM | 1082 | O | VAL | 1 | 120 | -4.360 | 62.293 | 32.613 | 1.00 | 0.00 |
| ATOM | 1083 | CB | VAL | 1 | 120 | -1.499 | 61.604 | 31.253 | 1.00 | 0.00 |
| ATOM | 1084 | CG1 | VAL | 1 | 120 | 0.035 | 61.659 | 31.162 | 1.00 | 0.00 |
| ATOM | 1085 | CG2 | VAL | 1 | 120 | -2.097 | 60.128 | 30.928 | 1.00 | 0.00 |
| ATOM | 1086 | H | VAL | 1 | 120 | -2.662 | 60.500 | 33.718 | 1.00 | 0.00 |
| ATOM | 1087 | N | PRO | 1 | 121 | -3.277 | 64.280 | 32.514 | 1.00 | 0.00 |
| ATOM | 1088 | CA | PRO | 1 | 121 | -4.501 | 65.112 | 32.553 | 1.00 | 0.00 |
| ATOM | 1089 | C | PRO | 1 | 121 | -5.183 | 65.158 | 31.223 | 1.00 | 0.00 |
| ATOM | 1090 | O | PRO | 1 | 121 | -5.005 | 66.142 | 30.408 | 1.00 | 0.00 |
| ATOM | 1091 | CB | PRO | 1 | 121 | -4.078 | 66.545 | 32.890 | 1.00 | 0.00 |
| ATOM | 1092 | CG | PRO | 1 | 121 | -2.593 | 66.574 | 32.951 | 1.00 | 0.00 |
| ATOM | 1093 | CD | PRO | 1 | 121 | -2.099 | 65.167 | 32.581 | 1.00 | 0.00 |
| ATOM | 1094 | N | GLU | 1 | 122 | -5.946 | 64.072 | 30.888 | 1.00 | 0.00 |
| ATOM | 1095 | CA | GLU | 1 | 122 | -6.357 | 64.028 | 29.506 | 1.00 | 0.00 |
| ATOM | 1096 | C | GLU | 1 | 122 | -7.790 | 64.010 | 29.329 | 1.00 | 0.00 |
| ATOM | 1097 | O | GLU | 1 | 122 | -8.390 | 64.999 | 28.991 | 1.00 | 0.00 |
| ATOM | 1098 | CB | GLU | 1 | 122 | -5.562 | 62.967 | 28.680 | 1.00 | 0.00 |
| ATOM | 1099 | CG | GLU | 1 | 122 | -5.508 | 61.536 | 29.110 | 1.00 | 0.00 |
| ATOM | 1100 | CD | GLU | 1 | 122 | -4.428 | 60.841 | 28.287 | 1.00 | 0.00 |
| ATOM | 1101 | OE1 | GLU | 1 | 122 | -4.533 | 59.662 | 28.084 | 1.00 | 0.00 |
| ATOM | 1102 | OE2 | GLU | 1 | 122 | -3.419 | 61.458 | 27.964 | 1.00 | 0.00 |
| ATOM | 1103 | H | GLU | 1 | 122 | -5.977 | 63.325 | 31.552 | 1.00 | 0.00 |
| ATOM | 1104 | N | ILE | 1 | 123 | -8.356 | 62.858 | 29.591 | 1.00 | 0.00 |
| ATOM | 1105 | CA | ILE | 1 | 123 | -9.817 | 62.884 | 29.471 | 1.00 | 0.00 |
| ATOM | 1106 | C | ILE | 1 | 123 | -10.637 | 62.807 | 30.714 | 1.00 | 0.00 |
| ATOM | 1107 | O | ILE | 1 | 123 | -11.593 | 63.548 | 30.791 | 1.00 | 0.00 |
| ATOM | 1108 | CB | ILE | 1 | 123 | -10.141 | 61.868 | 28.403 | 1.00 | 0.00 |
| ATOM | 1109 | CG1 | ILE | 1 | 123 | -11.547 | 62.072 | 27.779 | 1.00 | 0.00 |
| ATOM | 1110 | CG2 | ILE | 1 | 123 | -10.056 | 60.403 | 28.786 | 1.00 | 0.00 |
| ATOM | 1111 | CD1 | ILE | 1 | 123 | -11.761 | 63.221 | 26.711 | 1.00 | 0.00 |
| ATOM | 1112 | H | ILE | 1 | 123 | -7.841 | 62.124 | 30.034 | 1.00 | 0.00 |
| ATOM | 1113 | N | ALA | 1 | 124 | -10.185 | 61.872 | 31.630 | 1.00 | 0.00 |
| ATOM | 1114 | CA | ALA | 1 | 124 | -10.610 | 61.878 | 33.046 | 1.00 | 0.00 |
| ATOM | 1115 | C | ALA | 1 | 124 | -12.162 | 62.048 | 33.276 | 1.00 | 0.00 |
| ATOM | 1116 | O | ALA | 1 | 124 | -13.048 | 61.516 | 32.542 | 1.00 | 0.00 |
| ATOM | 1117 | CB | ALA | 1 | 124 | -9.795 | 63.009 | 33.690 | 1.00 | 0.00 |
| ATOM | 1118 | H | ALA | 1 | 124 | -9.351 | 61.353 | 31.444 | 1.00 | 0.00 |
| ATOM | 1119 | N | ARG | 1 | 125 | -12.434 | 62.735 | 34.377 | 1.00 | 0.00 |
| ATOM | 1120 | CA | ARG | 1 | 125 | -13.795 | 63.212 | 34.682 | 1.00 | 0.00 |
| ATOM | 1121 | C | ARG | 1 | 125 | -14.747 | 63.817 | 33.616 | 1.00 | 0.00 |
| ATOM | 1122 | O | ARG | 1 | 125 | -15.960 | 63.759 | 33.744 | 1.00 | 0.00 |
| ATOM | 1123 | CB | ARG | 1 | 125 | -13.769 | 64.204 | 35.773 | 1.00 | 0.00 |
| ATOM | 1124 | CG | ARG | 1 | 125 | -13.675 | 63.377 | 37.072 | 1.00 | 0.00 |
| ATOM | 1125 | CD | ARG | 1 | 125 | -14.972 | 62.537 | 37.191 | 1.00 | 0.00 |

FIG. 1Y

| | | | | | | | | | |
|---|---|---|---|---|---|---|---|---|---|
| ATOM | 1126 | NE | ARG | 1 | 125 | -14.854 | 61.500 | 38.232 | 1.00 | 0.00 |
| ATOM | 1127 | CZ | ARG | 1 | 125 | -15.861 | 60.967 | 38.847 | 1.00 | 0.00 |
| ATOM | 1128 | NH1 | ARG | 1 | 125 | -15.655 | 59.990 | 39.749 | 1.00 | 0.00 |
| ATOM | 1129 | NH2 | ARG | 1 | 125 | -17.122 | 61.349 | 38.534 | 1.00 | 0.00 |
| ATOM | 1130 | H | ARG | 1 | 125 | -11.855 | 63.259 | 35.001 | 1.00 | 0.00 |
| ATOM | 1131 | HE | ARG | 1 | 125 | -13.919 | 61.221 | 38.454 | 1.00 | 0.00 |
| ATOM | 1132 | 1HH1 | ARG | 1 | 125 | -16.416 | 59.493 | 40.167 | 1.00 | 0.00 |
| ATOM | 1133 | 2HH1 | ARG | 1 | 125 | -14.748 | 59.735 | 40.086 | 1.00 | 0.00 |
| ATOM | 1134 | 1HH2 | ARG | 1 | 125 | -17.856 | 61.089 | 39.162 | 1.00 | 0.00 |
| ATOM | 1135 | 2HH2 | ARG | 1 | 125 | -17.314 | 61.932 | 37.745 | 1.00 | 0.00 |
| ATOM | 1136 | N | ILE | 1 | 126 | -14.127 | 64.432 | 32.608 | 1.00 | 0.00 |
| ATOM | 1137 | CA | ILE | 1 | 126 | -14.788 | 64.980 | 31.466 | 1.00 | 0.00 |
| ATOM | 1138 | C | ILE | 1 | 126 | -15.410 | 63.856 | 30.692 | 1.00 | 0.00 |
| ATOM | 1139 | O | ILE | 1 | 126 | -16.523 | 63.970 | 30.167 | 1.00 | 0.00 |
| ATOM | 1140 | CB | ILE | 1 | 126 | -13.766 | 65.724 | 30.522 | 1.00 | 0.00 |
| ATOM | 1141 | CG1 | ILE | 1 | 126 | -13.082 | 66.752 | 31.461 | 1.00 | 0.00 |
| ATOM | 1142 | CG2 | ILE | 1 | 126 | -14.467 | 66.385 | 29.299 | 1.00 | 0.00 |
| ATOM | 1143 | CD1 | ILE | 1 | 126 | -11.753 | 67.296 | 30.873 | 1.00 | 0.00 |
| ATOM | 1144 | H | ILE | 1 | 126 | -13.135 | 64.303 | 32.601 | 1.00 | 0.00 |
| ATOM | 1145 | N | TYR | 1 | 127 | -14.624 | 62.715 | 30.636 | 1.00 | 0.00 |
| ATOM | 1146 | CA | TYR | 1 | 127 | -15.167 | 61.452 | 30.126 | 1.00 | 0.00 |
| ATOM | 1147 | C | TYR | 1 | 127 | -16.529 | 61.083 | 30.734 | 1.00 | 0.00 |
| ATOM | 1148 | O | TYR | 1 | 127 | -17.440 | 60.554 | 30.100 | 1.00 | 0.00 |
| ATOM | 1149 | CB | TYR | 1 | 127 | -14.051 | 60.272 | 30.134 | 1.00 | 0.00 |
| ATOM | 1150 | CG | TYR | 1 | 127 | -14.489 | 59.022 | 30.878 | 1.00 | 0.00 |
| ATOM | 1151 | CD1 | TYR | 1 | 127 | -15.254 | 58.078 | 30.129 | 1.00 | 0.00 |
| ATOM | 1152 | CD2 | TYR | 1 | 127 | -14.209 | 58.796 | 32.260 | 1.00 | 0.00 |
| ATOM | 1153 | CE1 | TYR | 1 | 127 | -15.911 | 56.995 | 30.838 | 1.00 | 0.00 |
| ATOM | 1154 | CE2 | TYR | 1 | 127 | -14.809 | 57.674 | 32.912 | 1.00 | 0.00 |
| ATOM | 1155 | CZ | TYR | 1 | 127 | -15.750 | 56.817 | 32.219 | 1.00 | 0.00 |
| ATOM | 1156 | OH | TYR | 1 | 127 | -16.381 | 55.818 | 32.877 | 1.00 | 0.00 |
| ATOM | 1157 | H | TYR | 1 | 127 | -13.751 | 62.624 | 31.115 | 1.00 | 0.00 |
| ATOM | 1158 | HH | TYR | 1 | 127 | -16.924 | 55.379 | 32.236 | 1.00 | 0.00 |
| ATOM | 1159 | N | GLN | 1 | 128 | -16.689 | 61.447 | 32.006 | 1.00 | 0.00 |
| ATOM | 1160 | CA | GLN | 1 | 128 | -17.972 | 61.076 | 32.613 | 1.00 | 0.00 |
| ATOM | 1161 | C | GLN | 1 | 128 | -18.820 | 62.307 | 32.767 | 1.00 | 0.00 |
| ATOM | 1162 | O | GLN | 1 | 128 | -19.700 | 62.437 | 33.627 | 1.00 | 0.00 |
| ATOM | 1163 | CB | GLN | 1 | 128 | -17.573 | 60.544 | 33.940 | 1.00 | 0.00 |
| ATOM | 1164 | CG | GLN | 1 | 128 | -18.401 | 59.339 | 34.361 | 1.00 | 0.00 |
| ATOM | 1165 | CD | GLN | 1 | 128 | -17.669 | 58.576 | 35.474 | 1.00 | 0.00 |
| ATOM | 1166 | OE1 | GLN | 1 | 128 | -17.437 | 59.077 | 36.587 | 1.00 | 0.00 |
| ATOM | 1067 | NE2 | GLN | 1 | 128 | -17.060 | 57.418 | 35.047 | 1.00 | 0.00 |
| ATOM | 1068 | H | GLN | 1 | 128 | -15.933 | 61.976 | 32.392 | 1.00 | 0.00 |
| ATOM | 1069 | 1HE2 | GLN | 1 | 128 | -17.400 | 56.974 | 34.218 | 1.00 | 0.00 |
| ATOM | 1070 | 2HE2 | GLN | 1 | 128 | -16.287 | 57.080 | 35.584 | 1.00 | 0.00 |

FIG. 1Z

| ATOM | 1171 | N | THR | 1 | 129 | -18.610 | 63.261 | 31.790 | 1.00 | 0.00 |
| ATOM | 1172 | CA | THR | 1 | 129 | -19.554 | 64.402 | 31.531 | 1.00 | 0.00 |
| ATOM | 1173 | C | THR | 1 | 129 | -20.034 | 64.338 | 30.090 | 1.00 | 0.00 |
| ATOM | 1174 | O | THR | 1 | 129 | -21.188 | 64.645 | 29.868 | 1.00 | 0.00 |
| ATOM | 1175 | CB | THR | 1 | 129 | -18.694 | 65.689 | 31.759 | 1.00 | 0.00 |
| ATOM | 1176 | OG1 | THR | 1 | 129 | -17.843 | 65.533 | 32.883 | 1.00 | 0.00 |
| ATOM | 1177 | CG2 | THR | 1 | 129 | -19.575 | 66.877 | 31.994 | 1.00 | 0.00 |
| ATOM | 1178 | H | THR | 1 | 129 | -17.822 | 63.069 | 31.205 | 1.00 | 0.00 |
| ATOM | 1179 | 1HG | THR | 1 | 129 | -17.276 | 64.776 | 32.808 | 1.00 | 0.00 |
| ATOM | 1180 | N | ASP | 1 | 130 | -19.100 | 63.839 | 29.242 | 1.00 | 0.00 |
| ATOM | 1181 | CA | ASP | 1 | 130 | -19.272 | 63.530 | 27.815 | 1.00 | 0.00 |
| ATOM | 1182 | C | ASP | 1 | 130 | -18.547 | 62.268 | 27.468 | 1.00 | 0.00 |
| ATOM | 1183 | O | ASP | 1 | 130 | -17.360 | 62.026 | 27.412 | 1.00 | 0.00 |
| ATOM | 1184 | CB | ASP | 1 | 130 | -18.822 | 64.757 | 26.978 | 1.00 | 0.00 |
| ATOM | 1185 | CG | ASP | 1 | 130 | -18.897 | 64.631 | 25.454 | 1.00 | 0.00 |
| ATOM | 1186 | OD1 | ASP | 1 | 130 | -19.920 | 64.947 | 24.888 | 1.00 | 0.00 |
| ATOM | 1187 | OD2 | ASP | 1 | 130 | 017.905 | 64.242 | 24.882 | 1.00 | 0.00 |
| ATOM | 1188 | H | ASP | 1 | 130 | -18.255 | 63.427 | 29.582 | 1.00 | 0.00 |
| ATOM | 1189 | N | ARG | 1 | 131 | -19.410 | 61.274 | 27.309 | 1.00 | 0.00 |
| ATOM | 1190 | CA | ARG | 1 | 131 | -18.935 | 59.959 | 26.768 | 1.00 | 0.00 |
| ATOM | 1191 | C | ARG | 1 | 131 | -18.469 | 60.154 | 25.366 | 1.00 | 0.00 |
| ATOM | 1192 | O | ARG | 1 | 131 | -17.594 | 59.446 | 24.815 | 1.00 | 0.00 |
| ATOM | 1193 | CB | ARG | 1 | 131 | -20.032 | 58.855 | 26.756 | 1.00 | 0.00 |
| ATOM | 1194 | CG | ARG | 1 | 131 | -20.416 | 58.478 | 28.193 | 1.00 | 0.00 |
| ATOM | 1195 | CD | ARG | 1 | 131 | -19.194 | 57.782 | 28.955 | 1.00 | 0.00 |
| ATOM | 1196 | NE | ARG | 1 | 131 | -18.986 | 56.441 | 28.423 | 1.00 | 0.00 |
| ATOM | 1197 | CZ | ARG | 1 | 131 | -19.071 | 55.351 | 29.184 | 1.00 | 0.00 |
| ATOM | 1198 | NH1 | ARG | 1 | 131 | -18.900 | 54.185 | 28.671 | 1.00 | 0.00 |
| ATOM | 1199 | NH2 | ARG | 1 | 131 | -19.376 | 55.517 | 30.503 | 1.00 | 0.00 |
| ATOM | 1200 | H | ARG | 1 | 131 | -20.369 | 61.548 | 27.370 | 1.00 | 0.00 |
| ATOM | 1201 | HE | ARG | 1 | 131 | -18.632 | 56.469 | 27.488 | 1.00 | 0.00 |
| ATOM | 1202 | 1HH1 | ARG | 1 | 131 | -18.956 | 53.332 | 29.191 | 1.00 | 0.00 |
| ATOM | 1203 | 2HH1 | ARG | 1 | 131 | -18.792 | 54.024 | 27.690 | 1.00 | 0.00 |
| ATOM | 1204 | 1HH2 | ARG | 1 | 131 | -19.481 | 54.718 | 31.095 | 1.00 | 0.00 |
| ATOM | 1205 | 2HH2 | ARG | 1 | 131 | -19.542 | 56.412 | 30.918 | 1.00 | 0.00 |
| ATOM | 1206 | N | GLU | 1 | 132 | -19.073 | 61.146 | 24.679 | 1.00 | 0.00 |
| ATOM | 1207 | CA | GLU | 1 | 132 | -19.097 | 61.123 | 23.223 | 1.00 | 0.00 |
| ATOM | 1208 | C | GLU | 1 | 132 | -17.704 | 61.256 | 22.550 | 1.00 | 0.00 |
| ATOM | 1209 | O | GLU | 1 | 132 | -17.303 | 60.476 | 21.676 | 1.00 | 0.00 |
| ATOM | 1210 | CB | GLU | 1 | 132 | -20.158 | 62.165 | 22.829 | 1.00 | 0.00 |
| ATOM | 1211 | CG | GLU | 1 | 132 | -20.663 | 62.490 | 21.437 | 1.00 | 0.00 |
| ATOM | 1212 | CD | GLU | 1 | 132 | -19.538 | 62.468 | 20.507 | 1.00 | 0.00 |
| ATOM | 1213 | OE1 | GLU | 1 | 132 | -18.751 | 63.417 | 20.464 | 1.00 | 0.00 |
| ATOM | 1214 | OE2 | GLU | 1 | 132 | -19.328 | 61.449 | 19.842 | 1.00 | 0.00 |
| ATOM | 1215 | H | GLU | 1 | 132 | -19.447 | 61.944 | 25.151 | 1.00 | 0.00 |

FIG. 1AA

| ATOM | 1216 | N    | LYS | 1 | 133 | -16.973 | 62.276 | 23.084  | 1.00 | 0.00 |
|------|------|------|-----|---|-----|---------|--------|---------|------|------|
| ATOM | 1217 | CA   | LYS | 1 | 133 | -15.616 | 62.452 | 22.586  | 1.00 | 0.00 |
| ATOM | 1218 | C    | LYS | 1 | 133 | -14.629 | 61.391 | 22.856  | 1.00 | 0.00 |
| ATOM | 1219 | O    | LYS | 1 | 133 | -13.837 | 60.980 | 22.044  | 1.00 | 0.00 |
| ATOM | 1220 | CB   | LYS | 1 | 133 | -15.115 | 63.846 | 22.950  | 1.00 | 0.00 |
| ATOM | 1221 | CG   | LYS | 1 | 133 | -15.678 | 64.917 | 22.035  | 1.00 | 0.00 |
| ATOM | 1222 | CD   | LYS | 1 | 133 | -16.243 | 66.106 | 22.825  | 1.00 | 0.00 |
| ATOM | 1223 | CE   | LYS | 1 | 133 | -17.623 | 66.499 | 22.255  | 1.00 | 0.00 |
| ATOM | 1224 | NZ   | LYS | 1 | 133 | -18.680 | 65.449 | 22.4551 | 1.00 | 0.00 |
| ATOM | 1225 | H    | LYS | 1 | 133 | -17.198 | 62.759 | 23.930  | 1.00 | 0.00 |
| ATOM | 1226 | 1HZ  | LYS | 1 | 133 | -18.725 | 64.799 | 21.645  | 1.00 | 0.00 |
| ATOM | 1227 | 2HZ  | LYS | 1 | 133 | -18.439 | 64.912 | 23.313  | 1.00 | 0.00 |
| ATOM | 1228 | 3HZ  | LYS | 1 | 133 | -19.642 | 65.786 | 22.663  | 1.00 | 0.00 |
| ATOM | 1229 | N    | TYR | 1 | 134 | -14.790 | 60.794 | 24.068  | 1.00 | 0.00 |
| ATOM | 1230 | CA   | TYR | 1 | 134 | -14.077 | 59.548 | 24.365  | 1.00 | 0.00 |
| ATOM | 1231 | C    | TYR | 1 | 134 | -14.477 | 58.281 | 23.495  | 1.00 | 0.00 |
| ATOM | 1232 | O    | TYR | 1 | 134 | -13.564 | 57.463 | 23.191  | 1.00 | 0.00 |
| ATOM | 1233 | CB   | TYR | 1 | 134 | -14.163 | 59.285 | 25.901  | 1.00 | 0.00 |
| ATOM | 1234 | CG   | TYR | 1 | 134 | -13.902 | 57.807 | 26.279  | 1.00 | 0.00 |
| ATOM | 1235 | CD1  | TYR | 1 | 134 | -12.616 | 57.238 | 26.234  | 1.00 | 0.00 |
| ATOM | 1236 | CD2  | TYR | 1 | 143 | -14.952 | 56.954 | 26.703  | 1.00 | 0.00 |
| ATOM | 1237 | CE1  | TYR | 1 | 134 | -12.308 | 55.950 | 26.691  | 1.00 | 0.00 |
| ATOM | 1238 | CE2  | TYR | 1 | 134 | -14.739 | 55.641 | 27.144  | 1.00 | 0.00 |
| ATOM | 1239 | CZ   | TYR | 1 | 134 | -13.388 | 55.147 | 27.137  | 1.00 | 0.00 |
| ATOM | 1240 | OH   | TYR | 1 | 134 | -13.089 | 53.833 | 27.509  | 1.00 | 0.00 |
| ATOM | 1241 | H    | TYR | 1 | 134 | -15.605 | 61.016 | 24.604  | 1.00 | 0.00 |
| ATOM | 1242 | HH   | TYR | 1 | 134 | -12.629 | 53.955 | 28.329  | 1.00 | 0.00 |
| ATOM | 1243 | N    | ASN | 1 | 135 | -15.732 | 58.290 | 23.026  | 1.00 | 0.00 |
| ATOM | 1244 | CA   | ASN | 1 | 135 | -16.023 | 57.578 | 21.793  | 1.00 | 0.00 |
| ATOM | 1245 | C    | ASN | 1 | 135 | -15.345 | 58.003 | 20.446  | 1.00 | 0.00 |
| ATOM | 1246 | O    | ASN | 1 | 135 | -16.007 | 57.968 | 19.385  | 1.00 | 0.00 |
| ATOM | 1247 | CB   | ASN | 1 | 135 | -17.458 | 57.139 | 21.710  | 1.00 | 0.00 |
| ATOM | 1248 | CG   | ASN | 1 | 135 | -17,585 | 55.762 | 22.262  | 1.00 | 0.00 |
| ATOM | 1249 | OD1  | ASN | 1 | 135 | -17.810 | 55.462 | 23.457  | 1.00 | 0.00 |
| ATOM | 1250 | ND2  | ASN | 1 | 135 | -17.359 | 54.819 | 21.344  | 1.00 | 0.00 |
| ATOM | 1251 | H    | ASN | 1 | 135 | -16.422 | 58.886 | 23.436  | 1.00 | 0.00 |
| ATOM | 1252 | 1HD2 | ASN | 1 | 135 | -17.077 | 54.977 | 20.398  | 1.00 | 0.00 |
| ATOM | 1253 | 2HD2 | ASN | 1 | 135 | -17.430 | 53.873 | 21.660  | 1.00 | 0.00 |
| ATOM | 1254 | N    | ARG | 1 | 136 | -14.053 | 58.370 | 20.478  | 1.00 | 0.00 |
| ATOM | 1255 | CA   | ARG | 1 | 136 | -13.385 | 58.938 | 19.318  | 1.00 | 0.00 |
| ATOM | 1256 | C    | ARG | 1 | 136 | -11.907 | 59.136 | 19.706  | 1.00 | 0.00 |
| ATOM | 1257 | O    | ARG | 1 | 136 | -11.120 | 58.192 | 19.624  | 1.00 | 0.00 |
| ATOM | 1258 | CB   | ARG | 1 | 136 | -13.963 | 60.323 | 18.860  | 1.00 | 0.00 |
| ATOM | 1259 | CG   | ARG | 1 | 136 | -13.759 | 60.585 | 17.391  | 1.00 | 0.00 |
| ATOM | 1260 | CD   | ARG | 1 | 136 | -15.027 | 60.276 | 16.539  | 1.00 | 0.00 |

FIG. 1BB

| | | | | | | | | | |
|---|---|---|---|---|---|---|---|---|---|
| ATOM | 1261 | NE | ARG | 1 | 136 | -16.001 | 61.343 | 16.710 | 1.00 | 0.00 |
| ATOM | 1262 | CZ | ARG | 1 | 136 | -16.953 | 61.385 | 17.722 | 1.00 | 0.00 |
| ATOM | 1263 | NH1 | ARG | 1 | 136 | -17.634 | 62.501 | 17.758 | 1.00 | 0.00 |
| ATOM | 1264 | NH2 | ARG | 1 | 136 | -17.160 | 60.427 | 18.572 | 1.00 | 0.00 |
| ATOM | 1265 | H | ARG | 1 | 136 | -13.577 | 58.270 | 21.352 | 1.00 | 0.00 |
| ATOM | 1266 | HE | ARG | 1 | 136 | -15.978 | 62.141 | 16.108 | 1.00 | 0.00 |
| ATOM | 1267 | 1HH1 | ARG | 1 | 136 | -18.194 | 62.691 | 18.565 | 1.00 | 0.00 |
| ATOM | 1268 | 2HH1 | ARG | 1 | 136 | -17.585 | 63.094 | 16.955 | 1.00 | 0.00 |
| ATOM | 1269 | 1HH2 | ARG | 1 | 136 | -17.955 | 60.445 | 19.178 | 1.00 | 0.00 |
| ATOM | 1270 | 2HH2 | ARG | 1 | 136 | -16.527 | 59.655 | 18.631 | 1.00 | 0.00 |
| ATOM | 1271 | N | ILE | 1 | 137 | -11.553 | 60.299 | 20.250 | 1.00 | 0.00 |
| ATOM | 1272 | CA | ILE | 1 | 137 | -10.216 | 60.181 | 20.894 | 1.00 | 0.00 |
| ATOM | 1273 | C | ILE | 1 | 137 | -10.249 | 59.245 | 22.086 | 1.00 | 0.00 |
| ATOM | 1274 | O | ILE | 1 | 137 | -10.876 | 59.502 | 23.085 | 1.00 | 0.00 |
| ATOM | 1275 | CB | ILE | 1 | 137 | -9.737 | 61.669 | 21.177 | 1.00 | 0.00 |
| ATOM | 1276 | CG1 | ILE | 1 | 137 | -10.160 | 62.400 | 22.437 | 1.00 | 0.00 |
| ATOM | 1277 | CG2 | ILE | 1 | 137 | -10.058 | 62.553 | 19.908 | 1.00 | 0.00 |
| ATOM | 1278 | CD1 | ILE | 1 | 137 | -9.379 | 63.684 | 22.863 | 1.00 | 0.00 |
| ATOM | 1279 | H | ILE | 1 | 137 | -12.189 | 61.029 | 20.500 | 1.00 | 0.00 |
| ATOM | 1280 | N | ALA | 1 | 138 | -9.665 | 58.091 | 21.783 | 1.00 | 0.00 |
| ATOM | 1281 | CA | ALA | 1 | 138 | -9.599 | 56.705 | 22.426 | 1.00 | 0.00 |
| ATOM | 1282 | C | ALA | 1 | 138 | -10.195 | 55.649 | 21.536 | 1.00 | 0.00 |
| ATOM | 1283 | O | ALA | 1 | 138 | -9.601 | 54.689 | 21.054 | 1.00 | 0.00 |
| ATOM | 1284 | CB | ALA | 1 | 138 | -10.297 | 56.767 | 23.804 | 1.00 | 0.00 |
| ATOM | 1285 | H | ALA | 1 | 138 | -9.100 | 58.150 | 20.960 | 1.00 | 0.00 |
| ATOM | 1286 | N | ARG | 1 | 139 | -11.487 | 55.821 | 21.280 | 1.00 | 0.00 |
| ATOM | 1287 | CA | ARG | 1 | 139 | -11.974 | 55.035 | 20.159 | 1.00 | 0.00 |
| ATOM | 1288 | C | ARG | 1 | 139 | -11.531 | 55.522 | 18.757 | 1.00 | 0.00 |
| ATOM | 1289 | O | ARG | 1 | 139 | -12.365 | 55.995 | 17.960 | 1.00 | 0.00 |
| ATOM | 1290 | CB | ARG | 1 | 139 | -13.446 | 54.877 | 20.345 | 1.00 | 0.00 |
| ATOM | 1291 | CG | ARG | 1 | 139 | -14.037 | 53.544 | 20.350 | 1.00 | 0.00 |
| ATOM | 1292 | CD | ARG | 1 | 139 | -13.777 | 52.739 | 19.100 | 1.00 | 0.00 |
| ATOM | 1293 | NE | ARG | 1 | 139 | -13.294 | 51.422 | 19.446 | 1.00 | 0.00 |
| ATOM | 1294 | CZ | ARG | 1 | 139 | -14.070 | 50.451 | 19.933 | 1.00 | 0.00 |
| ATOM | 1295 | NH1 | ARG | 1 | 139 | -15.376 | 50.557 | 20.176 | 1.00 | 0.00 |
| ATOM | 1296 | NH2 | ARG | 1 | 139 | -13.546 | 49.286 | 20.238 | 1.00 | 0.00 |
| ATOM | 1297 | H | ARG | 1 | 139 | -11.953 | 56.599 | 21.701 | 1.00 | 0.00 |
| ATOM | 1298 | HE | ARG | 1 | 139 | -12.325 | 51.217 | 19.213 | 1.00 | 0.00 |
| ATOM | 1299 | 1HH1 | ARG | 1 | 139 | -15.852 | 49.744 | 20.511 | 1.00 | 0.00 |
| ATOM | 1300 | 2HH1 | ARG | 1 | 139 | -15.778 | 51.473 | 20.172 | 1.00 | 0.00 |
| ATOM | 1301 | 1HH2 | ARG | 1 | 139 | -14.068 | 48.524 | 20.623 | 1.00 | 0.00 |
| ATOM | 1302 | 2HH2 | ARG | 1 | 139 | -12.550 | 49.203 | 20.209 | 1.00 | 0.00 |
| ATOM | 1303 | N | GLU | 1 | 140 | -10.248 | 55.319 | 18.431 | 1.00 | 0.00 |
| ATOM | 1304 | CA | GLU | 1 | 140 | -9.561 | 55.842 | 17.254 | 1.00 | 0.00 |
| ATOM | 1305 | C | GLU | 1 | 140 | -8.281 | 54.950 | 17.238 | 1.00 | 0.00 |

FIG. 1CC

| ATOM | 1306 | O    | GLU | 1 | 140 | -8.151  | 54.134 | 16.315 | 1.00 | 0.00 |
| ATOM | 1307 | CB   | GLU | 1 | 140 | -9.381  | 57.331 | 17.443 | 1.00 | 0.00 |
| ATOM | 1308 | CG   | GLU | 1 | 140 | -9.055  | 58.269 | 16.321 | 1.00 | 0.00 |
| ATOM | 1309 | CD   | GLU | 1 | 140 | -7.581  | 57.782 | 15.971 | 1.00 | 0.00 |
| ATOM | 1310 | OE1  | GLU | 1 | 140 | -6.649  | 57.991 | 16.665 | 1.00 | 0.00 |
| ATOM | 1311 | OE2  | GLU | 1 | 140 | -7.440  | 57.213 | 14.940 | 1.00 | 0.00 |
| ATOM | 1312 | H    | GLU | 1 | 140 | -9.824  | 54.778 | 19.157 | 1.00 | 0.00 |
| ATOM | 1313 | N    | TRP | 1 | 141 | -7.528  | 55.060 | 18.298 | 1.00 | 0.00 |
| ATOM | 1314 | CA   | TRP | 1 | 141 | -6.370  | 54.173 | 18.571 | 1.00 | 0.00 |
| ATOM | 1315 | C    | TRP | 1 | 141 | -6.737  | 52.782 | 18.944 | 1.00 | 0.00 |
| ATOM | 1316 | O    | TRP | 1 | 141 | -5.982  | 51.968 | 19.452 | 1.00 | 0.00 |
| ATOM | 1317 | CB   | TRP | 1 | 141 | -5.483  | 54.663 | 19.722 | 1.00 | 0.00 |
| ATOM | 1318 | CG   | TRP | 1 | 141 | -4.774  | 55.962 | 19.326 | 1.00 | 0.00 |
| ATOM | 1319 | CD1  | TRP | 1 | 141 | -3.685  | 56.131 | 18.409 | 1.00 | 0.00 |
| ATOM | 1320 | CD2  | TRP | 1 | 141 | -5.095  | 57.289 | 19.700 | 1.00 | 0.00 |
| ATOM | 1321 | NE1  | TRP | 1 | 141 | -3.327  | 57.468 | 18.247 | 1.00 | 0.00 |
| ATOM | 1322 | CE2  | TRP | 1 | 141 | -4.213  | 58.240 | 19.050 | 1.00 | 0.00 |
| ATOM | 1323 | CE3  | TRP | 1 | 141 | -6.038  | 57.792 | 20.591 | 1.00 | 0.00 |
| ATOM | 1324 | CZ2  | TRP | 1 | 141 | -4.413  | 59.642 | 19.300 | 1.00 | 0.00 |
| ATOM | 1325 | CZ3  | TRP | 1 | 141 | -6.247  | 59.169 | 20.882 | 1.00 | 0.00 |
| ATOM | 1326 | CH2  | TRP | 1 | 141 | -5.415  | 60.068 | 20.154 | 1.00 | 0.00 |
| ATOM | 1327 | H    | TRP | 1 | 141 | -7.623  | 55.892 | 18.845 | 1.00 | 0.00 |
| ATOM | 1328 | 1HE  | TRP | 1 | 141 | -2.570  | 57.837 | 17.746 | 1.00 | 0.00 |
| ATOM | 1329 | N    | THR | 1 | 142 | -7.945  | 52.388 | 18.669 | 1.00 | 0.00 |
| ATOM | 1330 | CA   | THR | 1 | 142 | -8.470  | 51.003 | 18.796 | 1.00 | 0.00 |
| ATOM | 1331 | C    | THR | 1 | 142 | -8.785  | 50.384 | 17.443 | 1.00 | 0.00 |
| ATOM | 1332 | O    | THR | 1 | 142 | -8.951  | 49.195 | 17.303 | 1.00 | 0.00 |
| ATOM | 1333 | CB   | THR | 1 | 142 | -9.836  | 51.112 | 19.635 | 1.00 | 0.00 |
| ATOM | 1334 | OG1  | THR | 1 | 142 | -10.085 | 52.512 | 20.129 | 1.00 | 0.00 |
| ATOM | 1335 | CG2  | THR | 1 | 142 | -9.646  | 50.189 | 20.902 | 1.00 | 0.00 |
| ATOM | 1336 | H    | THR | 1 | 142 | -8.557  | 53.070 | 18.268 | 1.00 | 0.00 |
| ATOM | 1337 | 1HG  | THR | 1 | 142 | -9.297  | 52.761 | 20.593 | 1.00 | 0.00 |
| ATOM | 1338 | N    | GLN | 1 | 143 | -8.798  | 51.237 | 16.420 | 1.00 | 0.00 |
| ATOM | 1339 | CA   | GLN | 1 | 143 | -8.800  | 50.759 | 15.056 | 1.00 | 0.00 |
| ATOM | 1340 | C    | GLN | 1 | 143 | -7.468  | 50.990 | 14.393 | 1.00 | 0.00 |
| ATOM | 1341 | O    | GLN | 1 | 143 | -6.836  | 49.990 | 14.069 | 1.00 | 0.00 |
| ATOM | 1342 | CB   | GLN | 1 | 143 | -9.874  | 51.493 | 14.234 | 1.00 | 0.00 |
| ATOM | 1343 | CG   | GLN | 1 | 143 | -10.095 | 50.582 | 13.074 | 1.00 | 0.00 |
| ATOM | 1344 | CD   | GLN | 1 | 143 | -10.628 | 51.426 | 11.972 | 1.00 | 0.00 |
| ATOM | 1345 | OE1  | GLN | 1 | 143 | -11.716 | 51.960 | 12.091 | 1.00 | 0.00 |
| ATOM | 1346 | NE2  | GLN | 1 | 143 | -9.832  | 51.593 | 10.953 | 1.00 | 0.00 |
| ATOM | 1347 | H    | GLN | 1 | 143 | -8.441  | 52.158 | 16.577 | 1.00 | 0.00 |
| ATOM | 1348 | 1HE2 | GLN | 1 | 143 | -8.858  | 51.392 | 10.856 | 1.00 | 0.00 |
| ATOM | 1349 | 2HE2 | GLN | 1 | 143 | -10.262 | 52.137 | 10.232 | 1.00 | 0.00 |
| ATOM | 1350 | N    | LYS | 1 | 144 | -7.185  | 52.353 | 14.272 | 1.00 | 0.00 |

FIG. 1DD

| ATOM | 1351 | CA  | LYS | 1 | 144 | -5.872 | 52.774 | 13.923 | 1.00 | 0.00 |
| ATOM | 1352 | C   | LYS | 1 | 144 | -4.944 | 52.505 | 15.064 | 1.00 | 0.00 |
| ATOM | 1353 | O   | LYS | 1 | 144 | -4.948 | 53.182 | 16.090 | 1.00 | 0.00 |
| ATOM | 1354 | CB  | LYS | 1 | 144 | -6.052 | 54.219 | 13.415 | 1.00 | 0.00 |
| ATOM | 1355 | CG  | LYS | 1 | 144 | -4.756 | 54.831 | 12.839 | 1.00 | 0.00 |
| ATOM | 1356 | CD  | LYS | 1 | 144 | -4.529 | 56.258 | 13.351 | 1.00 | 0.00 |
| ATOM | 1357 | CE  | LYS | 1 | 144 | -4.289 | 56.135 | 14.821 | 1.00 | 0.00 |
| ATOM | 1358 | NZ  | LYS | 1 | 144 | -4.298 | 57.465 | 15.486 | 1.00 | 0.00 |
| ATOM | 1359 | H   | LYS | 1 | 144 | -7.735 | 53.032 | 14.760 | 1.00 | 0.00 |
| ATOM | 1360 | 1HZ | LYS | 1 | 144 | -5.272 | 57.787 | 15.657 | 1.00 | 0.00 |
| ATOM | 1361 | 2HZ | LYS | 1 | 144 | -3.709 | 57.497 | 16.342 | 1.00 | 0.00 |
| ATOM | 1362 | 3HZ | LYS | 1 | 144 | -3.674 | 58.052 | 14.895 | 1.00 | 0.00 |
| ATOM | 1363 | N   | TYR | 1 | 145 | -4.035 | 51.523 | 14.725 | 1.00 | 0.00 |
| ATOM | 1364 | CA  | TYR | 1 | 145 | -2.783 | 51.563 | 15.405 | 1.00 | 0.00 |
| ATOM | 1365 | C   | TYR | 1 | 145 | -1.705 | 51.911 | 14.373 | 1.00 | 0.00 |
| ATOM | 1366 | O   | TYR | 1 | 145 | -1.262 | 51.077 | 13.622 | 1.00 | 0.00 |
| ATOM | 1367 | CB  | TYR | 1 | 145 | -2.651 | 50.166 | 16.073 | 1.00 | 0.00 |
| ATOM | 1368 | CG  | TYR | 1 | 145 | -1.338 | 50.008 | 16.760 | 1.00 | 0.00 |
| ATOM | 1369 | CD1 | TYR | 1 | 145 | -1.119 | 50.509 | 18.043 | 1.00 | 0.00 |
| ATOM | 1370 | CD2 | TYR | 1 | 145 | -0.302 | 49.394 | 16.035 | 1.00 | 0.00 |
| ATOM | 1371 | CE1 | TYR | 1 | 145 |  0.150 | 50.465 | 18.579 | 1.00 | 0.00 |
| ATOM | 1372 | CE2 | TYR | 1 | 145 |  0.972 | 49.409 | 16.589 | 1.00 | 0.00 |
| ATOM | 1373 | CZ  | TYR | 1 | 145 |  1.210 | 49.922 | 17.847 | 1.00 | 0.00 |
| ATOM | 1374 | OH  | TYR | 1 | 145 |  2.486 | 49.934 | 18.410 | 1.00 | 0.00 |
| ATOM | 1375 | H   | TYR | 1 | 145 | -4.122 | 50.802 | 14.038 | 1.00 | 0.00 |
| ATOM | 1376 | HH  | TYR | 1 | 145 |  2.907 | 50.776 | 18.294 | 1.00 | 0.00 |
| ATOM | 1377 | N   | ALA | 1 | 146 | -1.219 | 53.200 | 14.453 | 1.00 | 0.00 |
| ATOM | 1378 | CA  | ALA | 1 | 146 | -0.018 | 53.540 | 13.627 | 1.00 | 0.00 |
| ATOM | 1379 | C   | ALA | 1 | 146 |  0.585 | 54.832 | 14.174 | 1.00 | 0.00 |
| ATOM | 1380 | O   | ALA | 1 | 146 |  1.508 | 54.792 | 14.958 | 1.00 | 0.00 |
| ATOM | 1381 | CB  | ALA | 1 | 146 | -0.347 | 53.708 | 12.163 | 1.00 | 0.00 |
| ATOM | 1382 | H   | ALA | 1 | 146 | -1.694 | 53.960 | 14.896 | 1.00 | 0.00 |
| ATOM | 1383 | N   | MET | 1 | 147 |  0.146 | 55.965 | 13.712 | 1.00 | 0.00 |
| ATOM | 1384 | CA  | MET | 1 | 147 |  0.072 | 57.199 | 14.504 | 1.00 | 0.00 |
| ATOM | 1385 | C   | MET | 1 | 147 | -1.165 | 57.157 | 15.439 | 1.00 | 0.00 |
| ATOM | 1386 | O   | MET | 1 | 147 | -1.746 | 58.134 | 15.774 | 1.00 | 0.00 |
| ATOM | 1387 | CB  | MET | 1 | 147 |  0.219 | 58.444 | 13.697 | 1.00 | 0.00 |
| ATOM | 1388 | CG  | MET | 1 | 147 | -0.769 | 58.439 | 12.499 | 1.00 | 0.00 |
| ATOM | 1389 | SD  | MET | 1 | 147 | -0.431 | 59.820 | 11.346 | 1.00 | 0.00 |
| ATOM | 1390 | CE  | MET | 1 | 147 | -2.099 | 59.928 | 10.616 | 1.00 | 0.00 |
| ATOM | 1391 | OXT | MET | 1 | 147 | -1.521 | 56.064 | 15.926 | 1.00 | 0.00 |
| ATOM | 1392 | H   | MET | 1 | 147 | -0.461 | 55.994 | 12.919 | 1.00 | 0.00 |

END

FIG. 1EE

| ATOM | 1 | N | CYS | *1 | 85 | 12.813 | -15.194 | 42.441 | 1.00 | 0.00 |
|------|---|---|-----|----|----|--------|---------|--------|------|------|
| ATOM | 2 | H | CYS | *1 | 85 | 13.027 | -15.873 | 41.738 | 1.00 | 0.00 |
| ATOM | 3 | CA | CYS | *1 | 85 | 13.822 | -14.593 | 43.296 | 1.00 | 0.00 |
| ATOM | 4 | CB | CYS | *1 | 85 | 14.815 | -15.616 | 43.734 | 1.00 | 0.00 |
| ATOM | 5 | SG | CYS | *1 | 85 | 15.117 | -15.447 | 45.437 | 1.00 | 0.00 |
| ATOM | 6 | C | CYS | *1 | 85 | 14.478 | -13.341 | 42.778 | 1.00 | 0.00 |
| ATOM | 7 | O | CYS | *1 | 85 | 13.994 | -12.195 | 43.023 | 1.00 | 0.00 |
| ATOM | 8 | N | LEU | 1 | 86 | 15.596 | -13.553 | 42.021 | 1.00 | 0.00 |
| ATOM | 9 | CA | LEU | 1 | 86 | 16.482 | -12.490 | 41.469 | 1.00 | 0.00 |
| ATOM | 10 | C | LEU | 1 | 86 | 17.155 | -11.557 | 42.453 | 1.00 | 0.00 |
| ATOM | 11 | O | LEU | 1 | 86 | 16.664 | -11.390 | 43.514 | 1.00 | 0.00 |
| ATOM | 12 | CB | LEU | 1 | 86 | 15.850 | -11.805 | 40.281 | 1.00 | 0.00 |
| ATOM | 13 | CG | LEU | 1 | 86 | 14.624 | -12.437 | 39.580 | 1.00 | 0.00 |
| ATOM | 14 | CD1 | LEU | 1 | 86 | 14.040 | -11.515 | 38.482 | 1.00 | 0.00 |
| ATOM | 15 | CD2 | LEU | 1 | 86 | 14.916 | -13.795 | 38.925 | 1.00 | 0.00 |
| ATOM | 16 | H | LEU | 1 | 86 | 15.932 | -14.493 | 41.961 | 1.00 | 0.00 |
| ATOM | 17 | N | ASP | 1 | 87 | 18.301 | -10.942 | 42.020 | 1.00 | 0.00 |
| ATOM | 18 | CA | ASP | 1 | 87 | 18.887 | -9.697 | 42.577 | 1.00 | 0.00 |
| ATOM | 19 | C | ASP | 1 | 87 | 17.933 | -8.538 | 42.215 | 1.00 | 0.00 |
| ATOM | 20 | O | ASP | 1 | 87 | 17.603 | -7.688 | 42.977 | 1.00 | 0.00 |
| ATOM | 21 | CB | ASP | 1 | 87 | 20.280 | -9.473 | 41.980 | 1.00 | 0.00 |
| ATOM | 22 | CG | ASP | 1 | 87 | 20.280 | -9.437 | 40.434 | 1.00 | 0.00 |
| ATOM | 23 | OD1 | ASP | 1 | 87 | 21.191 | -8.936 | 39.856 | 1.00 | 0.00 |
| ATOM | 24 | OD2 | ASP | 1 | 87 | 19.409 | -9.977 | 39.792 | 1.00 | 0.00 |
| ATOM | 25 | H | ASP | 1 | 87 | 18.468 | -11.284 | 41.095 | 1.00 | 0.00 |
| ATOM | 26 | N | ILE | 1 | 88 | 17.532 | -8.458 | 40.922 | 1.00 | 0.00 |
| ATOM | 27 | CA | ILE | 1 | 88 | 16.874 | -7.254 | 40.484 | 1.00 | 0.00 |
| ATOM | 28 | C | ILE | 1 | 88 | 15.486 | -7.061 | 40.987 | 1.00 | 0.00 |
| ATOM | 29 | O | ILE | 1 | 88 | 14.834 | -5.995 | 40.819 | 1.00 | 0.00 |
| ATOM | 30 | CB | ILE | 1 | 88 | 16.911 | -7.193 | 38.904 | 1.00 | 0.00 |
| ATOM | 31 | CG1 | ILE | 1 | 88 | 16.078 | -8.320 | 38.291 | 1.00 | 0.00 |
| ATOM | 32 | CG2 | ILE | 1 | 88 | 18.322 | -7.055 | 38.472 | 1.00 | 0.00 |
| ATOM | 33 | CD | ILE | 1 | 88 | 14.676 | -8.014 | 37.765 | 1.00 | 0.00 |
| ATOM | 34 | H | ILE | 1 | 88 | 17.739 | -9.251 | 40.349 | 1.00 | 0.00 |
| ATOM | 35 | N | ARG | 1 | 90 | 14.426 | -7.619 | 44.251 | 1.00 | 0.00 |
| ATOM | 36 | CA | ARG | 1 | 90 | 14.634 | -7.627 | 45.688 | 1.00 | 0.00 |
| ATOM | 37 | C | ARG | 1 | 90 | 15.897 | -6.845 | 46.216 | 1.00 | 0.00 |
| ATOM | 38 | O | ARG | 1 | 90 | 15.818 | -5.995 | 47.079 | 1.00 | 0.00 |
| ATOM | 39 | CB | ARG | 1 | 90 | 14.624 | -9.055 | 46.305 | 1.00 | 0.00 |
| ATOM | 40 | CG | ARG | 1 | 90 | 15.765 | -10.003 | 46.039 | 1.00 | 0.00 |
| ATOM | 41 | CD | ARG | 1 | 90 | 15.221 | -11.397 | 46.218 | 1.00 | 0.00 |
| ATOM | 42 | NE | ARG | 1 | 90 | 14.864 | -11.584 | 47.622 | 1.00 | 0.00 |
| ATOM | 43 | CZ | ARG | 1 | 90 | 13.976 | -12.617 | 47.838 | 1.00 | 0.00 |
| ATOM | 44 | NH1 | ARG | 1 | 90 | 13.824 | -13.004 | 49.063 | 1.00 | 0.00 |
| ATOM | 45 | NH2 | ARG | 1 | 90 | 13.426 | -13.227 | 46.779 | 1.00 | 0.00 |

FIG. 3A

| | | | | | | | | | |
|---|---|---|---|---|---|---|---|---|---|
| ATOM | 46 | H | ARG | 1 | 90 | 14.907 | -6.934 | 43.703 | 1.00 0.00 |
| ATOM | 47 | HE | ARG | 1 | 90 | 15.187 | -11.015 | 48.378 | 1.00 0.00 |
| ATOM | 48 | 1HH1 | ARG | 1 | 90 | 13.264 | -13.807 | 49.262 | 1.00 0.00 |
| ATOM | 49 | 2HH1 | ARG | 1 | 90 | 14.153 | -12.435 | 49.817 | 1.00 0.00 |
| ATOM | 50 | 2HH1 | ARG | 1 | 90 | 12.658 | -13.824 | 47.013 | 1.00 0.00 |
| ATOM | 51 | 2HH2 | ARG | 1 | 90 | 13.676 | -13.086 | 45.821 | 1.00 0.00 |
| ATOM | 52 | N | SER | 1 | 91 | 17.097 | -7.261 | 45.695 | 1.00 0.00 |
| ATOM | 53 | CA | SER | 1 | 91 | 18.257 | -6.643 | 46.299 | 1.00 0.00 |
| ATOM | 54 | C | SER | 1 | 91 | 19.180 | -5.852 | 45.357 | 1.00 0.00 |
| ATOM | 55 | O | SER | 1 | 91 | 20.364 | -5.736 | 45.486 | 1.00 0.00 |
| ATOM | 56 | CB | SER | 1 | 91 | 19.094 | -7.651 | 47.083 | 1.00 0.00 |
| ATOM | 57 | OG | SER | 1 | 91 | 18.260 | -8.522 | 47.886 | 1.00 0.00 |
| ATOM | 58 | H | SER | 1 | 91 | 17.222 | -7.822 | 44.876 | 1.00 0.00 |
| ATOM | 59 | HG | SER | 1 | 91 | 17.859 | -7.970 | 48.544 | 1.00 0.00 |
| ATOM | 60 | N | LEU | 1 | 109 | 18.852 | -18.359 | 38.255 | 1.00 0.00 |
| ATOM | 61 | CA | LEU | 1 | 109 | 18.365 | -18.942 | 39.568 | 1.00 0.00 |
| ATOM | 62 | C | LEU | 1 | 109 | 17.179 | -19.841 | 39.495 | 1.00 0.00 |
| ATOM | 63 | O | LEU | 1 | 109 | 16.540 | -20.333 | 40.413 | 1.00 0.00 |
| ATOM | 64 | CB | LEU | 1 | 109 | 18.387 | -17.901 | 40.725 | 1.00 0.00 |
| ATOM | 65 | CG | LEU | 1 | 109 | 19.746 | -17.216 | 40.897 | 1.00 0.00 |
| ATOM | 66 | CD1 | LEU | 1 | 109 | 19.834 | -15.819 | 40.391 | 1.00 0.00 |
| ATOM | 67 | CD2 | LEU | 1 | 109 | 20.454 | -17.598 | 42.195 | 1.00 0.00 |
| ATOM | 68 | H | LEU | 1 | 109 | 18.274 | -17.735 | 37.728 | 1.00 0.00 |
| ATOM | 69 | N | ASN | 1 | 114 | 17.767 | -21.723 | 43.157 | 1.00 0.00 |
| ATOM | 70 | CA | ASN | 1 | 114 | 17.585 | -21.498 | 44.611 | 1.00 0.00 |
| ATOM | 71 | C | ASN | 1 | 114 | 16.288 | -22.097 | 45.204 | 1.00 0.00 |
| ATOM | 72 | O | ASN | 1 | 114 | 15.110 | -21.738 | 44.968 | 1.00 0.00 |
| ATOM | 73 | CB | ASN | 1 | 114 | 17.738 | -20.004 | 44.811 | 1.00 0.00 |
| ATOM | 74 | CG | ASN | 1 | 114 | 17.761 | -19.604 | 46.263 | 1.00 0.00 |
| ATOM | 75 | OD1 | ASN | 1 | 114 | 17.013 | -18.825 | 46.820 | 1.00 0.00 |
| ATOM | 76 | ND2 | ASN | 1 | 114 | 18.754 | -20.204 | 46.933 | 1.00 0.00 |
| ATOM | 77 | H | ASN | 1 | 114 | 17.244 | -21.387 | 42.373 | 1.00 0.00 |
| ATOM | 78 | 1HD2 | ASN | 1 | 114 | 19.381 | -20.849 | 46.496 | 1.00 0.00 |
| ATOM | 79 | 2HD2 | ASN | 1 | 114 | 19.079 | -20.336 | 47.869 | 1.00 0.00 |
| ATOM | 80 | N | ASP | 1 | 116 | 16.009 | -21.817 | 48.288 | 1.00 0.00 |
| ATOM | 81 | CA | ASP | 1 | 116 | 16.037 | -21.119 | 49.574 | 1.00 0.00 |
| ATOM | 82 | C | ASP | 1 | 116 | 15.396 | -19.793 | 49.630 | 1.00 0.00 |
| ATOM | 83 | O | ASP | 1 | 116 | 15.774 | -18.837 | 50.337 | 1.00 0.00 |
| ATOM | 84 | CB | ASP | 1 | 116 | 17.464 | -20.968 | 50.072 | 1.00 0.00 |
| ATOM | 85 | CG | ASP | 1 | 116 | 18.319 | -22.224 | 49.976 | 1.00 0.00 |
| ATOM | 86 | OD1 | ASP | 1 | 116 | 18.006 | -23.130 | 50.730 | 1.00 0.00 |
| ATOM | 87 | OD2 | ASP | 1 | 116 | 19.236 | -22.263 | 49.180 | 1.00 0.00 |
| ATOM | 88 | H | ASP | 1 | 116 | 16.323 | -21.489 | 47.396 | 1.00 0.00 |
| ATOM | 89 | N | ASP | 1 | 117 | 14.372 | -19.664 | 48.769 | 1.00 0.00 |
| ATOM | 90 | CA | ASP | 1 | 117 | 13.409 | -18.653 | 49.009 | 1.00 0.00 |

FIG. 3B

```
ATOM    91  C    ASP  1  117    12.024  -19.105  48.641  1.00  0.00
ATOM    92  O    ASP  1  117    11.645  -19.083  47.471  1.00  0.00
ATOM    93  CB   ASP  1  117    13.801  -17.459  48.181  1.00  0.00
ATOM    94  CG   ASP  1  117    13.342  -16.211  48.889  1.00  0.00
ATOM    95  OD1  ASP  1  117    13.889  -15.978  49.966  1.00  0.00
ATOM    96  OD2  ASP  1  117    12.577  -15.397  48.399  1.00  0.00
ATOM    97  H    ASP  1  117    14.092  -20.522  48.339  1.00  0.00
END
```

FIG. 3C

HUMAN UBIQUITIN CONJUGATING ENZYME

RELATED APPLICATIONS

This application is a continuation-in-part of U.S. Ser. No. 08/176,937 filed Jan. 4, 1994, abandoned, entitled "Assay and Reagents for Detecting Inhibitors of Ubiquitin-dependent Degradation of Cell Cycle Regulatory Proteins", the specification of which is incorporated by reference herein.

BACKGROUND OF THE INVENTION

The ubiquitin-mediated proteolysis system is the major pathway for the selective, controlled degradation of intracellular proteins in eukaryotic cells. Ubiquitin modification of a variety of protein targets within the cell appears to be important in a number of basic cellular functions such as regulation of gene expression, regulation of the cell-cycle, modification of cell surface receptors, biogenesis of ribosomes, and DNA repair. One major function of the ubiquitin-mediated system is to control the half-lives of cellular proteins. The half-life of different proteins can range from a few minutes to several days, and can vary considerably depending on the cell-type, nutritional and environmental conditions, as well as the stage of the cell-cycle.

Targeted proteins undergoing selective degradation, presumably through the actions of a ubiquitin-dependent proteosome, are covalently tagged with ubiquitin through the formation of an isopeptide bond between the C-terminal glycyl residue of ubiquitin and a specific lysyl residue in the substrate protein. This process is catalyzed by a ubiquitin-activating enzyme (E1) and a ubiquitin-conjugating enzyme (E2), and in some instances may also require auxiliary substrate recognition proteins (E3s). Following the linkage of the first ubiquitin chain, additional molecules of ubiquitin may be attached to lysine side chains of the previously conjugated moiety to form branched multi-ubiquitin chains.

The conjugation of ubiquitin to protein substrates is a multi-step process. In an initial ATP requiring step, a thioester is formed between the C-terminus of ubiquitin and an internal cysteine residue of an E1 enzyme. Activated ubiquitin is then transferred to a specific cysteine on one of several E2 enzymes. Finally, these E2 enzymes donate ubiquitin to protein substrates. Substrates are recognized either directly by ubiquitin-conjugated enzymes or by associated substrate recognition proteins, the E3 proteins, also known as ubiquitin ligases.

Ubiquitin is itself a substrate for ubiquitination. Depending on the ubiquitin-conjugating enzyme and the nature of the substrate, specific lysine residues of ubiquitin are used as acceptor sites for further ubiquitinations. This can lead to either a linear multi-ubiquitin chain (when a single lysine residue of ubiquitin is used) or multi-ubiquitin "trees" (when more than one lysine reside of ubiquitin is used). Although the attachment of a single ubiquitin moiety to a substrate can be sufficient for degradation, multi-ubiquitination appears to be required in most cases.

Many proteins that control cell-cycle progression are short-lived. For example, regulation of oncoproteins and anti-oncoproteins clearly plays an important role in determining steady-state levels of protein expression, and alterations in protein degradation are as likely as changes in transcription and/or translation to cause either the proliferative arrest of cells, or alternatively, the transformation of cells.

SUMMARY OF THE INVENTION

The present invention relates to the discovery in eukaryotic cells, particularly human cells, a novel ubiquitin conjugating enzyme (hereinafter "hUCE") which can function to mediate ubiquitination of cell check regulatory proteins, e.g. p53, and is therefore involved in regulating cell cycle progression, e.g. cell growth.

One aspect of the invention features a substantially pure preparation of an hUCE polypeptide, or a fragment thereof, which can function as a ubiquitin conjugating enzyme. In a preferred embodiment: the polypeptide has an amino acid sequence at least 90% homologous to the amino acid sequence of SEQ ID No. 2; the polypeptide has an amino acid sequence at least 95% homologous to the amino acid sequence of SEQ ID No. 2; the polypeptide has an amino acid sequence at least 97% homologous to the amino acid sequence of SEQ ID No. 2; the polypeptide has an amino acid sequence identical to the amino acid sequence of SEQ ID No. 2. In a preferred embodiment: the fragment comprises at least 5 contiguous amino acid residues of SEQ ID No. 2; the fragment comprises at least 20 contiguous amino acid residues of SEQ ID No. 2; the fragment comprises at least 50 contiguous amino acid residues of SEQ ID No. 2. In a preferred embodiment, the fragment comprises at least a portion of amino acid residues Cys-107 through Met-147, e.g. 5 amino acid residues, e.g. 15 amino acid residues, e.g. 25 amino acid residues.

Another aspect of the present invention features an hUCE polypeptide which functions in one of either role of an agonist of cell-cycle regulation or an antagonist of cell-cycle regulation. In a preferred embodiment the hUCE polypeptide has: an ability to mediate ubiquitination of cellular proteins, e.g. cell-cycle regulatory proteins, e.g. p53; an ability to mediate ubiquitin-dependent degradation of cellular proteins, e.g. cell-cycle regulatory proteins, e.g. p53; an ability to affect the cellular half-life of a cell-cycle regulatory protein, e.g. a cell-cycle checkpoint protein, e.g. p53, e.g. in normal cells, e.g. in normal proliferating cells, e.g. in virally-infected cells, e.g. in papillomavirus infected cells, e.g. in HPV-infected cells, e.g. in HPV-16, HPV-18, HPV-31, or HPV-33 infected cells, e.g. in cells expressing a papillomavirus E6 protein, e.g. in transformed cells, e.g. in cancerous cells.

Yet another aspect of the present invention concerns an immunogen comprising a hUCE polypeptide, or a fragment thereof, in an immunogenic preparation, the immunogen being capable of eliciting an immune response specific for the subject hUCE polypeptide; e.g. a humoral response, eg. an antibody response; e.g. a cellular response.

A still further aspect of the present invention features an antibody preparation specifically reactive with an epitope of the hUCE immunogen.

Another aspect of the present invention features recombinant hUCE polypeptide, or a fragment thereof, having an amino acid sequence preferably: at least 90% homologous to SEQ ID No. 2; at least 95% homologous to SEQ ID No. 2; at least 97% homologous to SEQ ID No. 2. In a preferred embodiment, the recombinant hUCE protein functions in one of either role of an agonist of cell cycle regulation or an antagonist of cell cycle regulation. In a more preferred embodiment: the hUCE polypeptide mediates ubiquitination of cellular proteins, e.g. cell-cycle regulatory proteins, e.g. p53; the hUCE polypeptide mediates ubiquitin-dependent degradation of cellular proteins, e.g. cell-cycle regulatory proteins, e.g. p53; the hUCE polypeptide affects the cellular half-life of a cell-cycle regulatory protein, e.g. a cell-cycle checkpoint protein, e.g. p53, e.g. in normal cells, e.g. in normal proliferating cells, e.g. in virally-infected cells, e.g. in papillomavirus infected cells, e.g. in HPV-infected cells, e.g. in HPV-16, HPV-18, HPV-31, or HPV-33 infected cells, e.g. in cells expressing a papillomavirus E6 protein, e.g. in transformed cells, e.g. in cancerous cells.

In yet other preferred embodiments, the recombinant hUCE protein is a fusion protein further comprising a second polypeptide portion having an amino acid sequence from a protein unrelated the protein of SEQ ID No. 2. Such fusion proteins can be functional in a two-hybrid assay.

Another aspect of the present invention provides a substantially pure nucleic acid having a nucleotide sequence which encodes an hUCE polypeptide, or a fragment thereof, having an amino acid sequence at least 90% homologous to SEQ ID NO. 2. In a more preferred embodiment, the nucleic acid encodes a protein having an amino acid sequence at least 95% homologous to SEQ ID No. 2; and more preferably at least 97% homologous to SEQ ID No. 2. The nucleic preferably encodes: a hUCE polypeptide which mediates ubiquitination of cellular proteins, e.g. cell-cycle regulatory proteins, e.g. p53; a hUCE polypeptide which mediates ubiquitin-dependent degradation of cellular proteins, e.g. cell-cycle regulatory proteins, e.g. p53; a hUCE polypeptide which affects the cellular half-life of a cell-cycle regulatory protein, e.g. a cell-cycle checkpoint protein, e.g. p53, e.g. in normal cells, e.g. in normal proliferating cells, e.g. in virally-infected cells, e.g. in papillomavirus infected cells, e.g. in HPV-infected cells, e.g. in HPV-16, HPV-18, HPV-31, or HPV-33 infected cells, e.g. in cells expressing a papillomavirus E6 protein, e.g. in transformed cells, e.g. in cancerous cells.

In yet a further preferred embodiment, the nucleic acid which encodes an hUCE polypeptide of the present invention, or a fragment thereof, hybridizes under stringent conditions to a nucleic acid probe corresponding to at least 12 consecutive nucleotides of SEQ ID No. 1; more preferably to at least 20 consecutive nucleotides of SEQ ID No. 1; more preferably to at least 40 consecutive nucleotides of SEQ ID No. 1. In yet a further preferred embodiment, the hUCE encoding nucleic acid hybridizes to a nucleic acid probe corresponding to a subsequence encoding at least 4 consecutive amino acids between residues 107 and 147 of SEQ ID No. 2, more preferably at least 10 consecutive amino acid residues, and even more preferably at least 20 amino acid residues. In yet a preferred embodiment, the nucleic acid encodes and hUCE polypeptide which includes Cys-107 through Cys-111.

Furthermore, in certain preferred embodiments, hUCE encoding nucleic acid will comprise a transcriptional regulatory sequence, e.g. at least one of a transcriptional promoter or transcriptional enhancer sequence, operably linked to the hUCE gene sequence so as to render the hUCE gene sequence suitable for use as an expression vector. In one embodiment, the hUCE gene is provided as a sense construct. In another embodiment, the hUCE gene is provided as an anti-sense construct.

The present invention also features transgenic non-human animals, e.g. mice, which either express a heterologous hUCE gene, e.g. derived from humans, or which mis-express their own homolog of the subject human gene, e.g. expression of the mouse hUCE homolog is disrupted. Such a transgenic animal can serve as an animal model for studying cellular disorders comprising mutated or mis-expressed hUCE alleles.

The present invention also provides a probe/primer comprising a substantially purified oligonucleotide, wherein the oligonucleotide comprises a region of nucleotide sequence which hybridizes under stringent conditions to at least 10 consecutive nucleotides of sense or antisense sequence of SEQ ID No. 1 or naturally occurring mutants thereof. In preferred embodiments, the probe/primer further comprises a label group attached thereto and able to be detected, e.g. the label group is selected from a group consisting of radioisotopes, fluorescent compounds, enzymes, and enzyme co-factors. Such probes can be used as a part of a diagnostic test kit for identifying transformed cells, such as for measuring a level of a hUCE nucleic acid in a sample of cells isolated from a patient; e.g. measuring the hUCE mRNA level in a cell; e.g. determining whether the genomic hUCE gene has been mutated or deleted.

The present invention also provides a method for treating an animal having unwanted cell growth characterized by a loss of wild-type p53 function, comprising administering a therapeutically effective amount of an agent able to inhibit a ubiquitin conjugating activity of the subject hUCE protein.

Another aspect of the present invention provides a method of determining if a subject, e.g. a human patient, is at risk for a disorder characterized by unwanted cell proliferation, comprising detecting, in a tissue of the subject, the presence or absence of a genetic lesion characterized by at least one of (i) a mutation of a gene encoding a protein represented by SEQ ID No. 2, or a homolog thereof; or (ii) the mis-expression of the hUCE gene. In preferred embodiments: detecting the genetic lesion comprises ascertaining the existence of at least one of a deletion of one or more nucleotides from the gene, an addition of one or more nucleotides to the gene, an substitution of one or more nucleotides of the gene, a gross chromosomal rearrangement of the gene, a gross alteration in the level of a messenger RNA transcript of the gene, the presence of a non-wild type splicing pattern of a messenger RNA transcript of the gene, or a non-wild type level of the protein. For example, detecting the genetic lesion can comprise (i) providing a probe/primer comprising an oligonucleotide containing a region of nucleotide sequence which hybridizes to a sense or antisense sequence of SEQ ID No. 1 or naturally occurring mutants thereof or 5' or 3' flanking sequences naturally associated with the gene; (ii) exposing the probe/primer to nucleic acid of the tissue; and (iii) detecting, by hybridization of the probe/primer to the nucleic acid, the presence or absence of the genetic lesion; e.g. wherein detecting the lesion comprises utilizing the probe/primer to determine the nucleotide sequence of the hUCE gene and, optionally, of the flanking nucleic acid sequences; e.g. wherein detecting the lesion comprises utilizing the probe/primer in a polymerase chain reaction (PCR); e.g. wherein detecting the lesion comprises utilizing the probe/primer in a ligation chain reaction (LCR). In alternate embodiments, the level of the protein is detected in an immunoassay.

Yet a further aspect of the present invention concerns three-dimensional molecular models of the subject hUCE protein, and their use as templates for the design of agents able to inhibit at least one biological activity of the ubiquitin conjugating enzyme. In preferred embodiments, the molecular models can be used to design pharmacophores by rational drug design; e.g. agents which can inhibit binding of the subject hUCE protein with any one of ubiquitin, an E1 enzyme, an E3 protein(s) such as E6 or E6AP, or the downstream target of the enzyme, such as p53.

For instance, one aspect of the present invention concerns a method for identifying inhibitors of the subject ubiquitin-conjugating enzyme by molecular modeling. In general, the method comprise providing a molecular model of the enzyme, such as the active site, as well as a molecular model of a candidate drug. The drug model is docked with the hUCE model and binding criteria, e.g. electrostatic interactions, hydrogen bonding, hydrophobic interactions, desolvation effects, cooperative motions of ligand and enzyme, of the docked models is determined. Based on the binding criteria of a particular candidate drug, the likelihood of the candidate drug being an inhibitor of said hUCE can be determined. Thus, the subject method can be used to design candidate agents, which when obtained, e.g. by chemical synthesis or from commercial sources, can be provided in an assay with the human ubiquitin-conjugating enzyme of the present invention in order to determine the actual inhibitory activity of the candidate drug. In preferred embodiments, the hUCE model includes the amino acid residues Cys-85, Leu-86, Asp-87, Ile-88, Arg-90, Ser-91, Leu-109, Asn-114, Asp-116, and Asp-117, the atomic coordinates of these residues, at 300° K, having an overall RMS within 2 Å of the atomic coordinates shown in FIG. 2, more preferably an overall RMS within 1 Å, and most preferably an overall RMS within 0.5 Å. Moreover, the hUCE model can include amino acid residues Arg-5 through Met-147 of SEQ ID No. 2. In preferred embodiments, the atomic coordinates for the C-α carbon for each of these residues, at 300° K, have an overall RMS within 2 Å of the C-α atomic coordinates shown in FIG. 1, more preferably an overall RMS within 1 Å, and most preferably an overall RMS within 0.5 Å. Moreover, the hUCE model can include the atomic coordinates for each atom of the amino acid residues Arg-5 through Met-147 of SEQ ID No. 2. In preferred embodiments, the atomic coordinates for each of these residues, at 300° K, have an overall RMS within 2 Å of the C-α atomic coordinates shown in FIG. 1, more preferably an overall RMS within 1 Å, and most preferably an overall RMS within 0.5 Å.

Yet a further aspect of this invention concerns addressable electronic memory means, e.g. RAM or ROM memory, magnetic disk devices, optical storage devices, having stored therein an addressable electronic representation of atomic coordinates of a molecular model of a human ubiquitin-conjugating enzyme. In preferred embodiments, the hUCE model comprises the amino acid residues Cys-85, Leu-86, Asp-87, Ile-88, Arg-90, Ser-91, Leu-109, Asn-114, Asp-116, and Asp-117, the atomic coordinates of these residues, at 300° K, having an overall RMS within 2 Å of the atomic coordinates shown in FIG. 2. In another embodiments, the human ubiquitin-conjugating enzyme model comprises amino acid residues Arg-5 through Met-147 of SEQ ID No. 2, the atomic coordinates of the residues, at 300° K, having an overall RMS within 2 Å of the atomic coordinates shown in FIG. 1.

Other features and advantages of the invention will be apparent from the following detailed description, and from the claims.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual,* 2nd Ed., ed. by Sambrook, Fritsch and Maniatis (Cold Spring Harbor Laboratory Press:1989); *DNA Cloning,* Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., New York); *Gene Transfer Vectors For Mammalian Cells* (J. H. Miller and M. P. Calos eds., 1987, Cold Spring Harbor Laboratory); *Methods In Enzymology,* Vols. 154 and 155 (Wu et al. eds.), *Immunochemical Methods In Cell And Molecular Biology* (Mayer and Walker, eds., Academic Press, London, 1987); *Handbook Of Experimental Immunology,* Volumes I–IV (D. M. Weir and C. C. Blackwell, eds., 1986); *Manipulating the Mouse Embryo,* (Cold Spring Harbor Laboratory Press, Cold Spring Harbor, N.Y., 1986).

BRIEF DESCRIPTION OF THE FIGURES

FIG. 1 is the atomic coordinates for Arg-5 through Met-147 of SEQ ID No. 2 in standard Brookhaven protein databank (pdb) format.

FIG. 3 is the atomic coordinates for Cys-85, Leu-86, Asp-87, Ile-88, Arg-90, Ser-91, Leu-109, Asn-114, Asp-116, and Asp-117 of SEQ ID No. 2 in standard Brookhaven protein databank (pdb) format.

DETAILED DESCRIPTION OF THE INVENTION

Figure 2:
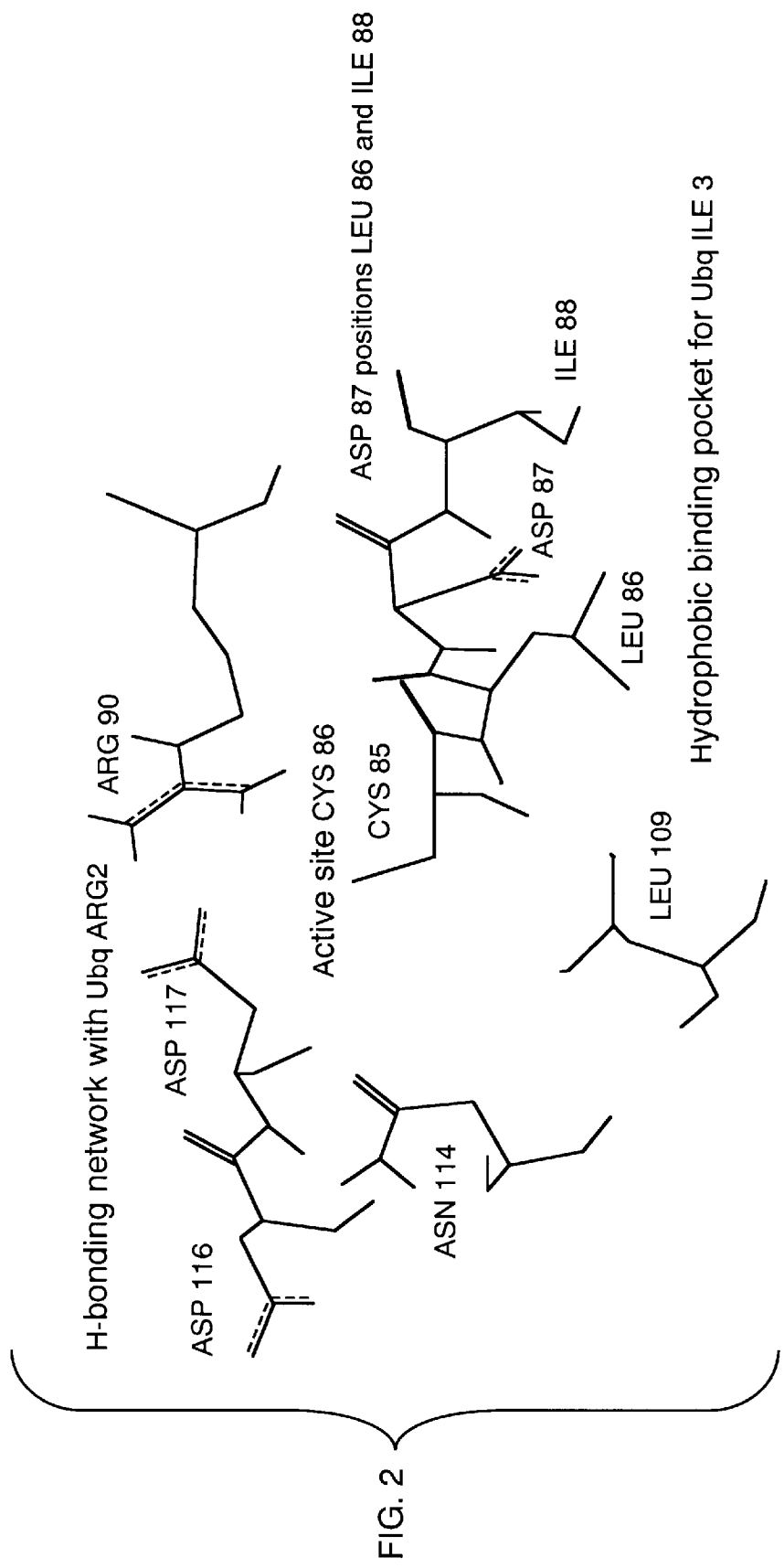
FIG. 2 is a stick figure illustrating the residues of the active site of hUCE.

The ubiquitin system is essential for a wide spectrum of cellular phenomena, and is a component of many biological regulatory mechanisms, including aspects of growth control, metabolic regulation, embryonic development, and cell-cycle progression. As described in Examples 1 and 2 below, we have cloned a novel human ubiquitin-conjugating enzyme (hUCE ) which is implicated in the ubiquitin-mediated inactivation of cell-cycle regulatory proteins, particularly p53. The present invention makes available diagnostic and therapeutic assays and reagents for detecting and treating transformed cells, such as may be useful in the detection of cancer. The present invention also provides reagents for altering the normal regulation of cell proliferation in untransformed cells, such as by upregulating certain cell-cycle checkpoints, e.g. to protect normal cells against DNA damaging reagents.

Accordingly, one aspect of this invention pertains to an isolated nucleic acid comprising the nucleotide sequence encoding the hUCE protein, fragments thereof encoding polypeptides having at least one biological activity of the hUCE protein, and/or equivalents of such nucleic acids. The term "nucleic acid" as used herein is intended to include such fragments and equivalents. The term "equivalent" is understood to include nucleotide sequences encoding functionally equivalent hUCE proteins or functionally equivalent peptides having an activity of an hUCE protein such as described herein. Equivalent nucleotide sequences will include sequences that differ by one or more nucleotide substitutions, additions or deletions, such as allelic variants; and will also include sequences that differ from the nucleotide sequence encoding the presently claimed hUCE protein shown in SEQ ID NO: 1 due to the degeneracy of the genetic code. Equivalents will also include nucleotide sequences that hybridize under stringent conditions (i.e., equivalent to about 20–27° C. below the melting temperature ($T_m$) of the DNA duplex formed in about 1M salt) to the nucleotide sequence of the presently claimed hUCE protein shown in SEQ ID NO: 1. In one embodiment, equivalents will further include nucleic acid sequences derived from and evolutionarily related to the nucleotide sequence shown in SEQ ID NO 1.

Polypeptides referred to herein as having an activity of an hUCE protein are defined as peptides that have an amino acid sequence corresponding to all or a portion of the amino acid sequence of the hUCE protein shown in SEQ ID NO: 2 and which have at least one biological activity of an hUCE protein: an ability to mediate ubiquitination of cellular proteins, e.g. cell-cycle regulatory proteins, e.g. p53; an ability to mediate ubiquitin-dependent degradation of cellular proteins, e.g. cell-cycle regulatory proteins, e.g. p53; an ability to affect the cellular half-life of a cell-cycle regulatory protein, e.g. a cell-cycle checkpoint protein, e.g. p53, e.g. in normal cells, e.g. in normal proliferating cells, e.g. in virally-infected cells, e.g. in papillomavirus infected cells, e.g. in HPV-infected cells, e.g. in HPV-16, HPV-18, HPV-31, or HPV-33 infected cells, e.g. in cells expressing a papillomavirus E6 protein, e.g. in transformed cells, e.g. in cancerous cells. Other biological activities of the subject hUCE proteins are described herein or will be reasonably apparent to those skilled in the art. It will be generally appreciated that it can be advantageous to provide, under various circumstances, homologs of the subject hUCE protein which are either agonists or antagonists of at least one of the biological activities of the naturally occurring hUCE, and such homologs are contemplated as part of the present invention. Homologs of the subject enzyme can be useful to either promote or inhibit only a subset of the biological activities of the naturally occurring hUCE protein, in order that, for example, specific effects can be elicited by treatment with fewer potential side effects, relative to treatment with agonists or antagonists directed to all hUCE-related biological activities.

The term "evolutionarily related to", with respect to nucleic acid sequences encoding hUCE protein, refers to nucleic acid sequences which have arisen naturally in an organism, including naturally occurring mutants. The term also refers to nucleic acid sequences which, while derived from a naturally occurring hUCE, have been altered by mutagenesis, as for example, combinatorial mutagenesis described below, yet still encode polypeptides which have at least one activity of an hUCE protein.

In one embodiment, the nucleic acid is a cDNA encoding a peptide having at least one biological activity of a naturally occurring form of the subject hUCE protein. Preferably, the nucleic acid is a cDNA molecule comprising at least a portion of the nucleotide sequence represented by SEQ ID NO: 1. Preferred portions of the cDNA molecule shown in SEQ ID NO: 1 include the coding region of the molecule.

In another embodiment, the nucleic acid of the invention encodes a peptide having an activity of an hUCE protein and comprises an amino acid sequence represented by SEQ ID NO: 2. Preferred nucleic acids encode a peptide having an hUCE protein activity and being at least 90% homologous, more preferably 95% homologous and most preferably 97% homologous with an amino acid sequence shown in SEQ ID NO: 2. Nucleic acids which encode peptides having an activity of an hUCE protein and having at least about 98–99% homology with a sequence shown in SEQ ID NO: 2 are also within the scope of the invention. Homology refers to sequence similarity between two peptides or between two nucleic acid molecules. Homology can be determined by comparing a position in each sequence which may be aligned for purposes of comparison. When a position in the compared sequence is occupied by the same base or amino acid, then the molecules arc homologous at that position. A degree of homology between sequences is a function of the number of matching or homologous positions shared by the sequences.

Another aspect of the invention provides a nucleic acid which hybridizes under high or low stringency conditions to a nucleic acid which encodes a peptide having all or a portion of an amino acid sequence shown in SEQ ID NO: 2. Appropriate stringency conditions which promote DNA hybridization, for example, 6.0× sodium chloride/sodium citrate (SSC) at about 45° C., followed by a wash of 2.0× SSC at 50° C., are known to those skilled in the art or can be found in *Current Protocols in Molecular Biology,* John Wiley & Sons, New York (1989), 6.3.1–6.3.6. For example, the salt concentration in the wash step can be selected from a low stringency of about 2.0× SSC at 50° C. to a high stringency of about 0.2× SSC at 50° C. In addition, the temperature in the wash step can be increased from low stringency conditions at room temperature, about 22° C., to high stringency conditions at about 65° C.

Isolated nucleic acids encoding peptides having hUCE biological activity, as described herein, and having a sequence which differs from the nucleotide sequence represented in SEQ ID NO: 1 due to degeneracy in the genetic code are also within the scope of the invention. Such nucleic acids encode functionally equivalent peptides (i.e., a peptide having a biological activity of an hUCE protein) but differ in sequence from the sequence shown in SEQ ID NO: 1 due to degeneracy in the genetic code. For example, a number of amino acids are designated by more than one triplet. Codons that specify the same amino acid, or synonyms (for example, CAU and CAC are synonyms for histidine) may result in "silent" mutations which do not affect the amino acid sequence of the subject hUCE protein. However, it is expected that DNA sequence polymorphisms that do lead to changes in the amino acid sequences of the present hUCE protein will exist from one human subject to the next. One skilled in the art will appreciate that these variations in one or more nucleotides (up to about 3–4% of the nucleotides) of the nucleic acids encoding peptides having an activity of an hUCE protein may exist among individuals due to natural allelic variation. Any and all such nucleotide variations and resulting amino acid polymorphisms are within the scope of this invention.

Fragments of the nucleic acid encoding the active portion of the presently claimed hUCE protein are also within the scope of the invention. As used herein, a fragment of the nucleic acid encoding the active portion of an hUCE protein refers to a nucleotide sequence having fewer nucleotides than the nucleotide sequence encoding the entire amino acid sequence of an hUCE protein and which encodes a peptide which possess agonistic or antagonistic activity relative to a naturally occurring form of the subject hUCE protein.

Nucleic acid fragments within the scope of the invention include those capable of hybridizing under high or low stringency conditions with nucleic acids from other species for use in screening protocols to detect hUCE homologs. Nucleic acids within the scope of the invention may also contain linker sequences, modified restriction endonuclease sites and other sequences useful for molecular cloning, expression or purification of recombinant peptides having at least one biological activity of an hUCE protein. In a preferred embodiment, the nucleic acid fragment comprises at least a portion of the nucleic acid sequence represented by nucleotide residues 319 through 441 of SEQ ID No. 1, corresponding to amino acid residues Cys-107 through Met-147. In preferred embodiments, the nucleic acid encodes an hUCE polypeptide which includes Cys-107 through Cys-111, and more preferably includes Cys-107 through Asp-117. As illustrated by FIG. 2, certain of the residues from Cys-107 to Asp-111 are important members of the ubiquitin-binding site of hUCE.

As will be apparent from the present disclosure, a nucleic acid encoding a peptide having an activity of an hUCE protein may be obtained from mRNA present in any of a number of human cell and tissue types. It should also be possible to obtain nucleic acids encoding hUCE proteins from genomic DNA obtained from both adults and embryos. For example, a gene encoding an hUCE protein of the present invention can be cloned from either a cDNA or a genomic library in accordance with protocols herein described, as well as those generally known to those skilled in the art. A cDNA encoding an hUCE protein can be obtained by isolating total mRNA from human cells, including both normal and tumor cells. Double stranded cDNAs can then be prepared from the total mRNA, and subsequently inserted into a suitable plasmid or bacteriophage vector using any one of a number of known techniques. The gene encoding the hUCE protein can also be cloned using established polymerase chain reaction techniques in accordance with the nucleotide sequence information provided by the invention. The nucleic acid of the invention can be DNA or RNA. A preferred nucleic acid is a cDNA encoding an hUCE protein having a sequence shown in SEQ ID NO: 1.

This invention also provides expression vectors containing a nucleic acid encoding the subject hUCE protein, operably linked to at least one transcriptional regulatory sequence. Operably linked is intended to mean that the nucleic acid is linked to a transcriptional regulatory sequence in a manner which allows expression of the hUCE protein encoded by the nucleic acid, and that expression is, for example, either constitutively or inducibly controlled by the transcriptional regulatory sequence. Regulatory sequences are art-recognized and are selected to direct expression of the peptide having an activity of an hUCE protein. Accordingly, the term regulatory sequence includes promoters, enhancers and other expression control elements. Such regulatory sequences are described in, for example, Goeddel; Gene Expression Technology: *Methods in Enzymology* 185, Academic Press, San Diego, Calif. (1990). It should be understood that the design of the expression vector may depend on such factors as the choice of the host cell to be transformed and/or the type of protein desired to be expressed. In preferred embodiments, the expression vector includes a DNA encoding the subject hUCE protein, e.g. a recombinant hUCE protein, e.g. a recombinant protein having an agonistic activity relative to a naturally-occurring form of hUCE, e.g. a recombinant protein having an antagonistic activity relative to a naturally-occurring form of hUCE. Such expression vectors can be used to transfect cells to thereby produce proteins or peptides, including fusion proteins or peptides encoded by nucleic acids as described herein.

Moreover, such vectors can be used as a part of a gene therapy protocol to reconstitute hUCE function in a cell in which hUCE is misexpressed, or alternatively, to provide an antagonist of the naturally-occurring hUCE activity in the cell—such as to inhibit the hUCE-mediated degradation of p53. Examples of therapeutic vehicles for delivery of an hUCE construct to a target cell are disclosed in, for example, PCT publication WO 93/04701, PCT publication WO 92/22635, PCT publication WO 92/20316, PCT publication WO 92/19749, and PCT publication WO 92/06180.

This invention also pertains to a host cell transfected or transformed to express a recombinant form of the subject hUCE protein. The host cell may be any prokaryotic or eukaryotic cell. For example, an hUCE protein of the present invention may be expressed in bacterial cells such as *E. coli*, insect cells (baculovirus), yeast, or mammalian cells. Other suitable host cells are known to those skilled in the art.

The term "recombinant protein" refers to a protein of the present invention which is produced by recombinant DNA techniques, wherein generally DNA encoding the hUCE protein is inserted into a suitable expression vector which is in turn used to transform a host cell to produce the heterologous protein. Moreover, the phrase "derived from", with respect to a recombinant gene encoding the recombinant hUCE, is meant to include within the meaning of "recombinant protein" those proteins having an amino acid sequence of a native hUCE, or an amino acid sequence similar thereto which is generated by mutations including substitutions and deletions of a naturally occurring hUCE protein of a organism. Recombinant proteins preferred by the present invention, in addition to native hUCE proteins, are at least 90% homologous, more preferably 95% homologous and most preferably 97% homologous with an amino acid sequence shown in SEQ ID NO: 2. Polypeptides having an activity of an hUCE protein and having at least about 90%, more preferably at least about 95%, and most preferably at least about 98–99% homology with a sequence shown in SEQ ID NO: 2 are also within the scope of the invention.

The present invention further pertains to recombinant hUCE homologs which are encoded by genes derived from other non-human mammals, e.g. mouse, rat, rabbit, or pig, and which have amino acid sequences evolutionarily related to an hUCE protein. Such recombinant hUCE proteins preferably are capable of functioning in one of either role of an agonist or antagonist of at least one biological activity of an hUCE. The term "evolutionarily related to", with respect to amino acid sequences of the present recombinant hUCE protein, refers to hUCE proteins having amino acid sequences which have arisen naturally, as well as mutational variants of hUCE proteins which are derived, for example, by combinatorial mutagenesis or scanning mutagenesis.

The present invention further pertains to methods of producing the subject hUCE proteins. For example, a host cell transfected with a nucleic acid vector directing expression of a nucleotide sequence encoding the subject hUCE protein can be cultured under appropriate conditions to allow expression of the peptide to occur. The peptide may be secreted (e.g. through use of recombinantly added signal sequence) and isolated from a mixture of cells and medium containing a secreted form of a recombinant hUCE protein. Alternatively, the peptide may be retained cytoplasmically, as it presumably is its naturally occurring form, and the cells harvested, lysed and the protein isolated. A cell culture includes host cells, media and other byproducts. Suitable media for cell culture are well known in the art. The subject hUCE polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for a peptide having an activity of an hUCE protein. In a preferred embodiment, the hUCE protein is a fusion protein containing a domain which facilitates its purification, such as an hUCE-GST fusion protein described below.

Thus, a nucleotide sequence derived from the cloning of the hUCE protein of the present invention, encoding all or a selected portion of the protein, can be used to produce a recombinant form of hUCE via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures used in producing other well-known proteins, e.g. insulin, interferons, human growth hormone, IL-1, IL-2, and the like. Similar procedures, or modifications thereof, can be employed to prepare recombinant hUCE proteins, or portions thereof, by microbial means or tissue-culture technology in accord with the subject invention.

The recombinant hUCE protein can be produced by ligating the cloned gene, or a portion thereof, into a vector suitable for expression in either prokaryotic cells, eukaryotic cells, or both. Expression vehicles for production of recombinant hUCE include plasmids and other vectors. For instance, suitable vectors for the expression of hUCE include plasmids of the types: pBR322-derived plasmids, pEMBL-derived plasmids, pEX-derived plasmids, pBTac-derived plasmids and pUC-derived plasmids for expression in prokaryotic cells, such as E. coli.

A number of vectors exist for the expression of recombinant proteins in yeast. For instance, YEP24, YIP5, YEP51, YEP52, pYES2, and YRP17 are cloning and expression vehicles useful in the introduction of genetic constructs into S. cerevisiae (see, for example, Broach et al. (1983) in Experimental Manipulation of Gene Expression, ed. M. Inouye Academic Press, p. 83, incorporated by reference herein). These vectors can replicate in E. coli due the presence of the pBR322 ori, and in S. cerevisiae due to the replication determinant of the yeast 2 micron plasmid. In addition, drug resistance markers such as ampicillin can be used.

The preferred mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art.

For other suitable expression systems for both prokaryotic and eukaryotic cells, as well as general recombinant procedures, see Molecular Cloning: A Laboratory Manual, 2nd Ed., ed. by Sambrook, Fritsch and Maniatis (Cold Spring Harbor Laboratory Press: 1989) Chapters 16 and 17. In some instances, it may be desirable to express the recombinant hUCE by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

When expression of a portion of hUCE is desired, i.e. a truncation mutant, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from E. coli (Ben-Bassat et al. (1987) J. Bacteriol. 169:751–757) and Salmonella typhimurium and its in vitro activity has been demonstrated on recombinant proteins (Miller et al. (1987) PNAS 84:2718–1722). Therefore, removal of an N-terminal methionine, if desired, can be achieved either in vivo by expressing hUCE-derived polypeptides in a host which produces MAP (e.g., E. coli or CM89 or S. cerevisiae), or in vitro by use of purified MAP (e.g., procedure of Miller et al.).

Alternatively, the coding sequences for the polypeptide can be incorporated as a part of a fusion gene including a nucleotide sequence encoding a different polypeptide. This type of expression system can be useful under conditions where it is desirable to produce an immunogenic fragment of an hUCE protein. For example, the VP6 capsid protein of rotavirus can be used as an immunologic carrier protein for portions of the hUCE polypeptide, either in the monomeric form or in the form of a viral particle. The nucleic acid sequences corresponding to the portion of the hUCE protein to which antibodies are to be raised can be incorporated into a fusion gene construct which includes coding sequences for a late vaccinia virus structural protein to produce a set of recombinant viruses expressing fusion proteins comprising a portion of the protein hUCE as part of the virion. It has been demonstrated with the use of immunogenic fusion proteins utilizing the Hepatitis B surface antigen fusion proteins that recombinant Hepatitis B virions can be utilized in this role as well. Similarly, chimeric constructs coding for fusion proteins containing a portion of an hUCE protein and the poliovirus capsid protein can be created to enhance immunogenicity of the set of polypeptide antigens (see, for example, EP Publication No. 0259149; and Evans et al. (1989) Nature 339:385; Huang et al. (1988) J. Virol. 62:3855; and Schlienger et al. (1992) J. Virol. 66:2).

The Multiple Antigen Peptide system for peptide-based immunization can be utilized, wherein a desired portion of an hUCE protein is obtained directly from organo-chemical synthesis of the peptide onto an oligomeric branching lysine core (see, for example, Posnett et al. (1988) J Biol Chem 263:1719 and Nardelli et al. (1992) J Immunol 148:914). Antigenic determinants of the hUCE proteins can also be expressed and presented by bacterial cells.

In addition to utilizing fusion proteins to enhance immunogenicity, it is widely appreciated that fusion proteins can also facilitate the expression of proteins, such as the hUCE protein of the present invention. For example, as described below, the hUCE protein can be generated as a glutathione-S-transferase (GST) fusion protein. Such GST fusion proteins can enable purification of the hUCE protein, such as by the use of glutathione-derivatized matrices (see, for example, *Current Protocols in Molecular Biology*, eds. Ausubel et al. (New York: John Wiley & Sons, 1991); Smith et al. (1988) *Gene* 67:31; and Kaelin et al. (1992) *Cell* 70:351). In another embodiment, a fusion gene coding for a purification leader sequence, such as a poly-(His)/enterokinase cleavage site sequence at the N-terminus of the desired portion of the hUCE protein, can allow purification of the expressed hUCE-fusion protein by affinity chromatography using a $Ni^{2+}$ metal resin. The purification leader sequence can then be subsequently removed by treatment with enterokinase (e.g., see Hochuli et al. (1987) *J Chromatography* 411:177; and Janknecht et al. *PNAS* 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al. John Wiley & Sons: 1992).

Another aspect of the invention pertains to isolated peptides having an activity of the naturally occurring form(s) of the subject hUCE protein or which are antagonists of at least one biological activity of the naturally occurring form of the subject hUCE protein. A peptide having an activity of an hUCE protein has at least one biological activity of an hUCE protein. In preferred embodiments, a biological activity of an hUCE protein includes: an ability to mediate ubiquitination of cellular proteins, e.g. cell-cycle regulatory proteins, e.g. p53; an ability to mediate ubiquitin-dependent degradation of cellular proteins, e.g. cell-cycle regulatory proteins, e.g. p53; an ability to affect the cellular half-life of a cell-cycle checkpoint protein, e.g. p53, e.g. in normal cells, e.g. in normal proliferating cells, e.g. in virally infected cells, e.g. in papilloma virus infected cells, e.g. in HPV-infected cells, e.g. in HPV-16, HPV-18, HPV-31, or HPV-33 infected cells, e.g. in PV E6 expressing cells, e.g. in transformed cells, e.g. in cancerous cells. Other biological activities of the subject hUCE protein are described herein or will be reasonably apparent to those skilled in the art. A peptide having at least one biological activity of the subject hUCE protein may differ in amino acid sequence from the sequence shown in SEQ ID NO: 2 but preferably, such differences result in a modified protein which functions in the same or similar manner (e.g. agonist) as a native hUCE protein or which has the same or similar characteristics of a native hUCE protein. Furthermore, as described herein, peptides having amino acid sequences homologous to SEQ ID No.2 yet which function as antagonists of a naturally occurring hUCE protein are also comtemplated by the present invention. Various modifications of the hUCE protein to produce these and other functionally equivalent peptides are described in detail herein. The term peptide, as used herein, refers to peptides, proteins, and polypeptides.

The present invention also makes available isolated hUCE protein, which is isolated from or otherwise substantially free of other extracellular proteins, especially other proteins of the human ubiquitin conjugating system (i.e. other E1 or E2 enzymes, as well as E3 proteins or ubiquitin) normally associated with the hUCE protein in the cellular milleau. The term "substantially free of other extracellular proteins" (also referred to herein as "contaminating proteins") is defined as encompassing preparations of the subject hUCE protein comprising less than 20% (by dry weight) contaminating protein, and preferably comprising less than 5% contaminating protein. Functional forms of the subject hUCE proteins can be prepared, for the first time, as purified preparations by using a cloned gene as described herein. By "purified", it is meant, when referring to a peptide or DNA or RNA sequence, that the indicated molecule is present in the substantial absence of other biological macromolecules, such as other proteins (particularly other enzymes of the ubiquitin system such as other E1 or E2 proteins, as well as other contaminating proteins). The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" do not encompass either natural materials in their native state or natural materials that have been separated into components (e.g., in an acrylamide gel) but not obtained either as pure (e.g. lacking contaminating proteins or chromatography reagents such as denaturing agents and polymers, e.g. acrylamide or agarose) substances or solutions. The term "isolated" as also used herein with respect to nucleic acids, such as DNA or RNA, refers to molecules separated from other DNAs, or RNAs, respectively, that are present in the natural source of the macromolecule. For example, an isolated nucleic acid encoding the subject hUCE protein preferably includes no more than 10 kilobases of sequence which naturally flanks the hUCE gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state.

Isolated peptides having an activity of an hUCE protein, or which can function as antagonists of a naturally occurring form of the hUCE protein described herein can also be obtained by screening peptides recombinantly produced from the corresponding fragment of the nucleic acid of hUCE encoding such peptides. In addition, fragments can be chemically synthesized using techniques known in the art such as conventional Merrifield solid phase f-Moc or t-Boc chemistry. For example, the hUCE protein may be arbitrarily divided into fragments of desired length with no overlap of the fragments, or preferably divided into overlapping fragments of a desired length. The fragments can be produced (recombinantly or by chemical synthesis) and tested to identify those peptides having an hUCE protein activity or alternatively to identify antagonists.

It is also possible to modify the structure of a peptide having an activity of an hUCE protein for such purposes as enhancing therapeutic or prophylactic efficacy, or stability (e.g., shelf life ex vivo and resistance to proteolytic degradation in vivo). Such modified peptides are considered functional equivalents of peptides having an activity of an hUCE protein as defined herein. A modified peptide can be produced in which the amino acid sequence has been altered, such as by amino acid substitution, deletion, or addition.

For instance, variations of the hUCE peptides and hUCE-encoding nucleic acid molecules are contemplated as being equivalent to those peptides and nucleic acid molecules that are set forth in more detail, as will be appreciated by those skilled in the art. To illustrate, it is reasonable to expect that an isolated replacement of a leucine with an isoleucine or valine, an aspartate with a glutamate, a threonine with a serine, or a similar replacement of an amino acid with a structurally related amino acid (i.e. conservative mutations) will not have a major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, *Biochemistry*, 2nd ed, Ed. by L. Stryer, W H Freeman and Co.: 1981). Whether a change in the amino acid sequence of a peptide results in a functional hUCE homolog can be readily determined by assessing the ability of the variant peptide to, e.g. mediate p53 ubiquitination in a fashion similar to the wild-type hUCE. Peptides in which more than one replacement has taken place can readily be tested in the same manner.

This invention further contemplates a method of generating sets of combinatorial mutants of hUCE, as well as truncation mutants, and is especially useful for identifying potential variant sequences (e.g. homologs) that are functional in ubiquitinating cellular proteins, especially cell-cycle regulatory proteins such as p53. In addition to generating novel hUCE agonists, another purpose of screening such combinatorial libraries can be to generate, for example, novel hUCE homologs which act as antagonist of normal hUCE activity, e.g. which inhibit p53 ubiquitination, or alternatively, possess novel activities all together. Such proteins, when expressed from recombinant DNA constructs, can be used in gene therapy protocols.

Likewise, mutagenesis can give rise to hUCE homologs which have intracellular half-lives dramatically different than the corresponding wild-type protein. For example, the altered protein can be rendered either more stable or less stable to proteolytic degradation or other cellular process which result in destruction of, or otherwise inactivation of, a naturally occurring form of the subject hUCE protein. Such hUCE homologs (either agonist or antagonist homologs), and the genes which encode them, can be utilized to alter the envelope of recombinant hUCE expression by modulating the half-life of the protein. For instance, a short half-life for the recombinant hUCE can give rise to more transient biological effects associated with that homolog and, when part of an inducible expression system, can allow tighter control of recombinant hUCE levels within the cell. As above, such proteins, and particularly their recombinant nucleic acid constructs, can be used in gene therapy protocols.

In one aspect of this method, the amino acid sequences for a population of hUCE homologs or other related proteins are aligned, preferably to promote the highest homology possible. Such a population of variants can include, for example, hUCE homologs from one or more species, or hUCE homologs from the same species but which differ due to mutation. Amino acids which appear at each position of the aligned sequences are selected to create a degenerate set of combinatorial sequences.

In a preferred embodiment, the combinatorial hUCE library is produced by way of a degenerate library of genes encoding a library of polypeptides which each include at least a portion of potential hUCE sequences. A mixture of synthetic oligonucleotides can be enzymatically ligated into gene sequences such that the degenerate set of potential hUCE sequences are expressible as individual polypeptides, or alternatively, as a set of larger fusion proteins (e.g. for phage display) containing the set of hUCE sequences therein.

There are many ways by which the library of potential hUCE homologs can be generated from a degenerate oligonucleotide sequence. Chemical synthesis of a degenerate gene sequence can be carried out in an automatic DNA synthesizer, and the synthetic genes then be ligated into an appropriate gene for expression. The purpose of a degenerate set of genes is to provide, in one mixture, all of the sequences encoding the desired set of potential hUCE sequences. The synthesis of degenerate oligonucleotides is well known in the art (see, for example, Narang, S A (1983) *Tetrahedron* 39:3; Itakura et al. (1981) *Recombinant DNA, Proc 3rd Cleveland Sympos. Macromolecules*, ed. A G Walton, Amsterdam: Elsevier pp273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815).

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis of hUCE homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate hUCE sequences created by combinatorial mutagenesis techniques.

In one illustrative screening assay, the candidate hUCE gene products are displayed on the surface of a cell or viral particle, and the ability of particular cells or viral particles to bind other components of the ubiquitin pathway, e.g. E1 or E3 proteins, ubiquitin, or p53, via this gene product is detected in a "panning assay". For instance, the gene library can be cloned into the gene for a surface membrane protein of a bacterial cell, and the resulting fusion protein detected by panning (Ladner et al., WO 88/06630; Fuchs et al. (1991) *Bio/Technology* 9:1370–1371; and Goward et al. (1992) *TIBS* 18:136–140). In a similar fashion, fluorescently labeled molecules which bind hUCE can be used to score for potentially functional hUCE homologs. Cells can be visually inspected and separated under a fluorescence microscope, or, where the morphology of the cell permits, separated by a fluorescence-activated cell sorter.

In an alternate embodiment, the gene library is expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at very high concentrations, a large number of phage can be screened at one time. Second, since each infectious phage displays the combinatorial gene product on its surface, if a particular phage is recovered from an affinity matrix in low yield, the phage can be amplified by another round of infection. The group of almost identical *E. coli* filamentous phages M 13, fd, and f1 are most often used in phage display libraries, as either of the phage gIII or gVIII coat proteins can be used to generate fusion proteins without disrupting the ultimate packaging of the viral particle (Ladner et al. PCT publication WO 90/02909; Garrard et al., PCT publication WO 92/09690; Marks et al. (1992) *J. Biol. Chem.* 267:16007–16010; Griffiths et al. (1993) *EMBO J* 12:725–734; Clackson et al. (1991) *Nature* 352:624–628; and Barbas et al. (1 992) *PNAS* 89:4457–4461).

In an illustrative embodiment, the recombinant phage antibody system (RPAS, Pharmacia Catalog number 27-9400-01) can be easily modified for use in expressing and screening hUCE combinatorial libraries. For instance, the pCANTAB 5 phagemid of the RPAS kit contains the gene which encodes the phage gIII coat protein. The hUCE combinatorial gene library can be cloned into the phagemid adjacent to the gIII signal sequence such that it will be expressed as a gIII fusion protein. After ligation, the phagemid is used to transform competent *E. coli* TG1 cells. Transformed cells are subsequently infected with M13KO7 helper phage to rescue the phagemid and its candidate hUCE gene insert. The resulting recombinant phage contain phagemid DNA encoding a specific candidate hUCE, and display one or more copies of the corresponding fusion coat protein. The phage-displayed candidate hUCE which are capable of binding a particular target protein, such as an E1 enzyme, an E3 protein (i.e. E6 or E6-AP), or p53, are selected or enriched by panning. For instance, the phage library can be panned on glutathione immobilized p53-GST fusion proteins or E6-GST or E6-AP-GST fusion proteins (described, for example, in U.S. patent application Ser. No. 08/176,937), and unbound phage washed away from the cells. The bound phage is then isolated, and if the recombinant phage express at least one copy of the wild type gIII coat protein, they will retain their ability to infect *E. coli*. Thus, successive rounds of reinfection of *E. coli*, and panning can be employed to greatly enrich for hUCE homologs that retain some ability to interact with normal targets of the wild-type hUCE, and which can then be screened for further biological activities in order to differentiate agonists and antagonists. In an exemplary embodiment, by use of two or more target proteins in sequential panning steps, the phage display library can be used to isolate hUCE homologs which are candidate antagonists of the normal cellular function of the naturally occurring hUCE. For instance, isolating from the library those variants which retain the ability to bind, for example, either the papillomavirus E6 protein or the cellular E6-AP protein, but which are unable to bind p53, provides a set of hUCE homologs some of which may be capable of antagonizing the ability of the wild-type hUCE to mediate ubiquitination of p53.

In yet another illustrative embodiment, the p53-dependent reporter construct described in Example 9 can be used to identify antagonists through their ability to enhance expression of the reporter gene by inhibiting the degradation of p53 wild-type hUCE. Thus, a combinatorial library can be screened by a detecting expression of the reporter gene, and appropriate clones isolated for further manipulation.

In light of the present disclosure, other forms of mutagenesis generally applicable will be apparent to those skilled in the art in addition to the aforementioned combinatorial mutagenesis based on conserved versus non-conserved residues. For example, hUCE homologs (both agonist and antagonist forms) can be generated and screened using, for example, alanine scanning mutagenesis and the like (Ruf et al. (1994) *Biochemistry* 33:1565–1572; Wang et al. (1994) *J Biol Chem* 269:3095–3099; Balint et al. (1993) *Gene* 137:109–118; Grodberg et al. (1993) *Eur J Biochem* 218:597–601; Nagashima et al. (1993) *J Biol Chem* 268:2888–2892; Lowman et al. (1991) *Biochemistry* 30:10832–10838; and Cunningham et al. (1989) *Science* 244:1081–1085), by linker scanning mutagenesis (Gustin et al. (1993) *Virology* 193:653–660; Brown et al. (1992) *Mol Cell Biol* 12:2644–2652; McKnight et al. (1982) *Science* 232:316); or by saturation mutagenesis (Meyers et al. (1986) *Science* 232:613).

An important goal of the present invention is to provide reduction of the hUCE protein to small functional units that can be ultimately used to generate hUCE mimetics, e.g. peptide or non-peptide agents, which are able to disrupt binding of hUCE with other cellular and/or viral proteins. Thus, such mutagenic techniques are particularly useful to map the determinants of the hUCE protein which participate in protein-protein interactions involved in, for example, binding of the subject hUCE to other proteins of the ubiquitin-conjugating system (both cellular and viral), as well as the target protein itself (e.g. p53). To illustrate, the critical residues of hUCE involved in molecular recognition of E6 and/or E6-AP can be determined and used to generate hUCE-derived peptidomimetics which competitively inhibit hUCE binding (see, for example, "Peptide inhibitors of human papillomavirus protein binding to retinoblastoma gene protein", European patent applications EP-412,762A and EP-531,080A). By employing, for example, scanning mutagenesis to map the residues of hUCE involved in ubiquitination of cellular proteins, peptidomimetic compounds, e.g. diazepine (benzodiazepine) or isoquinoline derivatives, can be generated which are capable of binding a papillomavirus E6 protein or cellular E6-AP, and thereby prevent their interaction with hUCE and disrupt hUCE-mediated destruction of, for example, p53. Furthermore, such data concerning protein-protein interactions can be used in conjunction with the molecular model of hUCE described below for rational design of mimetics of this interaction.

Another aspect of the invention pertains to an antibody specifically reactive with the subject hUCE protein. For example, by using immunogens derived from the hUCE protein of the present invention, anti-protein/anti-peptide antisera or monoclonal antibodies can be made by standard protocols (See, for example, *Antibodies: A Laboratory Manual* ed. by Harlow and Lane (Cold Spring Harbor Press: 1988)). A mammal such as a mouse, a hamster or rabbit can be immunized with an immunogenic form of the peptide (e.g., the whole hUCE protein or an antigenic fragment which is capable of eliciting an antibody response). Techniques for conferring immunogenicity on a protein or peptide include conjugation to carriers or other techniques well known in the art. An immunogenic portion of the subject hUCE protein can be administered in the presence of adjuvant. The progress of immunization can be monitored by detection of antibody titers in plasma or serum. Standard ELISA or other immunoassays can be used with the immunogen as an antigen to assess the levels of antibodies. In a preferred embodiment, the subject antibodies are immunospecific for hUCE antigenic determinants, e.g. antigenic determinants of a protein represented by SEQ ID No. 2 or a closely related human or non-human mammalian homolog (e.g. 90 percent homologous to SEQ ID No. 2, more preferably at least 95 percent homologous to SEQ ID No.2). In yet a further preferred embodiment of the present invention, the anti-hUCE antibodies does not substantially cross react with a protein which is: e.g. less than 90 percent homologous with SEQ ID No. 2; e.g. less than 95 percent homologous with SEQ ID No. 2; e.g. less than 98–99 percent homologous with SEQ ID No.2. By "does not substantially cross-react", it is meant that: the antibody has a binding affinity for a non-homologous E2 enzyme which is less than 10 percent, more preferably less than 5 percent, and most preferably less than about 1–2 percent of the binding affinity of that antibody for the protein of SEQ ID No. 2; the antibody does not specifically bind a protein which is non-homologous to SEQ ID No. 2.

Following immunization, anti-hUCE antisera can be obtained and, if desired, polyclonal anti-hUCE antibodies isolated from the serum. To produce monoclonal antibodies, antibody producing cells (lymphocytes) can be harvested from an immunized animal and fused by standard somatic cell fusion procedures with immortalizing cells such as myeloma cells to yield hybridoma cells. Such techniques are well known in the art, an include, for example, the hybridoma technique (originally developed by Kohler and Milstein, (1975) *Nature*, 256: 495–497), the human B cell hybridoma technique (Kozbar et al., (1983) *Immunology Today*, 4: 72), and the EBV-hybridoma technique to produce human monoclonal antibodies (Cole et al., (1985) *Monoclonal Antibodies and Cancer Therapy*, Alan R. Liss, Inc. pp. 77–96). Hybridoma cells can be screened immunochemically for production of antibodies specifically reactive with the subject hUCE protein and monoclonal antibodies isolated from a culture comprising such hybridoma cells.

The term antibody as used herein is intended to include fragments thereof which are also specifically reactive with the hUCE protein of the present invention. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments. The antibody of the present invention is further intended to include bispecific and chimeric molecules having an anti-hUCE portion.

Both monoclonal and polyclonal antibodies (Ab) directed against hUCE or hUCE variants, and antibody fragments such as Fab' and F(ab')$_2$, can be used as specialty chemicals to block the action of hUCE and allow the study of, for example, the cell cycle or cell proliferation when hUCE inhibits, e.g. by microinjection of anti-hUCE antibodies.

Antibodies which specifically bind hUCE epitopes can also be used in immunohistochemical staining of tissue samples in order to evaluate the abundance and pattern of expression of hUCE. Anti-hUCE antibodies can be used diagnostically in immuno-precipitation and immuno-blotting to detect and evaluate hUCE levels in tissue or bodily fluid as part of a clinical testing procedure. For instance, such measurements can be useful in predictive valuations of the onset or progression of tumors. Likewise, the ability to monitor hUCE levels in an individual can allow determination of the efficacy of a given treatment regimen for an individual afflicted with such a disorder. The level of hUCE can be measured in cells isolated from bodily fluid, such as in samples of cerebral spinal fluid or blood, or can be measured in tissue, such as produced by biopsy. Diagnostic assays using anti-hUCE antibodies can include, for example, immunoassays designed to aid in early diagnosis of a neoplastic or hyperplastic disorder, e.g. the presence of cancerous cells in the sample, e.g. to detect cells in which a lesion of the hUCE gene has occurred.

Another application of anti-hUCE antibodies is in the immunological screening of cDNA libraries constructed in expression vectors, such as λgt11, λgt18–23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of hUCE can then be detected with antibodies, as, for example, reacting nitrocellulose filters lifted from infected plates with anti-hUCE antibodies. Phage, scored by this assay, can then be isolated from the infected plate. Thus, the presence of hUCE homologs can be detected and cloned from other human sources, i.e. to identified other closely homologous human isoforms, as well as to identify hUCE homologs in other mammals.

Moreover, the nucleotide sequence determined from the cloning of subject hUCE from a human cell line will further allow for the generation of probes designed for use in identifying hUCE homologs in other human cell-types, particularly cancer or other transformed or immortalized cells, as well as hUCE homologs from other non-human mammals.

In addition, nucleotide probes can be generated from the cloned sequence of the hUCE protein, which allow for histological screening of intact tissue and tissue samples for the presence of hUCE mRNA. Similar to the diagnostic uses of anti-hUCE antibodies, the use of probes directed to hUCE mRNA, or to genomic hUCE sequences, can be used for both predictive and therapeutic evaluation of allelic mutations which might be manifest in, for example, neoplastic or hyperplastic disorders (e.g. unwanted cell growth). Used in conjunction with anti-hUCE antibody immunoassays, the nucleotide probes can help facilitate the determination of the molecular basis for a developmental disorder which may involve some abnormality associated with expression (or lack thereof) of an hUCE protein. For instance, variation in hUCE synthesis can be differentiated from a mutation in the hUCE coding sequence.

For example, the present method provides a method for determining if a subject is at risk for a disorder characterized by unwanted cell proliferation. In preferred embodiments, the subject method can be generally characterized as comprising detecting, in a tissue of a subject (e.g. a human patient), the presence or absence of a genetic lesion characterized by at least one of (i) a mutation of a gene encoding hUCE or (ii) the mis-expression of the hUCE gene. To illustrate, such genetic lesions can be detected by ascertaining the existence of at least one of (i) a deletion of one or more nucleotides from the hUCE gene, (ii) an addition of one or more nucleotides to the hUCE gene, (iii) a substitution of one or more nucleotides of the hUCE gene, (iv) a gross chromosomal rearrangement of the hUCE gene, (v) a gross alteration in the level of a messenger RNA transcript of the hUCE gene, (vi) the presence of a non-wild type splicing pattern of a messenger RNA transcript of the hUCE gene, and (vii) a non-wild type level of the hUCE protein. In one aspect of the invention there is provided A probe/primer comprising an oligonucleotide containing a region of nucleotide sequence which is capable of hybridizing to a sense or antisense sequence of SEQ ID NO: 1 or naturally occurring mutants thereof, or 5' or 3' flanking sequences or intronic sequences naturally associated with the hUCE gene. The probe is exposed to nucleic acid of a tissue sample; and the hybridization of the probe to the sample nucleic acid is detected. In certain embodiments, detection of the lesion comprises utilizing the probe/primer in, for example, a polymerase chain reaction (PCR) (see, e.g., U.S. Pat. Nos. 4,683,195 and 4,683,202), or, alternatively, in a ligation chain reaction (LCR) (see, e.g., Landegran et al. (1988) *Science* 241:1077–1080; and Nakazawa et al. (1994) *PNAS* 91:360–364), the later of which ]can be particularly useful for detecting even point mutations in the hUCE gene. Alternatively, or additionally, the level of hUCE protein can be detected in an immunoassay.

Also, the use of anti-sense techniques (e.g. microinjection of antisense molecules, or transfection with plasmids whose transcripts are anti-sense with regard to, e.g. hUCE mRNA) can be used to investigate the role of hUCE in the cell cycle and cell proliferation, by inhibiting endogenous hUCE production. Such techniques can be utilized in cell culture, but can also be used in the creation of transgenic animals.

In another aspect, the invention features transgenic non-human animals which express an hUCE gene of the present invention, or which have had one or more copies of their gene(s) which encode a non-human isoform of the subject hUCE disrupted, e.g. heterozygous or homozygous disruption, in at least one of the tissue or cell-types of the animal. In another aspect, the invention features an animal model for developmental diseases, which mis-expresses one or more allelic copies of their gene(s) which encode a non-human isoform of the subject hUCE, e.g. its transcription is controlled by transcriptional regulatory sequences which are not naturally associated with the wild-type hUCE gene. For example, a mouse can be bred in which the gene encoding the mouse isoform of the subject hUCE protein is deleted, or in which all or part of one or more its exons are deleted. Such a mouse model can then be used to study disorders arising from mis-expression of hUCE genes.

Furthermore, the present invention, by making available purified and recombinant forms of the subject hUCE protein, will allow the development of assays which can be used to screen for drugs which are either agonists or antagonists. For instance, in addition to agents which disrupt binding of the hUCE protein to other cellular (or viral) proteins, inhibitors of the enzymatic activity of the subject hUCE can be used to prevent transfer of ubiquitin to hUCE and/or inhibit any downstream transfer of ubiquitin from hUCE (e.g. to p53 or an intermediary E3 complex, e.g. E6/E6-AP). In a preferred embodiment, the hUCE inhibitor is a mechanism based inhibitor which chemically alters the enzyme, e.g. covalently binds Cys-85, and which is a specific inhibitor of hUCE, e.g. has an inhibition constant 10-fold, 100-fold, or more preferably, 1000-fold different for human E2 enzymes other than the subject hUCE protein. Inhibitor specificity can be improved, for example, by utilizing specificity sub-sites of the hUCE enzyme involved in interactions between hUCE and p53 or hUCE and E1, which are unique to one of those complexes relative to other human E2 enzymes.

Assays for the measurement of ubiquitination are disclosed in U.S. patent application Ser. No. 08/176,937, filed on Jan. 4, 1994, and herein incorporated by reference. Such assays can be used in conjunction with the subject hUCE protein to generate a ubiquitin-conjugating system to detect agents able to inhibit hUCE-mediated ubiquitination of a cellular or target protein. Such agents can be used to, for example, treat papillomavirus infected cells.

The subject assay comprises a ubiquitin-conjugating system that includes the regulatory protein and ubiquitin, and provides conditions which promote the ubiquitination of the target protein. The level of ubiquitination of the subject protein brought about by the system is measured in the presence and absence of a candidate agent, and a decrease in the level ubiquitin conjugation is indicative of an inhibitory activity for the candidate agent. As described below, the level of ubiquitination of the regulatory protein can be measured by determining the actual concentration of protein:ubiquitin conjugates formed; or inferred by detecting some other quality of the subject protein affected by ubiquitination, including the proteolytic degradation of the protein. In certain embodiments, the present assay comprises an in vivo ubiquitin-conjugating system, such as a cell able to conduct the regulatory protein through at least a portion of a ubiquitin-mediated proteolytic pathway. In other embodiments, the present assay comprises an in vitro ubiquitin-conjugating system in which at least the ability to transfer ubiquitin to the regulatory protein is constituted. Moreover, the present assay may further comprise auxiliary proteins which influence the level of ubiquitin-mediated degradation, including viral oncogenic proteins, such as the E6 protein of high-risk HPVs, which influence the level of the regulatory protein in an infected cell by enhancing or otherwise altering the proteolysis of the protein.

As described herein, inhibitors of the ubiquitin-mediated proteolysis of the regulatory protein refer generally to those agents which may act anywhere along the ubiquitin degradation pathway; from the reaction steps leading up to an including conjugation of ubiquitin to the protein of interest, to the interaction and degradation of the ubiquitin conjugate by a proteosome complex. A subset of this class of inhibitors comprises the ubiquitination inhibitors, which include those agents that act at the level of preventing conjugation of ubiquitin to the subject protein, rather than at the steps of proteolytic degradation of the protein. As more fully illustrated below, this subset of inhibitors is directed more particularly to such steps as the activation of ubiquitin by E1, transfer of ubiquitin from E1 to E2, or transfer of the activated ubiquitin to the target regulatory protein from the E2:Ub conjugate. Likewise, protease inhibitors refer to that subset of inhibitors which act at the step of proteosome-catalyzed degradation of the regulatory protein:ubiquitin conjugate. Moreover, as will be clear from the following description, particular embodiments of the present assay can be chosen so as to discriminate between ubiquitination inhibitors and protease inhibitors.

In one embodiment of the subject assay, the target regulatory protein is the tumor suppressor p53, and the assay is used to identify inhibitors of ubiquitin-mediated destruction of p53. Many lines of evidence point to the importance of p53 in human carcinogenesis. For instance, mutations within the p53 gene are the most frequent genetic aberration thus far associated with human cancer. Although p53 can block the progression of the cell cycle when artificially expressed at high levels, it appears to be dispensable for normal development. Thus, for mice containing homozygous deletions and humans harboring germline mutations of p53, development is normal and p53 protein is expressed at very low levels in most cell types. Emerging evidence, however, suggests that p53 is a checkpoint protein that plays an important role in sensing DNA damage or regulating cellular response to stress. Under normal conditions, p53 is an unstable protein and is present at very low levels in the cell, and the level of p53 in a cell appears to be controlled at least in party by degradation involving the ubiquitin system. Treating cells with UV light or X rays dramatically reduces the rate of p53 degradation, leading to a rapid increase in its concentration in the cell and presumably inducing the transcription of genes that block passage through the restriction point. However, while normal cell lines irradiated in G1 fail to enter S phase, many tumor lines do not. In fact, there is a perfect correlation between cell lines that lack this feedback control and cells that have mutations in the p53 gene. These mutations are of two sorts: recessive mutations that inactivate the gene, and dominant mutations that produce abnormal proteins. An inhibitor developed using the subject assay could be used therapeutically to enhance the function of the p53 checkpoint by increasing the steady state concentration of p53 in the treated cell. The anti-proliferative activity of such an inhibitor can be employed in the treatment of hyperplasias or neoplasias by increasing the fortitude of the checkpoint in transformed cells which contain wild-type p53 (i.e. can induce apoptosis in cells overexpressing c-myc), or by offsetting a diminishment in p53 activity by increasing the level of (mutant) p53. Moreover, such agents can also be used prophylactically to increase p53 levels and thereby enhance the protection against DNA damaging agents when it is known that exposere to damaging agents, such as radiation, is imminent.

Moreover, the oncogenic activity of certain viruses, such as the simian virus 40 (SV40), the adenovirus type 5 (Ad5), and the high human papilloma virus types 16 and 18 (HPV16 and HPV18), has been correlated with the virus' ability to interact with and inactivate the cellular p53 protein. In the instance of the high-risk papilloma viruses, the association of the viral oncoprotein E6 with p53 leads to the specific ubiquitination and degradation of p53. This has suggested a model in which E6 immortalizes cells by deregulating cell growth control through the elimination of the p53 tumor suppressor protein. This models accounts for the observations that p53 levels are very low in HPV-immortalized cells and that the half-life of p53 in HPV16-immortalized keratinocytes is shorter than in primary keratinocytes. Thus, the present method can be employed in the identification of an agent that can block the ubiquitin dependent degradation of p53 as mediated by E6, and thereby block proliferation of HPV-transformed cells. Moreover, to increase the specificity of such agents for HPV-infected cells, the assay especially, the reconstituted protein mixture described below, can be derived so as to favor discovery of inhibitors, including active site inhibitors, of the specific E2 enzyme involved in ubiquitin conjugation. Alternatively, the assay can detect agents which disrupt the interaction of E6 with either p53 or E2, as well as agents which disrupt the ability of E6-AP, a cellular protein, to mediate the interaction of E6 with p53.

In another embodiment, the targeted regulatory protein is the myc oncoprotein. The myc regulatory protein is activated by translocation or mutation in many B-cell lymphomas or by amplification in tumor types, such as small cell lung cancer and breast cancer. The c-myc gene is the cellular homolog of the viral oncogene v-myc, which is found in a number of avian and feline retroviruses which induce leukemia and carcinomas. Myc has been implicated in the control of normal cell proliferation by many studies. In particular, it is one of the immediate early growth response genes that are rapidly induced in quiescent cells upon mitogenic induction, suggesting that it plays some role in mediating the transition from quiescence to proliferation. However, increased levels of myc itself is not sufficient to cause proliferation. In fact, in normal cells the opposite happens and the cell undergoes apoptosis. Therefore, inhibitors identified in the present assay can be used to effectively induce apoptosis in cells which do not normally overexpress myc. For example, specific delivery of these agents to lymphocytes can be used to inhibit proliferation of B- and/or T-cells in order to induce clonal deletion and generate tolerance to particular antigens.

In tumor cells, on the other hand, elevated or deregulated expression of c-myc is so widespread as to suggest a critical role for myc gene activation in multi-stage carcinomas (Field et all. (1990) *Anticancer Res* 10:1–22; and Spencer et al. (1991) *Adv Cancer Res* 56:1–48). However, such overexpression of myc in these cells is typically believed to be accompanied by expression of other cellular proteins, such as bcl-2. Interestingly, however, almost all tumor cells tested that overexpress myc readily undergo apoptosis in the presence of cytotoxic and growth-inhibitory drugs (Cotter et al. (1990) *Anticancer Res* 10: 1153–1159; and Lennon et al. (1990) *Biochem Soc Trans* 18:343–345). Therefore, inhibitors of the ubiquitin-mediated degradation of myc can be used to further deregulate the expression of myc in order to render the cells even more sensitive to a chemotherapeutic treatment, or to possibly upset the careful balance of the transformed cell and cause apoptosis to occur even in the absence of a second cytotoxic drug.

Cyclin degradation is a key step governing exit from mitosis and progression into the next cell-cycle. For example, the transition from metaphase to anaphase which marks the end of mitosis in induced by the degradation of cyclin by a ubiquitin-mediated pathway, which in turn leads to the inactivation of cyclin-dependent kinases (cdk) operational at that cycle-cycle stage. As cells enter interphase, cyclin degradation ceases, cyclin accumulates and, as a result of a complex series of post-translational modifications, cyclin /cdk complexes are activated as kinases which drive the cell through mutosis. Cyclin degradation is thus one of the crucial events in exiting mitosis. Indeed, cyclin mutants that retain the ability to activate the cdk complexes, but which cannot be degraded, arrest the cell-cycle in mitosis. Similar cyclin-dependence exists at other points of the cel-cycle as well. Thus, inhibitors of ubiquitin-mediated degradation of a cyclin (such as where the cyclin is chosen from cyclin A, B, C, D1, D2, D3, E or F) can be used as antiproliferative agents. In one aspect of the invention, an inhibitor of ubiquitin-mediated cyclin degradation can be generated for use as fungal antiproliterative agents. For instance, genetic screens have identified three yeast cyclins, CLN1, CLN2, and CLN3, in *S. cerevisiae* that cooperate with cdc28 at start. The cdc34 gene has been identiified in *S. cerevisiae* to encode a ubiquitin-conjugating enzyme which involved in ubiquitination of CLN3. Inhibitors of cdc34 identifed in the present invention can therefore be of potential use in treating, for example, mycotic infections.

The fos oncogene product, which can undergo ubiquitin-mediated degradation in a cell, has been implicated in neoplastic transformation as well as in mediating the action of a variety of extracellular stimuli. The control of gene expression by c-fos is believed to play a critical role in cellular proliferation and developmental responses, and alterations in the normal pattern of c-fos can lead to oncogenesis.

Given the prominence of c-fos as an early response gone, apparent over-expression and prolonged lifetime of c-fos, as may be caused by an inhibitor of the ubiquitin-mediated degradation of c-fos, might sufficiently unbalance the cell-cycle and cause cell death. Alternatively, such inhibitors can be used to mimic the effects of an external stimulus on the cell, such as treatment with a cytokine.

Another regulatory protein that is short-lived due to ubiquitin-mediated degradation is for the yeast MATα2 transcriptional regulator of *S. cervesiae,* which governs the cell identity between the haploid forms, a and α, and the a/α diploid. Mutants deficient in the degradation of MATα2 have been found to have a number of defects, including inhibition of growth (Hochstrasser et al. (1990). *Cell* 61:697–708; and Chen et al. (1993) *Cell* 74: 357–369). Thus, the subject method can be used to identify inhibitors of ubiquitin-mediated degradation of MATα2, particularly which inhibit UBC4, UBC5, UBC6, and/or UBC7-mediated conjugation of ubiquitin with MATα2. Such inhibitors can be useful in, for example, the treatment of mycotic infections, as well as the preservation of foodstuff.

In preferred in vitro embodiments of the present assay, the ubiquitin-conjugating system comprises a reconstituted protein mixture of at least semi-purified proteins. By semi-purified, it is meant that the proteins utilized in the reconstituted mixture have been previously separated from other cellular or viral proteins. For instance, in contrast to cell lysates, the proteins involved in conjugation of ubiquitin to a target protein, together with the target protein, are present in the mixture to at least 50% purity relative to all other proteins in the mixture, and more preferably are present at 90–95% purity. In certain embodiments of the subject method, the reconstituted protein mixture is derived by mixing highly purified proteins such that the reconstituted mixture substantially lacks other proteins (such as of cellular or viral origin) which might interfere with or otherwise alter the ability to measure specific ubiquitination or ubiquitin-mediated degradation of the target regulatory protein.

Each of the protein components utilized to generate the reconstituted ubiquitin-conjugating system are preferably isolated from, or otherwise substantially free of, other proteins normally associated with the proteins in a cell or cell lysate. The term "substantially free of other cellular proteins" (also refered to herein as "contaminating proteins") is defined as encompassing individual preparations of each of the component proteins comprising less than 20% (by dry weight) contaminating protein, and preferably comprises less than 5% contaminating protein. Functional forms of each of the component proteins can be prepared as purified preparations by using a cloned gene as described in the attached examples. By "purified", it is meant, when referring to the component proteins preparations used to generate the reconstituted protein mixture, that the indicated molecule is present in the substantial absence of other biological macromolecules, such as other proteins (particularly other proteins which may substantially mask, diminish, confuse or alter the characteristics of the component proteins either as purified preparations or in thier function in the subject reconstituted mixture). The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" do not encompass either protein in its native state (e.g. as a part of a cell), or as part of a cell lysate, or that have been separated into components (e.g., in an acrylamide gel) but not obtained either as pure (e.g. lacking contaminating proteins) substances or solutions. The term isolated as used herein also refers to a component protein that is substantially free of cellular material or culture medium when produced by recombinant DNA techniques, or chemical precursors or other chemicals when chemically synthesized.

With respect to measuring ubiquitination, the purified protein mixture can substantially lack any proteolytic activity which would degrade the target protein and/or components of the ubiquitin conjugating system. For instance, the reconstituted system can be generated to have less than 10% of the proteolytic activity associated with a typical reticulocyte lysate, and preferably no more than 5%, and most preferably less than 2%. Alternatively, the mixture can be generated to include, either from the onset of ubiquitination or from some point after ubiquitin conjugation of the regulatory protein, a ubiquitin-dependent proteolytic activity, such as a purified proteosome complex, that is present in the mixture at measured amounts.

In the subject method, ubiquitin conjugating systems derived from purified proteins hold a number of significant advantages over cell lysate or wheat germ extract based assays (collectively referred to hereinafter as "lysates"). Unlike the reconstituted protein system, the synthesis and destruction of the target protein cannot be readily controlled for in lysate-based assays. Without knowledge of particular kinetic parameters for Ub-independant and Ub-dependent degradation of the target protein in the lysate, discerning between the two pathways can be extremely difficult. Measuring these parameters, if at all possible, is further made tedious by the fact that cell lysates tend to be inconsistent from batch to batch, with potentially significant variation between preparations. Evaluation of a potential inhibitor using a lysate system is also complicated in those circumstances where the lysate is charged with mRNA encoding the target protein, as such lysates may continue to synthesize the protein during the assay, and will do so at unpredictable rates.

Using similar considerations, knowledge of the concentration of each component of the ubiquitin conjugation pathway can be required for each lysate batch, along with the degradative kinetic data, in order to determine the necessary time course and calculate the sensitivity of experiments performed from one lysate preparation to the next.

Furthermore, the lysate system can be unsatisfactory where the target protein itself has a relatively short half-life, especially if due to degradative processes other than the ubiquitin-mediated pathway to which an inhibitor is sought. For example, in assays for an inhibitor of HPV-induced ubiquitination of p53, lysate based systems can be difficult to use, in addition to the reasons set forth above, due to the short half-life of p53 even in extracts which lack HPV proteins. In such systems, the ability to measure HPV-mediated ubiquitination of p53 is made difficult by the already rapid, ongoing degradation of p53 presumably occurring by proteolytic processes which are not mediated by any HPV proteins.

The use of reconstituted protein mixtures allows more careful control of the reaction conditions in the ubiquitin-conjugating system. Moreover, the system can be derived to favor discovery of inhibitors of particular steps of the ubiquitination process. For instance, a reconstituted protein assay can be generated which does not facilitate degradation of the ubiquitinated protein. The level of ubiquitin conjugated protein can easily be measured directly in such as system, both in the presence and absence of a candidate agent, thereby enhancing the ability to detect a ubiquitination inhibitor. Alternatively, the Ub-conjugating system can be allowed to develop a steady state level of regulatory protein:Ub conjugates in the absence of a proteolytic activity, but then shifted to a degradative system by addition of purified Ub-dependent proteases. Such degradative systems would be amenable to identifying proteosome inhibitors.

The purified protein mixture includes a purified preparation of the regulatory protein and ubiquitin under conditions which drive the conjugation of the two molecules. For instance, the mixture can include a ubiquitin-activating enzyme (E1), a ubiquitin-conjugating enzyme (E2), and a nucleotide triphosphate (e.g. ATP). Alternatively, the E1 enzyme, the ubiquitin, and the nucleotide triphosphate can be substituted in the system with a pre-activated ubiquitin in the form of an E1::Ub conjugate. Likewise, a pre-activated ubiquitin can instead comprise an E2::Ub conjugate which can directly transfer the pre-activated ubiquitin to the target protein substrate.

Furthermore, the reconstituted mixture can also be generated to include at least one auxiliary substrate recognition protein (E3) which may be, for example, of cellular or viral origin. In illustrative embodiments described below, in order to generate an assay which approximates the ubiquitination of p53 in HPV-16 or HPV-18 infected cells, the reconstitutated ubiquitin conjugating system may further include an E6 protein of HPV origin, as well as an E6-associated protein (E6-AP) of cellular origin.

Ubiquitination of the target regulatory protein via an in vitro ubiquitin-conjugating system, in the presence and absence of a candidate inhibitor, can be accomplished in any vessel suitable for containing the reactants. Examples include microtitre plates, test tubes, and micro-centrifuge tubes. In certain embodiments of the present assay, the in vitro assay system is generated to lack the ability to degrade the ubiquitinated target protein. In such an embodiments, a wide range of detection means can be practiced to score for the presence of the ubiquitinated protein.

In one embodiment of the present assay, the products of a non-degradative ubiquitin-conjugating system are separated by gel electrophoresis, and the level of ubiquitinated target protein assessed, using standard electrophaesis protocols, by measuring an increase in molecular weight of the target protein that corresponds to the addition of one or more ubiquitin chains. For example, one or both of the target protein and ubiquitin can be labeled with a radioisotope such as $^{35}S$, $^{14}C$, or $^{3}H$, and the isotopically labeled protein bands quantified by autoradiographic techniques. Standardization of the assay samples can be accomplished, for instance, by adding known quantities of labeled proteins which are not themselves subject to ubiquitination or degradation under the conditions which the assay is performed. Similarly, other means of detecting electrophoretically separated proteins can be employed to quantify the level of ubiquitination of the regulatory protein, including immunoblot analysis using antibodies specific for either the regulatory protein or ubiquitin, or derivatives thereof. As described below, the antibody can be replaced with another molecule able to bind one of either the regulatory protein or ubiquitin. By way of illustration, one embodiment of the present assay comprises the use of biotinylated ubiquitin in the conjugating system. The biotin label is detected in a gel during a subsequent detection step by contacting the electrophoretic products (or a blot thereof) with a streptavidin-conjugated label, such as a streptavidin linked fluorochrome or enzyme, which can be readily detected by conventional techniques. Moreover, where a reconstituted protein mixture is used (rather than a lysate) as the conjugating system, it may be possible to simply detect the regulatory protein and ubiquitin conjugates in the gel by standard staining protocols, including coomassie blue and silver staining.

In another embodiment, an immunoassay or similar binding assay, is used to detect and quantify the level of ubiquitinated regulatory protein produced in the ubiquitin-conjugating system. Many different immunoassay techniques are amenable for such use and can be employed to detect and quantitate the regulatory protein:Ub conjugates. For example, the wells of a microtitre plate (or other suitable solid phase) can be coated with an antibody which specifically binds one of either the regulatory protein or ubiquitin. After incubation of the ubiquitin-conjugated system with and without the candidate agent, the products are contacted with the matrix bound antibody, unbound material removed by washing, and ubiquitin conjugates of the regulatory protein specifically detected. To illustrate, if an antibody which binds the regulatory protein is used to sequester the protein on the matrix, then a detectable anti-ubiquitin antibody can be used to score for the presence of ubiquitinated regulatory protein on the matrix.

However, it will be clear to those skilled in the art that the use of antibodies in these binding assays is merely illustrative of binding molecules in general, and that the antibodies are readily substituted in the assay with any suitable molecule that can specifically detect one of either the regulatory protein or the ubiquitin. As described below, a biotin-derivative of ubiquitin can be used, and streptavidin (or avidin) employed to bind the biotinylated ubiquitin. In an illustrative embodiment, wells of a microtitre plate are coated with streptavidin and contacted with the developed ubiquitin-conjugating system under conditions wherein the biotinylated ubiquitin binds to and is sequestered in the wells. Unbound material is washed from the wells, and the level of regulatory protein (bound to the matrix via a conjugated ubiquitin moiety) is detected in each well. Alternatively, the microtitre plate wells can be coated with an antibody (or other binding molecule) which binds and sequesters the regulatory protein on the solid support, and detection of ubiquitinated conjugates of the matrix-bound regulatory protein are subsequently carried out using a detectable streptavidin derivative, such as an alkaline phosphatase/streptavidin complex.

In similar fashion, epitope-tagged ubiquitin, such as myc-Ub (see Ellison et al. (1991) *J. Biol. Chem.* 266:21150–21157; ubiquitin which includes a 10-residue sequence encoding a protein of c-myc) can be used in conjunction with antibodies to the epitope tag. A major advantage of using such an epitope-tagged ubiquitin approach for detecting Ub:protein conjugates is the ability of an N-terminal tag sequences to inhibit ubiquitin-mediated proteolysis of the conjugated regulatory protein.

Other ubiquitin derivatives include detectable labels which do not interfere greatly with the conjugation of ubiquitin to the regulatory protein. Such detectable lables can include fluorescently-labeled (e.g. FITC) or enzymatically-labeled ubiquitin fusion proteins. These derivatives can be produced by chemical cross-linking, or, where the label is a protein, by generation of a fusion protein. Several labeled ubiquitin derivatives are commercially available.

Likewise, other binding molecules can be employed in place of the antibodies that bind the regulatory protein. For example, the regulatory protein can be generated as a glutathione-S-transferase (GST) fusion protein. As a practical matter, such GST fusion protein can enable easy purification of the regulatory protein in the preparation of components of the ubiquitin-conjugating system (see, for example, *Current Protocols in Molecular Biology*, eds. Ausubel et al. (New York: John Wiley & Sons, 1991); Smith et al. (1988) *Gene* 67:31; and Kaelin et al. (1992) *Cell* 70:351) Moreover, glutathione derivatized matrices (e.g. glutathione-sepharose or glutathione-coated microtitre plates) can be used to sequester free and ubiquitinated forms of the regulatory protein from the ubiguitin-conjugating system, and the level of ubiquitin immobilized can be measured as described. Likewise, where the matrix is generated to bind ubiquitin, the level of sequestered GST-regulatory protein can be detected using agents which bind to the GST moiety (such as anti-GST antibodies), or, alternatively, using agents which are enzymatically acted upon by GST to produce detectable products (e.g. 1-chloro-2,4-dinitrobenzene; Habig et al. (1974) *J Biol Chem* 249:7130). Similarly, other fusion proteins involving the regulatory protein and an enzymatic activity are contemplated by the present method. For example, fusion proteins containing β-galactosidase or luciferase, to name but a few, can be employed as labels to determine the amount of regulatory protein sequestered on a matrix by virtue of a conjugated ubiquitin chain.

Moreover, such enzymatic fusion proteins can be used to detect and quantitate ubiquitinated regulatory protein in a heterogeneous assay, that is one which does not require separation of the components of the conjugating system. For example, ubiquitin conjugating systems can be generated to have a ubiquitin-dependent protease which degrades the regulatory protein. The enzymatic activity of the fusion protein provides a detectable signal, in the presence of substrate, for measuring the level of the regulatory protein ubiquitination. Similarly, in a non-degradative conjugating system, ubiquitination of the regulatory protein portion of the fusion protein can allosterically influence the enzymatic activity associated with the fusion the protein and thereby provides a means for monitoring the level of ubiquitin conjugation.

In binding assay-type detection steps set out above, the choice of which of either the regulatory protein or ubiquitin should be specifically sequestered on the matrix will depend on a number of factors, including the relative abundance of both components in the conjugating system. For instance, where the reaction conditions of the ubiquitin conjugating system provide ubiquitin at a concentration far in excess of the level of the regulatory protein, (e.g., one order of magnitude or greater) sequestering the ubiquitin and detecting the amount of regulatory protein bound with the ubiquitin can provide less dynamic range to the detection step of the present method than the converse embodiment of sequestering the regulatory protein and detecting ubiquitin conjugates from the total regulatory protein bound to the matrix. That is, where ubiquitin is provided in great excess relative to the regulatory protein, the percentage of ubiquitin conjugated regulatory protein in the total ubiquitin bound to the matrix can be small enough that any diminishment in ubiquitination caused by an inhibitor can be made difficult to detect by the fact that, for example, the statistical error of the system (e.g. the noise) can be a significant portion of the measured change in concentration of bound regulatory protein. Furthermore, it is clear that manipulating the reaction conditions and reactant concentrations in the ubiquitin-conjugating system can be carried out to provide, at the detection step, greater sensitivity by ensuring that a strong ubiquitinated protein signal exists in the absence of any inhibitor.

In still further embodiments of the present invention, the ubiquitin-conjugating system is generated in whole cells, taking advantage of cell culture techniques to support the subject assay. For example, as described below, the ubiquitin-conjugating system (including the target protein and detection means) can be constituted in a eukaryotic cell culture system, including mammalian and yeast cells. Advantages to generating the subject assay in an intact cell include the ability to detect inhibitors which are functional in an environment more closely approximating that which therapeutic use of the inhibitor would require, including the ability of the agent to gain entry into the cell. Furthermore, certain of the in vivo embodiments of the assay, such as examples given below, are amenable to high through-put analysis of candidate agents.

The components of the ubiquitin-conjugating system, including the regulatory protein, can be endogenous to the cell selected to support the assay. Alternatively, some or all of the components can be derived from exogenous sources. For instance, a virally derived E3 protein, such as an HPV E6 protein, can be introduced into the cell by recombinant techniques (such as through the use of an expression vector), as well as by microinjecting the E3 protein itself or mRNA encoding the E3 protein.

In any case, the cell is ultimately manipulated after incubation with a candidate inhibitor in order to facilitate detection of ubiquitination or ubiquitin-mediated degradation of the regulatory protein. As described above for assays performed in reconstituted protein mixtures or lysate, the effectiveness of a candidate inhibitor can be assessed by measuring direct characteristics of the regulatory protein, such as shifts in molecular weight by electrophoretic means or detection in a binding assay. For these embodiments, the cell will typically be lysed at the end of incubation with the candidate agent, and the lysate manipulated in a detection step in much the same manner as might be the reconstituted protein mixture or lysate.

Indirect measurement of ubiquitination of the target protein can also be accomplished by detecting a biological activity associated with the regulatory protein that is either attenuated by ubiquitin-conjugation or destroyed along with the regulatory protein by ubiquitin-dependent proteolytic processes. As set out above, the use of fusion proteins comprising the regulatory protein and an enzymatic activity are representative embodiments of the subject assay in which the detection means relies on indirect measurement of ubiquitination of the regulatory protein by quantitating an associated enzymatic activity.

Where the regulatory protein has a relatively short half-life due to ubiquitin-dependent or independent degradation in the cell, preferred embodiments of the assay either do not require cell lysis, or, alternatively, generate a longer lived detection signal that is independent of the regulatory protein's fate after lysis of the cell. With respect to the latter embodiment, the detection means can comprise, for example, a reporter gene construct which includes a positive transcriptional regulatory element that binds and is responsive to the regulatory protein. For instance, where the regulatory protein of interest is p53, p53 responsive elements can be used to construct the reporter gene. These include p53 binding seuquences set put in Example 9, as well as a creatine kinase enhancer, an interleukin-6 promoter, a c-fos promoter, a β-actin promoter, an hsc70 promoter, a c-jun promoter, a p53 promoter, and a CYC1 hybrid promoter containing a p53-binding sequence. The gene product is a detectable label, such as luciferase or β-galactosidase, and is produced in the intact cell. The label can be measured in a subsequent lysate of the cell. However, the lysis step is preferably avoided, and providing a step of lysing the cell to measure the label will typically only be employed where detection of the label cannot be accomplished in whole cells.

Moreover, in the whole cell embodiments of the subject assay, the reporter gene construct can provide, upon expression, a selectable marker. For instance, the product of the reporter gene can be an enzyme which confers resistance to antibiotic or other drug, or an enzyme which complements a deficiency in the host cell (i.e. thymidine kinase or dihydrofolate reductase). To illustrate, the aminoglcycoside phosphotransferase encoded by the bacterial transposon gene Tn5 neo can be placed under transcriptional control of a promoter element responsive to the level of target regulatory protein present in the cell. Thus, the level of expression of the phenotypic marker gene is lower in the absence of an inhibitor of ubiquitin-mediated proteolysis of the regulatory protein, and such inhibitors can be detected in the assay by an ability to confer the measured phenotypic trait. Such embodiments of the subject assay are particularly amenable to high through-put analysis in that proliferation of the cell can provide a simple measure of inhibition of the ubiquitin-mediated degradation of the regulatory protein.

In yet a further embodiment of the subject assay, the ubiquitin-conjugating system comprises a cell in which the biological activity of the target regulatory protein has been substantially impaired, the impairment being the result of abnormal ubiquitination of the regulatory protein. The cell, in the presence or absence of a candidate inhibitor, is subject to growth conditions that would ordinarily required the function of the regulatory protein for viability of the cell. Thus, an inhibitor of the ubiquitin-mediated degradation of the regulatory protein would restore the biological activity of the protein to the cell, and could easily be detected by the ability of the cell to proliferate. To further illustrate, the impairment of the regulatory protein can be the result of over expression of a cellular protein of the ubiquitin pathway, such as an E2 or E3 protein, which results in hyper-ubiquitination of the regulatory protein. Alternatively, the impairment can result from non-cellular agents, such as viral proteins, which increase the ubiquitin-mediated degradation of the regulatory protein. For example, as described above, expression of the HPV E6 protein can result in decreased levels of p53 in the cell due to the increased ubiquitin-dependent inactivation of the protein.

In embodiments of the subject method in which the target regulatory protein ordinarily acts as a negative regulator of mitotic events, impairment of the regulatory protein can result in a hyper-mitotic cell. The term hyper-mitotic cell denotes a cell having an impaired cell-cycle checkpoint which can allow the cell to proceed abherently toward subsequent mitotic stages and ultimately inhibits faithful proliferation of the cell. In the present of an agent able to inhibit the ubiquitin-mediated inactivation of the regulatory protein, progression of the hyper-mitotic cell through the cell-cycle can be reestablished under control of the regulatory protein and permit the cell to appropriately proliferate.

To illustrate, a p53-impaired cell can be generated by expression of the HPV viral protein E6. The concomitant decrease in p53 levels brought about by E6 expression does not in and of itself cause abherent mitotic events to occur. However, exposure of the impaired cell to an agent (i.e. chemical or environmental) that ordinarily induces cell-cycle arrest at the p53 checkpoint can result in inappropriate exit of the cell from the chemically or environmentally induced arrest. This type of checkpoint override can ultimately be lethal to the cell. Such arresting agents can include exposure to DNA damaging radiation or DNA damaging agents; inhibition of DNA synthesis or repairmen using DNA polymerase inhibitors such as hydroxyurea or aphidicolin; topoisomerase inhibitors such as 4'-dimethylepipodophyllotoxin (VM-26); or agents which interfere with microtubule assembly, such as nocadazole and taxol.

With respect to embodiments in which the regulatory protein ordinarily acts as a mitotic activator, impairment of the protein's activity by ubiquitination can generate a hypomitotic cell in which progression of the cell through at least a portion of the cell-cycle is repressed. In the presence of an inhibitor of ubiquitin-dependent degradation of the regulatory protein, the activity of the mitotic activator is restored and the cell can proliferate at an greater rate relative to the untreated cell. Agents to be tested for their ability to act as inhibitor of ubiquitin-dependent degradation of the regulatory protein in the present assay can be those produced by bacteria, yeast or other organisms, or those produced chemically.

With respect to sources for the proteins constituting the ubiquitin-conjugating system, particularly to generate the reconstituted protein mixture, many species of the enzymes and other proteins involved in ubiquitination have been identified, and in a significant number of instances, have been cloned so that recombinant sources exist. Isolation of enzymes of the ubiquitin-conjugating system has been greatly assisted by "covalent" ubiquitin-affinity chromatography (Crechanover et al. (1982) *J. Biol. Chem.* 257:2537–2542; and Pickart et al. (1985) *J. Biol. Chem.* 260:1573–1581). This method takes advantage of the fact that the E1 enzyme is capable of forming a thiol ester with immobilized ubiquitin (e.g. ubiquitin-sepharase) in the presence of ATP. As described in Example 4, such a protocol can be used to purify recombinantly expressed E1. Moreover, E1 enzymes bound to the immobilized ubiquitin can be exchanged with E2 enzymes. Thus, both E1 and E2 enzymes can be specifically purified on such columns, and can be recovered after elution with, for example, dithiothreitol. Under appropriate elution conditions, ubiquitin activated E1 or E2 complexes can be isolated and, as described herein, used in the present assay to increase the selectivity of the assay for an inhibitor of a particular step of ubiquitin-conjugation. Moreover, with minor changes, this protocol can be used to isolate E1:Ub or E2:Ub conjugates (e.g.

activated ubiquitin conjugates) for use in the reconstituted protein mixture.

Identification of enzymes involved in the ubiquitin pathway from different sources have facilitated the cloning of corresponding genes. For instance, genes encoding E1 enzymes have been cloned from various organisms (see, for example, Adams et al. (1992) *Nature* 355:632–634; Handley et al. (1991) *PNAS* 88:258–262; Handley et al. (1991) *PNAS* 88:7456; Hatfield et al. (1990) *J. Biol. Chem.* 265:15813–15817; Kay et al. (1991) *Nature* 354:486–489; McCrath eg al. (1991) *EMBO J* 10:227–236; Mitchell et al. (1991) *Nature* 354:483–486; and Zacksenhaus et al. (1990) *EMBO J* 9:2923–2929). The sequences of various cloned E1 enzymes predict proteins of roughly 100 kd, and which contain the nucleotide-binding consensus sequence Gly-Xaa-Gly-Xaa-Xaa-Gly (McGrath et al. (1991) *EMBO J* 10:227–236). For example, the gene UBA1 has been cloned from *S. cerevisiae* and shown to encode a 114 kd E1 enzyme (McGrath et al., supra). Moreover, more than one E1 species has been detected in the same cell-type, suggesting that two or more different E1 enzymes can exist. It is not yet known whether the different E1 enzymes are enzymatically similar, or if they collaborate with specific sets of ubiquitin-conjugating enzymes. In either case, each of the E1 species can be used to generate the ubiquitin-conjugating system of the subject method.

In contrast to the ubiquitin-activating enzyme (E1), where it is generally believed that there are relatively few different species of the enzyme in a given cell, eukaryotic cells can express a large and diverse array of E2 enzymes. This remarkable variety of E2 enzymes, along with experimental evidence, has implicated the E2 enzyme as the principle determinant of substrate selectivity in the ubiquitin system. The E2 enzyme, as set out above, catalyzes isopeptide bond formation between ubiquitin and substrate proteins, either with or without the aid of a substrate recognition factor (ubiquitin-ligase protein; E3). So far, several major species of E2 enzymes have been identified and purifed by ubiquitin-affinity chromatography of extracts from rabbit reticulocytes (Pickart et al. (1985) *J Biol Chem* 260:1573–1581), yeast (Jentsch et al. (1987) *Nature* 329:131–134), and wheat (Sullivan et al. (1989) *PNAS* 86:9861–9865). Furthermore, many genes encoding E2 enzymes have been cloned and characterized, most notably in the yeast *Sacchromyces cerevisiae*, where the phenotypic consequences of their inactivation can be readily assessed. More than 10 yeast E2 genes have been identified to date (see Table I below; also see Jentsch (1992) *Annu Rev Genet* 26:179–207; and Jentsch (1992) *Trends Cell Biol* 2:98–103), and there evidence for over 20 E2 genes in the plant *Arabipodopsis* (Cook et al. (1992) *J Bio Chem* 267:15116–15121). Additionally, E2 enzymes have been cloned from nematode (Zhen et al. (1993) *Mol Cell Biol* 13:1371–1377), drosophila (Muralidher et al. (1993) *Neuron* 11:253–266; and Koken et al. (1991) *PNAS* 88:3832–3836), bovine (Chen et al. (1991) *J Biol Chem* 266:15698–15704) and human cells (Koken et al. (1992) *Genomics* 12:447–453; Koken et al. (1991) *PNAS* 88:8865–8869; and Schneider et al. (1990) *EMBO J* 9:1431–1435).

TABLE I

| Yeast ubiquitin-conjugating enzymes (E2) | |
|---|---|
| UBC1 | Seufert et al. (1990) EMBO J9:4535 |
| UBC2/Rad6 | Jensch et al. (1987) Nature 329:131; and |
| UBC3/CDC34 | Goebl et al. (1988) Science 241:1331 |
| UBC4 | Suefert et al. (1990) EMBO J9:543–550; Chen et al. (1991) J Biol Chem 266:15698 |
| UBC5 | Suefert et al. (1990) EMBO J9:543–550; Seufert et al. (1990) EMBO J9:4535 |
| UBC6 | Chen et al. (1993) Cell 74:357 |
| UBC7 | Vassal et al. (1992) Biochem Biophys Acta 1132:211 |
| UBC8 | Qin et al. (1991) J Biol Chem 266:15549 |
| UBC9 | Chen et al. (1993) Cell 74:357 |
| UBC10/PAS2 | Wiebel et al. (1992) Nature 359:73 |

Some ubiquitin-conjugating enzymes require accessory factors, E3 proteins, for the recognition of certain protein substrates. Two E3 proteins, E3α and E3β, have been identified from rabbit reticulocytes (Reiss et al. (1989) *J. Biol. Chem.* 264:10378–10383; and Reiss et al. (1990) *J. Biol. Chem.* 265:3685–3690). A yeast gene (UBRI) encoding an E3 functionally similar to rabbit E3α has also been cloned (Bartel et al. (1990) *EMBO J* 9:3179–3189). Rabbit E3α and yeast UBR1 bind to substrates with N-terminal amino acid residues that are basic or have bulky hydrophobic side chains, while the E3β recognizes small unchanged residues at the N-terminus of substrates. In addition to the E3 proteins that recognize the N-terminus of protein substrates, other E3 proteins (collectively know as E3γ, capable of recognizing internally located signals, have been suspected.

Proteins that facilitate ubiquitin-conjugation reactions without physically interacting with E2 enzymes can also be classed as E3 proteins. By this definition, the E6 oncoprotein of the papillomavirus is regarded as an E3 protein, as binding of E6 triggers the ubiquitination and degradation of p53. As set out in Example 4, recombinant E6 protein from the high-risk HPV-18 (SEQ ID No. 4), as well as the cellular factor E6-AP (SEQ ID No. 2), are available for use in the subject assay.

The regulatory protein provided in the subject assay can be derived by purification from a cell in which it is exogenously expressed, or from a recombinant source of the protein. For example, cDNA clones are available for a number of regulatory proteins, including p53 (Oren et al. (1983) *EMBO J* 2:1633–1639); c-myc (Hann et al. (1988) *Cell* 52:185–195); N-myc (Curran et al. (1987) *Oncogene* 2:79–84); MATα2 (Hochstrasser et al. (1990) *Cell* 61:697–708); and E1A (Salvicek et al. (1988) *EMBO J* 7:3171–3180).

In each instance where a recombinant source of a protein is used in the subject assay, the manipulation of the gene encoding the protein and the subsequent expression of the protein can be carried out by standard molecular biological techniques. Ligating the polynucleotide sequence encoding the recombinant protein into a gene construct, such as an expression vector, and transforming or transfecting into host cells, either eukaryotic (yeast, avian, insect or mammalian) or prokaryotic (bacterial cells), are standard procedures used in producing other well-known proteins, e.g. insulin, interferons, human growth hormone, IL-1, IL-2, and the like. Similar procedures, or obvious modifications thereof, can be employed to prepare and purify recombinant proteins of the ubiquitin-conjugating system by microbial means or tissue-culture technology for use in the subject assay.

The recombinant protein (e.g. E1, E2, E3, the regulatory protein, etc.) can be produced by ligating the cloned gene, or a portion thereof, into a vector suitable for expression in either prokaryotic cells, eukaryotic cells, or both. Expression vehicles for production of recombinant proteins include plasmids and other vectors. For instance, suitable vectors for the expression of these proteins include plasmids of the types: pBR322-derived plasmids, pEMBL-derived plasmids, pEX-derived plasmids, pBTac-derived plasmids and pUC-derived plasmids for expression in prokaryotic cells, such as E. coli.

A number of vectors exist for the expression of recombinant proteins in yeast. For instance, YEP24, YIP5, YEP51, YEP52, pYES2, and YRP17 are cloning and expression vehicles useful in the introduction of genetic constructs into S. cerevisiae (see for example Broach et al. (1983) in Experimental Manipulation of Gene Expression, ed M. Inouye Academic Press, p. 83+). These vectors can replicate in E. coli due the presence of the pBR322 ori, and in S. cerevisiae due to the replication determinant of the yeast 2 micron plasmid. In addition, drug resistance markers such as ampicillin can be used.

The preferred mammalian expression vectors contain both prokaryotic sequences to facilitate the propagation of the vector in bacteria, and one or more eukaryotic transcription units that are expressed in eukaryotic cells. The pHβ APr-1-neo, EBO-pcD-XN, pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic, as well as general recombinant procedures, see Molecular Cloning A Laboratory Manual, 2nd Ed., ed. by Sambrook, Fritsch and Maniatis (Cold Spring Harbor Laboratory Press:1989) Chapters 16 and 17.

In some instances, as described below in Example 4, it may be desirable to express the recombinant protein by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In preferred embodiments, the expression vectors used to produce the recombinant proteins of the present invention are chosen to include at least one selectable marker for each cell line in which the vector is to be replicated or expressed. For instance, the vectors can be derived with sequences conferring resistance to ampicillin, chloramphenicol or kanomycin to facilitate amplification in E. coli. For selection in mammalian cells, such markers as the mammalian expressible E. coli ecogpt gene—which codes for a xanthine-guanine phosphoribosyl transferase (XGPRT) and allows selection of transfected HPRT⁻ mammalian cells with mycophenolic acid—can be utilized.

Furthermore, the recombinant protein can be encoded by a fusion gene created to have additional sequences coding for a polypeptide portion of a fusion protein which would facilitate its purification. For instance, Example 4 describes a fusion gene coding for a purification leader sequence comprising a poly-(His)/enterokinase cleavage site sequence at the N-terminus of the desired portion the E6-AP protein, thereby enabling purification of the expressed E6-AP fusion protein by affinity chromatography using a $Ni^{2+}$ metal resin. The purification leader sequence can then be subsequently removed by treatment with enterokinase (e.g., see Hochuli et al. 1987 J. Chromatography 411:177; and Janknecht et al. PNAS 88:8972).

Additionally, the subject ubiquitin conjugating enzyme can be used to generate an interaction trap assay for subsequently detecting inhibitors of hUCE biological activity (see, for example, U.S. Pat. No. 5,283,317; Zervos et al. (1993) Cell 72:223–232; Madura et al. (1993) J Biol Chem 268:12046–12054; Bartel et al. (1993) Biotechniques 14:920–924; and Iwabuchi et al. (1993) Oncogene 8:1693–1696) In an illustrative embodiment, Saccharomyces cerevisiae YPB2 cells are transformed simultaneously with a plasmid encoding a GAL4db-hUCE fusion and with a plasmid encoding the GAL4ad domain fused to p53. Moreover, the strain is transformed such that the GAL4-responsive promoter drives expression of a phenotypic marker. For example, the ability to grow in the absence of histidine can depends on the expression of the HIS3 gene if it is under control of a GAL4-responsive promoter and, therefore, indicates that a functional GAL4 activator has been reconstituted through the interaction of hUCE and p53. Thus, agent able to inhibit hUCE interaction with p53 will result in yeast cells unable to growth in the absence of histidine. Alternatively, the phenotypic marker can be one which provides a negative selection when expressed such that agents which disrupt hUCE/p53 interactions confer positive growth selection to the cells.

Another aspect of the present invention concerns three-dimensional molecular models of the subject hUCE protein, and their use as templates for the design of agents able to inhibit at least one biological activity of the ubiquitin conjugating enzyme. An integral step to our approach to designing inhibitors of the subject ubiquitin-conjugating enzyme involves construction of computer graphics models of the ubiquitin conjugating enzyme which can be used to design pharmacophores by rational drug design. For instance, for an inhibitor to interact optimally with the subject enzyme, it will generally be desirable that it have a shape which is at least partly complimentary to that of a particular binding site of the enzyme, as for example those portions of the enzyme which are involved in recognition of ubiquitin, an E1 enzyme, an E3 protein(s) such as E6 or E6AP, or the downstream target of the enzyme, such as p53. Additionally, other factors, including electrostatic interactions, hydrogen bonding, hydrophobic interactions, desolvation effects, and cooperative motions of ligand and enzyme, all influence the binding effect and should be taken into account in attempts to design bioactive inhibitors.

As described in Example 3, a computer-generated molecular model of the subject enzyme can be created. In preferred embodiments, at least the Cα-carbon positions of the hUCE sequence of interest are mapped to a particular coordinate pattern, such as the coordinates shown in FIG. 1, by homology modeling, and the structure of the protein and velocities of each atom are calculated at a simulation temperature ($T_o$) at which the docking simulation is to be determined. Typically, such a protocol involves primarily the prediction of side-chain conformations in the modeled protein, while assuming a main-chain trace taken from a tertiary structure such as provided in FIG. 1. Computer programs for performing energy minimization routines are commonly used to generate molecular models. For example, both the CHARMM (Brooks et al. (1983) J Comput Chem 4:187–217) and AMBER (Weiner et al (1981) *J. Comput. Chem.* 106: 765) algorithms handle all of the molecular system setup, force field calculation, and analysis (see also, Eisenfield et al. (1991) *Am J Physiol* 261:C376–386; Lybrand (1991) *J Pharm Belg* 46:49–54; Froimowitz (1990) *Biotechniques* 8:640–644; Burbam et al. (1990) *Proteins* 7:99–111; Pedersen (1985) *Environ Health Perspect* 61:185–190; and Kini et al. (1991) *J Biomol Struct Dyn* 9:475–488). At the heart of these programs is a set of subroutines that, given the position of every atom in the model, calculate the total potential energy of the system and the force on each atom. These programs may utilize a starting set of atomic coordinates, such as the model coordinates provided in FIG. 1, the parameters for the various terms of the potential energy function, and a description of the molecular topology (the covalent structure). Common features of such molecular modeling methods include: provisions for handling hydrogen bonds and other constraint forces; the use of periodic boundary conditions; and provisions for occasionally adjusting positions, velocities, or other parameters in order to maintain or change temperature, pressure, volume, forces of constraint, or other externally controlled conditions.

Most conventional energy minimization methods use the input data described above and the fact that the potential energy function is an explicit, differentiable function of Cartesian coordinates, to calculate the potential energy and its gradient (which gives the force on each atom) for any set of atomic positions. This information can be used to generate a new set of coordinates in an effort to reduce the total potential energy and, by repeating this process over and over, to optimize the molecular structure under a given set of external conditions. These energy minimization methods are routinely applied to molecules similar to the subject hUCE protein as well as nucleic acids, polymers and zeolites.

In general, energy minimization methods can be carried out for a given temperature, $T_i$, which may be different than the docking simulation temperature, $T_o$. Upon energy minimization of the molecule at $T_i$, coordinates and velocities of all the atoms in the system are computed. Additionally, the normal modes of the system are calculated. It will be appreciated by those skilled in the art that each normal mode is a collective, periodic motion, with all parts of the system moving in phase with each other, and that the motion of the molecule is the superposition of all normal modes. For a given temperature, the mean square amplitude of motion in a particular mode is inversely proportional to the effective force constant for that mode, so that the motion of the molecule will often be dominated by the low frequency vibrations.

After the molecular model has been energy minimized at $T_i$, the system is "heated" or "cooled" to the simulation temperature, $T_o$, by carrying out an equilibration run where the velocities of the atoms are scaled in a step-wise manner until the desired temperature, $T_o$, is reached. The system is further equilibrated for a specified period of time until certain properties of the system, such as average kinetic energy, remain constant. The coordinates and velocities of each atom are then obtained from the equilibrated system.

Further energy minimization routines can also be carried out. For example, a second class of methods involves calculating approximate solutions to the constrained EOM for the protein. These methods use an iterative approach to solve for the Lagrange multipliers and, typically, only need a few iterations if the corrections required are small. The most popular method of this type, SHAKE (Ryckaert et al. (1977) *J Comput Phys* 23:327; and Van Gunsteren et al. (1977) *Mol Phys* 34:1311) is easy to implement and scales as O(N) as the number of constraints increases. Therefore, the method is applicable to macromolecules such as the hUCE protein. An alternative method, RATTLE (Anderson (1983) *J Comput Phys* 52:24) is based on the velocity version of the Verlet algorithm. Like SHAKE, RATTLE is an iterative algorithm and can be used to energy minimize the model of the subject protein.

The increasing availability of biomacromolecule structures of potential pharmacophoric molecules that have been solved crystallographically has prompted the development of a variety of direct computational methods for molecular design, in which the steric and electronic properties of substrate binding sites are use to guide the design of potential inhibitors (Cohen et al. (1990) *J. Med. Cam.* 33: 883–894; Kuntz et al. (1982) *J. Mol. Biol* 161: 269–288; DesJarlais (1988) *J. Med. Cam.* 31: 722–729; Bartlett et al. (1989) (*Spec. Publ., Roy. Soc. Chem.*) 78: 182–196; Goodford et al. (1985) *J. Med. Cam.* 28: 849–857; DesJarlais et al. *J. Med. Cam.* 29: 2149–2153). Directed methods generally fall into two categories: (1) design by analogy in which 3-D structures of known molecules (such as from a crystallographic database) are docked to the enzyme structure and scored for goodness-of-fit; and (2) de novo design, in which the ligand model is constructed piece-wise in the enzyme. The latter approach, in particular, can facilitate the development of novel molecules, uniquely designed to bind to the subject human ubiquitin-conjugating enzyme.

In an illustrative embodiment, the design of potential hUCE inhibitors begins from the general perspective of shape complimentary for the active site and substrate specificity subsites of the enzyme, and a search algorithm is employed which is capable of scanning a database of small molecules of known three-dimensional structure for candidates which fit geometrically into the target protein site. It is not expected that the molecules found in the shape search will necessarily be leads themselves, since no evaluation of chemical interaction necessarily be made during the initial search. Rather, it is anticipated that such candidates might act as the framework for further design, providing molecular skeletons to which appropriate atomic replacements can be made. Of course, the chemical complimentary of these molecules can be evaluated, but it is expected that atom types will be changed to maximize the electrostatic, hydrogen bonding, and hydrophobic interactions with the enzyme. Most algorithms of this type provide a method for finding a wide assortment of chemical structures that are complementary to the shape of a binding site of the subject enzyme. Each of a set of small molecules from a particular data-base, such as the Cambridge Crystallographic Data Bank (CCDB) (Allen et al. (1973) *J. Chem. Doc.* 13: 119), is individually docked to the binding site of the hUCE enzyme in a number of geometrically permissible orientations with use of a docking algorithm. In a preferred embodiment, a set of computer algorithms called DOCK, can be used to characterize the shape of invaginations and grooves that form the active sites and recognition surfaces of the subject enzyme (Kuntz et al. (1982) *J. Mol. Biol* 161: 269–288). The program can also search a database of small molecules for templates whose shapes are complementary to particular binding sites of the enzyme (DesJarlais et al. (1988) *J Med Chem* 31: 722–729). These templates normally require modification to achieve good chemical and electrostatic interactions (DesJarlais et al. (1989) *ACS Symp Ser* 413: 60–69). However, the program has been shown to position accurately known cofactors for inhibitors based on shape constraints alone.

The orientations are evaluated for goodness-of-fit and the best are kept for further examination using molecular mechanics programs, such as AMBER or CHARMM. Such algorithms have previously proven successful in finding a variety of molecules that are complementary in shape to a given binding site of a receptor-enzyme, and have been shown to have several attractive features. First, such algorithms can retrieve a remarkable diversity of molecular architectures. Second, the best structures have, in previous applications to other proteins, demonstrated impressive shape complementarity over an extended surface area. Third, the overall approach appears to be quite robust with respect to small uncertainties in positioning of the candidate atoms.

Goodford (1985, *J Med Chem* 28:849–857) and Boobbyer et al. (1989, *J Med Chem* 32:1083–1094) have produced a computer program (GRID) which seeks to determine regions of high affinity for different chemical groups (termed probes) on the molecular surface of the binding site. GRID hence provides a tool for suggesting modifications to known ligands that might enhance binding. It may be anticipated that some of the sites discerned by GRID as regions of high affinity correspond to "pharmacophoric patterns" determined inferentially from a series of known ligands. As used herein, a pharmacophoric pattern is a geometric arrangement of features of the anticipated ligand that is believed to be important for binding. Attempts have been made to use pharmacophoric patterns as a search screen for novel ligands (Jakes et al. (1987) *J Mol Graph* 5:41–48; Brint et al. (1987) *J Mol Graph* 5:49–56; Jakes et al. (1986) *J Mol Graph* 4:12–20); however, the constraint of steric and "chemical" fit in the putative (and possibly unknown) receptor binding site is ignored. Goodsell and Olson (1990, *Proteins: Struct Funct Genet* 8:195–202) have used the Metropolis (simulated annealing) algorithm to dock a single known ligand into a target protein. They allow torsional flexibility in the ligand and use GRID interaction energy maps as rapid lookup tables for computing approximate interaction energies. Given the large number of degrees of freedom available to the ligand, the Metropolis algorithm is time-consuming and is unsuited to searching a candidate database of a few thousand small molecules.

Yet a further embodiment of the present invention utilizes a computer algorithm such as CLIX which searches such databases as CCDB for small molecules which can be oriented in the receptor binding site in a way that is both sterically acceptable and has a high likelihood of achieving favorable chemical interactions between the candidate molecule and the surrounding amino acid residues. The method is based on characterizing the receptor site in terms of an ensemble of favorable binding positions for different chemical groups and then searching for orientations of the candidate molecules that cause maximum spatial coincidence of individual candidate chemical groups with members of the ensemble. The current availability of computer power dictates that a computer-based search for novel ligands follows a breadth-first strategy. A breadth-first strategy aims to reduce progressively the size of the potential candidate search space by the application of increasingly stringent criteria, as opposed to a depth-first strategy wherein a maximally detailed analysis of one candidate is performed before proceeding to the next. CLIX conforms to this strategy in that its analysis of binding is rudimentary—it seeks to satisfy the necessary conditions of steric fit and of having individual groups in "correct" places for bonding, without imposing the sufficient condition that favorable bonding interactions actually occur. A ranked "shortlist" of molecules, in their favored orientations, is produced which can then be examined on a molecule-by-molecule basis, using computer graphics and more sophisticated molecular modeling techniques. CLIX is also capable of suggesting changes to the substituent chemical groups of the candidate molecules that might enhance binding.

The algorithmic details of CLIX is described in Lawerence et al. (1992) *Proteins* 12:31–41, and the CLIX algorithm can be summarized as follows. The GRID program is used to determine discrete favorable interaction positions (termed target sites) in the binding site of the protein for a wide variety of representative chemical groups. For each candidate ligand in the CCDB an exhaustive attempt is made to make coincident, in a spatial sense in the binding site of the protein, a pair of the candidate's substituent chemical groups with a pair of corresponding favorable interaction sites proposed by GRID. All possible combinations of pairs of ligand groups with pairs of GRID sites are considered during this procedure. Upon locating such coincidence, the program rotates the candidate ligand about the two pairs of groups and checks for steric hindrance and coincidence of other candidate atomic groups with appropriate target sites. Particular candidate/orientation combinations that are good geometric fits in the binding site and show sufficient coincidence of atomic groups with GRID sites are retained.

Consistent with the breadth-first strategy, this approach involves simplifying assumptions. Rigid protein and small molecule geometry is maintained throughout. As a first approximation rigid geometry is acceptable as the energy minimized coordinates of the hUCE deduced structure, as described in Example 3, describe an energy minimum for the molecule, albeit a local one. If the surface residues of the site of interest are not involved in crystal contacts then the crystal configuration of those residues. We believe that the deduced structure described in Example 3 should reasonably mimic the mean solution configuration.

A further assumption implicit in CLIX is that the potential ligand, when introduced into the binding site of ubiquitin-conjugating enzyme, does not induce change in the protein's stereochemistry or partial charge distribution and so alter the basis on which the GRID interaction energy maps were computed. It must also be stressed that the interaction sites predicted by GRID are used in a positional and type sense only, i.e., when a candidate atomic group is placed at a site predicted as favorable by GRID, no check is made to ensure that the bond geometry, the state of protonation, or the partial charge distribution favors a strong interaction between the protein and that group. Such detailed analysis should form part of more advanced modeling of candidates identified in the CLIX shortlist.

Yet another embodiment of a computer-assisted molecular design method for identifying inhibitors of the subject human ubiquitin-conjugating enzyme comprises the de novo synthesis of potential inhibitors by algorithmic connection of small molecular fragments that will exhibit the desired structural and electrostatic complementarity with the active site of the enzyme. The methodology employs a large template set of small molecules with are iteratively pieced together in a model of the hUCE active site. Each stage of ligand growth is evaluated according to a molecular mechanics-based energy function, which considers van der Waals and coulombic interactions, internal strain energy of the lengthening ligand, and desolvation of both ligand and enzyme. The search space can be managed by use of a data tree which is kept under control by pruning according to the binding criteria.

In an illustrative embodiment, the search space is limited to consider only amino acids and amino acid analogs as the molecular building blocks. Such a methodology generally employs a large template set of amino acid conformations, though need not be restricted to just the 20 natural amino acids, as it can easily be extended to include other related fragments of interest to the medicinal chemist, e.g. amino acid analogs. The putative ligands that result from this construction method are peptides and peptide-like compounds rather than the small organic molecules that are typically the goal of drug design research. The appeal of the peptide building approach is not that peptides are preferable to organics as potential pharmaceutical agents, but rather that: (1) they can be generated relatively rapidly de novo; (2) their energetics can be studied by well-parameterized force field methods; (3) they are much easier to synthesize than are most organics; and (4) they can be used in a variety of ways, for peptidomimetic inhibitor design, protein-protein binding studies, and even as shape templates in the more commonly used 3D organic database search approach described above.

Such a de novo peptide design method has been incorporated in a software package called GROW (Moon et al. (1991) *Proteins* 11:314–328). In a typical design session, standard interactive graphical modeling methods are employed to define the structural environment in which GROW is to operate. For instance, environment could be the active site cleft of hUCE, or it could be a set of features on the protein's surface to which the user wishes to bind a peptide-like molecule, e.g. a p53 mimetic. The GROW program then operates to generate a set of potential ligand molecules. Interactive modeling methods then come into play again, for examination of the resulting molecules, and for selection of one or more of them for further refinement.

To illustrate, GROW operates on an atomic coordinate file generated by the user in the interactive modeling session, such as the coordinates provided in FIG. 1, or the coordinates of the active site provided in FIG. 3, plus a small fragment (e.g., an acetyl group) positioned in the active site to provide a starting point for peptide growth. These are referred to as "site" atoms and "seed" atoms, respectively. A second file provided by the user contains a number of control parameters to guide the peptide growth (Moon et al. (1991) *Proteins* 11:314–328).

Figure 4:
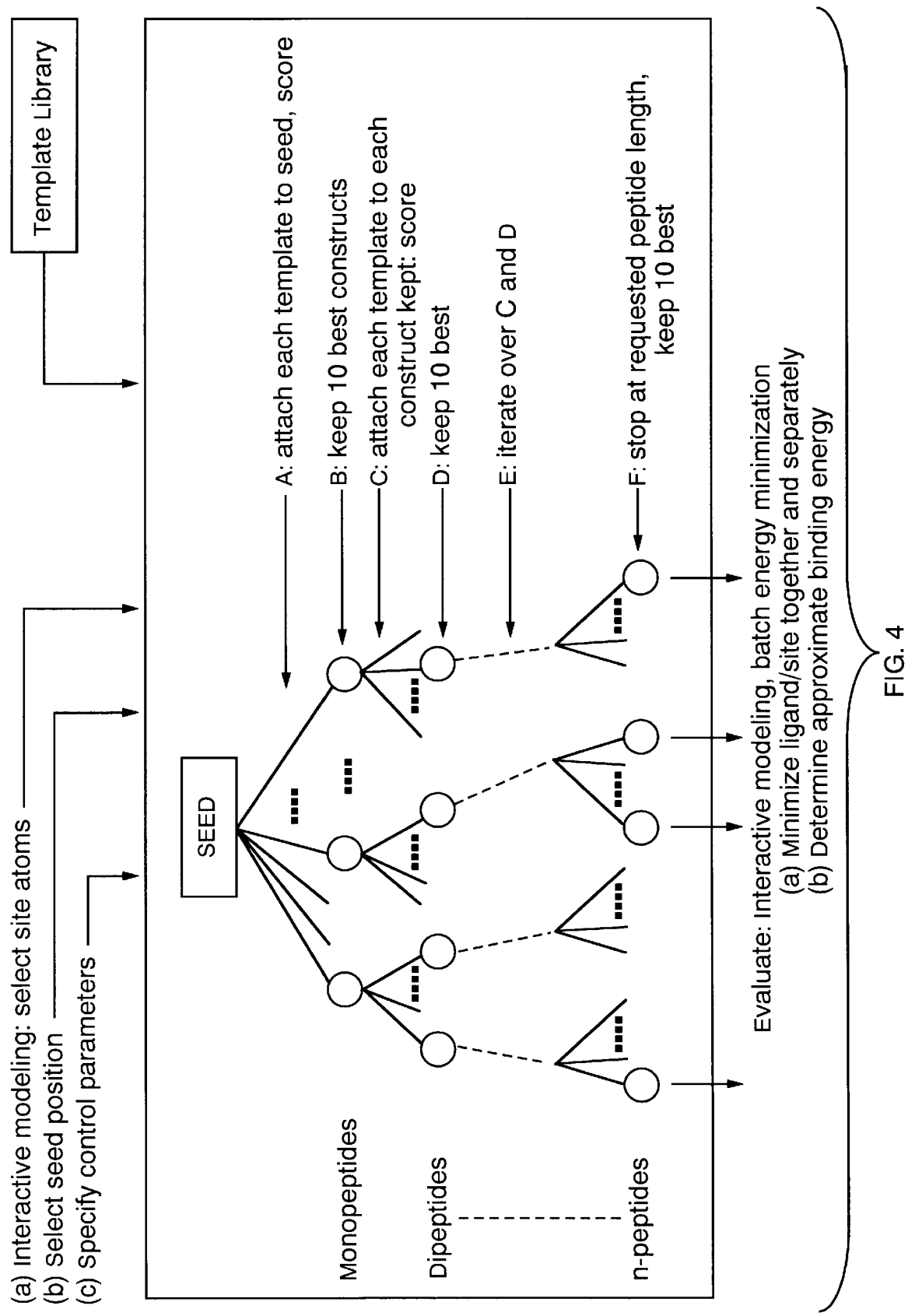
FIG. 4 is the schematic overview of the operation of the GROW method of drug design. The site and seed coordinate file and command file are provided to the GROW procedure by the user. Growth can be visualized as a tree process in which each library template is attached to the seed (A) and then evaluated bu the scoring function (e.g. binding criteria). Of the resulting constructs, a given number of best constructs (e.g. 10) are kept for the next level (B). To each retained monopeptide/seed construct are attached all library templates, which are again scored (C). After pruning(D), the process is repeated (E) until the specified peptide length us reached (F). In this tree diagram, circles represent those nodes selected (based on best binding criteria evaluation) for further growth. Uncircled nodes are pruned. Horizontal dots denote continuation across all template additions (e.g. other members of a series), and vertical dots represent the iterative process of tree growth.

The operation of the GROW algorithm is conceptually fairly simple, and is summarized in FIG. 4. GROW proceeds in an iterative fashion, to systematically attach to the seed fragment each amino acid template in a large preconstructed library of amino acid conformations. When a template has been attached, it is scored for goodness-of-fit to the receptor site, and then the next template in the library is attached to the seed. After all the templates have been tested, only the highest scoring ones are retained for the next level of growth. This procedure is repeated for the second growth level; each library template is attached in turn to each of the bonded seed/amino acid molecules that were retained from the first step, and is then scored. Again, only the best of the bonded seed/dipeptide molecules that result are retained for the third level of growth. The growth of peptides can proceed in the N-to-C direction only, the reverse direction only, or in alternating directions, depending on the initial control specifications supplied by the user. Successive growth levels therefore generate peptides that are lengthened by one residue. The procedure terminates when the user-defined peptide length has been reached, at which point the user can select from the constructed peptides those to be studied further. The resulting data provided by the GROW procedure include not only residue sequences and scores, but also atomic coordinates of the peptides, related directly to the coordinate system of the receptor site atoms.

In yet another embodiment, potential pharmacophoric compounds can be determined using a method based on an energy minimization-quenched molecular dynamics algorithm for determining energetically favorable positions of functional groups in the binding cites of the subject ubiquitin-conjugating enzyme. The method can aid in the design of molecules that incorporate such functional groups by modification of known ligands or de novo construction.

For example, the multiple copy simultaneous search method (MCSS) described by Miranker et al. (1991) *Proteins* 11: 29–34. To determine and characterize a local minima of a functional group in the forcefield of the protein, multiple copies of selected functional groups are first distributed in a binding site of interest on the hUCE protein. Energy minimization of these copies by molecular mechanics or quenched dynamics yields the distinct local minima. The neighborhood of these minima can then be explored by a grid search or by constrained minimization. In one embodiment, the MCSS method uses the classical time dependent Hartee (TDH) approximation to simultaneously minimize or quench many identical groups in the forcefield of the protein.

Implementation of the MCSS algorithm requires a choice of functional groups and a molecular mechanics model for each of them. Groups must be simple enough to be easily characterized and manipulated (3–6 atoms, few or no dihedral degrees of freedom), yet complex enough to approximate the steric and electrostatic interactions that the functional group would have in binding to the site of interest in the hUCE protein. A preferred set is, for example, one in which most organic molecules can be described as a collection of such groups (*Patai's Guide to the Chemistry of Functional Groups,* ed. S. Patai (New York: John Wiley, and Sons, (1989)). This includes fragments such as acetonitrile, methanol, acetate, methyl ammonium, dimethyl ether, methane, and acetaldehyde.

Determination of the local energy minima in the binding site requires that many starting positions be sampled. This can be achieved by distributing, for example, 1,000–5,000 groups at random inside a sphere centered on the binding site; only the space not occupied by the protein needs to be considered. If the interaction energy of a particular group at a certain location with the protein is more positive than a given cut-off (e.g. 5.0 kcal/mole) the group is discarded from that site. Given the set of starting positions, all the fragments are minimized simultaneously by use of the TDH approximation (Elber et al. (1990) *J Am Chem Soc* 112: 9161–9175). In this method, the forces on each fragment consist of its internal forces and those due to the protein. The essential element of this method is that the interactions between the fragments are omitted and the forces on the protein are normalized to those due to a single fragment. In this way simultaneous minimization or dynamics of any number of functional groups in the field of a single protein can be performed.

Minimization is performed successively on subsets of, e.g. 100, of the randomly placed groups. After a certain number of step intervals, such as 1,000 intervals, the results can be examined to eliminate groups converging to the same minimum. This process is repeated until minimization is complete (e.g. RMS gradient of 0.01 kcal/mole/A). Thus the resulting energy minimized set of molecules comprises what amounts to a set of disconnected fragments in three dimensions representing potential pharmacophores.

The next step then is to connect the pharmacophoric pieces with spacers assembled from small chemical entities (atoms, chains, or ring moieties). In a preferred embodiment, each of the disconnected can be linked in space to generate a single molecule using such computer programs as, for example, NEWLEAD (Tschinke et al. (1993) *J Med Chem* 36: 3863,3870). The procedure adopted by NEWLEAD executes the following sequence of commands (1) connect two isolated moieties, (2) retain the intermediate solutions for further processing, (3) repeat the above steps for each of the intermediate solutions until no disconnected units are found, and (4) output the final solutions, each of which is single molecule. Such a program can use for example, three types of spacers: library spacers, single-atom spacers, and fuse-ring spacers. The library spacers are optimized structures of small molecules such as ethylene, benzene and methylamide. The output produced by programs such as NEWLEAD consist of a set of molecules containing the original fragments now connected by spacers. The atoms belonging to the input fragments maintain their original orientations in space. The molecules are chemically plausible because of the simple makeup of the spacers and functional groups, and energetically acceptable because of the rejection of solutions with van-der Waals radii violations.

In one embodiment of the invention, the target regulatory protein is the tumor suppressor p53, and any one of the above assays or molecular modeling protocols is used to identify inhibitors of ubiquitin-mediated destruction of p53, such as by disrupting interaction of hUCE with p53, or interactions between hUCE an other proteins of the ubiquitin system, or alternatively, by mechanistically inhibiting the enzymatic activity of the enzyme. Many lines of evidence point to the importance of p53 in human carcinogenesis. For instance, mutations within the p53 gene are the most frequent genetic aberration thus far associated with human cancer. Although p53 can block the progression of the cell cycle when artificially expressed at high levels, it appears to be dispensable for normal development. Thus, for mice containing homozygous deletions and humans harboring germline mutations of p53, development is normal and p53 protein is expressed at very low levels in most cell types. Emerging evidence, however, suggests that p53 is a checkpoint protein that plays an important role in sensing DNA damage or regulating cellular response to stress. Under normal conditions, p53 is an unstable protein and is present at very low levels in the cell, and the level of p53 in a cell appears to be controlled at least in party by degradation involving the ubiquitin system and, based on data presented herein, is likely to be mediated by the subject hUCE. Treating cells with UV light or X rays dramatically reduces the rate of p53 degradation, leading to a rapid increase in its concentration in the cell and presumably inducing the transcription of genes that block passage through the restriction point. However, while normal cell lines irradiated in G1 fail to enter S phase, many tumor lines do not. In fact, there is a perfect correlation between cell lines that lack this feedback control and cells that have mutations in the p53 gene. These mutations are of two sorts: recessive mutations that inactivate the gene, and dominant mutations that produce abnormal proteins. An inhibitor developed using the subject hUCE in a ubiquitin-conjugating assay or by rational drug design could subsequently be used therapeutically to enhance the function of the p53 checkpoint by increasing the steady state concentration of p53 in the treated cell. The anti-proliferative activity of such an inhibitor can be employed in the treatment of hyperplasias or neoplasias by increasing the fortitude of the checkpoint in transformed cells which contain wild-type p53 (i.e. can induce apoptosis in cells overexpressing c-myc), or by offsetting a diminishment in p53 activity by increasing the level of (mutant) p53. Moreover, such agents can also be used prophylactically in normal cells to increase p53 levels and thereby enhance the protection against DNA damaging agents when it is known that exposure to damaging agents, such as radiation, is imminent.

Moreover, the oncogenic activity of certain viruses, such as the simian virus 40 (SV40), the adenovirus type 5 (Ad5), and the high human papilloma virus types 16 and 18 (HPV16 and HPV18), has been correlated with the virus' ability to interact with and inactivate the cellular p53 protein. In the instance of the high-risk papilloma viruses, the association of the viral oncoprotein E6 with p53 leads to the specific ubiquitination and degradation of p53. This has suggested a model in which E6 immortalizes cells by deregulating cell growth control through the elimination of the p53 tumor suppressor protein. This models accounts for the observations that p53 levels are very low in HPV-immortalized cells and that the half-life of p53 in HPV16-immortalized keratinocytes is shorter than in primary keratinocytes. Thus, the present invention can be employed in the identification of an agent that can block the ubiquitin dependent degradation of p53 as mediated by E6, and thereby block proliferation of HPV-transformed cells.

The subject human ubiquitin conjugating enzyme is likely to be involved in altering the activity of other cellular proteins, particularly proteins which seem to have short half-lives, and the present invention contemplates the use of hUCE inhibitors, including antagonistic forms of the hUCE protein, to inhibit the ubiquitination of other cellular proteins by hUCE. For example, in another embodiment, the regulatory protein ubiquitinated by hUCE is the myc oncoprotein. The myc regulatory protein is activated by translocation or mutation in many B-cell lymphomas or by amplification in tumor types, such as small cell lung cancer and breast cancer. The c-myc gene is the cellular homolog of the viral oncogene v-myc, which is found in a number of avian and feline retroviruses which induce leukemia and carcinomas. Myc has been implicated in the control of normal cell proliferation by many studies. In particular, it is one of the immediate early growth response genes that are rapidly induced in quiescent cells upon mitogenic induction, suggesting that it plays some role in mediating the transition from quiescence to proliferation. However, increased levels of myc itself is not sufficient to cause proliferation. In fact, in normal cells the opposite happens and the cell undergoes apoptosis. Therefore, inhibitors identified in the present assay can be used to effectively induce apoptosis in cells which do not normally overexpress myc. For example, specific delivery of these agents to lymphocytes can be used to inhibit proliferation of B- and/or T-cells in order to induce clonal deletion and generate tolerance to particular antigens.

In tumor cells, on the other hand, elevated or deregulated expression of c-myc is so widespread as to suggest a critical role for myc gene activation in multi-stage carcinomas (Field et all. (1990) *Anticancer Res* 10:1–22; and Spencer et al. (1991) *Adv Cancer Res* 56:1–48). However, such overexpression of myc in these cells is typically believed to be accompanied by expression of other cellular proteins, such as bcl-2. Interestingly, however, almost all tumor cells tested that overexpress myc readily undergo apoptosis in the presence of cytotoxic and growth-inhibitory drugs (Cotter et al. (1990) *Anticancer Res* 10:1153–1159; and Lennon et al. (1990) *Biochem Soc Trans* 18:343–345). Therefore, inhibitors of the ubiquitin-mediated degradation of myc can be used to further deregulate the expression of myc in order to render the cells even more sensitive to a chemotherapeutic treatment, or to possibly upset the careful balance of the transformed cell and cause apoptosis to occur even in the absence of a second cytotoxic drug.

The regulation of cyclin by ubiquitination is yet another therapeutic target which may implicate hUCE inhibitors. Cyclin degradation is a key step governing exit from mitosis and progression into the next cell-cycle. For example, the transition from metaphase to anaphase which marks the end of mitosis in induced by the degradation of cyclin by a ubiquitin-mediated pathway, which in turn leads to the inactivation of cyclin-dependent kinases (cdk) operational at that cycle—cycle stage. As cells enter interphase, cyclin degradation ceases, cyclin accumulates and, as a result of a complex series of post-translational modifications, cyclin /cdk complexes are activated as kinases which drive the cell through mitosis. Cyclin degradation is thus one of the crucial events in exiting mitosis. Indeed, cyclin mutants that retain the ability to activate the cdk complexes, but which cannot be degraded, arrest the cell-cycle in mitosis. Similar cyclin-dependence exists at other points of the cell-cycle as well. Thus, inhibitors of ubiquitin-mediated degradation of a cyclin (such as where the cyclin is chosen from cyclin A, B, C, D1, D2, D3, E or F) can be used as antiproliterative agents.

Yet a further possible substrate of the subject hUCE is the fos oncogene product, which can undergo ubiquitin-mediated degradation in a cell and has been implicated in neoplastic transformation as well as in mediating the action of a variety of extracellular stimuli. The control of gene expression by c-fos is believed to play a critical role in cellular proliferation and developmental responses, and alterations in the normal pattern of c-fos can lead to onco-genesis. Given the prominence of c-fos as an early response gene, apparent over-expression and prolonged lifetime of c-fos, as may be caused by an inhibitor of the ubiquitin-mediated degradation of c-fos, might sufficiently unbalance the cell-cycle and cause cell death. Alternatively, such inhibitors can be used to mimic the effects of an external stimulus on the cell, such as treatment with a cytokine.

EXAMPLE 1

Cloning and Expression of a Novel Human Ubiquitin-conjugating Enzyme

The cDNA encoding the human ubiquitin-conjugating enzyme of the present invention was cloned from HeLa cells (ATCC CCL2). Briefly, polvadenylated RNA was isolated from cultured HeLa cells and first strand cDNA was prepared following standard protocols (c.f., Chomczynski U.S. Pat. No. 4,843,155; and Sambrook et al. *Molecular Cloning: A Laboratory Manual,* CSHL Press, Cold Spring Harbor, N.Y. (1989)). Using the nested PCR primer sets 5'-(GC)$_3$AAGCTTTAYGARGGWGGWGTYTTYTT-3' (SEQ ID No. 3), 5'-(GC)$_3$GAATTCACNGCRTAYTT-YTTNGTCCCAYTC-3' (SEQ ID No. 4) and 5'-(GC)$_3$AAGCTTCCNGTNGGNGAYTTRTTYCAYTG-GCA-3' (SEQ ID No. 5), 5-(GC)$_3$GAATTCATN-GTNARNGCNGGCGACCA-3' (SEQ ID No. 6), which also provided convenient restriction sites in the PCR products, the coding sequences for the hUCE gene was amplified from the HeLa cDNA library, and a HindIII-EcoRI fragment therefrom was subsequently ligated into a pBluescript II KS+ phagemid (PKS+ Stratagene catalog no. 212207) for further manipulation. The resulting pKS-hUCE construct was amplified in XL1-Blue Cells (Strategene Catalog no. 260268), and double stranded construct purified. The nucleic acid sequence determined for the hUCE clone is represented in SEQ ID NO. 1, and the corresponding deduced amino acid sequence is provided in SEQ ID No. 2.

The hUCE gene was subsequently sub-cloned from pKS+ into other expression vectors to generate gene constructs for producing the recombinant hUCE protein in either bacterial or insect cells. In some instances, the recombinant hUCE was provided with exogenous sequences to produce fusion proteins, where the additional sequences of the fusion protein facilitate its purification. For example, after further amplification, the pKS-E2 construct was cut with XhoI and EcoRI, and the fragment containing the hUCE coding sequence sub-cloned into a pGEX vector (Pharmacia catalog no. PGEX-4T) previously digested with SalI and EcoRI. The resulting pGEX-hUCE construct encoded a glutathione-S-transferase (GST)/hUCE fusion (Smith et al. (1988) *Gene* 67:31–40). The pGEX construct was introduced into *E.coli* by transformation, and the transformants grown in liquid media (LB) in the presence of IPTG. Purification of GST/hUCE fusion protein was by standard protocols (*Current Protocols in Molecular Biology,* eds. Ausubel et al. (New York:John Wiley & Sons, 1991); Pharmacia instruction booklet (for catalog no. 27-4570)) using a glutathione-sepharose column (Pharmacia catalog no. 27-4570). Treatment with thrombin removed the GST domain from the fusion protein.

Alternatively, the hUCE coding sequence was excised from the pKS-hUCE construct as a HindIII-EcoRI fragment and ligated into pVL1393 cut with Sma I and Eco I. Briefly, the hUCE gene fragment was purified by agarose gel separation, and ligated into the baculorvirus vector pVL1393 (Invitrogen catalog no. V1392-20) previously cut with Sma I and Bgl II. The pVL1393-hUCE construct was then used to transfect spodoptera frugiperda (Sf9 cells, ATCC CRL 1711), and the cells maintained in insect cell culture media (Grace's Antheraea medium) supplemented with 10% FBS, lactal bumin hydrolysate, TC yeastolate and glutamate (Invitrogen catalog no. B823) following standard protocols (Invitrogen product guide; Summers and Smith (1987); *Texas Agricultural Experiment Station Bulletin No. 1555,* College Station, Tex.; Luckow et al. (1988) *Bio/technology* 6:47–55; and Miller et al., in *Genetic Engineering,* Vol. 8 ed. Setlow and Hollaender (Plenum Press: New York) pages 277–298). Transfected cells are grown until cells begin to lose their adherence to the culture plate surface, at which time the cells are harvested, collected by centrifugation, and lysed. The lysate is clarified by centrifugation to remove the cell wall debris, and the hUCE can be purified from the lysate.

For instance, the hUCE protein was isolated on an E1:ubiquitin charged column. Isolation of enzymes of the ubiquitin-conjugating system has been greatly assisted by "covalent" ubiquitin-affinity chromatography (Crechanover et al. (1982) *J. Biol. Chem.* 257:2537–2542; and Pickart et al. (1985) *J. Biol. Chem.* 260:1573–1581). This method takes advantage of the fact that the E1 enzyme is capable of forming a thiol ester with immobilized ubiquitin (e.g. ubiquitin-Sepharose) in the presence of ATP. Moreover, E1 enzymes bound to the immobilized ubiquitin can be exchanged with the subject hUCE protein. Thus, both E1 and the subject hUCE protein can be specifically purified on such columns, and can be recovered after elution with, for example, dithiothreitol. Moreover, with minor changes, this protocol can be used to isolate hUCE:Ub conjugates (e.g. activated ubiquitin conjugates) for use in therapeutic target assays.

As described in U.S. patent application Ser. No. 08/176, 937, the an E1-containing lysate was applied to a sepharose-ubiquitin column (Hershko et al. (1983) *J. Biol. Chem.* 257:2537–2542) in the presence of ATP (e.g. 5 mM ATP, 10 mM $MgCl_2$, and 0.2 mM dithiothreitol, 500 mM Tris-HCl (pH 7.2)). The column was washed several times with this buffer. A clarified lysate of the hUCE-producing insect cells, adjusted to 50 mM Tris-HCl (pH 7.2), 5 mM ATP, 10 mM $MgCl_2$, and 0.2 mM dithiothreitol, was then applied to the Ub:E1 column, washed, then eluted to remove any remaining Ub:E1 (e.g. hUCE will be exchanged for E1 on the column). The subject hUCE protein was then eluted from the column by washing with 50 mM Tris-HCl (pH 9.0) containing 2 mM dithiothreitol.

In another exemplary embodiment, the recombinant hUCE protein is generated as a poly(His) fusion protein for purification on a $Ni^{2+}$ metal column. An XhoI to EcoRI fragment of the pKS construct is cloned into the pBlueBac A baculovirus (Intvitrogen catalog no. V360-20) previously digested with XhoI and EcoRI. Following the manufacturer's protocols, the $His_6$-hUCE fusion protein is then expressed in Sf9 insect cells, and purified on a $Ni^{2+}$ charged sepharose resin (Invitrogen catalog no. R801; see also Hochuli et al. (1987) *J. Chromatography* 411:177–184; and Janknecht et al. (1991) *PNAS* 88:8972–8976). Following purification of the fusion protein, the $His_6$ tag can be removed by treatment with entrokinase.

EXAMPLE 2

Microinjection of Sense and Anti-sense constructs of the hUCE Gene

In order to confirm the role of hUCE in p53 degradation, we performed microinjection experiments using sense and anti-sense constructs of the hUCE gene. The CMV expression vectors were obtained by inserting the entire open-reading frame of one of HPV-18 E6, human E1, human E6-AP, hUCE, or a Cys-85 mutant of hUCE, in either a sense or anti-sense orientation (as indicated in Table I) in the pX-plasmid (Baldin et al. (1993) *Genes & Devel.,* 7:812–821). Plasmids were purified with a Promega Wizard Maxi-prep kit and injected at a concentration of 50 to 100 $\mu g/\mu l$ in the presence of normal affinity-purified rabbit or mouse antibody (5 mg/ml in PBS) used as microinjection marker.

Cell monolayers growing on glass coverslips (at ca. 60% density) were microinjected with an automated microinjection system (AIS, Zeiss; Ansorge et al. (1988) *J. Biochem. Biophys. Meth.,* 16:283–292). All microinjection experiments were carried out in 3.5 cm Petri dishes containing 3 ml of DMEM medium carbonate free, in order to avoid the decrease in pH of the medium during the injection. Each cell was injected at a pressure between 50 and 150 hPa. Approximately 100–150 cells were microinjected for each experimental point. Protein levels of p53 were monitored by incubating the cells with FITC-conjugated anti-p53 antibody. Cells were washed again three times with PBS and incubated with Texas red-conjugated streptavidin (Vector Laboratories, dilution 1:100) or FITC-conjugated streptavidin (Vector Laboratories, dilution 1:50). After a final wash with PBS, immunofluorescence samples were directly mounted in Crystal/mount medium (Biomeda Corp.).

TABLE II

Detection of p53 protein levels in microinjected MDA-MB-468 cells

| Microinjected | *Injected Cells p53+ | Uninjected Cells p53+ |
|---|---|---|
| pX sense E6 (100 µg/ml) Rabbit IgG (5 mg/ml) | 31/129 cells or 24.0% | 100% |
| pX sense E6 (50 µg/ml) pX Antisense hUCE (50 µg/ml) Rabbit IgG (5 mg/ml) | 69/112 cells or 61.6% | 100% |
| pX sense E6 (50 µg/ml) and pX sense hUCE mutant (50 µg/ml) Rabbit IgG (5 mg/ml) | 66/103 cells or 64.1% | 100% |
| pX sense E6 (50 µg/ml) pX Antisense E6AP (50 µg/ml) Rabbit IgG (5 mg/ml) | 53/123 cells or 43.1% | 100% |
| pX sense E6 (50 µg/ml) pX Antisense E1 (50 µg/ml) Rabbit IgG (5 mg/ml) | 67/118 cells or 56.8% | 100% |

*p53 positive cells were those which stained as bright as the noninjected cells. p53 negative cells were less bright or completely negative MDA-MB-408 cells stably express p53 to levels which are detectable by immunoflourescence means. As demostrated in Tabel II, the level of p53 is significantly reduced by the expression of E6, e.g. mimicking HPV infection, presumably by ubiquitin-mediated pathways. The role of hUCE in the destruction of p53 brought about by E6 expression is demonstrated by the ability of an anti-sense hUCE construct to at least partially protect p53 from degradation. Moreover, the data of Table 1 reveals that an hUCE mutant, Cys-85→Ser, which produces an inactive form of the enzyme, is possibly a dominant negative mutant able to at least partially rescue p53.

EXAMPLE 3

Generating a Molecular Model of the hUCE protein

The three dimenstional coordinates of the protein backbone from the structure of UBC1 from A. thaliana (Brookhaven databank file IAAK.pdb) were used for homology modeling of hUCE. Modeling was performed with the Protein Workbench software package of QUANTA, version 4 (MSI, Burlington Mass.).

Briefly, the amino acid sequence of hUCE (SEQ ID No. 2) and UBC1 were aligned using the alignment program in QUANTA. This alignment shows a 44% match of similar residues. The coordinates of the backbone non-hydrogen atoms were then copied onto the hUCE sequence, sidechain coordinates for the hUCE model were a ignored at this point. The resulting hUCE structure was then energy minimized using 200 steps of the steepest descent algorithm followed by 5000 steps of the adopted-base Newton Raphson algorithm. All atoms, including polar hydrogens and all side chains were allowed to move. The resulting CHARMM energy of the system was −7084.2 kcal.

In the next step, the structure was heated up to 500° K using 2000 steps or a total time of 2 psec. After heating, the system was then allowed to equilibrate for 9 psec (9000 steps). The final CHARMM energy after 10 psec was around −5750 kcal. Finally, the system was cooled down to 300° K in steps of 50° K (1 psec cooling, 4 psec equilibration) and finally equilibrated at 300° K for 6 psec. The final total CHARMM energy was around −6650 kcal. The final structure hsowed no serious conformational strains or improper angles. The atomic coordinates for the full length model are shown in FIG. 1.

In the next step we modeled the 4-meric peptide Ala-Ile-Arg-Gly into the active site. This peptide was derived from the c-terminal sequence of ubiquitin (RIRG). A thioester bond was manually constructed in both cases between the C-terminal Gly and the active site cyteseines. The system was energy-minimized and subsequently subjected to molecular dynamics simulations. In both cases the Ile residue of the peptide settles into the hydrophobic pocket. There are two backbone—backbone hydrogen bonds between the loops and the peptide. The Arg of the peptide forms hydrogen bonds with a conserved Asp residue (between the conserved Val and Ile residues) in both cases.

The general tight fit of the peptide into the active-site cleft makes us very confident that this area is also the docking site for ubiquitin. We will use this structural information for the construction of various mutants which we believe will no longer bind ubiquitin. We will also use this three-dimensional information for the design of inhibitory peptides or peptidomimetics. The coordinates for the subset of residues determined to be of greatest import in rational drug design are shown in FIG. 2.

EXAMPLE 4

Ubiquitin was obtained from commercial sources, and the remaining protein components of the reconstituted protein system were cloned from HeLa cells (ATCC CCL2). Briefly, polyadenylated RNA was isolated from cultured HeLa cells and first strand cDNA was prepared following standard protocols (c.f., Chomczynski U.S. Pat. No. 4,843,155; and Sambrook et al. *Molecular Cloning. A Laboratory Manual,* CSHL Press, Cold Spring harbor, N.Y. (1989)). PCR primers, designed to amplify DNA sequences encoding each of the component proteins, as well as provide convenient restriction sites to the PCR products, were used to isolate coding sequences for a human E1, human p53, HPV-18 E6, human E6-AP, and various human E2's, which were subsequently liguated into a pBluescript II KS+ phagemid (pKS+ Stratagene catalog no. 212207) for further manipulation. As described below, each of the component proteins genes were subsequently sub-cloned from pKS+ into other expression vectors to generate gene constructs for producing the recombinant proteins in either bacterial or insect cells. In some instances, the recombinant proteins have been provided with exogenous sequences to produce fusion proteins, where the additional sequences of the fusion protein facilitate its purification.

i) Human E1

Utilizing the primers 5'-(GC)$_3$AAGCTTATGTC-CAGCTCGCCGCTGTCCAAG-3' and 5'-(GC)$_3$GGATCCTCAGCGGATGGTGTATCGGACATA-3'. The coding sequence for a human E1 (SEQ ID Nos. 13 and 14) was amplified from a HeLa cell cDNA library. The PCR amplification product containing the E1 coding sequences was purified and cut with Hind III and Bam HI (restriction sites provided by the PCR primers), and ligated into the pKS+ phagemid. The resulting pKS-E1 construct was amplified in XL1-Blue Cells (Strategen catalog no. 260268), and double stranded construct purified.

A Hind III/fill to BamHI fragments containing the E1 coding sequence was isolated from the pKS-E1 construct, where "Hind III/fill" indicates that a Hind III overhand generated in the fragment has been filled to form a blunt-end using Klenow and dNTPs. The E1 gene fragment was purified by agarose gel separation, and ligated into the baculorvirus vector pVL1393 (Invitrogen catalog no. V1392-20) previously cut with Sma I and Bgl II. The pVL1393-E1 construct was used to transfect spodoptera frugiperda (Sf9) cells) (ATCC CRL 1711), and the cells maintained in insect cell culture media (Grace's Antheraea medium) supplemented with 10% FBS, lactal bumin hydrolysate, TC yeastolate and glutamate (Invitrogen catalog no. B823) following standard protocols (Invitrogen product guide; Summers and Smith (1987); *Texas Agricultural Experiment Station Bulletin No.* 1555, College Station, Tex.; Luckow et al. (1988) Bio/technology 6:47–55; and Miller et al., in *Genetic Engineering,* Vol. 8 (Setlow and Hollaender, eds) pp. 277–298, Plenum, N.Y.). Transfected cells are grown until cells begin to lose their adherence to the culture plate surface, at which time the cells are harvested, collected by centrifugation, and lysed. The lysate is clarified by centrifugation to remove the cell wall debris, and the E1 containing lysate is applied to a sepharose-ubiquitin column (Hershko et al. (1983) *J. Biol. Chem.* 257:2537–2542) in the presence of ATP (e.g. 5 m MATP, 10 mM MgCl$_2$, and 0.2 mM clithiothreitol, 50 mM Tris-HCl (pH 7.2)). The column is washed several times with this buffer, and the E1 protein eluted with the following solutions: 1M KCl containing 50 mM Tris-HCl, pH 7.2 (KCl eluate); the above Tris buffer, to remove salt; and finally 2 mM ATP and 0.04 mM sodium pyrophosphate in the above Tri buffer. The E1-containing eluate can be concentrated, as well as placed in new buffer solution, by centrifuge ultrafiltration with CentriPrep or Centricon membranes (Amicon Corp., Massachusetts). Alternatively, the ubiquitin-immoblized E1 can be used, as described below, in the purification of E2 enzymes.

ii) Human E2

A human rad6 homolog (SEQ ID Nos. 15 and 16) was amplified from the HeLa cel cDNA using the primers 5'-(GC)$_3$AAGCTTATGTCGACCCCGGCCCGGAG-GAGG-3' and 5'-(GC)$_3$GAATTCTTATGAATCATTCCAGCTTTGTTC-3' and cloned into pBluescript II pKS+ as a Hind III-EcoRI fragment. After further amplification, the pKS-E2 construct was cut with XhoI and NotI, and the fragment containing E2 coding sequence sub-cloned into a pGEX vector (Pharmacia catalog no. PGEX-4T-3) previously digested with SalI and NotI. The resulting pGEX-E2 construct encoded a glutathione-S-transferase (GST)/E2 fusion (Smith et al. (1988) Gene 67:31-40). The pGEX construct was introduced into *E.coli* by transfromation, and the transformants grown in liquid media (LB) in the presence of IPTG. Purification of GST/E2 fusion protein was by standard protocols (*Current Protocols in Molecular Biology,* eds. Ausubel et al. (New York:John Wiley & Sons, 1991); Pharmacia instruction booklet (for catalog no. 27-4570)) using a glutathione-sepharose column (Pharmacia catalog no. 27-4570). Treatment with thrombin removed the GST domain from the fusion protein.

Alternatively, the rad6 coding sequence was excised from the pKS-rad6 construct as a HindIII-EcoRI fragment and ligated into pVL1393 cut with Sma I and Eco 1. The E2 protein is produced in Sf9 cells, as described above, and purified on a sepharose-uibiquitin:E1 column. As above, a clarified lysate of the E2-producing insect cells, adjusted to 50 mM Tris-HCl (pH 7.2), 5 mM ATP, 10 mM MgCl$_2$, and 0.2 mM dithiothreitol, is applied to the Ub:E1 column, washed, then eluted to remove any remaining Ub:E1 (e.g. E2 will be exchanged for E1 on the column). Rad6 is then eluted from the column by washing with 50 mM Tris-HCl (pH 9.0) containing 2 mM dithiothreitol.

iii) HPV-18E6

The coding-sequence for HPV-18 E6 (SEQ ID Nos. 9 and 10) was amplified from the HeLa cell cDNA library using the primers 5'-(GC)₃AAGCTTATGGCGCGCTTTG-AGGATCCAACA-3' and 5'-(GC)₃GAATTCTT-ATACTTGTGTTTCTCTGCGTCG-3', the PCR products purified, and the amplified E6 sequences digested with Hind III and EcoRI and ligated into a pBlueScript II pKS+ phagemid. Several different expression vectors were generated by subcloning the E6 sequences from the pKS-E6 construct. For example, a Hind III to EcoRI fragment containing E6 coding sequences was ligated into pVL1393 cut with Sma I and EcoRI to produce baculovirus expression system as described above.

Alternatively, E6 has been generated as $His_6$ fusion protein for purification on a $Ni^{2+}$ metal column. An XhoI to EcoRI fragment of the pKS construct was cloned into the pBlueBac A baculovirus (intvitrogen catalog no. V360-20) previously digested with XhoI and EcoRI. Following the manufacturer's protocols, the $His_6$-E6 fusion protein was expressed in Sf9 insect cells, and purified on a $Ni^{2+}$ charged sepharose resin (Invitrogen catalog no. R801; sell also Hochuli et al. (1987) *J. Chromatography* 411:177–184; and Janknecht et al. (1991) *PNAS* 88:8972–8976). Following purification of the fusion protein, the $His_6$ tag can be removed by treatment with entrokinase.

iv) Human E6-AP

E6-AP (SEQ ID Nos. 7 and 8) was cloned from the HeLa cell cDNA library using the PCR primers 5'-(GC)₃-AAGCTTTCAGGACCTCAGTCTGACGAC-3' and 5'(GC)₃ GGATCCTTACAGCATGCCAAATCCTTTGGC-3', wherein the amplified E6-AP sequences were digested with Hind III and Bam HI and ligated into pBluescript II pkst. Constructs for expressing both $HIS_6$ tagged and GST tagged versions of E6-AP were generated. In one instance, an NheI to BamHI E6-AP containing fragment was cloned into pBlueBacA (cut with NheI and BamHII), and the construct expressed in insect cells. As above, the His-tagged E6-AP protein was purified by $Ni^{+2}$ affinity, and the his-tag subsequently removed by treatment with enterokinase.

Alternatively, a HindIII (fill) to NotI fragment has been isolated from the pKS-E6AP construct and subsequently ligated into the SmaI-Not I sites of pGEX-4T-3, to produce a GST fusion protein in *E. coli* which was purified using a gluathione-sepharose resin.

v) Human p53

Human p53 (SEQ ID Nos. 11 and 12) was cloned into pBluescript II pKS+ from the HeLa cell cDNA library using the primers 5' (GC)₃GAATTCGCCATGGA-GGAGCCGCAGTCAGATCCT-3' and 5'-(GC)₃AAGCTT-TCAGTCTGAGTCAGGCCCTTCTGT-3'. In similar fashion to the other component proteins above, several different expression constructs were generated for p53, some of which included extra polypeptide sequence to facilitate purification. For expression in insect cells, two baculoviral constructs were made. For native p53, a BamHI fragment of the pKS-p53 vector was ligated into BamHI digested pVL1393. For $His_6$-tagged p53, the BamHIII fragment was ligated into pBlueBacA previously cut with BamHI. Likewise, a GST-p53 was generated in *E. coli* by expression of a pGEX construct made by ligating a p53-containing EcoRI to NotI fragment of the pKS-p53 construct into pGEX-4T-1.

In the instance of each of the two fusion proteins, standard protocols were used to purify p53 from lysed transformants. For the native p53 produced by the pVL1393-p53 construct, the method of Hupp et al. was used to purify the p53 on a heparin-sepharose column (Hupp et al. (192) *Cell* 71:875–886).

vi) Ubiquitin

Ubiquitin is available from commercial sources (Bovine ubiquitin, Sigma catalog no. 6253; yeast ubiquitin, Sigma catalog no. 2129). Various modified forms of ubiquitin are also available as for example, fluorescein-labeled ubiquitin (Sigma catalog no. U5504), and horseradish-peroxidase labeled ubiquitin (Sigma catalog no. U9879). Biotinylated ubiquitin can be prepared from biotin-NHS (N-hydroxy-succinimide ester) using well-known techniques (biotinylation kit; Pierce catalog no. 214206, 203188 (6 atom spacer), or 203114 (14 atom spacer)).

vii) Additional Reagents

For generating certain of the detection means as described herein, some of the following reagents can be employed: polyclonal sera to ubiquitin (Sigma catalog no. U5379); labeled antibodies to biotin (Sigma catalog nos. A4541 (peroxidase conjugated) and F6762 (FITC conjugated)); labeled avidin (Sigma catalog nos. A7294, E2636 (peroxidase conjugated) and A2050, E2761 (FITC conjugated)); streptavidin (Sigma catalog no. S3762 (FITC conjugated) and S5512 (peroxidase conjugated)); Streptavidin-coated beads (Sigma catalog no. 400996; Pierce catalog no. 20347G); Streptavidin-coated 96 well microtrite plates (Pierce catalog no. 15124); Maleic anhydride-activated polystyrene 96 well plates (Pierce catalog no. 15110); and antibody to human p53 (PharMingen catalog Nos. 14091A and 14211 A).

EXAMPLE 5

To generate the ubiquitin-conjugating system comprising a reconstituted protein mixture, portions of each of the preparations of purified components (described above), along with ubiquitin, are mixed together in a conjugation buffer comprising 50 mM Tris·HCl (pH7.4), 5 mM $MgCl_2$, 2 mM ATP, 0.1 mM DTT, and 5 μM ubiquitin. In a typical reaction, E1, E2, the target protein (p53), and (optionally) E6 and E6-AP, are added to the conjugation buffer at approximately 100 ng each in a final reaction volume of 20–50 μL. The reconstituted ubiquitin-conjugating system is incubated at 25° C. for varying lengths of time (e.g. 0.5 to 30 minutes), in the presence of varying concentrations of a candidate agent (e.g. 0 to 50 mM), and the reaction quenched with iodoacetate and/or arsenite. Where either preconjugated E1:Ub or E2:Ub is used to genereate the mixture, the level of the conjugate in the reaction system can be increased to 5–10 μM, and free ubiquitin left out of the conjugation buffer. The levels of p53:Ub conjugates in the presence and absence of a candidate agent can be determined as described herein, taking into account statistical significance (e.g. the error of the particular assay employed) and appropriate controls.

EXAMPLE 6

$^{35}S$-labeled p53, prepared by cell culture technique utilizing $^{35}S$-methionine, is incubated with combined purified components of a ubiquitin conjugating system as described in Example 5, including biotinylated ubiquitin. The reaction is conducted in a 96 well microtitre plate and stopped with iodoacetate. The reaction mixture is transferred to the wells of a streptavidin-coated microtitre plate and incubated to capture the complex of biotinylated ubiquitin and p53 (free biotinylated ubiquitin will also compete for binding sites on the well). The wells are washed with buffer (e.g. phosphate-buffered saline, or conjugation buffer lacking ubiquitin and ATP) to remove uncomplexed p53. Ubiquinated p53 is detected by addition of scintillant to the well and counting in a scintillation instrument. Inhibition of the ubiquitin conjugation system by an added candidate agent is indicated by a reduced radioactive count.

EXAMPLE 7 p53 is incubated with combined purified components of a ubiquitin conjugating system as desribed above, including biotinylated ubiquitin. The reaction is conducted in a 96 well microtitre plate and stopped with iodoacetate. The reaction mixture is transferred to the wells of a streptavidin coated microtitre plate and incubated to capture the complex of biotinylated ubiquitin and p53 (free biotinylated ubiquitin will also compete for binding sites on the well). The wells are washed with buffer to remove uncomplexed p53. Next, the Ub:p53 complexes capatured on the plate are decorated with a murine monoclonal antibody to p53. The wells are washed and binding of monoclonal antibody is detected by addition of peroxidase-conjugated antibody to mouse IgG (H+L) (Pierce catalog nos. 91430G and 91450G) and contacting with an appropriate substrate system, such as o-phenylenediamine dihydrochloride (Sigma catalog no. P9187).

EXAMPLE 8

The glutathione S-transferase (GST)-p53 fusion product is incubated with combined purified components of a ubiquitin conjugating system, including biotinylated ubiquitin. The reaction is conducted in a 96 well microtitre plate and stopped with iodoacetate. The reaction mixture is transferred to the wells of a streptavidin coated microtitre plate and incubated to capture the complex of biotinylated ubiquitin and GST-p53 (free biotinylated ubiquitin will also compete for binding sites on the well). The wells are washed with buffer to remove uncomplexed GST-p53. Binding of ubiquitinated GST-p53 is monitored with a detection system, based either on a biochemical assay for GST (e.g., 1-chloro-2,4-dinitrobenzene, Pharmacia catalog no. 27-4590-01) or an immunological assay using goat anti-GST antibody (Pharmacia catalog no. 27-4590-01).

EXAMPLE 9

The plasmid pTKluc comprises a luciferase gene whose expression is driven by the core Herpes simplex virus thymidine-kinase (TK) promoter which has been modified with either p53 (p53RE/TK), myc (mycRE/TK), or Sp1 (Sp1RE/TK) binding sites. When the construct lacking any of the modifications to the TK promoter is transfected into mammalian cells, the detectable luciferase activity is low because this core TK promoter fragment does not contain the upstream activating sequences necessary for efficient transcriptional activation of the luciferase gene. However transfection with the constructs in which TK is further modified to contain either 3 or 6 response-elements (RE) for one of p53, myc or Sp1, the detectable luciferase activity increases in cells which express the appropriate protein. For example, the level of luciferase expression is significantly higher in p53-producing cells (e.g. ML1 cells) transfected with the p53RETK-containing construct than with the TK construct. likewise, endogenous myc and Sp1 proteins can drive expression of the mycRE/TK and Sp1RE/TK constructs. As set out above, both p53 and myc can be degraded by the ubiquitin pathway. However, Sp1 is not known to be degraded by any ubiquitin-mediated pathway, and the SP1RE/TK construct can therefore be used as a control in the present assays. Thus, in the presence of an agent which inhibits ubiquitin-mediated degradation of p53 in a cell harboring the p53RE/TK construct, the level of luciferase activity would increase relative to that in the cell not treated with the candidate agent.

To construct the luciferase reporter constructs, the pGL2-Basic vector (Promega catalog no. E1641) was modified by addition, in the multiple cloning region, of a SalI to BamHII fragment containing the TK promoter sequence with either 3 or 6 tandemly arranged binding sites placed upstream of the TK promoter. Prior to addition of the RE/TK promoter sequences, a SalI restriction site at 2744 of pGL2-Basic was destroyed by oligonucleotide site-directed mutagenesis. The resulting constructs, designated p53RE/TK, mycRE/TK, and Sp1RE/TK, were each subsequently used to transfect mammalian cells following the manufacturer's suggests (Technical notes, Part #TM003 of Promega Catalog no. E164).

In an alternative embodiment, a SalI to BamHI fragment of p53/RE/TK containing the luciferase reporter gene was isolated and sub-cloned into another eukaryotic expression vector pcDNAIII (Invitrogen, San Diego, Calif.) previously digested with BglII and XhoI.

The vector p53RE/TK is transfected into the human chronic leukemia cell line ML1 that expresses wild-type p53. In this in vivo situation, luciferase expression is upregulated by the presence of p53, which functions as a transcriptional activating factor by binding to the p53 response clement upstream of the TK promoter. The ubiquitin conjugating system participates in the degradation of p53 and, when functional, down regulates the expression of luciferase in this system. Measurement of luciferase activity are carried out by standard protocols (see, for example, Promega Technical Bulletin #TB161). Cells are grown and transfected in a tissue culture grade 96 well microtitre plate. The cultured cells are incubated in the presence and absence of a candidate agent, then harvested and centrifuged. The harvested cells are then lysed with lysis buffer. The lysates clarified by centrifugation, and the supernatants transferred to luminescent grade microtitre plates. Luciferase assay sustrate (Beetle luciferin, Promega catalog no. E1603) is added, and the reaction in each well monitored in a luminometer or scintillation counter. Inhibition of the ubiquitin conjugating system results in a greater luminescence signal than the uninhibited system. Although an in vivo assay, this screen will ignore general cytotoxic compounds.

All of the above-cited references and publications are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A substantially pure preparation of an hUCE polypeptide comprising an amino acid sequence at least 95% homologous to SEQ ID NO. 2, which polypeptide catalyzes ubiquitin conjugation.

2. The polypeptide of claim 1, having an amino acid sequence at least 97% homologous to the amino acid sequence of SEQ ID No. 2.

3. The polypeptide of claim 1, wherein said polypeptide mediates ubiquitination of a p53 protein.

4. A recombinant hUCE polypeptide comprising an amino acid sequence at least 95% homologous to SEQ ID NO. 2, which polypeptide specifically binds at least one of an E6-AP protein, a papillomavirus E6 protein, or p53.

5. The polypeptide of claim 4, wherein said polypeptide contains at least one amino acid residue different from SEQ ID No. 2 and which inhibits ubiquitination of a p53 or E6-AP protein by an enzyme having a sequence represented by SEQ ID No. 2.

6. An immunogen comprising the polypeptide of claim 1, in an immunogenic preparation, said immunogen being capable of eliciting an immune response specific for said ubiquitin conjugating enzyme polypeptide.

7. An immunogen comprising the polypeptide of claim 1 in an immunogenic preparation, said immunogen being capable of eliciting antibodies specific for said ubiquitin conjugating enzyme polypeptide.

8. The polypeptide of claim 5, wherein said ubiquitin conjugating enzyme has an ubiquitin conjugating activity which is less than 5 percent of a ubiquitin conjugating enzyme identical to SEQ ID No. 2.

9. The polypeptide of claim 1, which polypeptide specifically binds at least one of an E6-AP protein, a papillomavirus E6 protein, or p53.

10. The polypeptide of claim 1, wherein said ubiquitin conjugating enzyme is of human origin.

11. The polypeptide of claim 7, wherein said ubiquitin conjugating enzyme is a fusion protein.

12. The polypeptide of claim 11, wherein said fusion protein is functional in a two-hybrid assay.

13. The polypeptide of claim 1, having an amino acid sequence identical to the amino acid sequence of SEQ ID No. 2.

14. The polypeptide of claim 1, wherein said polypeptide mediates ubiquitination of an E6-AP polypeptide.

15. The polypeptide of claim 1, wherein said polypeptide can be encoded by a gene which hybridizes under stringent conditions to the coding sequence of SEQ ID No. 1.

16. The polypeptide of claim 4, wherein said polypeptide catalyzes ubiquitin conjugation.

17. The polypeptide of claim 16, wherein said polypeptide mediates ubiquitin conjugation to a p53 polypeptide.

18. The polypeptide of claim 16, wherein said polypeptide mediates ubiquitin conjugation to an E6-AP polypeptide.

19. The polypeptide of claim 4, having an amino acid sequence at least 97% homologous to the amino acid sequence of SEQ ID No. 2.

20. The polypeptide of claim 4, having an amino acid sequence identical to the amino acid sequence of SEQ ID No. 2.

21. The polypeptide of claim 11, wherein said fusion protein is glutathione-S-transferase (GST) fusion protein.

22. The polypeptide of claim 11, wherein said fusion protein includes a purification leader sequence.

23. The polypeptide of claim 1, wherein said polypeptide further comprises a label group attached thereto and able to be detected.

24. The polypeptide of claim 23, wherein said label group being selected from a group consisting of radioisotopes, fluorescent compounds, enzymes, and enzyme co-factors.

25. The polypeptide of claim 4, wherein said polypeptide can be encoded by a gene which hybridizes under stringent conditions to coding sequence of the human hUCE gene of SEQ ID No. 1.

26. The polypeptide of claim 5, wherein said polypeptide comprises a dominant negative mutation at the active site cysteine.

* * * * *

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
       (A) LENGTH: 444 base pairs
       (B) TYPE: nucleic acid
       (C) STRANDEDNESS: both
       (D) TOPOLOGY: linear (ii) MOLECULE TYPE: cDNA (ix) FEATURE:
       (A) NAME/KEY: CDS
       (B) LOCATION: 1..441

(xi) SEQUENCE DESCRIPTION: SEQ ID NO:1:

```
ATG GCG CTG AAA CGG ATC CAC AAG GAA TTG AAT GAT CTG GCA CGG GAC        48
Met Ala Leu Lys Arg Ile His Lys Glu Leu Asn Asp Leu Ala Arg Asp
 1               5                  10                  15

CCT CCA GCA CAG TGT TCA GCA GGT CCT GTT GGA GAT GAT ATG TTC CAT        96
Pro Pro Ala Gln Cys Ser Ala Gly Pro Val Gly Asp Asp Met Phe His
             20                  25                  30

TGG CAA GCT ACA ATA ATG GGG CCA AAT GAC AGT CCC TAT CAG GGT GGA       144
Trp Gln Ala Thr Ile Met Gly Pro Asn Asp Ser Pro Tyr Gln Gly Gly
         35                  40                  45

GTA TTT TTC TTG ACA ATT CAT TTC CCA ACA GAT TAC CCC TTC AAA CCA       192
Val Phe Phe Leu Thr Ile His Phe Pro Thr Asp Tyr Pro Phe Lys Pro
 50                  55                  60

CCT AAG GTT GCA TTT ACC ACA AGA ATT TAT CAT CCA AAT ATT AAC AGT       240
Pro Lys Val Ala Phe Thr Thr Arg Ile Tyr His Pro Asn Ile Asn Ser
 65                  70                  75                  80

AAT GGC AGC ATT TGT CTT GAT ATT CTA CGA TCA CAG TGG TCT CCA GCA       288
Asn Gly Ser Ile Cys Leu Asp Ile Leu Arg Ser Gln Trp Ser Pro Ala
                 85                  90                  95

CTA ACT ATT TCA AAA GTA CTC TTG TCC ATC TGT TCT CTG TTG TGT GAT       336
Leu Thr Ile Ser Lys Val Leu Leu Ser Ile Cys Ser Leu Leu Cys Asp
            100                 105                 110

CCC AAT CCA GAT GAT CCT TTA GTG CCT GAG ATT GCT CGG ATC TAC CAA       384
Pro Asn Pro Asp Asp Pro Leu Val Pro Glu Ile Ala Arg Ile Tyr Gln
        115                 120                 125

ACA GAT AGA GAA AAG TAC AAC AGA ATA GCT CGG GAA TGG ACT CAG AAG       432
Thr Asp Arg Glu Lys Tyr Asn Arg Ile Ala Arg Glu Trp Thr Gln Lys
    130                 135                 140

TAT GCG ATG TAA                                                       444
Tyr Ala Met
145
```

(2) INFORMATION FOR SEQ ID NO:2:

(i) SEQUENCE CHARACTERISTICS:
       (A) LENGTH: 147 amino acids
       (B) TYPE: amino acid
       (D) TOPOLOGY: linear (ii) MOLECULE TYPE: protein (xi) SEQUENCE DESCRIPTION: SEQ ID NO:2:

```
Met Ala Leu Lys Arg Ile His Lys Glu Leu Asn Asp Leu Ala Arg Asp
 1               5                  10                  15

Pro Pro Ala Gln Cys Ser Ala Gly Pro Val Gly Asp Asp Met Phe His
```

```
            20                  25                  30
Trp Gln Ala Thr Ile Met Gly Pro Asn Asp Ser Pro Tyr Gln Gly Gly
            35                  40                  45
Val Phe Phe Leu Thr Ile His Phe Pro Thr Asp Tyr Pro Phe Lys Pro
 50                  55                  60
Pro Lys Val Ala Phe Thr Thr Arg Ile Tyr His Pro Asn Ile Asn Ser
 65                  70                  75                  80
Asn Gly Ser Ile Cys Leu Asp Ile Leu Arg Ser Gln Trp Ser Pro Ala
                 85                  90                  95
Leu Thr Ile Ser Lys Val Leu Leu Ser Ile Cys Ser Leu Leu Cys Asp
                100                 105                 110
Pro Asn Pro Asp Asp Pro Leu Val Pro Glu Ile Ala Arg Ile Tyr Gln
                115                 120                 125
Thr Asp Arg Glu Lys Tyr Asn Arg Ile Ala Arg Glu Trp Thr Gln Lys
    130                 135                 140
Tyr Ala Met
145
```

(2) INFORMATION FOR SEQ ID NO:3:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:3:

GCGCGCAAGC TTTAYGARGG WGGWGTYTTY TT                                  32

(2) INFORMATION FOR SEQ ID NO:4:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:4:

GCGCGCGAAT TCACNGCRTA YTTYTTNGTC CCAYTC                          36

(2) INFORMATION FOR SEQ ID NO:5:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:5:

GCGCGCAAGC TTCCNGTNGG NGAYTTRTTY CAYTGGCA                       38

(2) INFORMATION FOR SEQ ID NO:6:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:6:

```
GCGCGCGAAT TCATNGTNAR NGCNGGCGAC CA                                   32
```

(2) INFORMATION FOR SEQ ID NO:7:

(i) SEQUENCE CHARACTERISTICS:
       (A) LENGTH: 2624 base pairs
       (B) TYPE: nucleic acid
       (C) STRANDEDNESS: both
       (D) TOPOLOGY: linear (ii) MOLECULE TYPE: cDNA (ix) FEATURE:
       (A) NAME/KEY: CDS
       (B) LOCATION: 1..2624

(xi) SEQUENCE DESCRIPTION: SEQ ID NO:7:

```
TCA GGA GAA CCT CAG TCT GAC GAC ATT GAA GCT AGC CGA ATG AAG CGA        48
Ser Gly Glu Pro Gln Ser Asp Asp Ile Glu Ala Ser Arg Met Lys Arg
 1               5                  10                  15

GCA GCT GCA AAG CAT CTA ATA GAA CGC TAC TAC CAC CAG TTA ACT GAG        96
Ala Ala Ala Lys His Leu Ile Glu Arg Tyr Tyr His Gln Leu Thr Glu
             20                  25                  30

GGC TGT GGA AAT GAA GCC TGC ACG AAT GAG TTT TGT GCT TCC TGT CCA       144
Gly Cys Gly Asn Glu Ala Cys Thr Asn Glu Phe Cys Ala Ser Cys Pro
         35                  40                  45

ACT TTT CTT CGT ATG GAT AAT AAT GCA GCA GCT ATT AAA GCC CTC GAG       192
Thr Phe Leu Arg Met Asp Asn Asn Ala Ala Ala Ile Lys Ala Leu Glu
     50                  55                  60

CTT TAT AAG ATT AAT GCA AAA CTC TGT GAT CCT CAT CCC TCC AAG AAA       240
Leu Tyr Lys Ile Asn Ala Lys Leu Cys Asp Pro His Pro Ser Lys Lys
 65                  70                  75                  80

GGA GCA AGC TCA GCT TAC CTT GAG AAC TCG AAA GGT GCC CCC AAC AAC       288
Gly Ala Ser Ser Ala Tyr Leu Glu Asn Ser Lys Gly Ala Pro Asn Asn
                 85                  90                  95

TCC TGC TCT GAG ATA AAA ATG AAC AAG AAA GGC GCT AGA ATT GAT TTT       336
Ser Cys Ser Glu Ile Lys Met Asn Lys Lys Gly Ala Arg Ile Asp Phe
            100                 105                 110

AAA GAT GTG ACT TAC TTA ACA GAA GAG AAG GTA TAT GAA ATT CTT GAA       384
Lys Asp Val Thr Tyr Leu Thr Glu Glu Lys Val Tyr Glu Ile Leu Glu
        115                 120                 125

TTA TGT AGA GAA AGA GAG GAT TAT TCC CCT TTA ATC CGT GTT ATT GGA       432
Leu Cys Arg Glu Arg Glu Asp Tyr Ser Pro Leu Ile Arg Val Ile Gly
    130                 135                 140

AGA GTT TTT TCT AGT GCT GAG GCA TTG GTA CAG AGC TTC CGG AAA GTT       480
Arg Val Phe Ser Ser Ala Glu Ala Leu Val Gln Ser Phe Arg Lys Val
145                 150                 155                 160

AAA CAA CAC ACC AAG GAA GAA CTG AAA TCT CTT CAA GCA AAA GAT GAA       528
Lys Gln His Thr Lys Glu Glu Leu Lys Ser Leu Gln Ala Lys Asp Glu
                165                 170                 175

GAC AAA GAT GAA GAT GAA AAG GAA AAA GCT GCA TGT TCT GCT GCT GCT       576
Asp Lys Asp Glu Asp Glu Lys Glu Lys Ala Ala Cys Ser Ala Ala Ala
            180                 185                 190

ATG GAA GAA GAC TCA GAA GCA TCT TCC TCA AGG ATA GGT GAT AGC TCA       624
Met Glu Glu Asp Ser Glu Ala Ser Ser Ser Arg Ile Gly Asp Ser Ser
        195                 200                 205

CAG GGA GAC AAC AAT TTG CAA AAA TTA GGC CCT GAT GAT GTG TCT GTG       672
Gln Gly Asp Asn Asn Leu Gln Lys Leu Gly Pro Asp Asp Val Ser Val
    210                 215                 220

GAT ATT GAT GCC ATT AGA AGG GTC TAC ACC AGA TTG CTC TCT AAT GAA       720
```

```
                                                                        -continued Asp Ile Asp Ala Ile Arg Arg Val Tyr Thr Arg Leu Leu Ser Asn Glu
225                 230                 235                 240

AAA ATT GAA ACT GCC TTT CTC AAT GCA CTT GTA TAT TTG TCA CCT AAC         768
Lys Ile Glu Thr Ala Phe Leu Asn Ala Leu Val Tyr Leu Ser Pro Asn
                245                 250                 255

GTG GAA TGT GAC TTG ACG TAT CAC AAT GTA TAC TCT CGA GAT CCT AAT         816
Val Glu Cys Asp Leu Thr Tyr His Asn Val Tyr Ser Arg Asp Pro Asn
            260                 265                 270

TAT CTG AAT TTG TTC ATT ATC GGA ATG GAG AAT AGA AAT CTC CAC AGT         864
Tyr Leu Asn Leu Phe Ile Ile Gly Met Glu Asn Arg Asn Leu His Ser
        275                 280                 285

CCT GAA TAT CTG GAA ATG GCT TTG CCA TTA TTT TGC AAA GCG ATG AGC         912
Pro Glu Tyr Leu Glu Met Ala Leu Pro Leu Phe Cys Lys Ala Met Ser
    290                 295                 300

AAG CTA CCC CTT GCA GCC CAA GGA AAA CTG ATC AGA CTG TGG TCT AAA         960
Lys Leu Pro Leu Ala Ala Gln Gly Lys Leu Ile Arg Leu Trp Ser Lys
305                 310                 315                 320

TAC AAT GCA GAC CAG ATT CGG AGA ATG ATG GAG ACA TTT CAG CAA CTT        1008
Tyr Asn Ala Asp Gln Ile Arg Arg Met Met Glu Thr Phe Gln Gln Leu
                325                 330                 335

ATT ACT TAT AAA GTC ATA AGC AAT GAA TTT AAC AGT CGA AAT CTA GTG        1056
Ile Thr Tyr Lys Val Ile Ser Asn Glu Phe Asn Ser Arg Asn Leu Val
            340                 345                 350

AAT GAA TTT AAC AGT CGA AAT CTA GTG AAT GAT GAT GAT GCC ATT GTT        1104
Asn Glu Phe Asn Ser Arg Asn Leu Val Asn Asp Asp Asp Ala Ile Val
        355                 360                 365

GCT GCT TCG AAG TGC TTG AAA ATG GTT TAC TAT GCA AAT GTA GTG GGA        1152
Ala Ala Ser Lys Cys Leu Lys Met Val Tyr Tyr Ala Asn Val Val Gly
    370                 375                 380

GGG GAA GTG GAC ACA AAT CAC AAT GAA GAA GAT GAT GAA GAG CCC ATC        1200
Gly Glu Val Asp Thr Asn His Asn Glu Glu Asp Asp Glu Glu Pro Ile
385                 390                 395                 400

CCT GAG TCC AGC GAG CTG ACA CTT CAG GAA CTT TTG GGA GAA GAA AGA        1248
Pro Glu Ser Ser Glu Leu Thr Leu Gln Glu Leu Leu Gly Glu Glu Arg
                405                 410                 415

AGA AAC AAG AAA GGT CTT CGA GTG GAC CCC CTG GAA ACT GAA CTT GGT        1296
Arg Asn Lys Lys Gly Leu Arg Val Asp Pro Leu Glu Thr Glu Leu Gly
            420                 425                 430

GTT AAA ACC CTG GAT TGT CGA AAA CCA CTT ATC CCT TTT GAA GAG TTT        1344
Val Lys Thr Leu Asp Cys Arg Lys Pro Leu Ile Pro Phe Glu Glu Phe
        435                 440                 445

ATT AAT GAA CCA CTG AAT GAG GTT CTA GAA ATG GAT AAA GAT TAT ACT        1392
Ile Asn Glu Pro Leu Asn Glu Val Leu Glu Met Asp Lys Asp Tyr Thr
    450                 455                 460

TTT TTC AAA GTA GAA ACA GAG AAC AAA TTC TCT TTT ATG ACA TGT CCC        1440
Phe Phe Lys Val Glu Thr Glu Asn Lys Phe Ser Phe Met Thr Cys Pro
465                 470                 475                 480

TTT ATA TTG AAT GCT GTC ACA AAG AAT TTG GGA TTA TAT TAT GAC AAT        1488
Phe Ile Leu Asn Ala Val Thr Lys Asn Leu Gly Leu Tyr Tyr Asp Asn
                485                 490                 495

AGA ATT CGC ATG TAC AGT GAA CGA AGA ATC ACT GTT CTC TAC AGC TTA        1536
Arg Ile Arg Met Tyr Ser Glu Arg Arg Ile Thr Val Leu Tyr Ser Leu
            500                 505                 510

GTT CAA GGA CAG CAG TTG AAT CCA TAT TTG AGA CTC AAA GTT AGA CGT        1584
Val Gln Gly Gln Gln Leu Asn Pro Tyr Leu Arg Leu Lys Val Arg Arg
        515                 520                 525

GAC CAT ATC ATA GAT GAT GCA CTT GTC CGG CTA GAG ATG ATC GCT ATG        1632
Asp His Ile Ile Asp Asp Ala Leu Val Arg Leu Glu Met Ile Ala Met
    530                 535                 540

GAA AAT CCT GCA GAC TTG AAG AAG CAG TTG TAT GTG GAA TTT GAA GGA        1680
```

-continued

```
Glu Asn Pro Ala Asp Leu Lys Lys Gln Leu Tyr Val Glu Phe Glu Gly
545                 550                 555                 560

GAA CAA GGA GTT GAT GAG GGA GGT GTT TCC AAA GAA TTT TTT CAG CTG        1728
Glu Gln Gly Val Asp Glu Gly Gly Val Ser Lys Glu Phe Phe Gln Leu
                565                 570                 575

GTT GTG GAG GAA ATC TTC AAT CCA GAT ATT GGT ATG TTC ACA TAC GAT        1776
Val Val Glu Glu Ile Phe Asn Pro Asp Ile Gly Met Phe Thr Tyr Asp
            580                 585                 590

GAA TCT ACA AAA TTG TTT TGG TTT AAT CCA TCT TCT TTT GAA ACA GAG        1824
Glu Ser Thr Lys Leu Phe Trp Phe Asn Pro Ser Ser Phe Glu Thr Glu
        595                 600                 605

GGT CAG TTT ACT CTG ATT GGC ATA GTA CTG GGT CTG GCT ATT TAC AAT        1872
Gly Gln Phe Thr Leu Ile Gly Ile Val Leu Gly Leu Ala Ile Tyr Asn
    610                 615                 620

AAC TGT ATA CTG GAT GTA CAT TTT CCC ATG GTT GTC TAC AGG AAG CTA        1920
Asn Cys Ile Leu Asp Val His Phe Pro Met Val Val Tyr Arg Lys Leu
625                 630                 635                 640

ATG GGG AAA AAA GGA CTT TTC GTC GAC TTG GGA GAC TCT CAC CCA GTT        1968
Met Gly Lys Lys Gly Leu Phe Val Asp Leu Gly Asp Ser His Pro Val
                645                 650                 655

CTA TAT CAG AGT TTA AAA GAT TTA TTG GAG TAT GTT GGG AAT GTG GAA        2016
Leu Tyr Gln Ser Leu Lys Asp Leu Leu Glu Tyr Val Gly Asn Val Glu
            660                 665                 670

GAT GAC ATG ATG ATC ACT TTC CAG ATA TCA CAG ACA AAT CTT TTT GGT        2064
Asp Asp Met Met Ile Thr Phe Gln Ile Ser Gln Thr Asn Leu Phe Gly
        675                 680                 685

AAC CCA ATG ATG TAT GAT CTA AAG GAA AAT GGT GAT AAA ATT CCA ATT        2112
Asn Pro Met Met Tyr Asp Leu Lys Glu Asn Gly Asp Lys Ile Pro Ile
    690                 695                 700

ACA AAT GAA AAC AGG AAG GAA TTT GTC AAT CTT TAT TCT GAC TAC ATT        2160
Thr Asn Glu Asn Arg Lys Glu Phe Val Asn Leu Tyr Ser Asp Tyr Ile
705                 710                 715                 720

CTC AAT AAA TCA GTA GAA AAA CAG TTC AAG GCT TTT CGG AGA GGT TTT        2208
Leu Asn Lys Ser Val Glu Lys Gln Phe Lys Ala Phe Arg Arg Gly Phe
                725                 730                 735

CAT ATG GTG ACC AAT GAA TCT CCC TTA AAG TAC TTA TTC AGA CCA GAA        2256
His Met Val Thr Asn Glu Ser Pro Leu Lys Tyr Leu Phe Arg Pro Glu
            740                 745                 750

GAA ATT GAA TTG CTT ATA TGT GGA AGC CGC AAT CTA GAT TTC CAA GCA        2304
Glu Ile Glu Leu Leu Ile Cys Gly Ser Arg Asn Leu Asp Phe Gln Ala
        755                 760                 765

CTA GAA GAA ACT ACA GAA TAT GAC GGT GGC TAT ACC AGG GAC TCT GTT        2352
Leu Glu Glu Thr Thr Glu Tyr Asp Gly Gly Tyr Thr Arg Asp Ser Val
    770                 775                 780

CTG ATT AGG GAG TTC TGG GAA ATC GTT CAT TCA TTT ACA GAT GAA CAG        2400
Leu Ile Arg Glu Phe Trp Glu Ile Val His Ser Phe Thr Asp Glu Gln
785                 790                 795                 800

AAA AGA CTC TTC TTG CAG TTT ACA ACG GGC ACA GAC AGA GCA CCT GTG        2448
Lys Arg Leu Phe Leu Gln Phe Thr Thr Gly Thr Asp Arg Ala Pro Val
                805                 810                 815

GGA GGA CTA GGA AAA TTA AAG ATG ATT ATA GCC AAA AAT GGC CCA GAC        2496
Gly Gly Leu Gly Lys Leu Lys Met Ile Ile Ala Lys Asn Gly Pro Asp
            820                 825                 830

ACA GAA AGG TTA CCT ACA TCT CAT ACT TGC TTT AAT GTG CTT TTA CTT        2544
Thr Glu Arg Leu Pro Thr Ser His Thr Cys Phe Asn Val Leu Leu Leu
        835                 840                 845

CCG GAA TAC TCA AGC AAA GAA AAA CTT AAA GAG AGA TTG TTG AAG GCC        2592
Pro Glu Tyr Ser Ser Lys Glu Lys Leu Lys Glu Arg Leu Leu Lys Ala
    850                 855                 860

ATC ACG TAT GCC AAA GGA TTT GGC ATG CTG TA                             2624
```

Ile Thr Tyr Ala Lys Gly Phe Gly Met Leu
865                 870                 875

(2) INFORMATION FOR SEQ ID NO:8:

(i) SEQUENCE CHARACTERISTICS:
        (A) LENGTH: 874 amino acids
        (B) TYPE: amino acid
        (D) TOPOLOGY: linear (ii) MOLECULE TYPE: protein (xi) SEQUENCE DESCRIPTION: SEQ ID NO:8:

Ser Gly Glu Pro Gln Ser Asp Asp Ile Glu Ala Ser Arg Met Lys Arg
1               5                   10                  15

Ala Ala Ala Lys His Leu Ile Glu Arg Tyr Tyr His Gln Leu Thr Glu
            20                  25                  30

Gly Cys Gly Asn Glu Ala Cys Thr Asn Glu Phe Cys Ala Ser Cys Pro
            35                  40                  45

Thr Phe Leu Arg Met Asp Asn Asn Ala Ala Ile Lys Ala Leu Glu
    50                  55                  60

Leu Tyr Lys Ile Asn Ala Lys Leu Cys Asp Pro His Pro Ser Lys Lys
65                  70                  75                  80

Gly Ala Ser Ser Ala Tyr Leu Glu Asn Ser Lys Gly Ala Pro Asn Asn
                85                  90                  95

Ser Cys Ser Glu Ile Lys Met Asn Lys Lys Gly Ala Arg Ile Asp Phe
            100                 105                 110

Lys Asp Val Thr Tyr Leu Thr Glu Glu Lys Val Tyr Glu Ile Leu Glu
            115                 120                 125

Leu Cys Arg Glu Arg Glu Asp Tyr Ser Pro Leu Ile Arg Val Ile Gly
130                 135                 140

Arg Val Phe Ser Ser Ala Glu Ala Leu Val Gln Ser Phe Arg Lys Val
145                 150                 155                 160

Lys Gln His Thr Lys Glu Glu Leu Lys Ser Leu Gln Ala Lys Asp Glu
                165                 170                 175

Asp Lys Asp Glu Asp Glu Lys Glu Lys Ala Ala Cys Ser Ala Ala Ala
            180                 185                 190

Met Glu Glu Asp Ser Glu Ala Ser Ser Ser Arg Ile Gly Asp Ser Ser
            195                 200                 205

Gln Gly Asp Asn Asn Leu Gln Lys Leu Gly Pro Asp Asp Val Ser Val
    210                 215                 220

Asp Ile Asp Ala Ile Arg Arg Val Tyr Thr Arg Leu Leu Ser Asn Glu
225                 230                 235                 240

Lys Ile Glu Thr Ala Phe Leu Asn Ala Leu Val Tyr Leu Ser Pro Asn
                245                 250                 255

Val Glu Cys Asp Leu Thr Tyr His Asn Val Tyr Ser Arg Asp Pro Asn
            260                 265                 270

Tyr Leu Asn Leu Phe Ile Ile Gly Met Glu Asn Arg Asn Leu His Ser
        275                 280                 285

Pro Glu Tyr Leu Glu Met Ala Leu Pro Leu Phe Cys Lys Ala Met Ser
    290                 295                 300

Lys Leu Pro Leu Ala Ala Gln Gly Lys Leu Ile Arg Leu Trp Ser Lys
305                 310                 315                 320

Tyr Asn Ala Asp Gln Ile Arg Arg Met Met Glu Thr Phe Gln Gln Leu
                325                 330                 335

Ile Thr Tyr Lys Val Ile Ser Asn Glu Phe Asn Ser Arg Asn Leu Val
            340                 345                 350

-continued

```
Asn Glu Phe Asn Ser Arg Asn Leu Val Asn Asp Asp Ala Ile Val
        355                 360                 365
Ala Ala Ser Lys Cys Leu Lys Met Val Tyr Ala Asn Val Val Gly
        370                 375                 380
Gly Glu Val Asp Thr Asn His Asn Glu Glu Asp Asp Glu Glu Pro Ile
385                 390                 395                 400
Pro Glu Ser Ser Glu Leu Thr Leu Gln Glu Leu Leu Gly Glu Arg
                405                 410                 415
Arg Asn Lys Lys Gly Leu Arg Val Asp Pro Leu Glu Thr Glu Leu Gly
                420                 425                 430
Val Lys Thr Leu Asp Cys Arg Lys Pro Leu Ile Pro Phe Glu Glu Phe
                435                 440                 445
Ile Asn Glu Pro Leu Asn Glu Val Leu Glu Met Asp Lys Asp Tyr Thr
        450                 455                 460
Phe Phe Lys Val Glu Thr Glu Asn Lys Phe Ser Phe Met Thr Cys Pro
465                 470                 475                 480
Phe Ile Leu Asn Ala Val Thr Lys Asn Leu Gly Leu Tyr Tyr Asp Asn
                485                 490                 495
Arg Ile Arg Met Tyr Ser Glu Arg Arg Ile Thr Val Leu Tyr Ser Leu
                500                 505                 510
Val Gln Gly Gln Gln Leu Asn Pro Tyr Leu Arg Leu Lys Val Arg Arg
                515                 520                 525
Asp His Ile Ile Asp Asp Ala Leu Val Arg Leu Glu Met Ile Ala Met
                530                 535                 540
Glu Asn Pro Ala Asp Leu Lys Lys Gln Leu Tyr Val Glu Phe Glu Gly
545                 550                 555                 560
Glu Gln Gly Val Asp Glu Gly Val Ser Lys Glu Phe Phe Gln Leu
                565                 570                 575
Val Val Glu Glu Ile Phe Asn Pro Asp Ile Gly Met Phe Thr Tyr Asp
                580                 585                 590
Glu Ser Thr Lys Leu Phe Trp Phe Asn Pro Ser Ser Phe Glu Thr Glu
                595                 600                 605
Gly Gln Phe Thr Leu Ile Gly Ile Val Leu Gly Leu Ala Ile Tyr Asn
                610                 615                 620
Asn Cys Ile Leu Asp Val His Phe Pro Met Val Val Tyr Arg Lys Leu
625                 630                 635                 640
Met Gly Lys Lys Gly Leu Phe Val Asp Leu Gly Asp Ser His Pro Val
                645                 650                 655
Leu Tyr Gln Ser Leu Lys Asp Leu Leu Glu Tyr Val Gly Asn Val Glu
                660                 665                 670
Asp Asp Met Met Ile Thr Phe Gln Ile Ser Gln Thr Asn Leu Phe Gly
                675                 680                 685
Asn Pro Met Met Tyr Asp Leu Lys Glu Asn Gly Asp Lys Ile Pro Ile
        690                 695                 700
Thr Asn Glu Asn Arg Lys Glu Phe Val Asn Leu Tyr Ser Asp Tyr Ile
705                 710                 715                 720
Leu Asn Lys Ser Val Glu Lys Gln Phe Lys Ala Phe Arg Arg Gly Phe
                725                 730                 735
His Met Val Thr Asn Glu Ser Pro Leu Lys Tyr Leu Phe Arg Pro Glu
                740                 745                 750
Glu Ile Glu Leu Leu Ile Cys Gly Ser Arg Asn Leu Asp Phe Gln Ala
                755                 760                 765
Leu Glu Glu Thr Thr Glu Tyr Asp Gly Gly Tyr Thr Arg Asp Ser Val
```

```
                    770              775              780
Leu Ile Arg Glu Phe Trp Glu Ile Val His Ser Phe Thr Asp Glu Gln
785              790              795              800

Lys Arg Leu Phe Leu Gln Phe Thr Thr Gly Thr Asp Arg Ala Pro Val
                805              810              815

Gly Gly Leu Gly Lys Leu Lys Met Ile Ile Ala Lys Asn Gly Pro Asp
                820              825              830

Thr Glu Arg Leu Pro Thr Ser His Thr Cys Phe Asn Val Leu Leu Leu
                835              840              845

Pro Glu Tyr Ser Ser Lys Glu Lys Leu Lys Glu Arg Leu Leu Lys Ala
    850              855              860

Ile Thr Tyr Ala Lys Gly Phe Gly Met Leu
865              870
```

(2) INFORMATION FOR SEQ ID NO:9:

(i) SEQUENCE CHARACTERISTICS:
        (A) LENGTH: 476 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..476

(xi) SEQUENCE DESCRIPTION: SEQ ID NO:9:

```
ATG GCG CGC TTT GAG GAT CCA ACA CGG CGA CCC TAC AAG CTA CCT GAT      48
Met Ala Arg Phe Glu Asp Pro Thr Arg Arg Pro Tyr Lys Leu Pro Asp
  1               5                  10                  15

CTG TGC ACG GAA CTG AAC ACT TCA CTG CAA GAC ATA GAA ATA ACC TGT      96
Leu Cys Thr Glu Leu Asn Thr Ser Leu Gln Asp Ile Glu Ile Thr Cys
                 20                  25                  30

GTA TAT TGC AAG ACA GTA TTG GAA CTT ACA GAG GTA TTT GAA TTT GCA     144
Val Tyr Cys Lys Thr Val Leu Glu Leu Thr Glu Val Phe Glu Phe Ala
             35                  40                  45

TTT AAA GAT TTA TTT GTG GTG TAT AGA GAC AGT ATA CCG CAT GCT GCA     192
Phe Lys Asp Leu Phe Val Val Tyr Arg Asp Ser Ile Pro His Ala Ala
 50                  55                  60

TGC CAT AAA TGT ATA GAT TTT TAT TCT AGA ATT AGA GAA TTA AGA CAT     240
Cys His Lys Cys Ile Asp Phe Tyr Ser Arg Ile Arg Glu Leu Arg His
 65                  70                  75                  80

TAT TCA GAC TCT GTG TAT GGA GAC ACA TTG GAA AAA CTA ACT AAC ACT     288
Tyr Ser Asp Ser Val Tyr Gly Asp Thr Leu Glu Lys Leu Thr Asn Thr
                 85                  90                  95

GGG TTA TAC AAT TTA TTA ATA AGG TGC CTG CGG TGC CAG AAA CCG TTG     336
Gly Leu Tyr Asn Leu Leu Ile Arg Cys Leu Arg Cys Gln Lys Pro Leu
            100                 105                 110

AAT CCA GCA GAA AAA CTT AGA CAC CTT AAT GAA AAA CGA CGA TTT CAC     384
Asn Pro Ala Glu Lys Leu Arg His Leu Asn Glu Lys Arg Arg Phe His
        115                 120                 125

AAC ATA GCT GGG CAC TAT AGA GGC CAG TGC CAT TCG TGC TGC AAC CGA     432
Asn Ile Ala Gly His Tyr Arg Gly Gln Cys His Ser Cys Cys Asn Arg
    130                 135                 140

GCA CGA CAG GAA CGA CTC CAA CGA CGC AGA GAA ACA CAA GTA TA          476
Ala Arg Gln Glu Arg Leu Gln Arg Arg Arg Glu Thr Gln Val
145                 150                 155
```

(2) INFORMATION FOR SEQ ID NO:10:

-continued (i) SEQUENCE CHARACTERISTICS:
    (A) LENGTH: 158 amino acids
    (B) TYPE: amino acid
    (D) TOPOLOGY: linear (ii) MOLECULE TYPE: protein (xi) SEQUENCE DESCRIPTION: SEQ ID NO:10:

Met Ala Arg Phe Glu Asp Pro Thr Arg Arg Pro Tyr Lys Leu Pro Asp
 1               5                  10                  15

Leu Cys Thr Glu Leu Asn Thr Ser Leu Gln Asp Ile Glu Ile Thr Cys
                20                  25                  30

Val Tyr Cys Lys Thr Val Leu Glu Leu Thr Glu Val Phe Glu Phe Ala
            35                  40                  45

Phe Lys Asp Leu Phe Val Val Tyr Arg Asp Ser Ile Pro His Ala Ala
        50                  55                  60

Cys His Lys Cys Ile Asp Phe Tyr Ser Arg Ile Arg Glu Leu Arg His
65                  70                  75                  80

Tyr Ser Asp Ser Val Tyr Gly Asp Thr Leu Glu Lys Leu Thr Asn Thr
                85                  90                  95

Gly Leu Tyr Asn Leu Leu Ile Arg Cys Leu Arg Cys Gln Lys Pro Leu
            100                 105                 110

Asn Pro Ala Glu Lys Leu Arg His Leu Asn Glu Lys Arg Arg Phe His
        115                 120                 125

Asn Ile Ala Gly His Tyr Arg Gly Gln Cys His Ser Cys Cys Asn Arg
130                 135                 140

Ala Arg Gln Glu Arg Leu Gln Arg Arg Arg Glu Thr Gln Val
145                 150                 155

(2) INFORMATION FOR SEQ ID NO:11:

(i) SEQUENCE CHARACTERISTICS:
        (A) LENGTH: 1181 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..1181

(xi) SEQUENCE DESCRIPTION: SEQ ID NO:11:

ATG GAG GAG CCG CAG TCA GAT CCT AGC GTC GAG CCC CCT CTG AGT CAG        48
Met Glu Glu Pro Gln Ser Asp Pro Ser Val Glu Pro Pro Leu Ser Gln
 1               5                  10                  15

GAA ACA TTT TCA GAC CTA TGG AAA CTA CTT CCT GAA AAC AAC GTT CTG        96
Glu Thr Phe Ser Asp Leu Trp Lys Leu Leu Pro Glu Asn Asn Val Leu
                20                  25                  30

TCC CCC TTG CCG TCC CAA GCA ATG GAT GAT TTG ATG CTG TCC CCG GAC       144
Ser Pro Leu Pro Ser Gln Ala Met Asp Asp Leu Met Leu Ser Pro Asp
            35                  40                  45

GAT ATT GAA CAA TGG TTC ACT GAA GAC CCA GGT CCA GAT GAA GCT CCC       192
Asp Ile Glu Gln Trp Phe Thr Glu Asp Pro Gly Pro Asp Glu Ala Pro
        50                  55                  60

AGA ATG CCA GAG GCT GCT CCC CCC GTG GCC CCT GCA CCA GCA GCT CCT       240
Arg Met Pro Glu Ala Ala Pro Pro Val Ala Pro Ala Pro Ala Ala Pro
65                  70                  75                  80

ACA CCG GCG GCC CCT GCA CCA GCC CCC TCC TGG CCC CTG TCA TCT TCT       288
Thr Pro Ala Ala Pro Ala Pro Ala Pro Ser Trp Pro Leu Ser Ser Ser
                85                  90                  95

| | | | | | | | | | | | | |
|---|---|---|---|---|---|---|---|---|---|---|---|---|
| GTC | CCT | TCC | CAG | AAA | ACC | TAC | CAG | GGC | AGC | TAC | GGT | TTC | CGT | CTG | GGC | 336 |
| Val | Pro | Ser | Gln | Lys | Thr | Tyr | Gln | Gly | Ser | Tyr | Gly | Phe | Arg | Leu | Gly | |
| | | | 100 | | | | | 105 | | | | 110 | | | | |

```
GTC CCT TCC CAG AAA ACC TAC CAG GGC AGC TAC GGT TTC CGT CTG GGC          336
Val Pro Ser Gln Lys Thr Tyr Gln Gly Ser Tyr Gly Phe Arg Leu Gly
            100                 105                 110

TTC TTG CAT TCT GGG ACA GCC AAG TCT GTG ACT TGC ACG TAC TCC CCT          384
Phe Leu His Ser Gly Thr Ala Lys Ser Val Thr Cys Thr Tyr Ser Pro
        115                 120                 125

GCC CTC AAC AAG ATG TTT TGC CAA CTG GCC AAG ACC TGC CCT GTG CAG          432
Ala Leu Asn Lys Met Phe Cys Gln Leu Ala Lys Thr Cys Pro Val Gln
130                 135                 140

CTG TGG GTT GAT TCC ACA CCC CCG CCC GGC ACC CGC GTC CGC GCC ATG          480
Leu Trp Val Asp Ser Thr Pro Pro Pro Gly Thr Arg Val Arg Ala Met
145                 150                 155                 160

GCC ATC TAC AAG CAG TCA CAG CAC ATG ACG GAG GTT GTG AGG CGC TGC          528
Ala Ile Tyr Lys Gln Ser Gln His Met Thr Glu Val Val Arg Arg Cys
            165                 170                 175

CCC CAC CAT GAG CGC TGC TCA GAT AGC GAT GGT CTG GCC CCT CCT CAG          576
Pro His His Glu Arg Cys Ser Asp Ser Asp Gly Leu Ala Pro Pro Gln
        180                 185                 190

CAT CTT ATC CGA GTG GAA GGA AAT TTG CGT GTG GAG TAT TTG GAT GAC          624
His Leu Ile Arg Val Glu Gly Asn Leu Arg Val Glu Tyr Leu Asp Asp
            195                 200                 205

AGA AAC ACT TTT CGA CAT AGT GTG GTG GTG CCC TAT GAG CCG CCT GAG          672
Arg Asn Thr Phe Arg His Ser Val Val Val Pro Tyr Glu Pro Pro Glu
210                 215                 220

GTT GGC TCT GAC TGT ACC ACC ATC CAC TAC AAC TAC ATG TGT AAC AGT          720
Val Gly Ser Asp Cys Thr Thr Ile His Tyr Asn Tyr Met Cys Asn Ser
225                 230                 235                 240

TCC TGC ATG GGC GGC ATG AAC CGG AGG CCC ATC CTC ACC ATC ATC ACA          768
Ser Cys Met Gly Gly Met Asn Arg Arg Pro Ile Leu Thr Ile Ile Thr
            245                 250                 255

CTG GAA GAC TCC AGT GGT AAT CTA CTG GGA CGG AAC AGC TTT GAG GTG          816
Leu Glu Asp Ser Ser Gly Asn Leu Leu Gly Arg Asn Ser Phe Glu Val
        260                 265                 270

CGT GTT TGT GCC TGT CCT GGG AGA GAC CGG CGC ACA GAG GAA GAG AAT          864
Arg Val Cys Ala Cys Pro Gly Arg Asp Arg Arg Thr Glu Glu Glu Asn
            275                 280                 285

CTC CGC AAG AAA GGG GAG CCT CAC CAC GAG CTG CCC CCA GGG AGC ACT          912
Leu Arg Lys Lys Gly Glu Pro His His Glu Leu Pro Pro Gly Ser Thr
290                 295                 300

AAG CGA GCA CTG CCC AAC AAC ACC AGC TCC TCT CCC CAG CCA AAG AAG          960
Lys Arg Ala Leu Pro Asn Asn Thr Ser Ser Ser Pro Gln Pro Lys Lys
305                 310                 315                 320

AAA CCA CTG GAT GGA GAA TAT TTC ACC CTT CAG ATC CGT GGG CGT GAG         1008
Lys Pro Leu Asp Gly Glu Tyr Phe Thr Leu Gln Ile Arg Gly Arg Glu
            325                 330                 335

CGC TTC GAG ATG TTC CGA GAG CTG AAT GAG GCC TTG GAA CTC AAG GAT         1056
Arg Phe Glu Met Phe Arg Glu Leu Asn Glu Ala Leu Glu Leu Lys Asp
        340                 345                 350

GCC CAG GCT GGG AAG GAG CCA GGG GGG AGC AGG GCT CAC TCC AGC CAC         1104
Ala Gln Ala Gly Lys Glu Pro Gly Gly Ser Arg Ala His Ser Ser His
            355                 360                 365

CTG AAG TCC AAA AAG GGT CAG TCT ACC TCC CGC CAT AAA AAA CTC ATG         1152
Leu Lys Ser Lys Lys Gly Gln Ser Thr Ser Arg His Lys Lys Leu Met
370                 375                 380

TTC AAG ACA GAA GGG CCT GAC TCA GAC TG                                  1181
Phe Lys Thr Glu Gly Pro Asp Ser Asp
385                 390
```

(2) INFORMATION FOR SEQ ID NO:12:

(i) SEQUENCE CHARACTERISTICS:

(A) LENGTH: 393 amino acids
(B) TYPE: amino acid
(D) TOPOLOGY: linear (ii) MOLECULE TYPE: protein (xi) SEQUENCE DESCRIPTION: SEQ ID NO:12:

```
Met Glu Glu Pro Gln Ser Asp Pro Ser Val Glu Pro Pro Leu Ser Gln
  1               5                  10                  15

Glu Thr Phe Ser Asp Leu Trp Lys Leu Leu Pro Glu Asn Asn Val Leu
                 20                  25                  30

Ser Pro Leu Pro Ser Gln Ala Met Asp Asp Leu Met Leu Ser Pro Asp
             35                  40                  45

Asp Ile Glu Gln Trp Phe Thr Glu Asp Pro Gly Pro Asp Glu Ala Pro
 50                  55                  60

Arg Met Pro Glu Ala Ala Pro Pro Val Ala Pro Ala Pro Ala Ala Pro
 65                  70                  75                  80

Thr Pro Ala Ala Pro Ala Pro Ala Pro Ser Trp Pro Leu Ser Ser Ser
                 85                  90                  95

Val Pro Ser Gln Lys Thr Tyr Gln Gly Ser Tyr Gly Phe Arg Leu Gly
                100                 105                 110

Phe Leu His Ser Gly Thr Ala Lys Ser Val Thr Cys Thr Tyr Ser Pro
            115                 120                 125

Ala Leu Asn Lys Met Phe Cys Gln Leu Ala Lys Thr Cys Pro Val Gln
130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
        355                 360                 365

Leu Lys Ser Lys Lys Gly Gln Ser Thr Ser Arg His Lys Lys Leu Met
370                 375                 380
```

```
Phe Lys Thr Glu Gly Pro Asp Ser Asp
385                 390
```

(2) INFORMATION FOR SEQ ID NO:13:

(i) SEQUENCE CHARACTERISTICS:
        (A) LENGTH: 3176 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..3176

(xi) SEQUENCE DESCRIPTION: SEQ ID NO:13:

```
ATG TCC AGC TCG CCG CTG TCC AAG AAA CGT CGC GTG TCC GGG CCT GAT        48
Met Ser Ser Ser Pro Leu Ser Lys Lys Arg Arg Val Ser Gly Pro Asp
1               5                   10                  15

CCA AAG CCG GGT TCT AAC TGC TCC CCT GCC CAG TCC GTG TTG TCC GAA        96
Pro Lys Pro Gly Ser Asn Cys Ser Pro Ala Gln Ser Val Leu Ser Glu
            20                  25                  30

GTG CCC TCG GTG CCA ACC AAC GGA ATG GCC AAG AAC GGC AGT GAA GCA       144
Val Pro Ser Val Pro Thr Asn Gly Met Ala Lys Asn Gly Ser Glu Ala
        35                  40                  45

GAC ATA GAC GAG GGC CTT TAC TCC CGG CAG CTG TAT GTG TTG GGC CAT       192
Asp Ile Asp Glu Gly Leu Tyr Ser Arg Gln Leu Tyr Val Leu Gly His
    50                  55                  60

GAG GCA ATG AAG CGG CTC CAG ACA TCC AGT GTC CTG GTA TCA GGC CTG       240
Glu Ala Met Lys Arg Leu Gln Thr Ser Ser Val Leu Val Ser Gly Leu
65                  70                  75                  80

CGG GGC CTG GGC GTG GAG ATC GCT AAG AAC ATC ATC CTT GGT GGG GTC       288
Arg Gly Leu Gly Val Glu Ile Ala Lys Asn Ile Ile Leu Gly Gly Val
                85                  90                  95

AAG GCT GTT ACC CTA CAT GAC CAG GGC ACT GCC CAG TGG GCT GAT CTT       336
Lys Ala Val Thr Leu His Asp Gln Gly Thr Ala Gln Trp Ala Asp Leu
            100                 105                 110

TCC TCC CAG TTC TAC CTG CGG GAG GAG GAC ATC GGT AAA AAC CGG GCC       384
Ser Ser Gln Phe Tyr Leu Arg Glu Glu Asp Ile Gly Lys Asn Arg Ala
        115                 120                 125

GAG GTA TCA CAG CCC CGC CTC GCT GAG CTC AAC AGC TAT GTG CCT GTC       432
Glu Val Ser Gln Pro Arg Leu Ala Glu Leu Asn Ser Tyr Val Pro Val
    130                 135                 140

ACT GCC TAC ACT GGA CCC CTC GTT GAG GAC TTC CTT AGT GGT TTC CAG       480
Thr Ala Tyr Thr Gly Pro Leu Val Glu Asp Phe Leu Ser Gly Phe Gln
145                 150                 155                 160

GTG GTG GTG CTC ACC AAC ACC CCC CTG GAG GAC CAG CTG CGA GTG GGT       528
Val Val Val Leu Thr Asn Thr Pro Leu Glu Asp Gln Leu Arg Val Gly
                165                 170                 175

GAG TTC TGT CAC AAC CGT GGC ATC AAG CTG GTG GTG GCA GAC ACG CGG       576
Glu Phe Cys His Asn Arg Gly Ile Lys Leu Val Val Ala Asp Thr Arg
            180                 185                 190

GGC CTG TTT GGG CAG CTC TTC TGT GAC TTT GGA GAG GAA ATG ATC CTC       624
Gly Leu Phe Gly Gln Leu Phe Cys Asp Phe Gly Glu Glu Met Ile Leu
        195                 200                 205

ACA GAT TCC AAT GGG GAG CAG CCA CTC AGT GCT ATG GTT TCT ATG GTT       672
Thr Asp Ser Asn Gly Glu Gln Pro Leu Ser Ala Met Val Ser Met Val
    210                 215                 220

ACC AAG GAC AAC CCC GGT GTG GTT ACC TGC CTG GAT GAG GCC CGA CAC       720
Thr Lys Asp Asn Pro Gly Val Val Thr Cys Leu Asp Glu Ala Arg His
225                 230                 235                 240
```

```
GGG TTT GAG AGC GGG GAC TTT GTC TCC TTT TCA GAA GTA CAG GGC ATG      768
Gly Phe Glu Ser Gly Asp Phe Val Ser Phe Ser Glu Val Gln Gly Met
            245                 250                 255

GTT GAA CTC AAC GGA AAT CAG CCC ATG GAG ATC AAA GTC CTG GGT CCT      816
Val Glu Leu Asn Gly Asn Gln Pro Met Glu Ile Lys Val Leu Gly Pro
        260                 265                 270

TAT ACC TTT AGC ATC TGT GAC ACC TCC AAC TTC TCC GAC TAC ATC CGT      864
Tyr Thr Phe Ser Ile Cys Asp Thr Ser Asn Phe Ser Asp Tyr Ile Arg
        275                 280                 285

GGA GGC ATC GTC AGT CAG GTC AAA GTA CCT AAG AAG ATT AGC TTT AAA      912
Gly Gly Ile Val Ser Gln Val Lys Val Pro Lys Lys Ile Ser Phe Lys
        290                 295                 300

TCC TTG GTG GCC TCA CTG GCA GAA CCT GAC TTT GTG GTG ACG GAC TTC      960
Ser Leu Val Ala Ser Leu Ala Glu Pro Asp Phe Val Val Thr Asp Phe
305                 310                 315                 320

GCC AAG TTT TCT CGC CCT GCC CAG CTG CAC ATT GGC TTC CAG GCC CTG     1008
Ala Lys Phe Ser Arg Pro Ala Gln Leu His Ile Gly Phe Gln Ala Leu
            325                 330                 335

CAC CAG TTC TGT GCT CAG CAT GGC CGG CCA CCT CGG CCC CGC AAT GAG     1056
His Gln Phe Cys Ala Gln His Gly Arg Pro Pro Arg Pro Arg Asn Glu
        340                 345                 350

GAG GAT GCA GCA GAA CTG GTA GCC TTA GCA CAG GCT GTG AAT GCT CGA     1104
Glu Asp Ala Ala Glu Leu Val Ala Leu Ala Gln Ala Val Asn Ala Arg
        355                 360                 365

GCC CTG CCA GCA GTG CAG CAA AAT AAC CTG GAC GAG GAC CTC ATC CGG     1152
Ala Leu Pro Ala Val Gln Gln Asn Asn Leu Asp Glu Asp Leu Ile Arg
        370                 375                 380

AAG CTG GCA TAT GTG GCT GCT GGG GAT CTG GCA CCC ATA AAC GCC TTC     1200
Lys Leu Ala Tyr Val Ala Ala Gly Asp Leu Ala Pro Ile Asn Ala Phe
385                 390                 395                 400

ATT GGG GGC CTG GCT GCC CAG GAA GTC ATG AAG GCC TGC TCC GGG AAG     1248
Ile Gly Gly Leu Ala Ala Gln Glu Val Met Lys Ala Cys Ser Gly Lys
            405                 410                 415

TTC ATG CCC ATC ATG CAG TGG CTA TAC TTT GAT GCC CTT GAG TGT CTC     1296
Phe Met Pro Ile Met Gln Trp Leu Tyr Phe Asp Ala Leu Glu Cys Leu
        420                 425                 430

CCT GAG GAC AAA GAG GTC CTC ACA GAG GAC AAG TGC CTC CAG CGC CAG     1344
Pro Glu Asp Lys Glu Val Leu Thr Glu Asp Lys Cys Leu Gln Arg Gln
        435                 440                 445

AAC CGT TAT GAC GGG CAA GTG GCT GTG TTT GGC TCA GAC CTG CAA GAG     1392
Asn Arg Tyr Asp Gly Gln Val Ala Val Phe Gly Ser Asp Leu Gln Glu
450                 455                 460

AAG CTG GGC AAG CAG AAG TAT TTC CTG GTG GGT GCG GGG GCC ATT GGC     1440
Lys Leu Gly Lys Gln Lys Tyr Phe Leu Val Gly Ala Gly Ala Ile Gly
465                 470                 475                 480

TGT GAG CTG CTC AAG AAC TTT GCC ATG ATT GGG CTG GGC TGC GGG GAG     1488
Cys Glu Leu Leu Lys Asn Phe Ala Met Ile Gly Leu Gly Cys Gly Glu
            485                 490                 495

GGT GGA GAA ATC ATC GTT ACA GAC ATG GAC ACC ATT GAG AAG TCA AAT     1536
Gly Gly Glu Ile Ile Val Thr Asp Met Asp Thr Ile Glu Lys Ser Asn
            500                 505                 510

CTG AAT CGA CAG TTT CTT TTC CGG CCC TGG GAT GTC ACG AAG TTA AAG     1584
Leu Asn Arg Gln Phe Leu Phe Arg Pro Trp Asp Val Thr Lys Leu Lys
        515                 520                 525

TCT GAC ACG GCT GCT GCA GCT GTG CGC CAA ATG AAT CCA CAT ATC CGG     1632
Ser Asp Thr Ala Ala Ala Ala Val Arg Gln Met Asn Pro His Ile Arg
        530                 535                 540

GTG ACA AGC CAC CAG AAC CGT GTG GGT CCT GAC ACG GAG CGC ATC TAT     1680
Val Thr Ser His Gln Asn Arg Val Gly Pro Asp Thr Glu Arg Ile Tyr
545                 550                 555                 560
```

```
GAT GAC GAT TTT TTC CAA AAC CTA GAT GGC GTG GCC AAT GCC CTG GAC     1728
Asp Asp Asp Phe Phe Gln Asn Leu Asp Gly Val Ala Asn Ala Leu Asp
            565                 570                 575

AAC GTG GAT GCC CGC ATG TAC ATG GAC CGC CGC TGT GTC TAC TAC CGG     1776
Asn Val Asp Ala Arg Met Tyr Met Asp Arg Arg Cys Val Tyr Tyr Arg
            580                 585                 590

AAG CCA CTG CTG GAG TCA GGC ACA CTG GGC ACC AAA GGC AAT GTG CAG     1824
Lys Pro Leu Leu Glu Ser Gly Thr Leu Gly Thr Lys Gly Asn Val Gln
            595                 600                 605

GTG GTG ATC CCC TTC CTG ACA GAG TCG TAC AGT TCC AGC CAG GAC CCA     1872
Val Val Ile Pro Phe Leu Thr Glu Ser Tyr Ser Ser Ser Gln Asp Pro
            610                 615                 620

CCT GAG AAG TCC ATC CCC ATC TGT ACC CTG AAG AAC TTC CCT AAT GCC     1920
Pro Glu Lys Ser Ile Pro Ile Cys Thr Leu Lys Asn Phe Pro Asn Ala
625                 630                 635                 640

ATC GAG CAC ACC CTG CAG TGG GCT CGG GAT GAG TTT GAA GGC CTC TTC     1968
Ile Glu His Thr Leu Gln Trp Ala Arg Asp Glu Phe Glu Gly Leu Phe
            645                 650                 655

AAG CAG CCA GCA GAA AAT GTC AAC CAG TAC CTC ACA GAC CCC AAG TTT     2016
Lys Gln Pro Ala Glu Asn Val Asn Gln Tyr Leu Thr Asp Pro Lys Phe
            660                 665                 670

GTG GAG CGA ACA CTG CGG CTG GCA GGC ACT CAG CCC TTG GAG GTG CTG     2064
Val Glu Arg Thr Leu Arg Leu Ala Gly Thr Gln Pro Leu Glu Val Leu
            675                 680                 685

GAG GCT GTG CAG CGC AGC CTG GTG CTG CAG CGA CCA CAG ACC TGG GCT     2112
Glu Ala Val Gln Arg Ser Leu Val Leu Gln Arg Pro Gln Thr Trp Ala
            690                 695                 700

GAC TGC GTG ACC TGG GCC TGC CAC CAC TGG CAC ACC CAG TAC TCG AAC     2160
Asp Cys Val Thr Trp Ala Cys His His Trp His Thr Gln Tyr Ser Asn
705                 710                 715                 720

AAC ATC CGG CAG CTG CTG CAC AAC TTC CCT CCT GAC CAG CTC ACA AGC     2208
Asn Ile Arg Gln Leu Leu His Asn Phe Pro Pro Asp Gln Leu Thr Ser
            725                 730                 735

TCA GGA GCG CCG TTC TGG TCT GGG CCC AAA CGC TGT CCA CAC CCG CTC     2256
Ser Gly Ala Pro Phe Trp Ser Gly Pro Lys Arg Cys Pro His Pro Leu
            740                 745                 750

ACC TTT GAT GTC AAC AAT CCC CTG CAT CTG GAC TAT GTG ATG GCT GCT     2304
Thr Phe Asp Val Asn Asn Pro Leu His Leu Asp Tyr Val Met Ala Ala
            755                 760                 765

GCC AAC CTG TTT GCC CAG ACC TAC GGG CTG ACA GGC TCT CAG GAC CGA     2352
Ala Asn Leu Phe Ala Gln Thr Tyr Gly Leu Thr Gly Ser Gln Asp Arg
            770                 775                 780

GCT GCT GTG GCC ACA TTC CTG CAG TCT GTG CAG GTC CCC GAA TTC ACC     2400
Ala Ala Val Ala Thr Phe Leu Gln Ser Val Gln Val Pro Glu Phe Thr
785                 790                 795                 800

CCC AAG TCT GGC GTC AAG ATC CAT GTT TCT GAC CAG GAG CTG CAG AGC     2448
Pro Lys Ser Gly Val Lys Ile His Val Ser Asp Gln Glu Leu Gln Ser
            805                 810                 815

GCC AAT GCC TCT GTT GAT GAC AGT CGT CTA GAG GAG CTC AAA GCC ACT     2496
Ala Asn Ala Ser Val Asp Asp Ser Arg Leu Glu Glu Leu Lys Ala Thr
            820                 825                 830

CTG CCC AGC CCA GAC AAG CTC CCT GGA TTC AAG ATG TAC CCC ATT GAC     2544
Leu Pro Ser Pro Asp Lys Leu Pro Gly Phe Lys Met Tyr Pro Ile Asp
            835                 840                 845

TTT GAG AAG GAT GAT GAC AGC AAC TTT CAT ATG GAT TTC ATC GTG GCT     2592
Phe Glu Lys Asp Asp Asp Ser Asn Phe His Met Asp Phe Ile Val Ala
850                 855                 860

GCA TCC AAC CTC CGG GCA GAA AAC TAT GAC ATT CCT TCT GCA GAC CGG     2640
Ala Ser Asn Leu Arg Ala Glu Asn Tyr Asp Ile Pro Ser Ala Asp Arg
865                 870                 875                 880
```

| | | | | | | | | | | | | | | | | |
|---|---|---|---|---|---|---|---|---|---|---|---|---|---|---|---|---|
| CAC | AAG | AGC | AAG | CTG | ATT | GCA | GGG | AAG | ATC | ATC | CCA | GCC | ATT | GCC | ACG | 2688 |
| His | Lys | Ser | Lys | Leu | Ile | Ala | Gly | Lys | Ile | Ile | Pro | Ala | Ile | Ala | Thr | |
| | | | | 885 | | | | | 890 | | | | | 895 | | |
| ACC | ACA | GCA | GCC | GTG | GTT | GGC | CTT | GTG | TGT | CTG | GAA | CTG | TAC | AAG | GTT | 2736 |
| Thr | Thr | Ala | Ala | Val | Val | Gly | Leu | Val | Cys | Leu | Glu | Leu | Tyr | Lys | Val | |
| | | | 900 | | | | | 905 | | | | | 910 | | | |
| GTG | CAG | GGG | CAC | CGA | CAG | CTT | GAC | TCC | TAC | AAG | AAT | GGT | TTC | CTC | AAC | 2784 |
| Val | Gln | Gly | His | Arg | Gln | Leu | Asp | Ser | Tyr | Lys | Asn | Gly | Phe | Leu | Asn | |
| | | 915 | | | | | 920 | | | | | 925 | | | | |
| TTG | GCC | CTG | CCT | TTC | TTT | GGT | TTC | TCT | GAA | CCC | CTT | GCC | GCA | CCA | CGT | 2832 |
| Leu | Ala | Leu | Pro | Phe | Phe | Gly | Phe | Ser | Glu | Pro | Leu | Ala | Ala | Pro | Arg | |
| | 930 | | | | | 935 | | | | | 940 | | | | | |
| CAC | CAG | TAC | TAT | AAC | CAA | GAG | TGG | ACA | TTG | TGG | GAT | CGC | TTT | GAG | GTA | 2880 |
| His | Gln | Tyr | Tyr | Asn | Gln | Glu | Trp | Thr | Leu | Trp | Asp | Arg | Phe | Glu | Val | |
| 945 | | | | | 950 | | | | | 955 | | | | | 960 | |
| CAA | GGG | CTG | CAG | CCT | AAT | GGT | GAG | GAG | ATG | ACC | CTC | AAA | CAG | TTC | CTC | 2928 |
| Gln | Gly | Leu | Gln | Pro | Asn | Gly | Glu | Glu | Met | Thr | Leu | Lys | Gln | Phe | Leu | |
| | | | | 965 | | | | | 970 | | | | | 975 | | |
| GAC | TAT | TTT | AAG | ACA | GAG | CAC | AAA | TTA | GAG | ATC | ACC | ATG | CTG | TCC | CAG | 2976 |
| Asp | Tyr | Phe | Lys | Thr | Glu | His | Lys | Leu | Glu | Ile | Thr | Met | Leu | Ser | Gln | |
| | | | 980 | | | | | 985 | | | | | 990 | | | |
| GGC | GTG | TCC | ATG | CTC | TAT | TCC | TTC | TTC | ATG | CCA | GCT | GCC | AAG | CTC | AAG | 3024 |
| Gly | Val | Ser | Met | Leu | Tyr | Ser | Phe | Phe | Met | Pro | Ala | Ala | Lys | Leu | Lys | |
| | | | 995 | | | | | 1000 | | | | | 1005 | | | |
| GAA | CGG | TTG | GAT | CAG | CCG | ATG | ACA | GAG | ATT | GTG | AGC | CGT | GTG | TCG | AAG | 3072 |
| Glu | Arg | Leu | Asp | Gln | Pro | Met | Thr | Glu | Ile | Val | Ser | Arg | Val | Ser | Lys | |
| | | 1010 | | | | | 1015 | | | | | 1020 | | | | |
| CGA | AAG | CTG | GGC | CGC | CAC | GTG | CGG | GCG | CTG | GTG | CTT | GAG | CTG | TGC | TGT | 3120 |
| Arg | Lys | Leu | Gly | Arg | His | Val | Arg | Ala | Leu | Val | Leu | Glu | Leu | Cys | Cys | |
| 1025 | | | | | 1030 | | | | | 1035 | | | | | 1040 | |
| AAC | GAC | GAG | AGC | GGC | GAG | GAT | GTC | GAG | GTT | CCC | TAT | GTC | CGA | TAC | ACC | 3168 |
| Asn | Asp | Glu | Ser | Gly | Glu | Asp | Val | Glu | Val | Pro | Tyr | Val | Arg | Tyr | Thr | |
| | | | | 1045 | | | | | 1050 | | | | | 1055 | | |
| ATC | CGC | TG | | | | | | | | | | | | | | 3176 |
| Ile | Arg | | | | | | | | | | | | | | | |

(2) INFORMATION FOR SEQ ID NO:14:

(i) SEQUENCE CHARACTERISTICS:
        (A) LENGTH: 1058 amino acids
        (B) TYPE: amino acid
        (D) TOPOLOGY: linear (ii) MOLECULE TYPE: protein (xi) SEQUENCE DESCRIPTION: SEQ ID NO:14:

```
Met Ser Ser Ser Pro Leu Ser Lys Lys Arg Arg Val Ser Gly Pro Asp
 1               5                  10                  15

Pro Lys Pro Gly Ser Asn Cys Ser Pro Ala Gln Ser Val Leu Ser Glu
             20                  25                  30

Val Pro Ser Val Pro Thr Asn Gly Met Ala Lys Asn Gly Ser Glu Ala
         35                  40                  45

Asp Ile Asp Glu Gly Leu Tyr Ser Arg Gln Leu Tyr Val Leu Gly His
     50                  55                  60

Glu Ala Met Lys Arg Leu Gln Thr Ser Ser Val Leu Val Ser Gly Leu
 65                  70                  75                  80

Arg Gly Leu Gly Val Glu Ile Ala Lys Asn Ile Ile Leu Gly Gly Val
                 85                  90                  95

Lys Ala Val Thr Leu His Asp Gln Gly Thr Ala Gln Trp Ala Asp Leu
            100                 105                 110
```

-continued

```
Ser Ser Gln Phe Tyr Leu Arg Glu Glu Asp Ile Gly Lys Asn Arg Ala
    115                 120                 125

Glu Val Ser Gln Pro Arg Leu Ala Glu Leu Asn Ser Tyr Val Pro Val
    130                 135                 140

Thr Ala Tyr Thr Gly Pro Leu Val Glu Asp Phe Leu Ser Gly Phe Gln
145                 150                 155                 160

Val Val Val Leu Thr Asn Thr Pro Leu Glu Asp Gln Leu Arg Val Gly
                165                 170                 175

Glu Phe Cys His Asn Arg Gly Ile Lys Leu Val Val Ala Asp Thr Arg
                180                 185                 190

Gly Leu Phe Gly Gln Leu Phe Cys Asp Phe Gly Glu Glu Met Ile Leu
                195                 200                 205

Thr Asp Ser Asn Gly Glu Gln Pro Leu Ser Ala Met Val Ser Met Val
    210                 215                 220

Thr Lys Asp Asn Pro Gly Val Val Thr Cys Leu Asp Glu Ala Arg His
225                 230                 235                 240

Gly Phe Glu Ser Gly Asp Phe Val Ser Phe Ser Glu Val Gln Gly Met
                245                 250                 255

Val Glu Leu Asn Gly Asn Gln Pro Met Glu Ile Lys Val Leu Gly Pro
                260                 265                 270

Tyr Thr Phe Ser Ile Cys Asp Thr Ser Asn Phe Ser Asp Tyr Ile Arg
                275                 280                 285

Gly Gly Ile Val Ser Gln Val Lys Val Pro Lys Lys Ile Ser Phe Lys
    290                 295                 300

Ser Leu Val Ala Ser Leu Ala Glu Pro Asp Phe Val Val Thr Asp Phe
305                 310                 315                 320

Ala Lys Phe Ser Arg Pro Ala Gln Leu His Ile Gly Phe Gln Ala Leu
                325                 330                 335

His Gln Phe Cys Ala Gln His Gly Arg Pro Pro Arg Pro Arg Asn Glu
                340                 345                 350

Glu Asp Ala Ala Glu Leu Val Ala Leu Ala Gln Ala Val Asn Ala Arg
                355                 360                 365

Ala Leu Pro Ala Val Gln Gln Asn Asn Leu Asp Glu Asp Leu Ile Arg
    370                 375                 380

Lys Leu Ala Tyr Val Ala Ala Gly Asp Leu Ala Pro Ile Asn Ala Phe
385                 390                 395                 400

Ile Gly Gly Leu Ala Ala Gln Glu Val Met Lys Ala Cys Ser Gly Lys
                405                 410                 415

Phe Met Pro Ile Met Gln Trp Leu Tyr Phe Asp Ala Leu Glu Cys Leu
                420                 425                 430

Pro Glu Asp Lys Glu Val Leu Thr Glu Asp Lys Cys Leu Gln Arg Gln
                435                 440                 445

Asn Arg Tyr Asp Gly Gln Val Ala Val Phe Gly Ser Asp Leu Gln Glu
    450                 455                 460

Lys Leu Gly Lys Gln Lys Tyr Phe Leu Val Gly Ala Gly Ala Ile Gly
465                 470                 475                 480

Cys Glu Leu Leu Lys Asn Phe Ala Met Ile Gly Leu Gly Cys Gly Glu
                485                 490                 495

Gly Gly Glu Ile Ile Val Thr Asp Met Asp Thr Ile Glu Lys Ser Asn
                500                 505                 510

Leu Asn Arg Gln Phe Leu Phe Arg Pro Trp Asp Val Thr Lys Leu Lys
    515                 520                 525

Ser Asp Thr Ala Ala Ala Ala Val Arg Gln Met Asn Pro His Ile Arg
530                 535                 540
```

-continued

Val Thr Ser His Gln Asn Arg Val Gly Pro Asp Thr Glu Arg Ile Tyr
545                 550                 555                 560

Asp Asp Asp Phe Phe Gln Asn Leu Asp Gly Val Ala Asn Ala Leu Asp
            565                 570                 575

Asn Val Asp Ala Arg Met Tyr Met Asp Arg Arg Cys Val Tyr Tyr Arg
            580                 585                 590

Lys Pro Leu Leu Glu Ser Gly Thr Leu Gly Thr Lys Gly Asn Val Gln
    595                 600                 605

Val Val Ile Pro Phe Leu Thr Glu Ser Tyr Ser Ser Gln Asp Pro
    610                 615                 620

Pro Glu Lys Ser Ile Pro Ile Cys Thr Leu Lys Asn Phe Pro Asn Ala
625                 630                 635                 640

Ile Glu His Thr Leu Gln Trp Ala Arg Asp Glu Phe Glu Gly Leu Phe
            645                 650                 655

Lys Gln Pro Ala Glu Asn Val Asn Gln Tyr Leu Thr Asp Pro Lys Phe
            660                 665                 670

Val Glu Arg Thr Leu Arg Leu Ala Gly Thr Gln Pro Leu Glu Val Leu
    675                 680                 685

Glu Ala Val Gln Arg Ser Leu Val Leu Gln Arg Pro Gln Thr Trp Ala
690                 695                 700

Asp Cys Val Thr Trp Ala Cys His His Trp His Thr Gln Tyr Ser Asn
705                 710                 715                 720

Asn Ile Arg Gln Leu Leu His Asn Phe Pro Pro Asp Gln Leu Thr Ser
            725                 730                 735

Ser Gly Ala Pro Phe Trp Ser Gly Pro Lys Arg Cys Pro His Pro Leu
            740                 745                 750

Thr Phe Asp Val Asn Asn Pro Leu His Leu Asp Tyr Val Met Ala Ala
        755                 760                 765

Ala Asn Leu Phe Ala Gln Thr Tyr Gly Leu Thr Gly Ser Gln Asp Arg
    770                 775                 780

Ala Ala Val Ala Thr Phe Leu Gln Ser Val Gln Val Pro Glu Phe Thr
785                 790                 795                 800

Pro Lys Ser Gly Val Lys Ile His Val Ser Asp Gln Glu Leu Gln Ser
            805                 810                 815

Ala Asn Ala Ser Val Asp Asp Ser Arg Leu Glu Glu Leu Lys Ala Thr
            820                 825                 830

Leu Pro Ser Pro Asp Lys Leu Pro Gly Phe Lys Met Tyr Pro Ile Asp
    835                 840                 845

Phe Glu Lys Asp Asp Ser Asn Phe His Met Asp Phe Ile Val Ala
850                 855                 860

Ala Ser Asn Leu Arg Ala Glu Asn Tyr Asp Ile Pro Ser Ala Asp Arg
865                 870                 875                 880

His Lys Ser Lys Leu Ile Ala Gly Lys Ile Ile Pro Ala Ile Ala Thr
            885                 890                 895

Thr Thr Ala Ala Val Val Gly Leu Val Cys Leu Glu Leu Tyr Lys Val
        900                 905                 910

Val Gln Gly His Arg Gln Leu Asp Ser Tyr Lys Asn Gly Phe Leu Asn
    915                 920                 925

Leu Ala Leu Pro Phe Phe Gly Phe Ser Glu Pro Leu Ala Ala Pro Arg
    930                 935                 940

His Gln Tyr Tyr Asn Gln Glu Trp Thr Leu Trp Asp Arg Phe Glu Val
945                 950                 955                 960

Gln Gly Leu Gln Pro Asn Gly Glu Glu Met Thr Leu Lys Gln Phe Leu

-continued

```
                            965                 970                 975
Asp Tyr Phe Lys Thr Glu His Lys Leu Glu Ile Thr Met Leu Ser Gln
                980                 985                 990

Gly Val Ser Met Leu Tyr Ser Phe Phe Met Pro Ala Ala Lys Leu Lys
            995                1000                1005

Glu Arg Leu Asp Gln Pro Met Thr Glu Ile Val Ser Arg Val Ser Lys
       1010                1015                1020

Arg Lys Leu Gly Arg His Val Arg Ala Leu Val Leu Glu Leu Cys Cys
1025                1030                1035                1040

Asn Asp Glu Ser Gly Glu Asp Val Glu Val Pro Tyr Val Arg Tyr Thr
                1045                1050                1055

Ile Arg
```

(2) INFORMATION FOR SEQ ID NO:15:

(i) SEQUENCE CHARACTERISTICS:
        (A) LENGTH: 458 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..458

(xi) SEQUENCE DESCRIPTION: SEQ ID NO:15:

```
ATG TCG ACC CCG GCC CGG AGG AGG CTC ATG CGG GAT TTC AAG CGG TTA        48
Met Ser Thr Pro Ala Arg Arg Arg Leu Met Arg Asp Phe Lys Arg Leu
 1               5                  10                  15

CAA GAG GAC CCA CCT GTG GGT GTC AGT GGC GCA CCA TCT GAA AAC AAC        96
Gln Glu Asp Pro Pro Val Gly Val Ser Gly Ala Pro Ser Glu Asn Asn
                20                  25                  30

ATC ATG CAG TGG AAT GCA GTT ATA TTT GGA CCA GAA GGG ACA CCT TTT       144
Ile Met Gln Trp Asn Ala Val Ile Phe Gly Pro Glu Gly Thr Pro Phe
            35                  40                  45

GAA GAT GGT ACT TTT AAA CTA GTA ATA GAA TTT TCT GAA GAA TAT CCA       192
Glu Asp Gly Thr Phe Lys Leu Val Ile Glu Phe Ser Glu Glu Tyr Pro
        50                  55                  60

AAT AAA CCA CCA ACT GTT AGG TTT TTA TCC AAA ATG TTT CAT CCA AAT       240
Asn Lys Pro Pro Thr Val Arg Phe Leu Ser Lys Met Phe His Pro Asn
 65                  70                  75                  80

GTG TAT GCT GAT GGT AGC ATA TGT TTA GAT ATC CTT CAG AAT CGA TGG       288
Val Tyr Ala Asp Gly Ser Ile Cys Leu Asp Ile Leu Gln Asn Arg Trp
                85                  90                  95

AGT CCA ACA TAT GAT GTA TCT TCT ATC TTA ACA TCA ATT CAG TCT CTG       336
Ser Pro Thr Tyr Asp Val Ser Ser Ile Leu Thr Ser Ile Gln Ser Leu
            100                 105                 110

CTG GAT GAA CCG AAT CCT AAC AGT CCA GCC AAT AGC CAG GCA GCA CAG       384
Leu Asp Glu Pro Asn Pro Asn Ser Pro Ala Asn Ser Gln Ala Ala Gln
        115                 120                 125

CTT TAT CAG GAA AAC AAA CGA GAA TAT GAG AAA AGA GTT CGG GCC ATT       432
Leu Tyr Gln Glu Asn Lys Arg Glu Tyr Glu Lys Arg Val Ser Ala Ile
130                 135                 140

GTT GAA CAA AGC TGG AAT GAT TCA TA                                    458
Val Glu Gln Ser Trp Asn Asp Ser
145                 150
```

(2) INFORMATION FOR SEQ ID NO:16:

(i) SEQUENCE CHARACTERISTICS:

-continued

```
        (A) LENGTH: 152 amino acids
        (B) TYPE: amino acid
        (D) TOPOLOGY: linear (ii) MOLECULE TYPE: protein (xi) SEQUENCE DESCRIPTION: SEQ ID NO:16:

Met Ser Thr Pro Ala Arg Arg Leu Met Arg Asp Phe Lys Arg Leu
  1               5                  10                  15

Gln Glu Asp Pro Pro Val Gly Val Ser Gly Ala Pro Ser Glu Asn Asn
             20                  25                  30

Ile Met Gln Trp Asn Ala Val Ile Phe Gly Pro Glu Gly Thr Pro Phe
         35                  40                  45

Glu Asp Gly Thr Phe Lys Leu Val Ile Glu Phe Ser Glu Glu Tyr Pro
     50                  55                  60

Asn Lys Pro Pro Thr Val Arg Phe Leu Ser Lys Met Phe His Pro Asn
 65                  70                  75                  80

Val Tyr Ala Asp Gly Ser Ile Cys Leu Asp Ile Leu Gln Asn Arg Trp
             85                  90                  95

Ser Pro Thr Tyr Asp Val Ser Ser Ile Leu Thr Ser Ile Gln Ser Leu
            100                 105                 110

Leu Asp Glu Pro Asn Pro Asn Ser Pro Ala Asn Ser Gln Ala Ala Gln
            115                 120                 125

Leu Tyr Gln Glu Asn Lys Arg Glu Tyr Glu Lys Arg Val Ser Ala Ile
    130                 135                 140

Val Glu Gln Ser Trp Asn Asp Ser
145                 150

(2) INFORMATION FOR SEQ ID NO:17:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO:17:

Ala Ile Arg Gly
```